(12) United States Patent
Kim et al.

(10) Patent No.: US 12,069,879 B2
(45) Date of Patent: Aug. 20, 2024

(54) ORGANIC LIGHT-EMITTING DEVICE

(71) Applicants: Samsung Electronics Co., Ltd., Suwon-si (KR); Samsung SDI Co., Ltd., Yongin-si (KR)

(72) Inventors: Jongsoo Kim, Seoul (KR); Joonghyuk Kim, Seoul (KR); Namheon Lee, Suwon-si (KR); Inkoo Kim, Suwon-si (KR); Daun Jeong, Anyang-si (KR); Sunghan Kim, Seongnam-si (KR); Myungsun Sim, Suwon-si (KR); Sooghang Ihn, Hwaseong-si (KR)

(73) Assignees: SAMSUNG ELECTRONICS CO., LTD., Gyeonggi-Do (KR); SAMSUNG SDI CO, LTD., Gyeonggi-Do (KR)

( * ) Notice: Subject to any disclaimer, the term of this patent is extended or adjusted under 35 U.S.C. 154(b) by 389 days.

(21) Appl. No.: 16/161,574

(22) Filed: Oct. 16, 2018

(65) Prior Publication Data
US 2019/0157603 A1    May 23, 2019

(30) Foreign Application Priority Data
Nov. 20, 2017   (KR) ........................ 10-2017-0154975

(51) Int. Cl.
| | |
|---|---|
| *H10K 50/805* | (2023.01) |
| *C07D 209/82* | (2006.01) |
| *C07D 219/14* | (2006.01) |
| *C07D 333/76* | (2006.01) |
| *C07D 401/10* | (2006.01) |
| *C07D 403/14* | (2006.01) |
| *C07D 405/10* | (2006.01) |
| *C07D 405/14* | (2006.01) |
| *C07D 409/10* | (2006.01) |
| *C07D 487/04* | (2006.01) |
| *C07D 491/048* | (2006.01) |
| *C07D 495/04* | (2006.01) |
| *C07D 519/00* | (2006.01) |
| *H10K 50/12* | (2023.01) |
| *H10K 50/13* | (2023.01) |
| *H10K 50/16* | (2023.01) |
| *H10K 85/30* | (2023.01) |
| *H10K 85/40* | (2023.01) |
| *H10K 85/60* | (2023.01) |
| *H10K 101/00* | (2023.01) |

(52) U.S. Cl.
CPC ......... *H10K 50/805* (2023.02); *C07D 209/82* (2013.01); *C07D 219/14* (2013.01); *C07D 333/76* (2013.01); *C07D 401/10* (2013.01); *C07D 403/14* (2013.01); *C07D 405/10* (2013.01); *C07D 405/14* (2013.01); *C07D 409/10* (2013.01); *C07D 487/04* (2013.01); *C07D 491/048* (2013.01); *C07D 495/04* (2013.01); *C07D 519/00* (2013.01); *H10K 50/13* (2023.02); *H10K 50/16* (2023.02); *H10K 85/342* (2023.02); *H10K 85/40* (2023.02); *H10K 85/654* (2023.02); *H10K 85/657* (2023.02); *H10K 85/6572* (2023.02); *H10K 85/6574* (2023.02); *H10K 85/6576* (2023.02); *H10K 50/12* (2023.02); *H10K 2101/90* (2023.02)

(58) Field of Classification Search
None
See application file for complete search history.

(56) References Cited

U.S. PATENT DOCUMENTS

| | | | |
|---|---|---|---|
| 2006/0251923 A1* | 11/2006 | Lin ............................... 428/690 |
| 2009/0072727 A1* | 3/2009 | Takeda .......................... 313/504 |
| 2010/0270916 A1* | 10/2010 | Xia ............................... 313/504 |
| 2011/0057559 A1* | 3/2011 | Xia ............................... 313/504 |
| 2013/0234119 A1* | 9/2013 | Mizuki ............... H01L 51/0072 |
| | | | 257/40 |
| 2016/0233440 A1* | 8/2016 | Bae ..................... H01L 51/0085 |
| 2017/0077421 A1 | 3/2017 | Ihn et al. |
| 2017/0213968 A1* | 7/2017 | Park ..................... H01L 51/006 |

(Continued)

FOREIGN PATENT DOCUMENTS

| | | |
|---|---|---|
| KR | 10-2011-0088457 A | 8/2011 |
| KR | 10-2015-0010387 A | 1/2015 |

(Continued)

OTHER PUBLICATIONS

Tao et al. "Thermally Activated Delayed Fluorescence Materials Towards the Breakthrough of Organoelectronics", Adv. Mater. 2014, vol. 26, p. 7931-7958 (Year: 2014).*

(Continued)

*Primary Examiner* — Jennifer A Boyd
*Assistant Examiner* — Seokmin Jeon
(74) *Attorney, Agent, or Firm* — CANTOR COLBURN LLP

(57) ABSTRACT

An organic light-emitting device including a first electrode, a second electrode facing the first electrode, and an emission layer disposed between the first electrode and the second electrode, wherein the emission layer includes a first material not including an electron transport moiety, a second material including at least one electron transport moiety, a third material having reorganization energy of about 0.4 eV or more, and a light-emitting material, wherein the first material, the second material, the third material, and the light-emitting material are different from one another, and wherein a ratio of a light-emitting component emitted from the light-emitting material to a total of light-emitting components emitted from the emission layer is about 90% or more.

16 Claims, 1 Drawing Sheet

(56) References Cited

U.S. PATENT DOCUMENTS

2017/0342057 A1   11/2017  Shim et al.
2019/0040314 A1*  2/2019  Ito ........................ C09K 11/06

FOREIGN PATENT DOCUMENTS

| | | |
|---|---|---|
| KR | 10-2016-0056298 A | 5/2016 |
| KR | 10-2016-0060569 A | 5/2016 |
| KR | 10-2017-0032148 A | 3/2017 |
| WO | 2016-080791 A1 | 5/2016 |

OTHER PUBLICATIONS

A screen shot of web page captured on Jun. 26, 2017 using the Wayback Machine, web page address—https://www.thoughtco.com/the-visible-light-spectrum-2699036 (Year: 2017).*

Machine translated English version of KR 20110088457 A, Ikuo Kinoshita (Year: 2011).*

English translation of JP 2010/215759 A and the original JP 2010/215759 A, Sep. 30, 2010, Masahito Nishizeki (Year: 2010).*

* cited by examiner

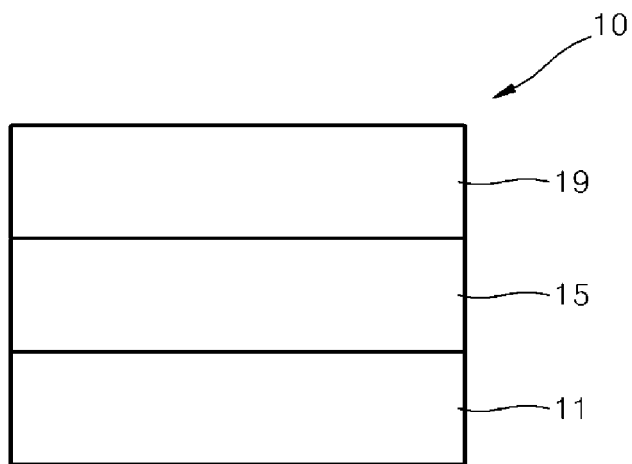

ORGANIC LIGHT-EMITTING DEVICE

CROSS-REFERENCE TO RELATED APPLICATION

This application claims priority to Korean Patent Application No. 10-2017-0154975, filed on Nov. 20, 2017, in the Korean Intellectual Property Office, and all the benefits accruing therefrom under 35 U.S.C. § 119, the content of which is incorporated herein in its entirety by reference.

BACKGROUND

1. Field

The present disclosure relates to an organic light-emitting device.

2. Description of the Related Art

Organic light-emitting devices (OLEDs) are self-emission devices that produce full-color images, and that also have wide viewing angles, high contrast ratios, short response times, and excellent characteristics in terms of brightness, driving voltage, and response speed, compared to devices in the art.

In an example, an organic light-emitting device includes an anode, a cathode, and an organic layer disposed between the anode and the cathode, wherein the organic layer includes an emission layer. A hole transport region may be disposed between the anode and the emission layer, and an electron transport region may be disposed between the emission layer and the cathode. Holes provided from the anode may move toward the emission layer through the hole transport region, and electrons provided from the cathode may move toward the emission layer through the electron transport region. The holes and the electrons recombine in the emission layer to produce excitons. These excitons transit from an excited state to a ground state, thereby generating light.

Various types of organic light emitting devices are known. However, there still remains a need in OLEDs having low driving voltage, high efficiency, high brightness, and long lifespan.

SUMMARY

Aspects of the present disclosure provide an organic light-emitting device with a long lifespan, which includes a first material, a second material, a third material, and a light-emitting material.

Additional aspects will be set forth in part in the description which follows and, in part, will be apparent from the description, or may be learned by practice of the presented embodiments.

An aspect provides an organic light-emitting device including:
a first electrode;
a second electrode facing the first electrode; and
an emission layer between the first electrode and the second electrode,
wherein the emission layer includes a first material, a second material, a third material, and a light-emitting material,
the first material does not include an electron transport moiety,
the second material includes at least one electron transport moiety,
the third material has reorganization energy of about 0.4 eV or more,
the first material, the second material, the third material, and the light-emitting material are different from one another, and
a ratio of a light-emitting component emitted from the light-emitting material to a total of light-emitting components emitted from the emission layer is 90% or more.

BRIEF DESCRIPTION OF THE DRAWING

These and/or other aspects will become apparent and more readily appreciated from the following description of the embodiments, taken in conjunction with the FIGURE which is a schematic view of an organic light-emitting device according to an embodiment.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the FIGURES, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

The term "or" means "and/or." It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the FIGURES are schematic in nature and their shapes are not intended to illustrate the precise shape of a region and are not intended to limit the scope of the present claims.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

In an embodiment, an organic light-emitting device is provided. The organic light-emitting device according to an embodiment may include a first electrode, a second electrode facing the first electrode, and an emission layer between the first electrode and the second electrode, wherein the emission layer may include a first material, a second material, a third material, and a light-emitting material.

The first material does not include an electron transport moiety, and the second material may include at least one electron transport moiety.

For example, the first material may include at least one π electron-depleted nitrogen-free cyclic group and may not include an electron transport moiety, and the second material may include at least one π electron-depleted nitrogen-free cyclic group and at least one electron transport moiety. The electron transport moiety may be selected from a cyano group, a π electron-depleted nitrogen-containing cyclic group, and a group represented by one of Formulae illustrated below:

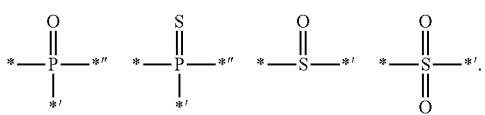

In Formulae, *, *', and *" each indicate a binding site to a neighboring atom.

The "π electron-depleted nitrogen-containing cyclic group" means a group including a cyclic group having at least one *—N=*' moiety and may be, for example, an imidazole group, a pyrazole group, a thiazole group, an isothiazole group, an oxazole group, an isoxazole group, a pyridine group, a pyrazine group, a pyridazine group, a pyrimidine group, an indazole group, a purine group, a quinoline group, an isoquinoline group, a benzoquinoline group, a benzoisoquinoline group, a phthalazine group, a naphthyridine group, a quinoxaline group, a benzoquinoxaline group, a quinazoline group, a cinnoline group, a phenanthridine group, a phenanthroline group, a phenazine group, a benzimidazole group, an iso-benzothiazole group, a benzoxazole group, an isobenzoxazole group, a triazole group, a tetrazole group, an oxadiazole group, a triazine group, a thiadiazole group, an imidazopyridine group, an imidazopyrimidine group, an azaindene group, an azaindole group, an azabenzofuran group, an azabenzothiophene group, an azabenzosilole group, an azafluorene group, an azacarbazole group, an azadibenzofuran group, an azadibenzothiophene group, an azadibenzosilole group, or a condensed group condensed with at least one of these groups and a cyclic group.

The π electron-depleted nitrogen-free cyclic group may be, for example, a benzene group, a heptalene group, an indene group, a naphthalene group, an azulene group, a heptalene group, an indacene group, an acenaphthylene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentacene group, a hexacene group, a pentaphene group, a rubicene group, a coronene group, an ovalene group, a pyrrole group, an iso-indole group, an indole group, a furan group, a thiophene group, a benzofuran group, a benzothiophene group, a benzosilole group, a benzocarbazole group, a dibenzocarbazole group, a dibenzofuran group, a dibenzothiophene group, a dibenzothiophene sulfone group, a carbazole group, a dibenzosilole group, an indeno carbazole group, an indolocarbazole group, a benzofurocarbazole group, a benzothienocarbazole group, a benzosilolocarbazole group, a triindolobenzene group, an acridine group, or a dihydroacridine group, but embodiments of the present disclosure are not limited thereto.

In an embodiment, the first material may include at least one of a compound represented by Formula H-1(1), a compound represented by Formula H-1(2), and a compound represented by Formula H-1(3):

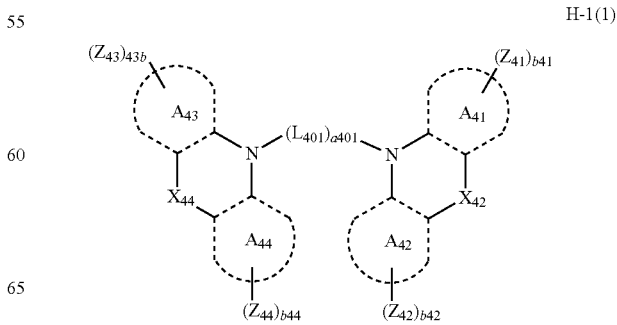

H-1(2)

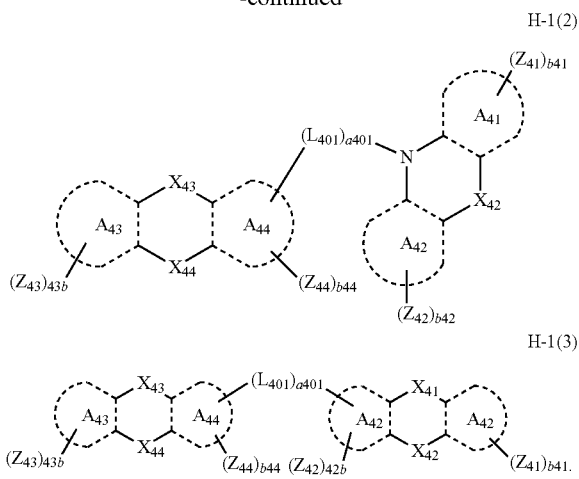

H-1(3)

$A_{41}$ to $A_{44}$ in Formulae H-1(1) to H-1(3) may each independently be a benzene group, a naphthalene group, an indene group, an indole group, a benzofuran group, a benzothiophene group, a benzosilole group, a fluorene group, a carbazole group, a dibenzofuran group, a dibenzothiophene group, or a dibenzosilole group.

For example, $A_{41}$ to $A_{44}$ may each independently be a benzene group, a fluorene group, a carbazole group, a dibenzofuran group, a dibenzothiophene group, or a dibenzosilole group, wherein at least one of $A_{41}$ and $A_{42}$ may be a benzene group, and at least one of $A_{43}$ and $A_{44}$ may be a benzene group.

In Formulae H-1(1) to H-1(3), $X_{41}$ may be N-$[(L_{411})_{c411}$-$Z_{411}]$, C($Z_{415}$)($Z_{416}$), O, or S, $X_{42}$ may be a single bond, N-$[(L_{412})_{c412}$-$Z_{412}]$, C($Z_{417}$)($Z_{418}$), O, or S, $X_{43}$ may be N-$[(L_{413})_{c413}$-$Z_{413}]$, C($Z_{419}$)($Z_{420}$), O, or S, and $X_{44}$ may be a single bond, N-$[(L_{414})_{c414}$-$Z_{414}]$, C($Z_{421}$)($Z_{422}$), O, or S.

$L_{401}$ and $L_{411}$ to $L_{414}$ may each independently be selected from:

a single bond; and a π electron-depleted nitrogen-free cyclic group, unsubstituted or substituted with at least one selected from deuterium, a $C_1$-$C_{10}$ alkyl group, a $C_1$-$C_{10}$ alkoxy group, a phenyl group, a naphthyl group, a fluorenyl group, a carbazolyl group, a dibenzofuranyl group, a dibenzothiophenyl group, a triphenylenyl group, a biphenyl group, a terphenyl group, a tetraphenyl group, and —Si($Q_{401}$)($Q_{402}$)($Q_{403}$) (for example, a benzene group, a heptalene group, an indene group, a naphthalene group, an azulene group, a heptalene group, an indacene group, an acenaphthylene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentacene group, a hexacene group, a pentaphene group, a rubicene group, a coronene group, an ovalene group, a pyrrole group, an isoindole group, an indole group, a furan group, a thiophene group, a benzofuran group, a benzothiophene group, a benzosilole group, a benzocarbazole group, a dibenzocarbazole group, a dibenzofuran group, a dibenzothi- ophene group, a dibenzothiophene sulfone group, a carbazole group, a dibenzosilole group, an indeno carbazole group, an indolocarbazole group, a benzofurocarbazole group, a benzothienocarbazole group, a benzosilolocarbazole group, a triindolobenzene group, an acridine group, or a dihydroacridine group, each unsubstituted or substituted with at least one selected from deuterium, a $C_1$-$C_{10}$ alkyl group, a $C_1$-$C_{10}$ alkoxy group, a phenyl group, a naphthyl group, a fluorenyl group, a carbazolyl group, a dibenzofuranyl group, a dibenzothiophenyl group, a triphenylenyl group, a biphenyl group, a terphenyl group, a tetraphenyl group, and —Si($Q_{401}$)($Q_{402}$)($Q_{403}$)).

a401 and c411 to c414 indicate the number of groups $L_{401}$ and groups $L_{411}$ to $L_{414}$, respectively, and may each independently be an integer from 1 to 10, wherein, when a401 is two or more, two or more groups $L_{401}$ may be identical to or different from each other, when c411 is two or more, two or more groups $L_{411}$ may be identical to or different from each other, when c412 is two or more, two or more groups $L_{412}$ may be identical to or different from each other, when c413 is two or more, two or more groups $L_{413}$ may be identical to or different from each other, and when c414 is two or more, two or more groups $L_{414}$ may be identical to or different from each other.

For example, a401 and c411 to c414 may each independently be 1, 2, or 3.

$Z_{41}$ to $Z_{44}$ and $Z_{411}$ to $Z_{422}$ may each independently be selected from:

hydrogen, deuterium, a $C_1$-$C_{10}$ alkyl group, and a $C_1$-$C_{10}$ alkoxy group; and a π electron-depleted nitrogen-free cyclic group, unsubstituted or substituted with at least one selected from deuterium, a $C_1$-$C_{10}$ alkyl group, a $C_1$-$C_{10}$ alkoxy group, a phenyl group, a naphthyl group, a fluorenyl group, a carbazolyl group, a dibenzofuranyl group, a dibenzothiophenyl group, a triphenylenyl group, a biphenyl group, a terphenyl group, a tetraphenyl group, and —Si($Q_{401}$)($Q_{402}$)($Q_{403}$) (for example, a phenyl group, a biphenyl group, a terphenyl group, a tetraphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, a chrysenyl group, a pyrrolyl group, an isoindolyl group, an indolyl group, a furanyl group, a thiophenyl group, a benzofuranyl group, a benzothiophenyl group, a benzosilolyl group, a benzocarbazolyl group, a dibenzocarbazolyl group, a dibenzofuranyl group, a dibenzothiophenyl group, a carbazolyl group, a dibenzosilolyl group, an indeno carbazolyl group, an indolocarbazolyl group, a benzofurocarbazolyl group, a benzothienocarbazolyl group, a benzosilolocarbazolyl group, an acridinyl group, or a dihydroacridinyl group, each unsubstituted or substituted with at least one selected from deuterium, a $C_1$-$C_{10}$ alkyl group, a $C_1$-$C_{10}$ alkoxy group, a phenyl group, a naphthyl group, a fluorenyl group, a carbazolyl group, a dibenzofuranyl group, a dibenzothiophenyl group, a triphenylenyl group, a biphenyl group, a terphenyl group, a tetraphenyl group, and —Si($Q_{401}$)($Q_{402}$)($Q_{403}$)).

b41 to b44 indicate the number of groups $Z_{41}$ to $Z_{44}$, respectively, and may each independently be 1, 2, 3, or 4. When b41 is two or more, two or more groups $Z_{41}$ may be identical to or different from each other, when b42 is two or more, two or more groups $Z_{42}$ may be identical to or different from each other, when b43 is two or more, two or more groups $Z_{43}$ may be identical to or different from each other, and when b44 is two or more, two or more groups $Z_{44}$ may be identical to or different from each other.

For example, b41 to b44 may each independently be 1 or 2, but embodiments of the present disclosure are not limited thereto.

$Q_{401}$ to $Q_{403}$ may each independently be hydrogen, deuterium, a $C_1$-$C_{10}$ alkyl group, a $C_1$-$C_{10}$ alkoxy group, a phenyl group, a naphthyl group, a fluorenyl group, a carbazolyl group, a dibenzofuranyl group, a dibenzothiophenyl group, a triphenylenyl group, a biphenyl group, a terphenyl group, or a tetraphenyl group.

In an embodiment, $L_{401}$ and $L_{411}$ to $L_{414}$ may each independently be selected from:
  a single bond; and
  a benzene group, a fluorene group, a dibenzofuran group, a dibenzothiophene group, a carbazole group, a dibenzosilole group, an indeno carbazole group, an indolocarbazole group, a benzofurocarbazole group, a benzothienocarbazole group, a benzosilolocarbazole group, an acridine group, or a dihydroacridine group, each unsubstituted or substituted with at least one selected from deuterium, a $C_1$-$C_{10}$ alkyl group, a $C_1$-$C_{10}$ alkoxy group, a phenyl group, a naphthyl group, a fluorenyl group, a carbazolyl group, a dibenzofuranyl group, a dibenzothiophenyl group, a triphenylenyl group, a biphenyl group, a terphenyl group, and a tetraphenyl group, and $Z_{41}$ to $Z_{44}$ and $Z_{411}$ to $Z_{422}$ may each independently be selected from:
  hydrogen, deuterium, a $C_1$-$C_{10}$ alkyl group, and a $C_1$-$C_{10}$ alkoxy group; and
  a phenyl group, a biphenyl group, a terphenyl group, a tetraphenyl group, a fluorenyl group, a dibenzocarbazolyl group, a dibenzofuranyl group, a dibenzothiophenyl group, a carbazolyl group, a dibenzosilolyl group, an indenocarbazolyl group, an indolocarbazolyl group, a benzofurocarbazolyl group, a benzothienocarbazolyl group, a benzosilolocarbazolyl group, an acridinyl group, or a dihydroacridinyl group, each unsubstituted or substituted with at least one selected from deuterium, a $C_1$-$C_{10}$ alkyl group, a $C_1$-$C_{10}$ alkoxy group, a phenyl group, a naphthyl group, a fluorenyl group, a carbazolyl group, a dibenzofuranyl group, a dibenzothiophenyl group, a triphenylenyl group, a biphenyl group, a terphenyl group, and a tetraphenyl group,
  but embodiments of the present disclosure are not limited thereto.

In an embodiment, the first material may include at least one compound selected from Compounds H1 to H32, but embodiments of the present disclosure are not limited thereto:

H1

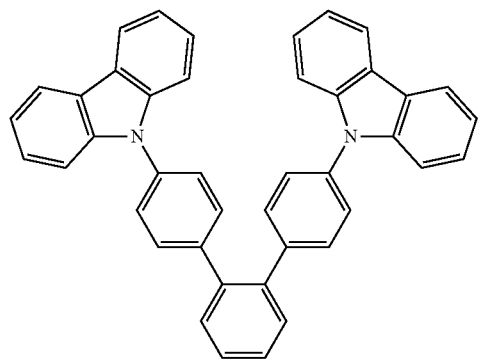

H2

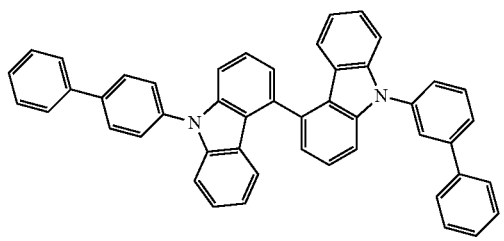

H3

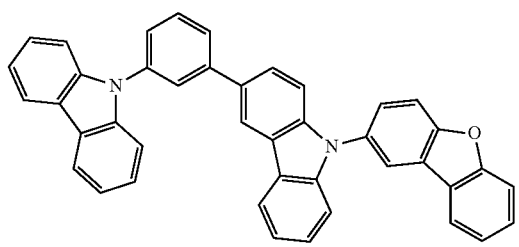

H4

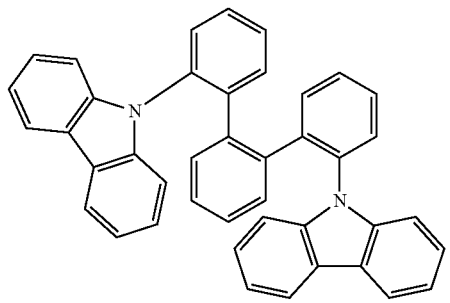

H5

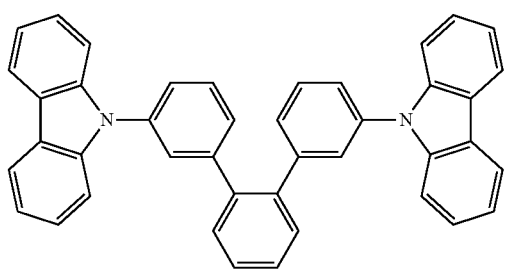

H6

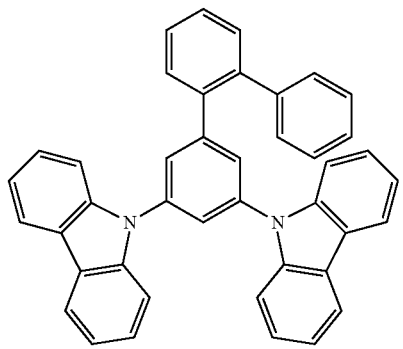

H7
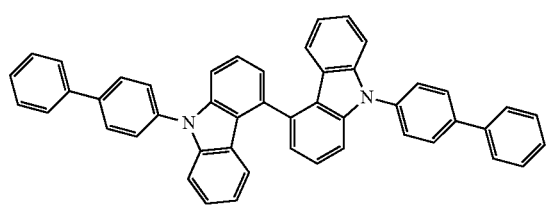
H8
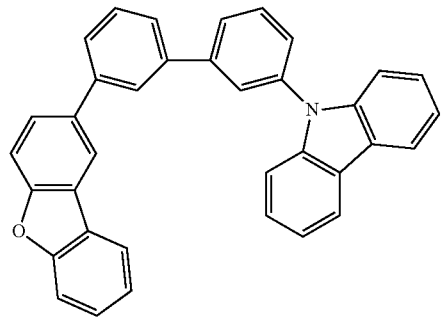
H9
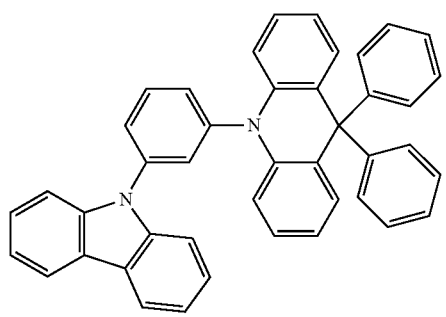
H10
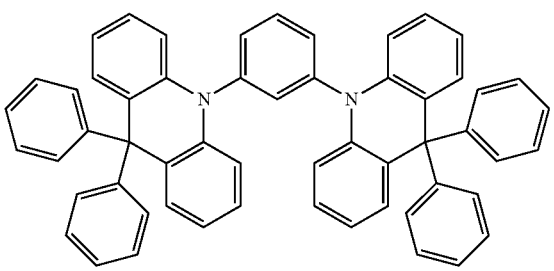
H11
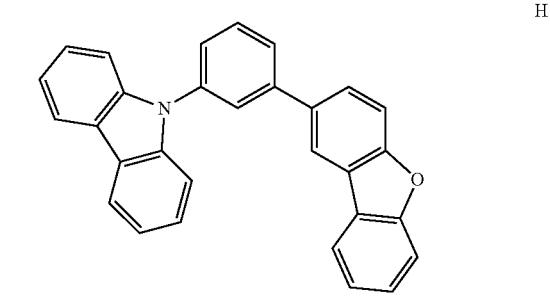
H12
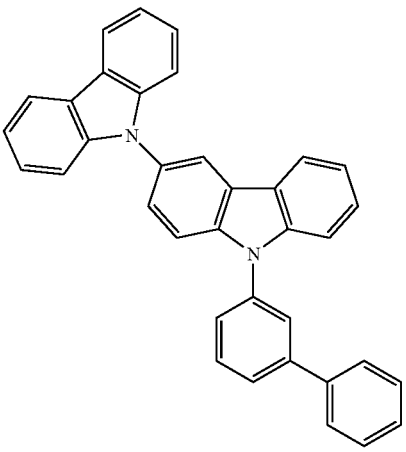
H13
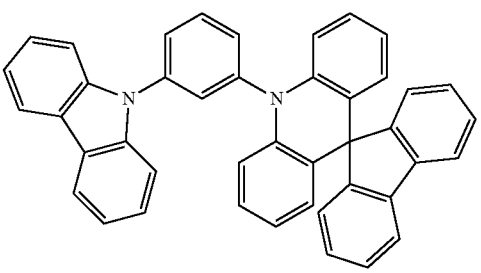
H14
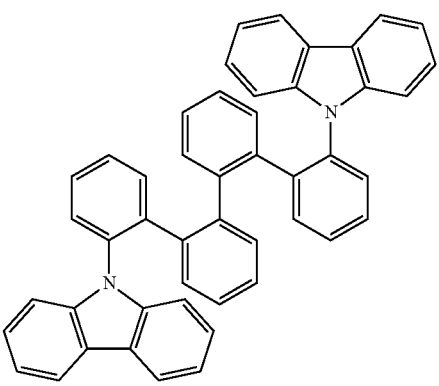
H15
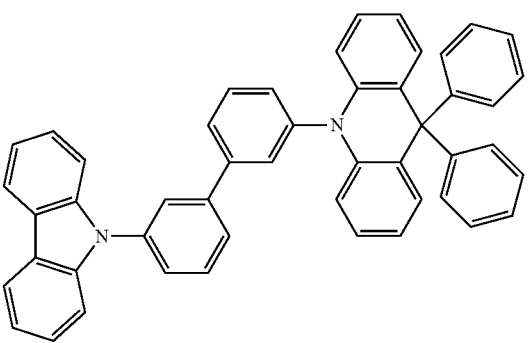

H16
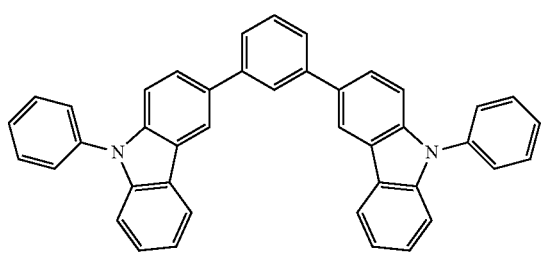
H17
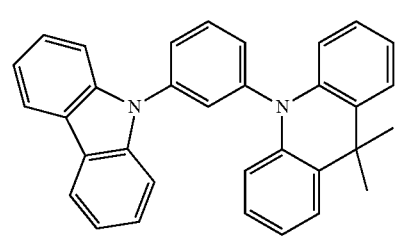
H18
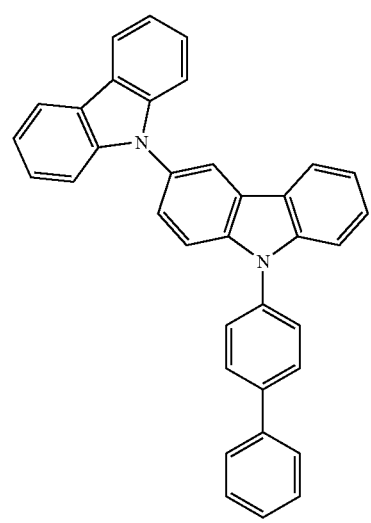
H19
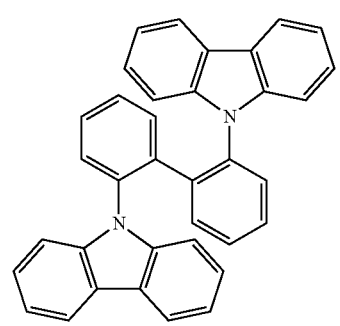
H20
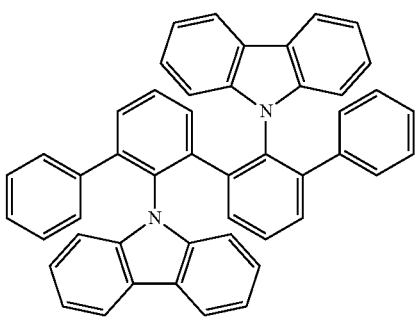
H21
H22
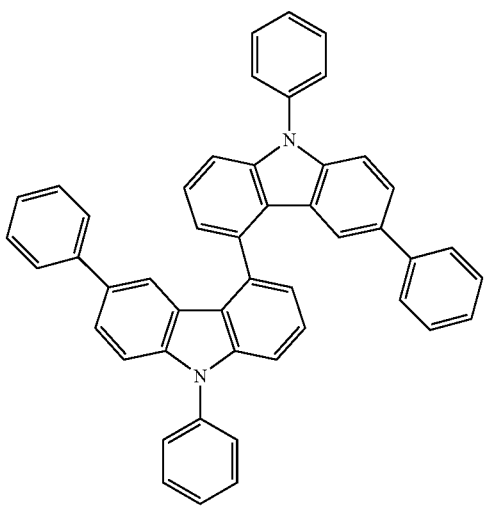

H23
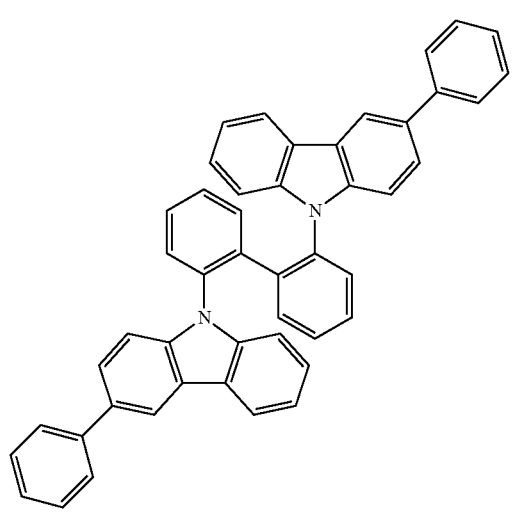
H24
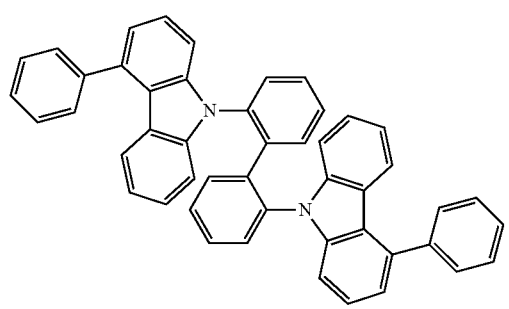
H25
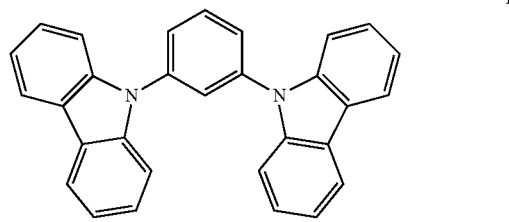
H26
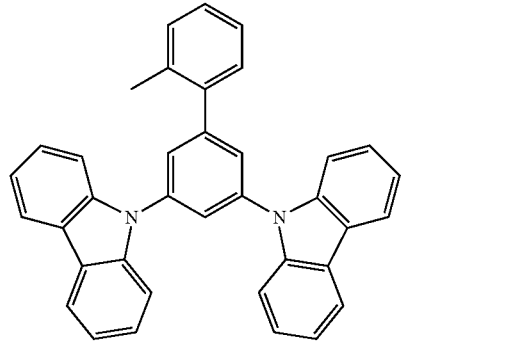
H27
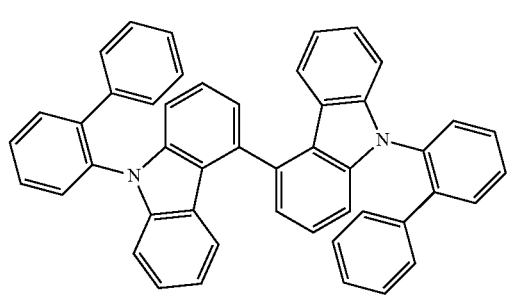
H28
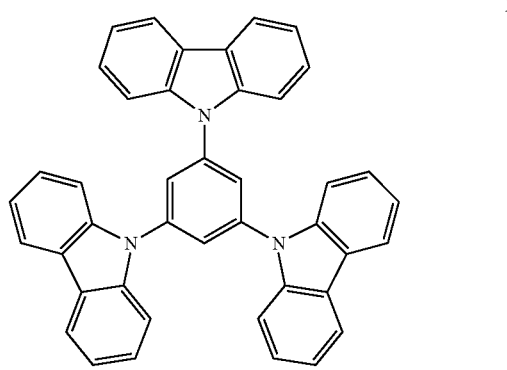
H29
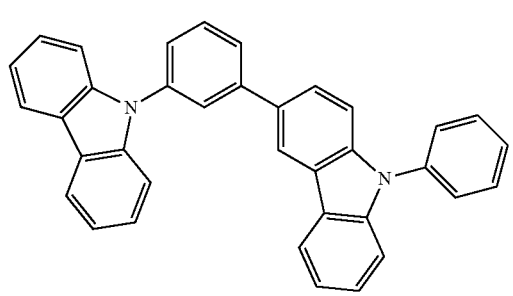
H30
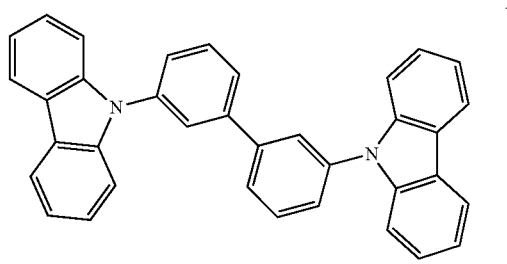
H31
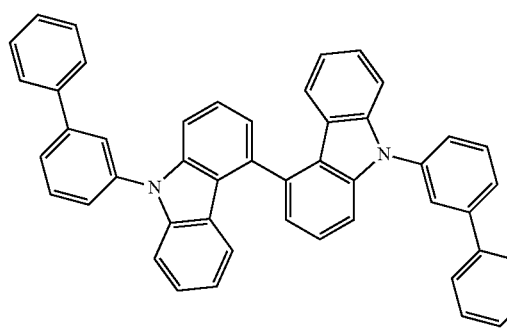

-continued

H32

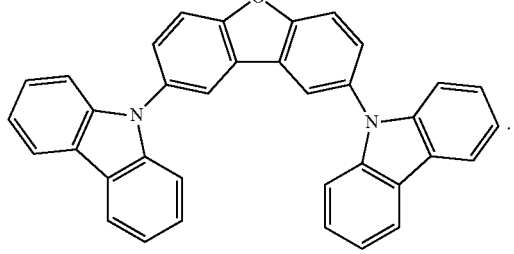

In one or more embodiments, the second material may include at least one cyano group.

In one or more embodiments, the second material may include at least one cyano group and at least one carbazole ring.

In one or more embodiments, the second material may include a compound represented by Formula E-1:

[Ar$_{301}$]$_{xb11}$-[(L$_{301}$)$_{xb1}$-R$_{301}$]$_{xb21}$.   Formula E-1

In Formula E-1,

Ar$_{301}$ may be selected from a substituted or unsubstituted C$_5$-C$_{60}$ carbocyclic group and a substituted or unsubstituted C$_1$-C$_{60}$ heterocyclic group, xb11 may be 1, 2, or 3, and L$_{301}$ may be selected from a single bond, a group represented by one of Formulae illustrated below, a substituted or unsubstituted C$_5$-C$_{60}$ carbocyclic group, and a substituted or unsubstituted C$_1$-C$_{60}$ heterocyclic group, and *, *', and *'' in Formulae each indicate a binding site to a neighboring atom:

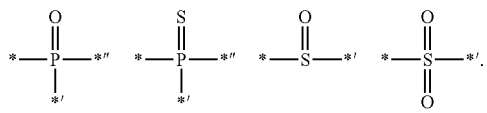

xb1 may be an integer from 1 to 5,

R$_{301}$ may be selected from hydrogen, deuterium, —F, —Cl, —Br, —I, a hydroxyl group, a cyano group, a nitro group, an amidino group, a hydrazino group, a hydrazono group, a substituted or unsubstituted C$_1$-C$_{60}$ alkyl group, a substituted or unsubstituted C$_2$-C$_{60}$ alkenyl group, a substituted or unsubstituted C$_2$-C$_{60}$ alkynyl group, a substituted or unsubstituted C$_1$-C$_{60}$ alkoxy group, a substituted or unsubstituted C$_3$-C$_{10}$ cycloalkyl group, a substituted or unsubstituted C$_1$-C$_{10}$ heterocycloalkyl group, a substituted or unsubstituted C$_3$-C$_{10}$ cycloalkenyl group, a substituted or unsubstituted C$_1$-C$_{10}$ heterocycloalkenyl group, a substituted or unsubstituted C$_6$-C$_{60}$ aryl group, a substituted or unsubstituted C$_6$-C$_{60}$ aryloxy group, a substituted or unsubstituted C$_6$-C$_{60}$ arylthio group, a substituted or unsubstituted C$_1$-C$_{60}$ heteroaryl group, a substituted or unsubstituted monovalent non-aromatic condensed polycyclic group, a substituted or unsubstituted monovalent non-aromatic condensed heteropolycyclic group, —Si(Q$_{301}$)(Q$_{302}$)(Q$_{303}$), —N(Q$_{301}$)(Q$_{302}$), —B(Q$_{301}$)(Q$_{302}$), —C(=O)(Q$_{301}$), —S(=O)$_2$(Q$_{301}$), —S(=O)(Q$_{301}$), —P(=O)(Q$_{301}$)(Q$_{302}$), and —P(=S)(Q$_{301}$)(Q$_{302}$), xb21 may be an integer from 1 to 5, Q$_{301}$ to Q$_{303}$ may each independently be selected from a C$_1$-C$_{10}$ alkyl group, a alkoxy group, a phenyl group, a biphenyl group, a terphenyl group, and a naphthyl group, and at least one of <Condition 1> to <Condition 3> is satisfied:

Condition 1 at least one of Ar$_{301}$, L$_{301}$, and R$_{301}$ in Formula E-1 includes a π electron-depleted nitrogen-containing cyclic group;

Condition 2

L$_{301}$ in Formula E-1 is a group represented by one of Formulae illustrated below:

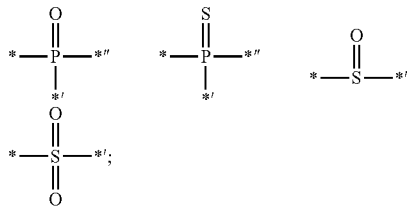

and

Condition 3

R$_{301}$ in Formula E-1 is selected from a cyano group, —S(=O)$_2$(Q$_{301}$), —S(=O)(Q$_{301}$), —P(=O)(Q$_{301}$)(Q$_{302}$), and —P(=S)(Q$_{301}$)(Q$_{302}$).

In one or more embodiments, the second material may include at least one of a compound represented by Formula E-1(1), a compound represented by Formula E-1(2), and a compound represented by Formula E-1(3):

E-1(1)

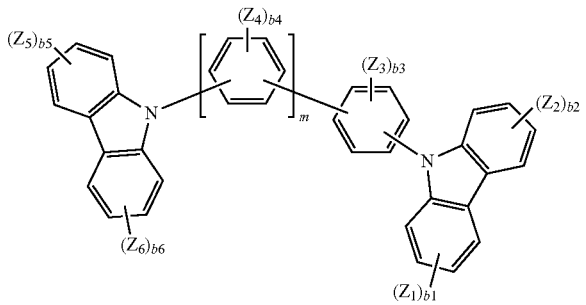

E-1(2)

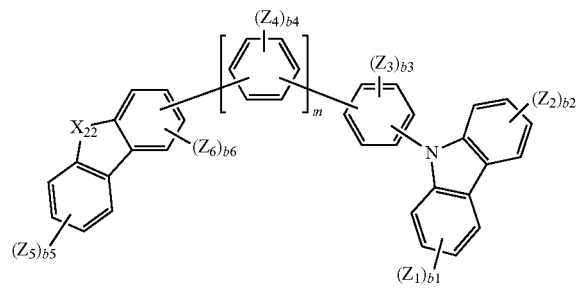

E-1(3)

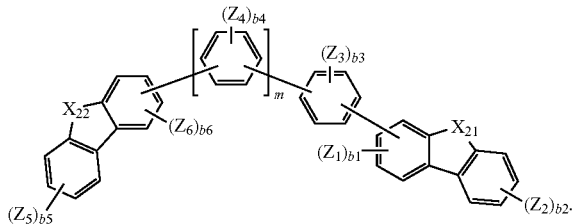

$Z_1$ to $Z_6$ in Formulae E-1(1) to E-1(3) may each independently be:
hydrogen, deuterium, or a cyano group (CN); or
a $C_1$-$C_{20}$ alkyl group, a phenyl group, a biphenyl group, a terphenyl group, a dibenzofuranyl group, or a dibenzothiophenyl group, each unsubstituted or substituted with at least one selected from deuterium, a cyano group, a $C_1$-$C_{20}$ alkyl group, a phenyl group, and a biphenyl group.

For example, $Z_1$ to $Z_6$ in Formulae E-1(1) to E-1(3) may each independently be:
hydrogen, deuterium, or a cyano group; or
a $C_3$-$C_{10}$ alkyl group, a phenyl group, a biphenyl group, a terphenyl group, a dibenzofuranyl group, or a dibenzothiophenyl group, each unsubstituted or substituted with at least one selected from deuterium, a cyano group, a $C_3$-$C_{10}$ alkyl group, a phenyl group, and a biphenyl group.

In an embodiment, $Z_1$ to $Z_6$ in Formulae E-1(1) to E-1(3) may each independently be:
hydrogen, deuterium, or a cyano group; or
an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, a biphenyl group, or a terphenyl group, each unsubstituted or substituted with at least one selected from deuterium, a cyano group, an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a biphenyl group.

b1 to b6 in Formulae E-1(1) to E-1(3) indicate the number of groups $Z_1$ to $Z_6$, respectively, and may each independently be 1, 2, or 3. When b1 to b6 are two or more, two or more groups $Z_1$ to $Z_6$ are identical to or different from each other, respectively.

In Formulae E-1(1) to E-1(3), at least one of groups $Z_1$ in the number of b1, groups $Z_2$ in the number of b2, groups $Z_3$ in the number of b3, groups $Z_4$ in the number of b4, groups $Z_5$ in the number of b5, and groups $R_6$ in the number of b6 may be a cyano group. That is, Formulae Formula E-1(1) to E-1(3) essentially includes at least one cyano group.

For example, the number of cyano groups included in the compound represented by Formula E-1(1), the number of cyano groups included in the compound represented by Formula E-1(2), and the number of cyano groups included in the compound represented by Formula E-1(3) may each independently be 1, 2, or 3, but embodiments of the present disclosure are not limited thereto.

In an embodiment, in Formulae E-1(1) to E-1(3),
at least one of groups $Z_1$ in the number of b1 and groups $Z_2$ in the number of b2 may be a cyano group, at least one of groups $Z_3$ in the number of b3 and groups $Z_4$ in the number of b4 may be a cyano group,
at least one of groups $Z_5$ in the number of b5 and groups $Z_6$ in the number of b6 may be a cyano group,
at least one of groups $Z_1$ in the number of b1 and groups $Z_2$ in the number of b2 may be a cyano group, and at least one of groups $Z_3$ in the number of b3 and groups $Z_4$ in the number of b4 may be a cyano group,
at least one of groups $Z_1$ in the number of b1 and groups $Z_2$ in the number of b2 may be a cyano group, and at least one of groups $Z_5$ in the number of b5 and groups $Z_6$ in the number of b6 may be a cyano group,
at least one of groups $Z_3$ in the number of b3 and groups $Z_4$ in the number of b4 may be a cyano group, and at least one of groups $Z_5$ in the number of b5 and groups $Z_6$ in the number of b6 may be a cyano group, or
at least one of groups $Z_1$ in the number of b1 and groups $Z_2$ in the number of b2 may be a cyano group, at least one of groups $Z_3$ in the number of b3 and groups $Z_4$ in the number of b4 may be a cyano group, and at least one of groups $Z_5$ in the number of b5 and groups $Z_6$ in the number of b6 may be a cyano group.

$X_{21}$ and $X_{22}$ in Formulae E-1(1) to E-1(3) may each independently be O or S, and m may be 0 or 1.

In an embodiment, a group represented by

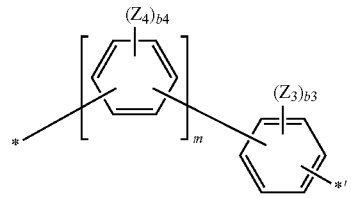

in Formulae E-1(1) to E-1(3) may be one of groups represented by Formulae PO1 to PO25, PM1 to PM25, PP1 to PP18, MO1 to MO37, MM1 to MM37, MP1 to MP25, OO1 to OO37, OM1 to OM37, OP1 to OP25, O1 to O16, M1 to M16, and P1 to P9:

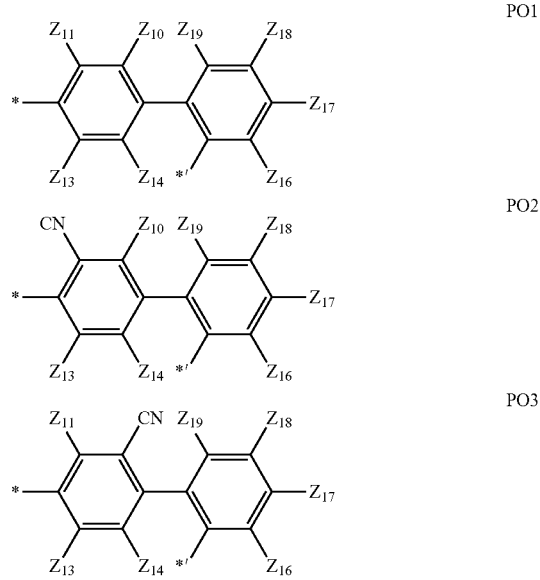

PO4 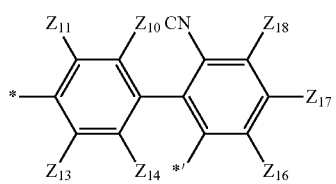
PO5 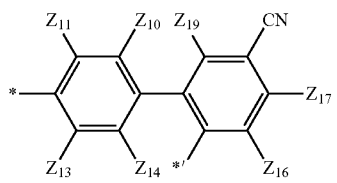
PO6 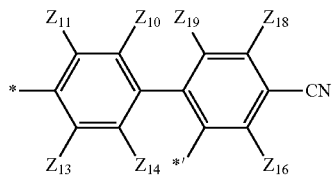
PO7 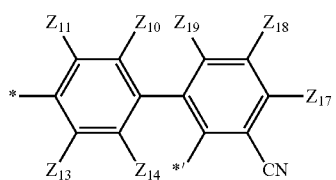
PO8 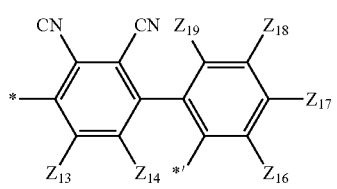
PO9 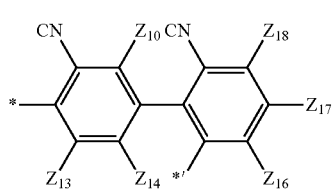
PO10 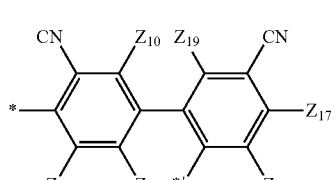
PO11 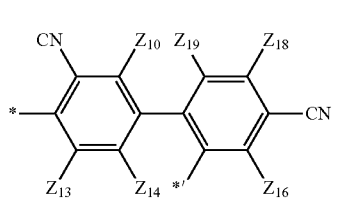
PO12 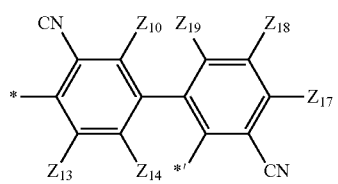
PO13 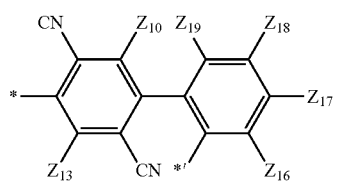
PO14 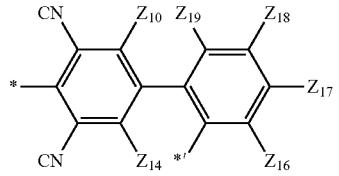
PO15 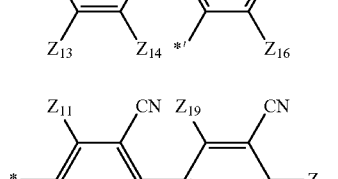
PO16 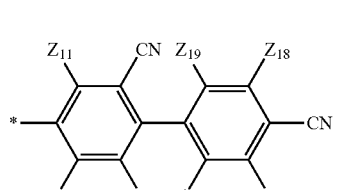
PO17 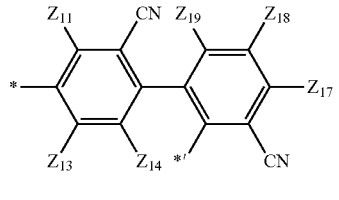
PO18 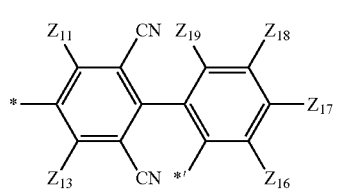
PO19

-continued
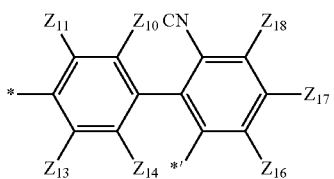 PO20
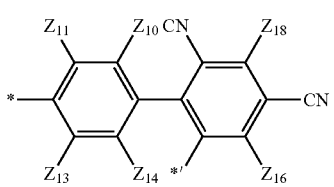 PO21
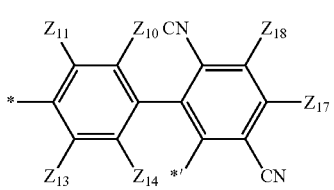 PO22
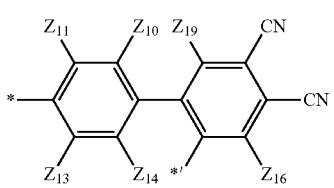 PO23
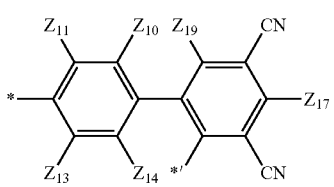 PO24
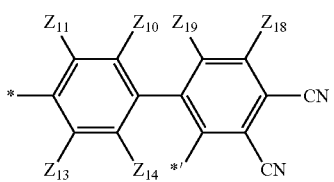 PO25
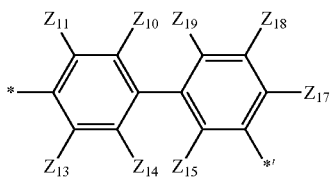 PM1
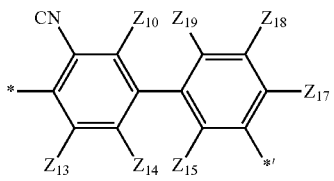 PM2
-continued
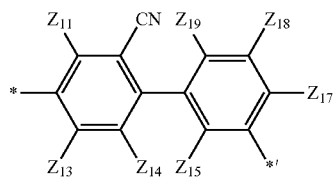 PM3
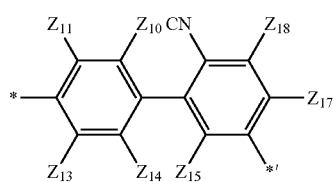 PM4
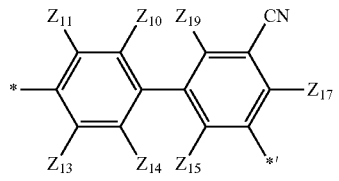 PM5
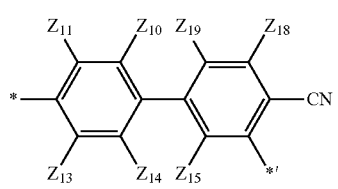 PM6
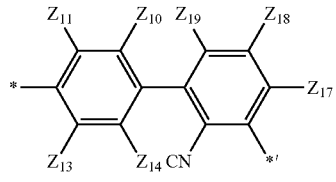 PM7
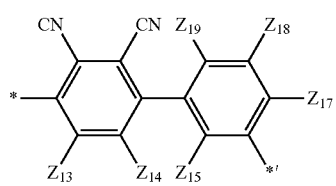 PM8
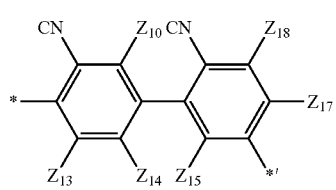 PM9
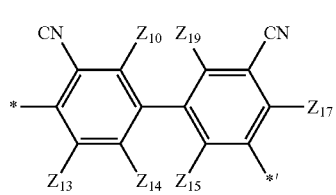 PM10

-continued
PM11
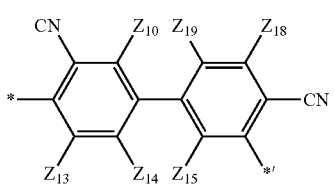
PM12
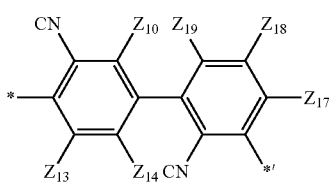
PM13
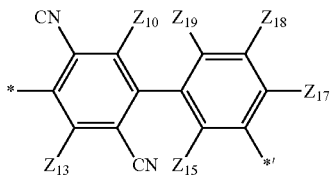
PM14
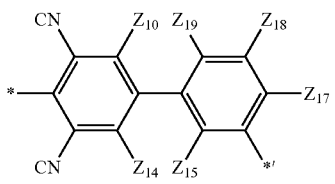
PM15
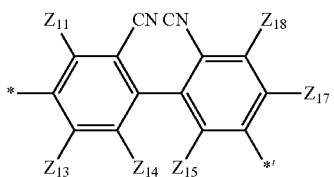
PM16
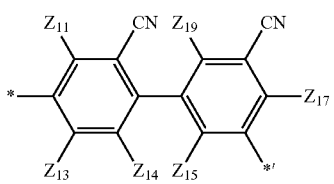
PM17
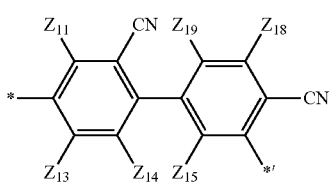
PM18
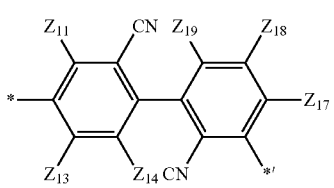
-continued
PM19
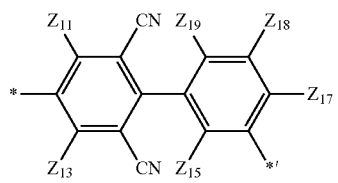
PM20
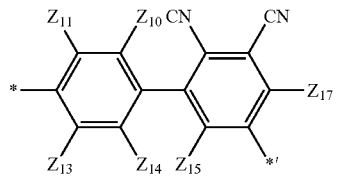
PM21
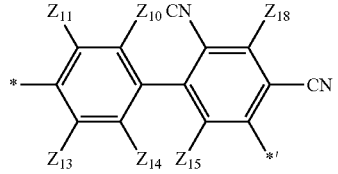
PM22
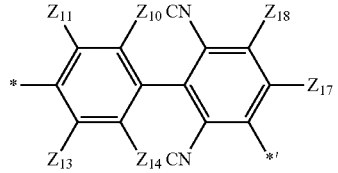
PM23
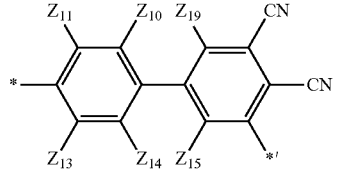
PM24
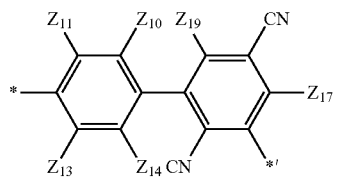
PM25
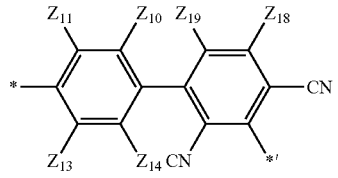
PP1
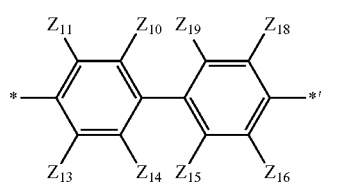

-continued
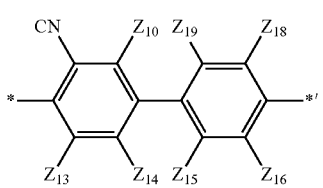
PP2
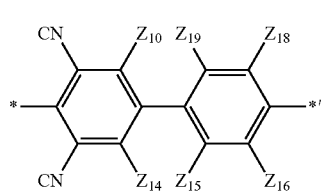
PP10
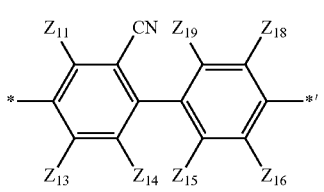
PP3
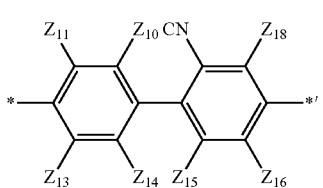
PP4
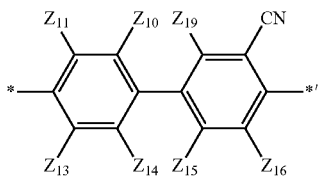
PP5
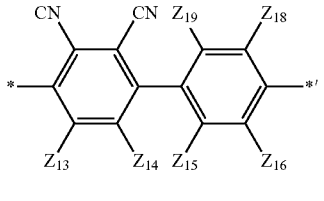
PP6
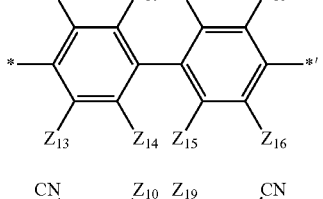
PP7
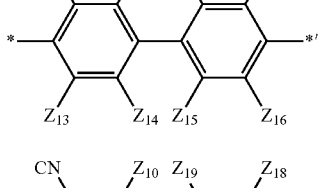
PP8
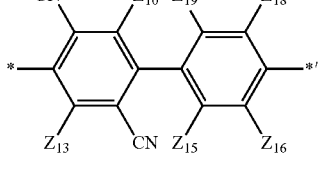
PP9

-continued
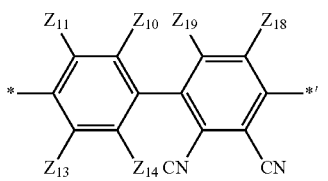
PP18
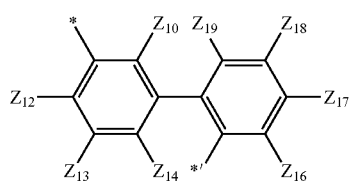
MO1
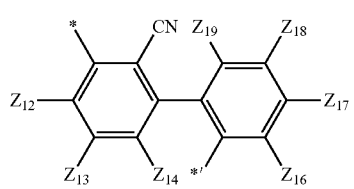
MO2
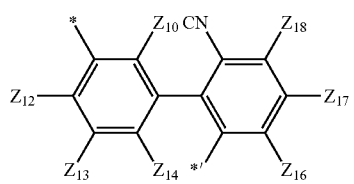
MO3
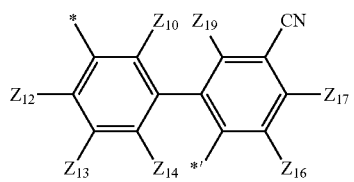
MO4
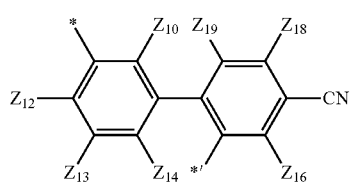
MO5
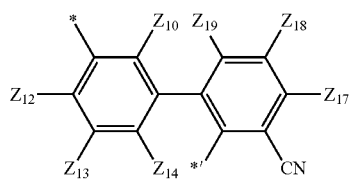
MO6
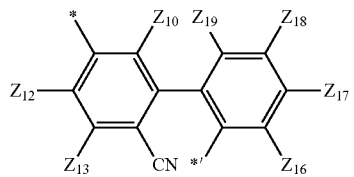
MO7
-continued
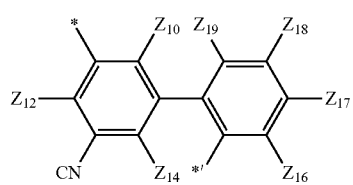
MO8
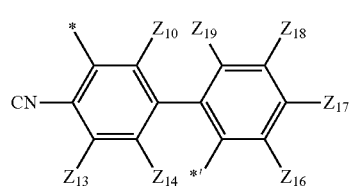
MO9
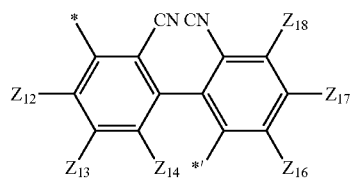
MO10
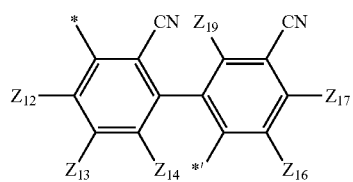
MO11
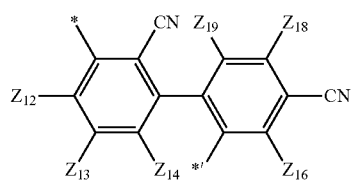
MO12
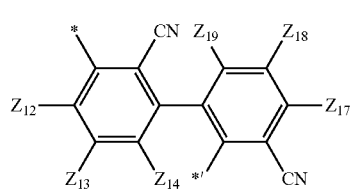
MO13
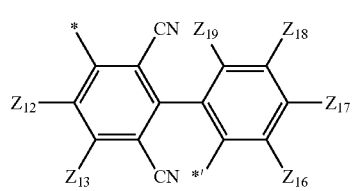
MO14
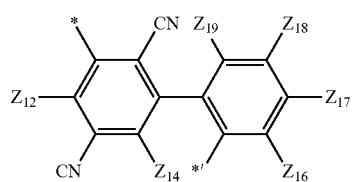
MO15

-continued
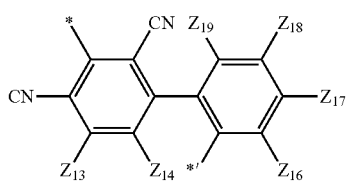
MO16
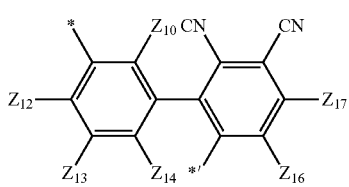
MO17
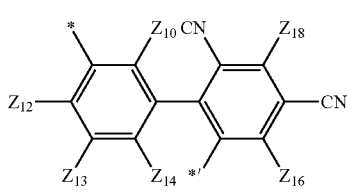
MO18
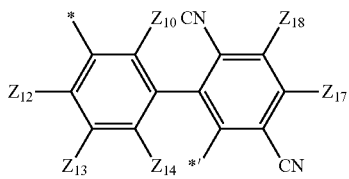
MO19
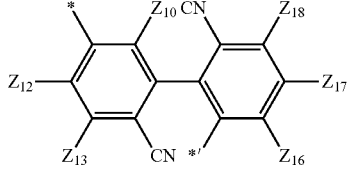
MO20
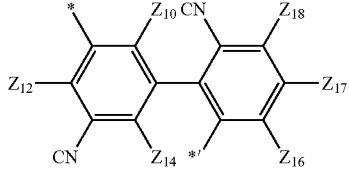
MO21
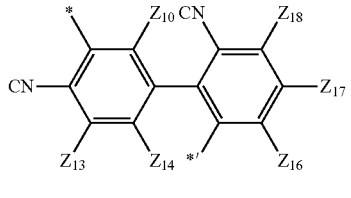
MO22
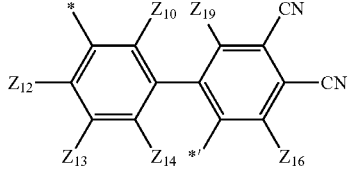
MO23
-continued
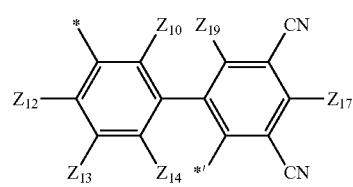
MO24
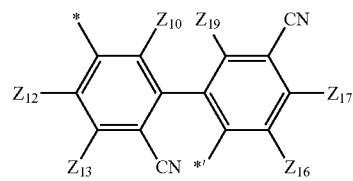
MO25
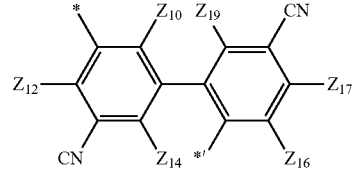
MO26
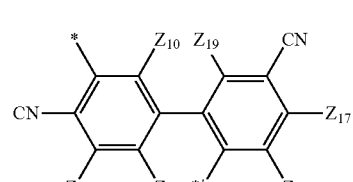
MO27
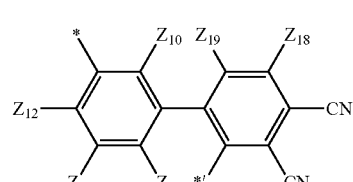
MO28
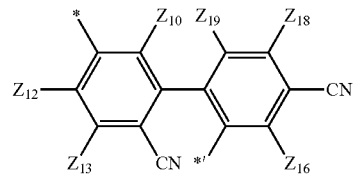
MO29
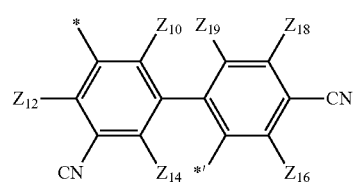
MO30
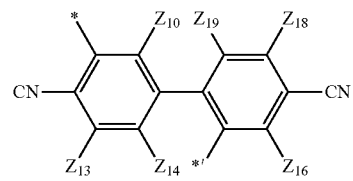
MO31

MO32
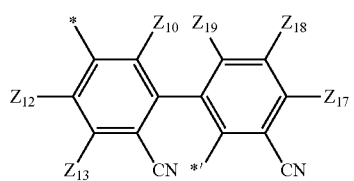
MO33
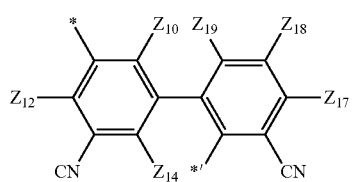
MO34
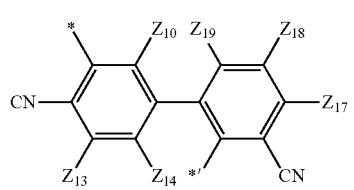
MO35
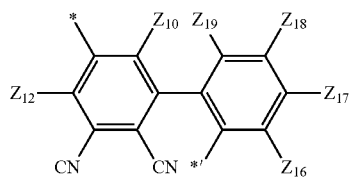
MO36
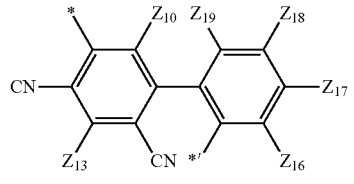
MO37
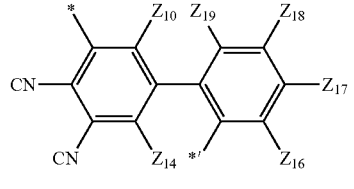
MM1
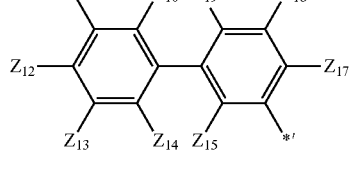
MM2
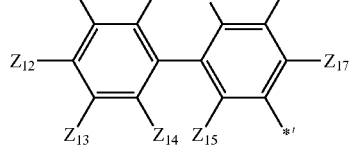
MM3
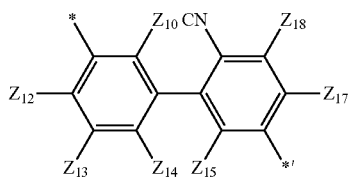
MM4
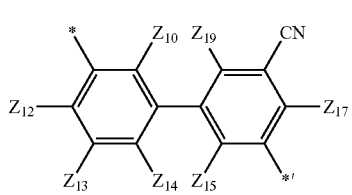
MM5
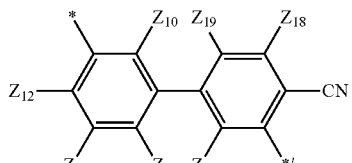
MM6
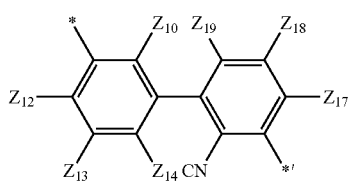
MM7
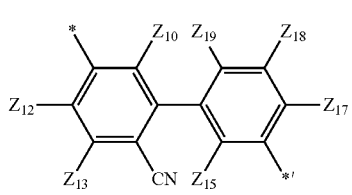
MM8
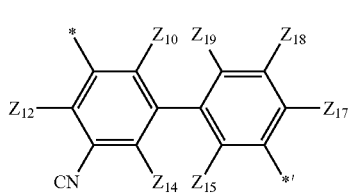
MM9
MM10

MM11 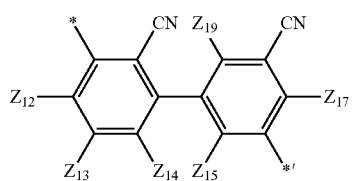
MM12 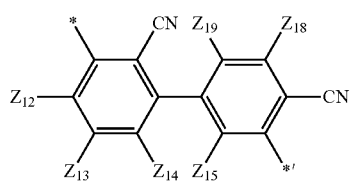
MM13 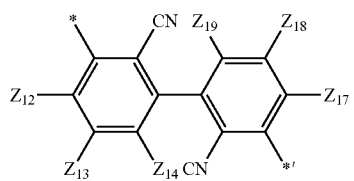
MM14 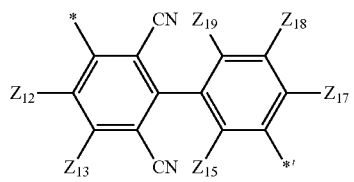
MM15 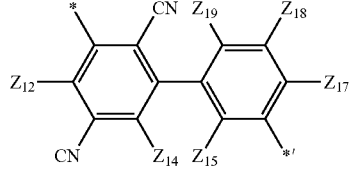
MM16 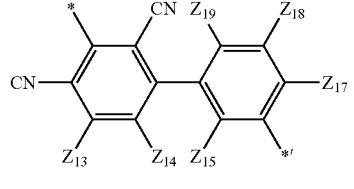
MM17 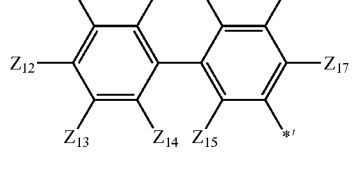
MM18 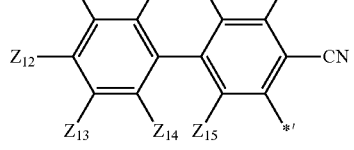
MM19 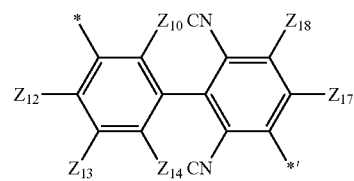
MM20 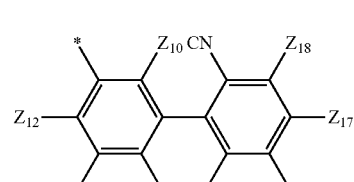
MM21 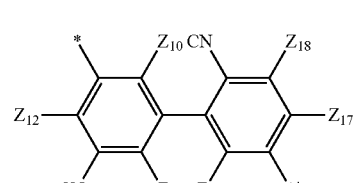
MM22 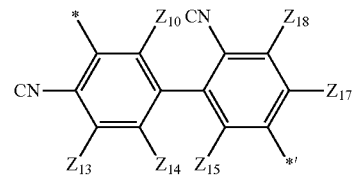
MM23 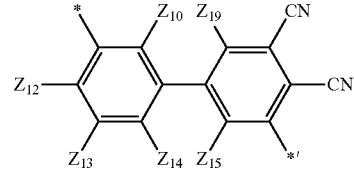
MM24 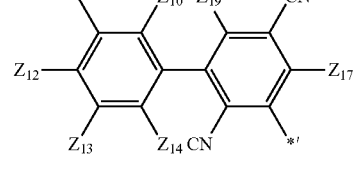
MM25 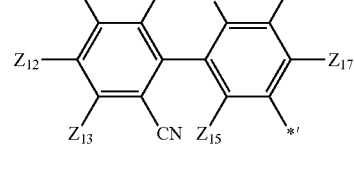
MM26 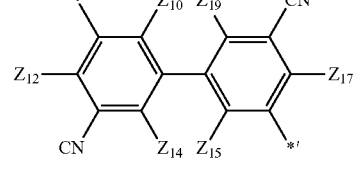

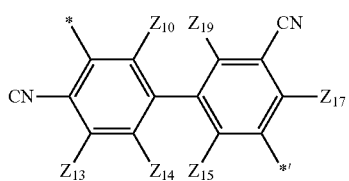 MM27
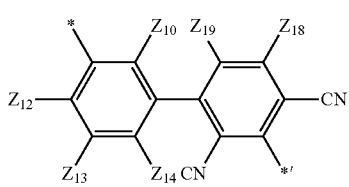 MM28
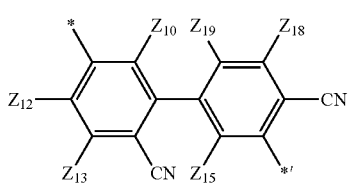 MM29
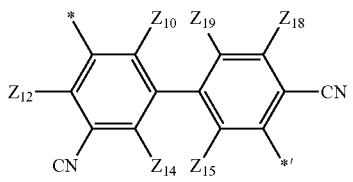 MM30
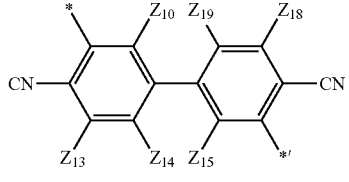 MM31
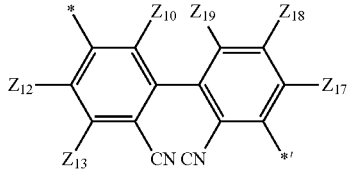 MM32
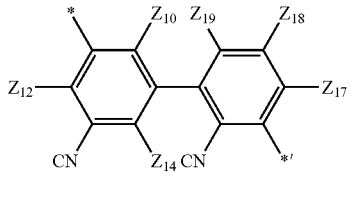 MM33
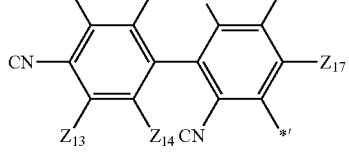 MM34
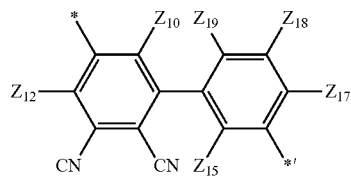 MM35
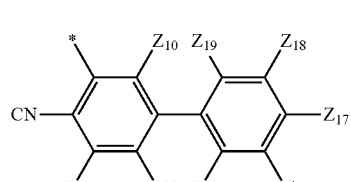 MM36
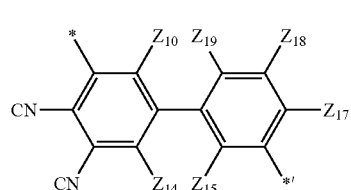 MM37
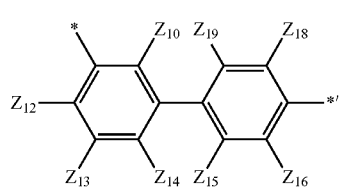 MP1
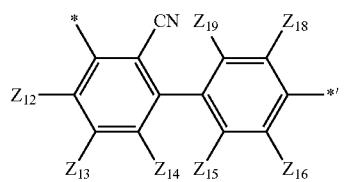 MP2
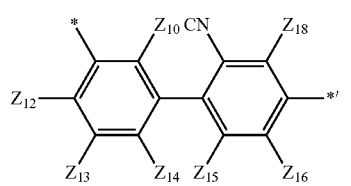 MP3
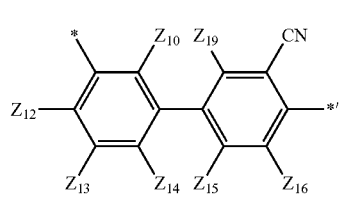 MP4
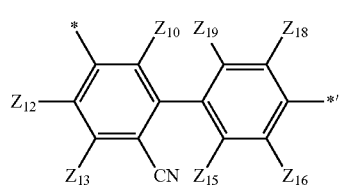 MP5

-continued
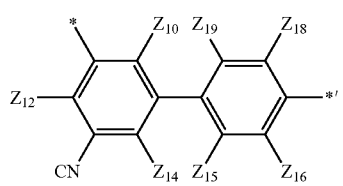 MP6
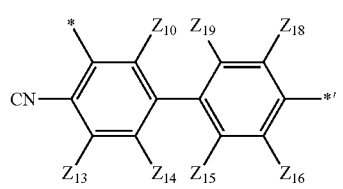 MP7
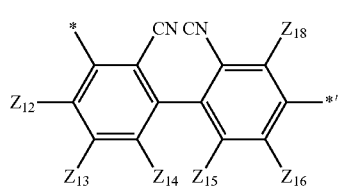 MP8
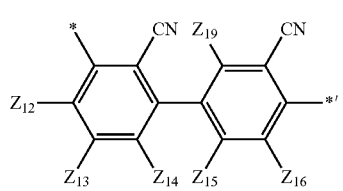 MP9
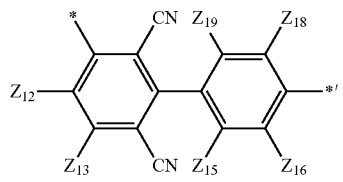 MP10
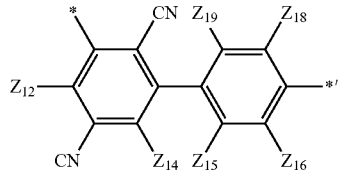 MP11
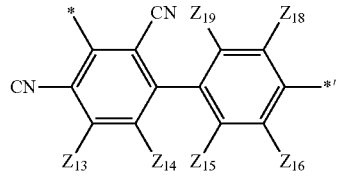 MP12
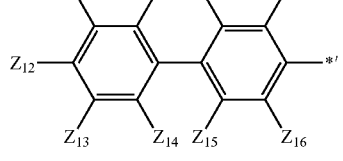 MP13
-continued
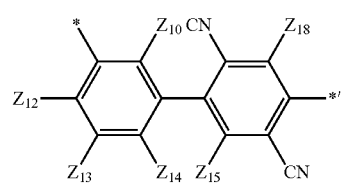 MP14
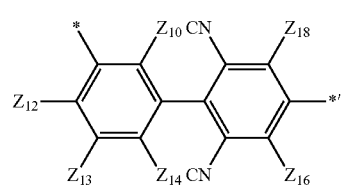 MP15
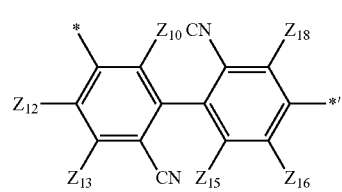 MP16
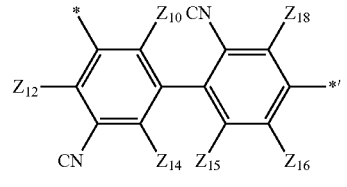 MP17
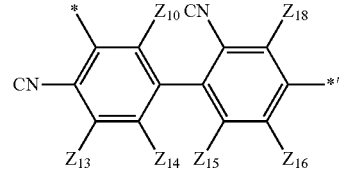 MP18
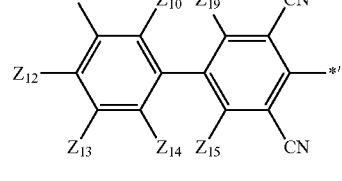 MP19
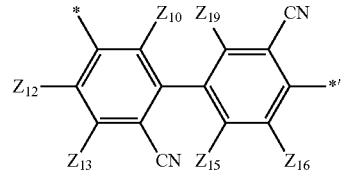 MP20
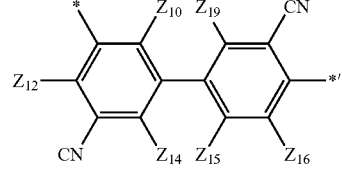 MP21

-continued
MP22
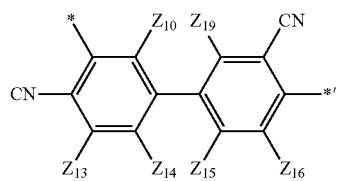
MP23
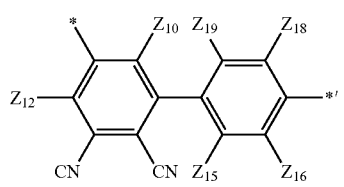
MP24
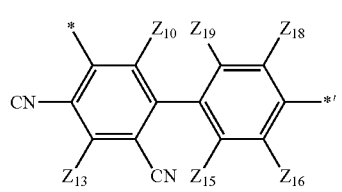
MP25
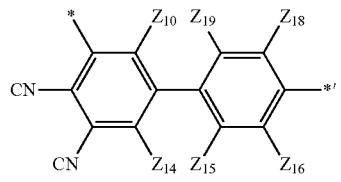
OO1
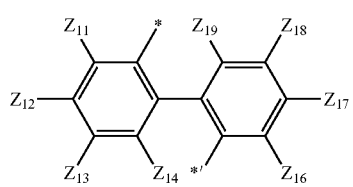
OO2
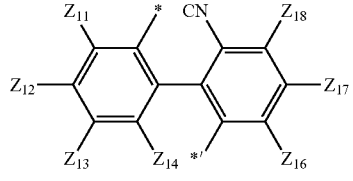
OO3
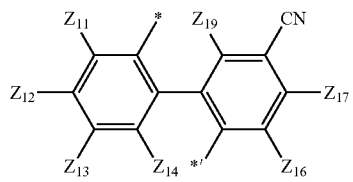
OO4
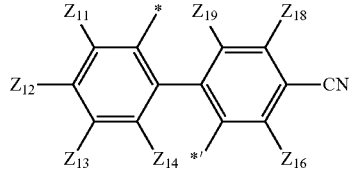
-continued
OO5
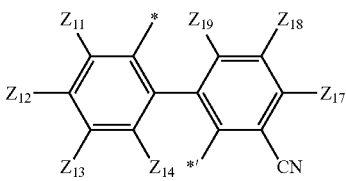
OO6
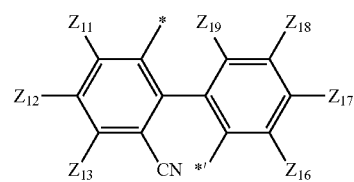
OO7
OO8
OO9

OO10
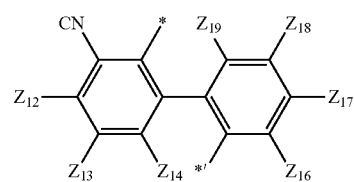
OO11
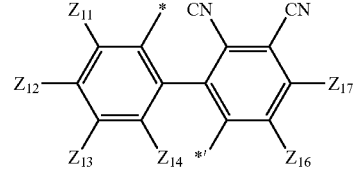
OO12
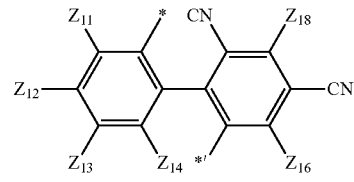
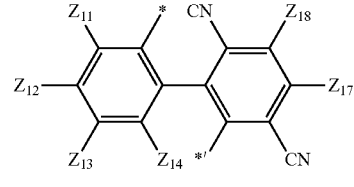

-continued
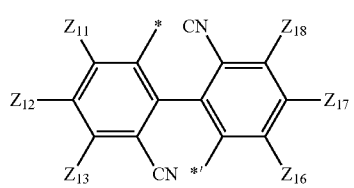
OO13
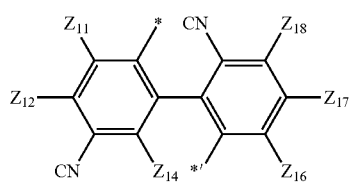
OO14
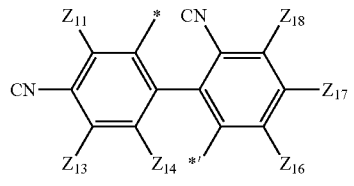
OO15
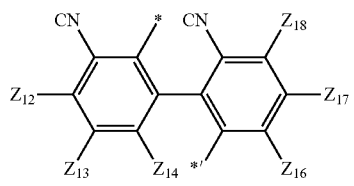
OO16
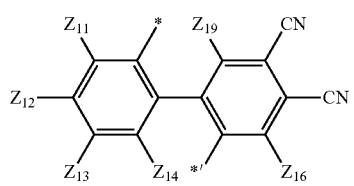
OO17
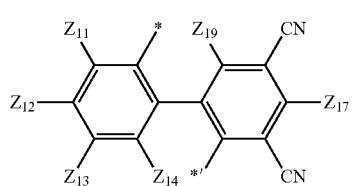
OO18
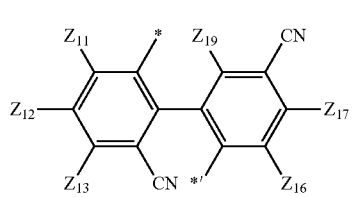
OO19
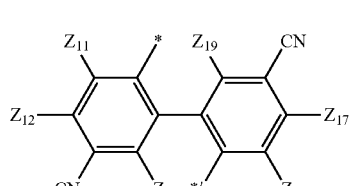
OO20
-continued
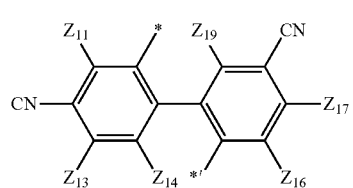
OO21
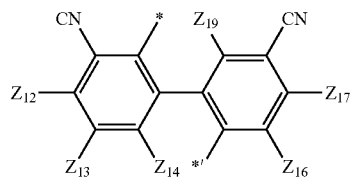
OO22
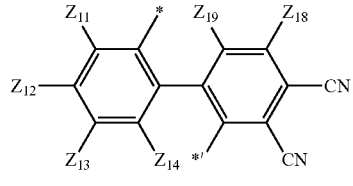
OO23
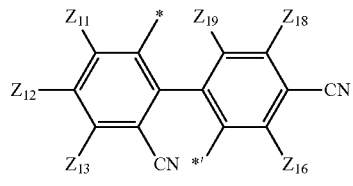
OO24
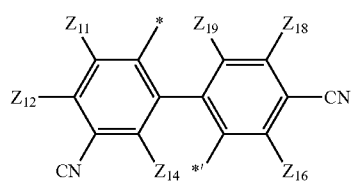
OO25
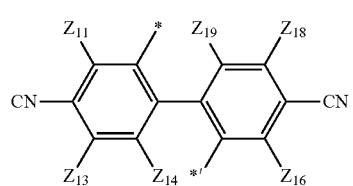
OO26
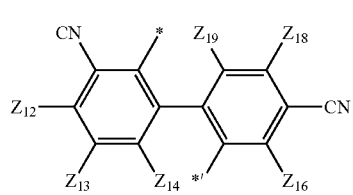
OO27
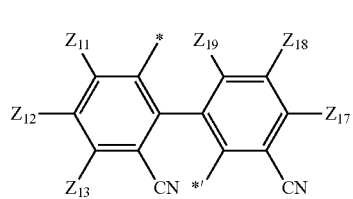
OO28

OO29 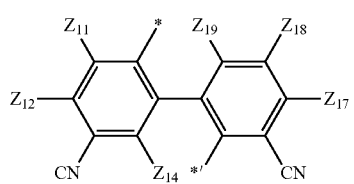
OO30 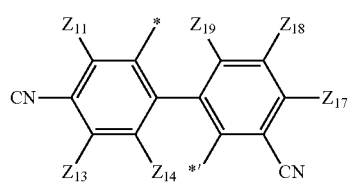
OO31 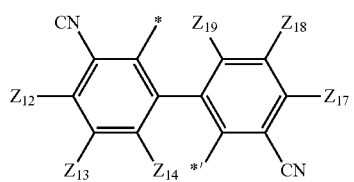
OO32 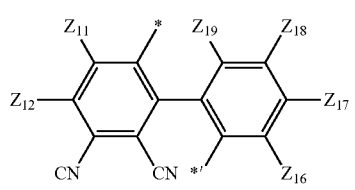
OO33 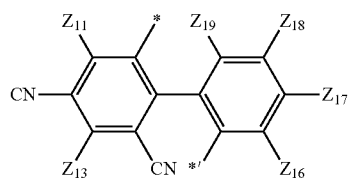
OO34 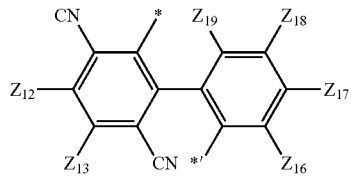
OO35 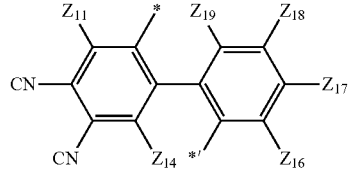
OO36 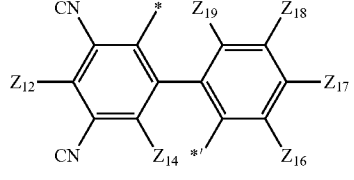
OO37 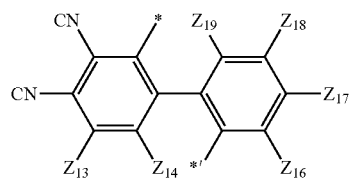
OM1 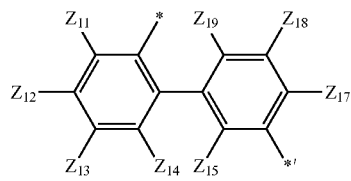
OM2 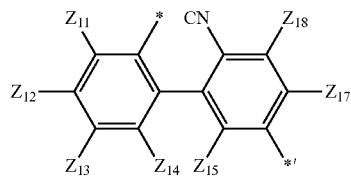
OM3
OM4
OM5
OM6
OM7

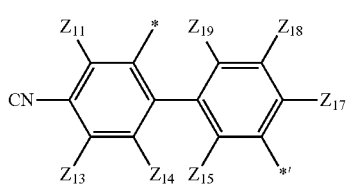
OM8
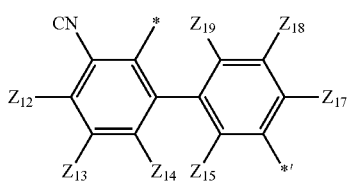
OM9
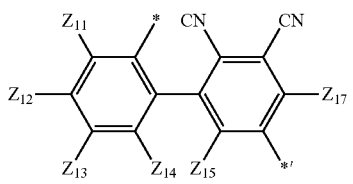
OM10
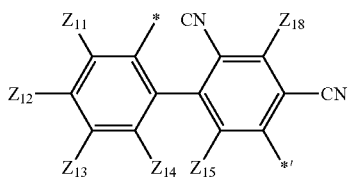
OM11
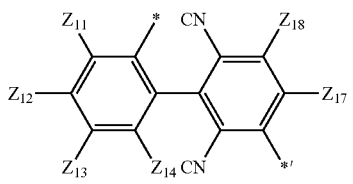
OM12
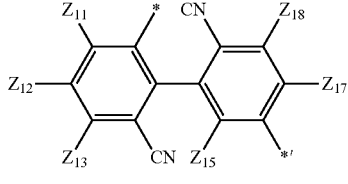
OM13
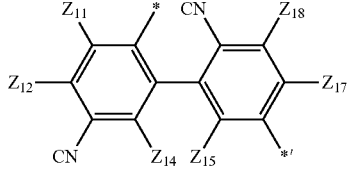
OM14
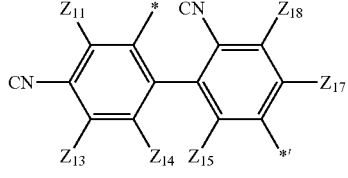
OM15
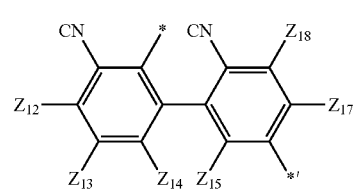
OM16
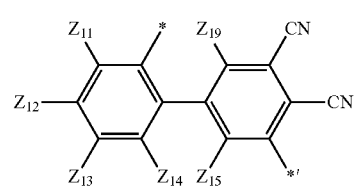
OM17
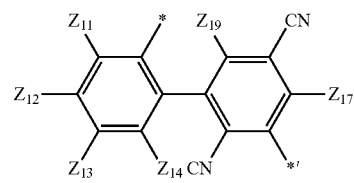
OM18
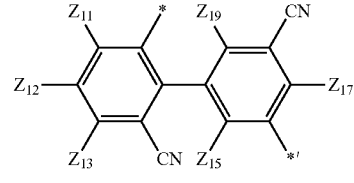
OM19
OM20
OM21
OM22
OM23

OM24
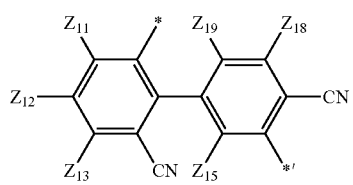
OM25
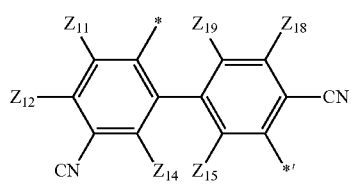
OM26
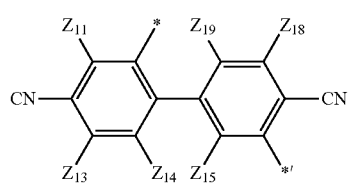
OM27
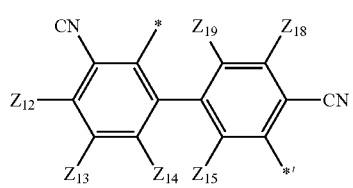
OM28
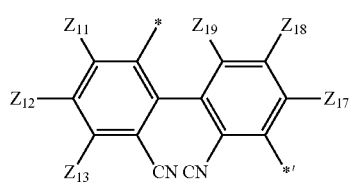
OM29
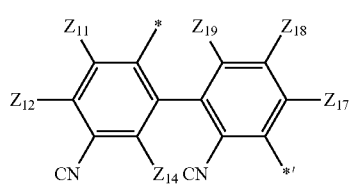
OM30
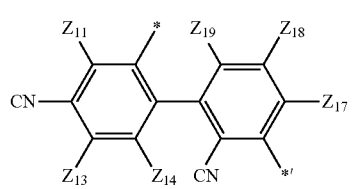
OM31
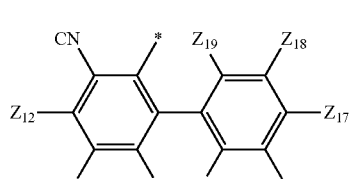
OM32
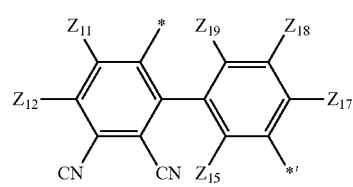
OM33
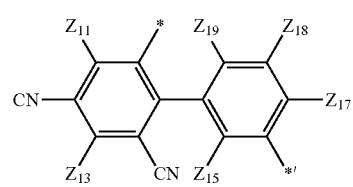
OM34
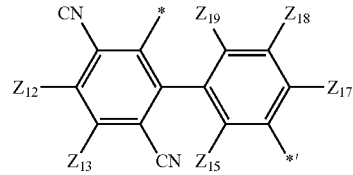
OM35
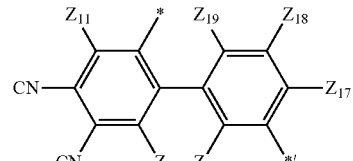
OM36
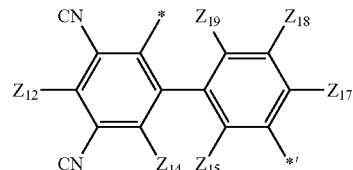
OM37
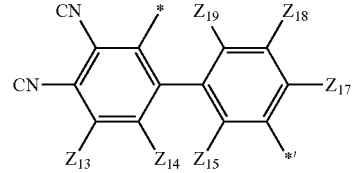
OP1
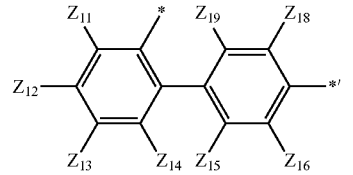
OP2
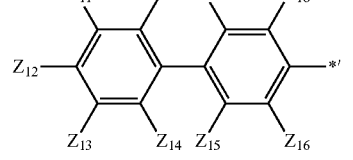

-continued
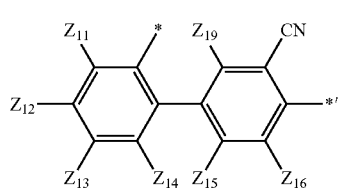
OP3
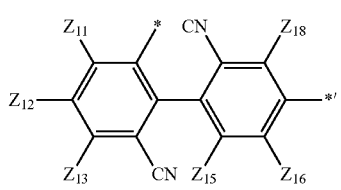
OP11
OP4
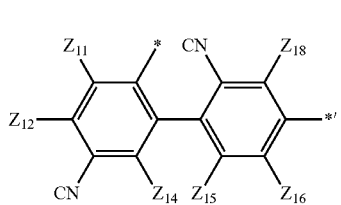
OP12
OP5
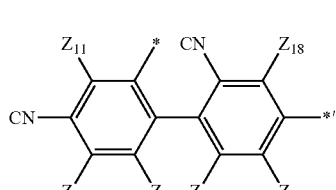
OP13
OP6
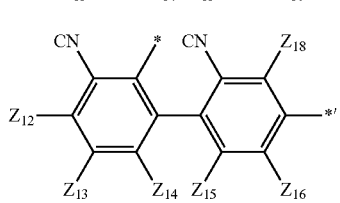
OP14
OP7
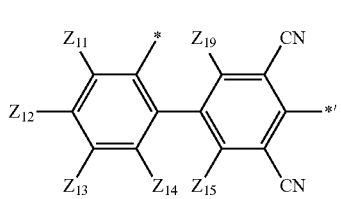
OP15
OP8
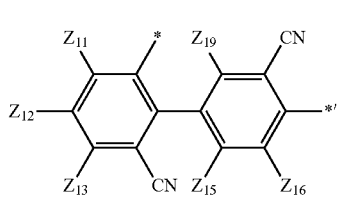
OP16
OP9
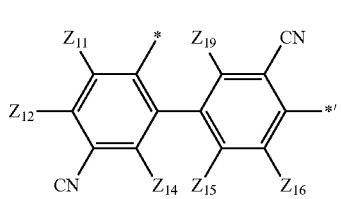
OP17
OP10
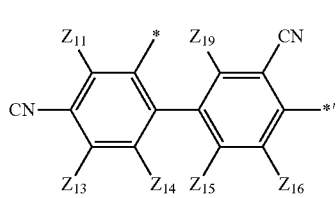
OP18

US 12,069,879 B2
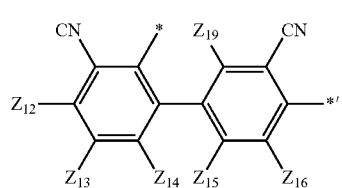  OP19
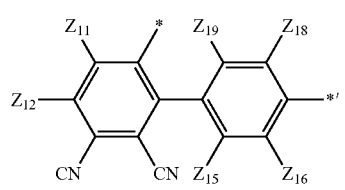  OP20
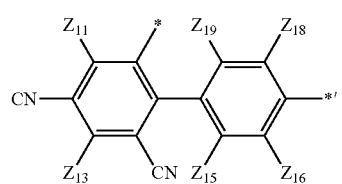  OP21
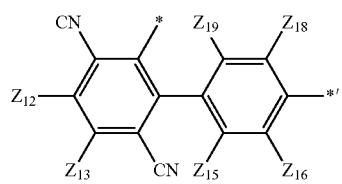  OP22
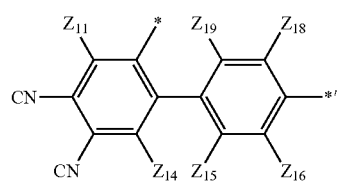  OP23
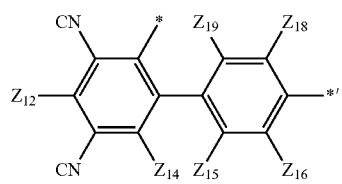  OP24
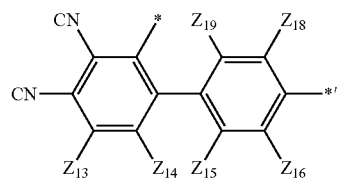  OP25
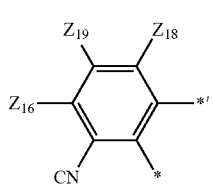  O1
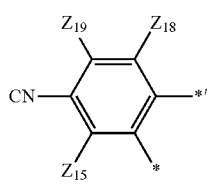  O2
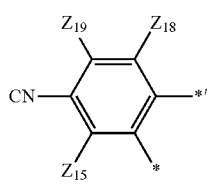  O3
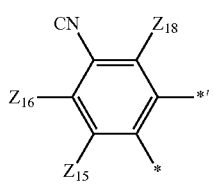  O4
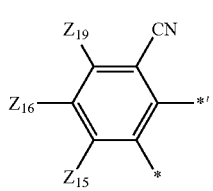  O5
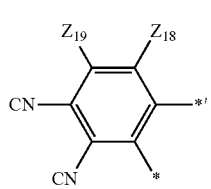  O6
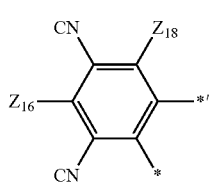  O7
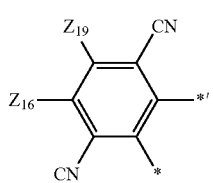  O8
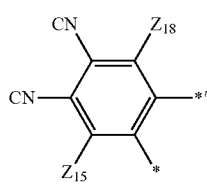  O9

| | |
|---|---|
| 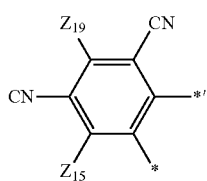 | O10 |
| 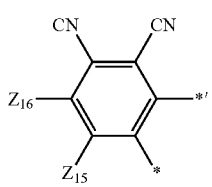 | O11 |
| 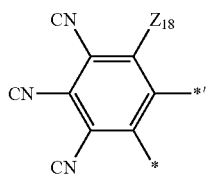 | O12 |
| 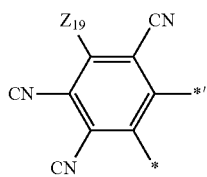 | O13 |
| 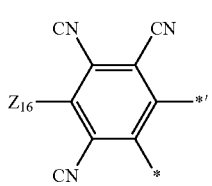 | O14 |
| 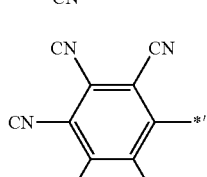 | O15 |
| 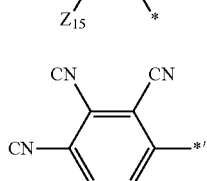 | O16 |
| 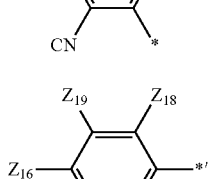<br>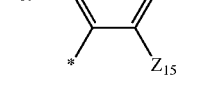 | M1 |
| | |
|---|---|
| 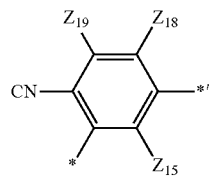 | M2 |
| 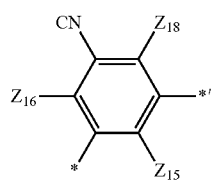 | M3 |
| 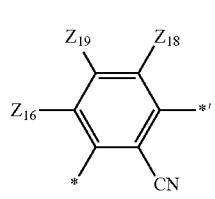 | M4 |
| 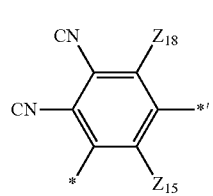 | M5 |
| 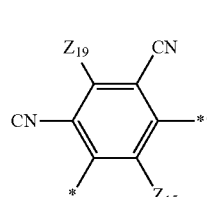 | M6 |
| 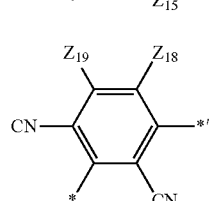 | M7 |
| 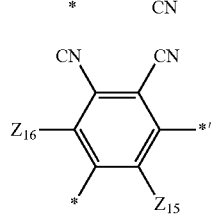 | M8 |
| 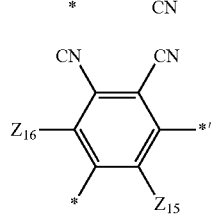 | M9 |

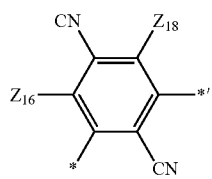 M10
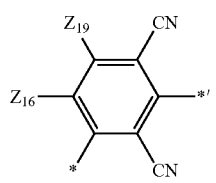 M11
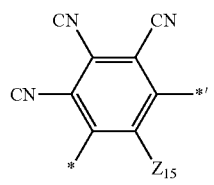 M12
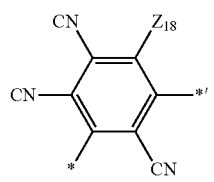 M13
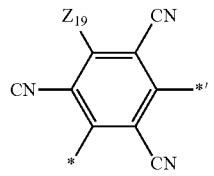 M14
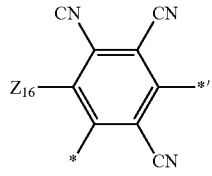 M15
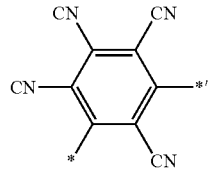 M16
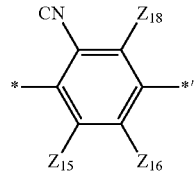 P1
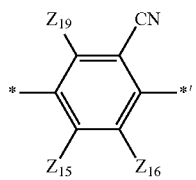 P2
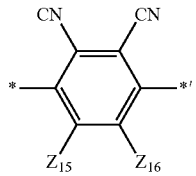 P3
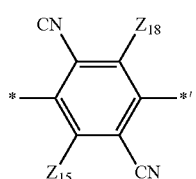 P4
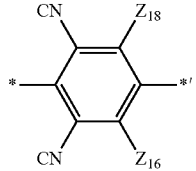 P5
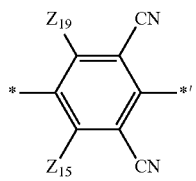 P6
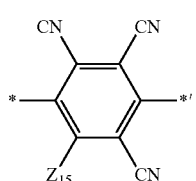 P7
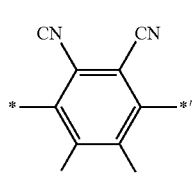 P8
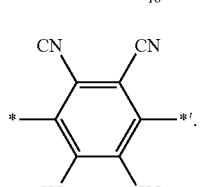 P9
$Z_{10}$ to $Z_{19}$ in Formulae PO1 to PO25, PM1 to PM25, PP1 to PP18, MO1 to MO37, MM1 to MM37, MP1 to MP25, OO1 to OO37, OM1 to OM37, OP1 to OP25, O1 to O16, M1 to M16, and P1 to P9 are the same as described in connection with $Z_3$ and $Z_4$, and * and *' each indicate a binding site to a neighboring atom.

In an embodiment, $Z_{10}$ to $Z_{19}$ in Formulae PO1 to PO25, PM1 to PM25, PP1 to PP18, MO1 to MO37, MM1 to MM37, MP1 to MP25, OO1 to OO37, OM1 to OM37, OP1 to OP25, O1 to O16, M1 to M16, and P1 to P9 may not be a cyano group.

In one or more embodiments, $Z_{10}$ to $Z_{19}$ in Formulae PO1 to PO25, PM1 to PM25, PP1 to PP18, MO1 to MO37, MM1 to MM37, MP1 to MP25, OO1 to OO37, OM1 to OM37, OP1 to OP25, O1 to O16, M1 to M16, and P1 to P9 may each independently be:

hydrogen, deuterium, or a cyano group; or an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, a biphenyl group, or a terphenyl group, each unsubstituted or substituted with at least one selected from deuterium, a cyano group, an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a biphenyl group.

In one or more embodiments, a group represented by

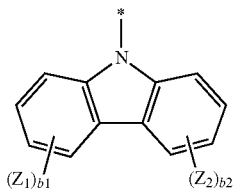

in Formulae E-1(1) and E-1(2) may be one of groups represented by Formulae A1-1 to A1-3, a group represented by

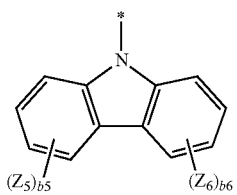

in Formula E-1(1) may be one of groups represented by Formulae A2-1 to A2-3, a group represented by

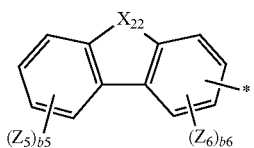

in Formulae E-1(2) and E-1(3) may be one of groups represented by Formulae A2-4 to A2-17, and a group represented by

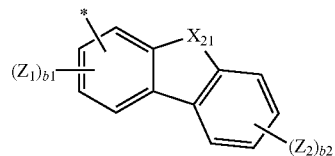

in Formula E-1(3) may be one of groups represented by Formulae A1-4 to A1-17:

A1-1

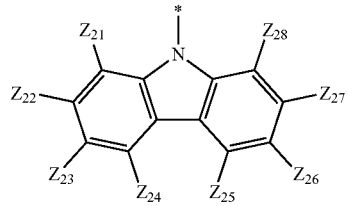

A1-2

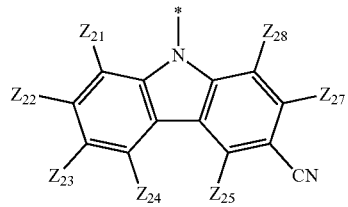

A1-3

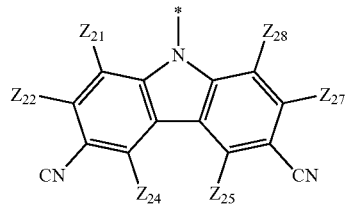

A1-4

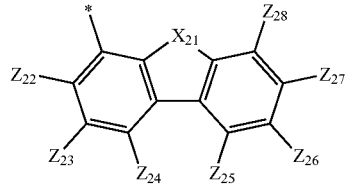

A1-5

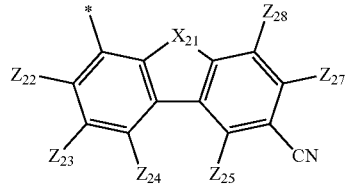

A1-6

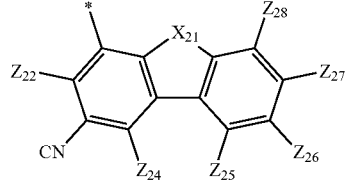

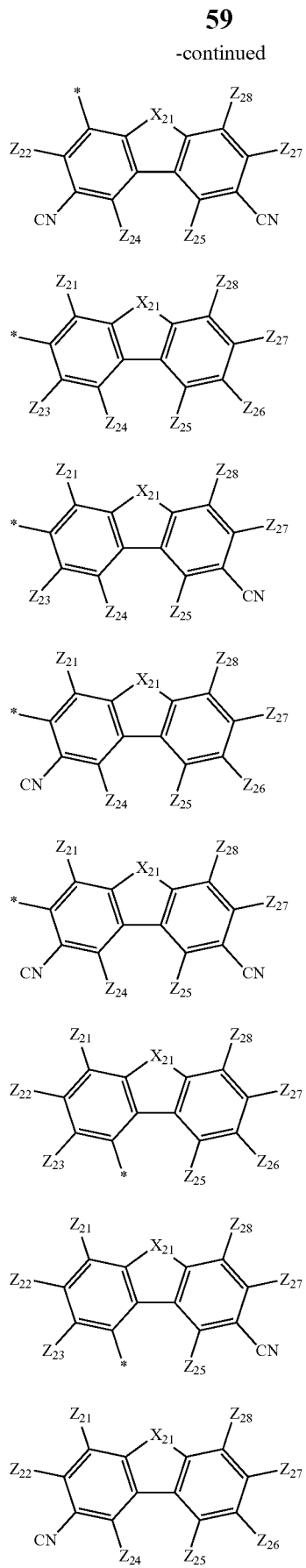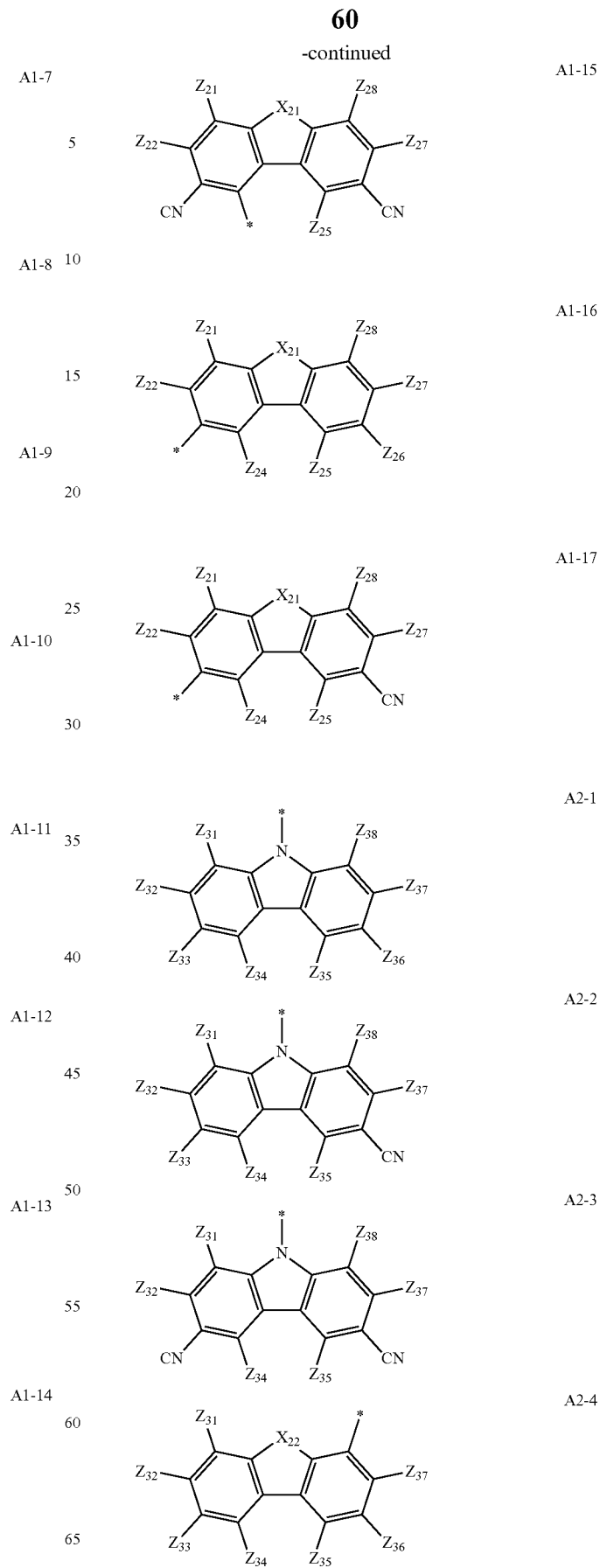

A2-5 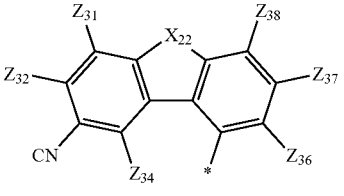

A2-6 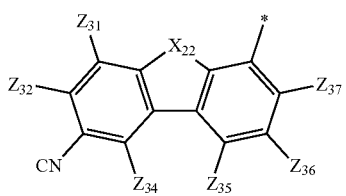

A2-7 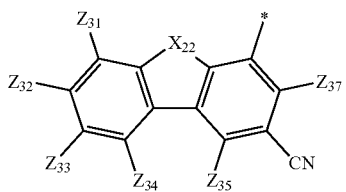

A2-8 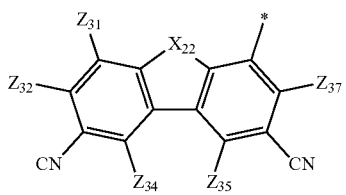

A2-9 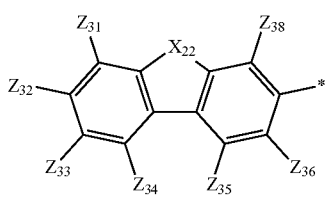

A2-10 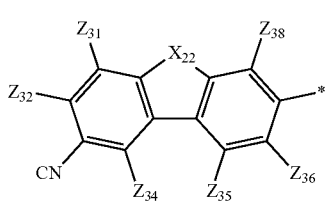

A2-11 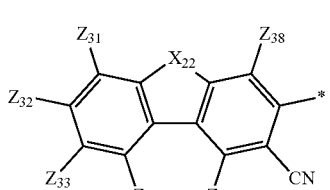

A2-12 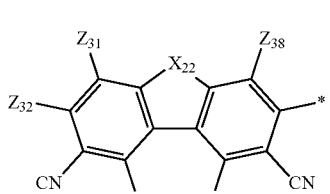

A2-13 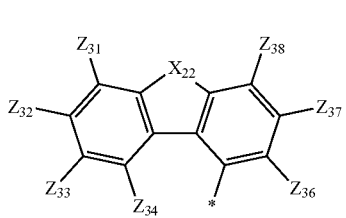

A2-14 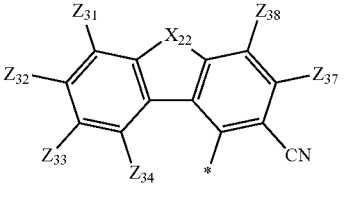

A2-15 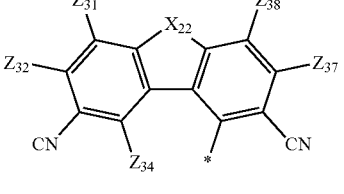

A2-16 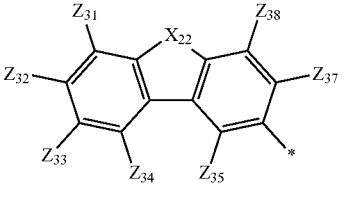

A2-17 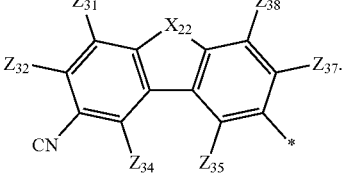

In Formulae A1-1 to A1-17 and A2-1 to A2-17, $Z_{21}$ to $Z_{28}$ are the same as described in connection with $Z_1$ and $Z_2$, $Z_{31}$ to $Z_{38}$ are the same as described in connection with $Z_5$ and $Z_6$, and * and *' each indicate a binding site to a neighboring atom.

In an embodiment, $Z_{21}$ to $Z_{28}$ and $Z_{31}$ to $Z_{38}$ in Formulae A1-1 to A1-17 and A2-1 to A2-17a are not a cyano group.

In one or more embodiments, $Z_{21}$ to $Z_{28}$ and $Z_{31}$ to $Z_{38}$ in Formulae A1-1 to A1-17 and A2-1 to A2-17 may each independently be:

hydrogen, deuterium, or a cyano group; or an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, a biphenyl group, or a terphenyl group, each unsubstituted or substituted with at least one selected from deuterium, a cyano group, an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a biphenyl group.

In an embodiment, the second material may include at least one compound selected from Compounds E1 to E8, but embodiments of the present disclosure are not limited thereto:

E1
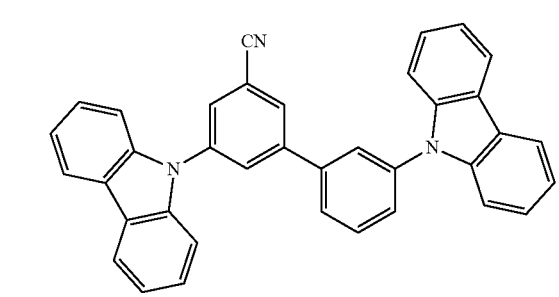
E2
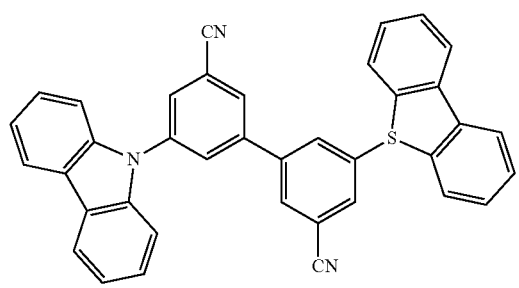
E3
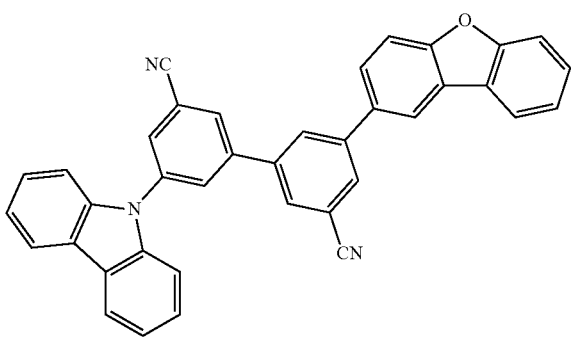
E4
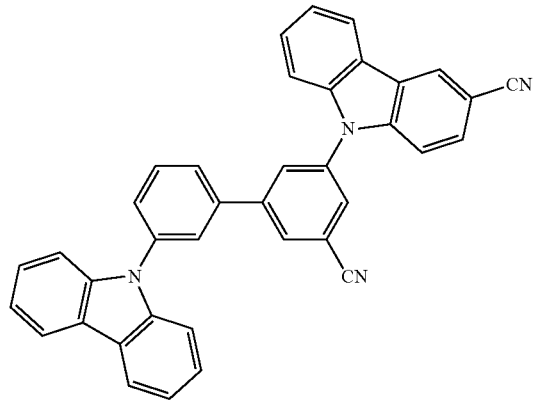
-continued
E5
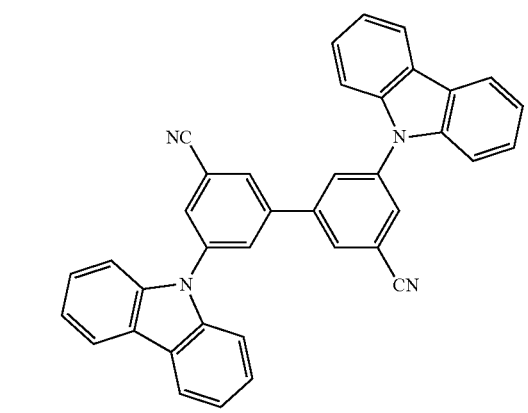
E6
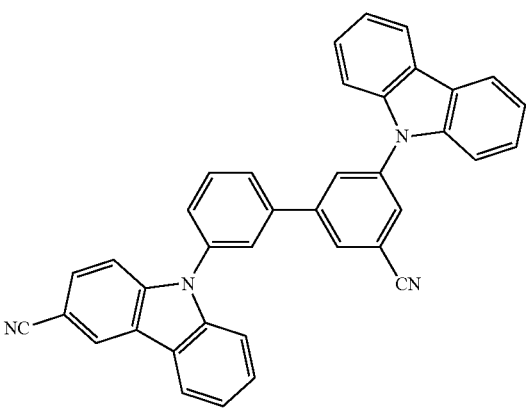
E7
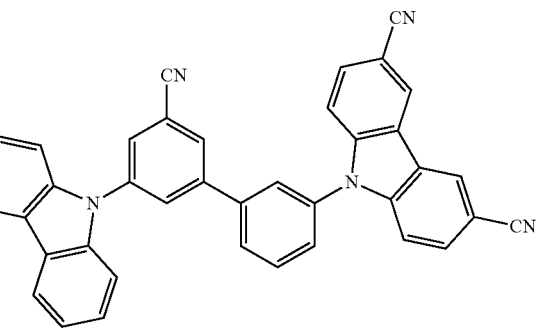
E8
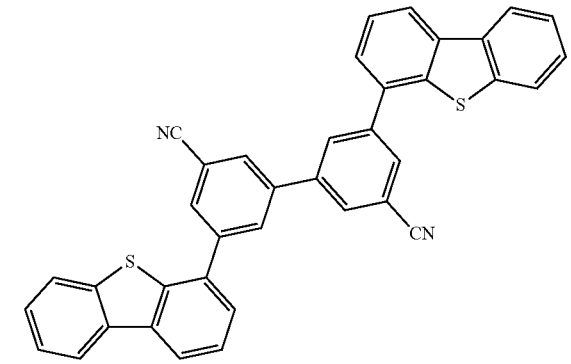
The third material may be selected from materials having reorganization energy of about 0.4 electron volts (eV) or more, for example, about 0.4 eV to about 1.0 eV, about 0.4 eV to about 0.9 eV, about 0.4 eV to about 0.8 eV, about 0.4 eV to about 0.7 eV, about 0.4 eV to about 0.6 eV, or about 0.4 eV to about 0.5 eV.

The "reorganization energy" means energy necessary for relaxation of a molecular structure due to movement of electrons. The third material, which has large reorganization energy in the above-described range, serves to reduce excess electrons in the emission layer and minimize polaron-triplet quenching in the emission layer. Thus, the emission layer including the third material as described above may have long lifespan characteristics.

The reorganization energy may be calculated and estimated by a density function theory using quantum chemical software (TURBOMOLE), and a more detailed evaluation method may be understood by referring to Evaluation Example 1 provided below.

In an embodiment, the third material may include a compound represented by Formula 11:

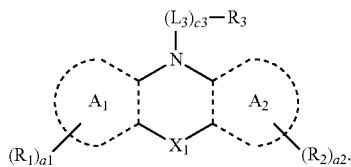

Formula 11

$X_1$ in Formula 11 may be a single bond, N-[$(L_4)_{c4}$-$R_4$], $C(R_5)(R_6)$, O, or S.

For example, $X_1$ may be a single bond, but embodiments of the present disclosure are not limited thereto.

$A_1$ and $A_2$ in Formula 11 may each independently be a benzene group, a naphthalene group, an indene group, an indole group, a benzofuran group, a benzothiophene group, a benzosilole group, a fluorene group, a carbazole group, a dibenzofuran group, a dibenzothiophene group, or a dibenzosilole group.

For example, $A_1$ and $A_2$ may each independently be a benzene group, a fluorene group, a carbazole group, a dibenzofuran group, a dibenzothiophene group, or a dibenzosilole group, and at least one of $A_1$ and $A_2$ may be a benzene group, but embodiments of the present disclosure are not limited thereto.

$L_3$ and $L_4$ may each independently be selected from a single bond, a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group.

For example, $L_3$ and $L_4$ may each independently be selected from:
a single bond, a phenylene group, a naphthylene group, a fluorenylene group, a pyridinylene group, a pyrimidinylene group, a pyrazinylene group, a pyridazinylene group, a triazinylene group, a quinolinylene group, an isoquinolinylene group, a carbazolylene group, a dibenzofuranylene group, a dibenzothiophenylene group, and an indolocarbazolylene group; and
a phenylene group, a naphthylene group, a fluorenylene group, a pyridinylene group, a pyrimidinylene group, a pyrazinylene group, a pyridazinylene group, a triazinylene group, a quinolinylene group, an isoquinolinylene group, a carbazolylene group, a dibenzofuranylene group, a dibenzothiophenylene group, and an indolocarbazolylene group, each substituted with at least one selected from deuterium, a $C_1$-$C_{10}$ alkyl group, a $C_1$-$C_{10}$ alkoxy group, a phenyl group, a biphenyl group, a terphenyl group, a naphthyl group, a fluorenyl group, a pyridinyl group, a pyrimidinyl group, a pyrazinyl group, a pyridazinyl group, a triazinyl group, a quinolinyl group, an isoquinolinyl group, a carbazolyl group, a dibenzofuranyl group, a dibenzothiophenyl group, an indolocarbazolyl group, —Si($Q_{31}$)($Q_{32}$)($Q_{33}$), and —N($Q_{34}$)($Q_{35}$), and $Q_{31}$ to $Q_{35}$ may each independently be selected from a $C_1$-$C_{10}$ alkyl group, a $C_1$-$C_{10}$ alkoxy group, a phenyl group, a biphenyl group, a terphenyl group, and a naphthyl group. However, embodiments of the present disclosure are not limited thereto.

c3 and c4 indicate the number of groups $L_3$ and the number of groups $L_4$, respectively, and may each independently be an integer from 0 to 4. When c3 is two or more, two or more groups $L_3$ may be identical to or different from each other, and when c4 is two or more, two or more groups $L_4$ may be identical to or different from each other. For example, c3 and c4 may each independently be 0, 1, or 2, but embodiments of the present disclosure are not limited thereto.

$R_1$ to $R_6$ in Formula 11 may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_4$)($Q_5$), and —B($Q_6$)($Q_7$).

In an embodiment, $R_3$ in Formula 11 may include at least one π electron-depleted nitrogen-containing cyclic group. The π electron-depleted nitrogen-containing cyclic group is the same as described above.

For example, $R_3$ in Formula 11 may be selected from a phenyl group, an indenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a pyrrolyl group, an isoindolyl group, an indolyl group, a furanyl group, a thiophenyl group, a silolyl group, a benzofuranyl group, a benzothiophenyl group, a benzosilolyl group, a carbazolyl group, a dibenzofuranyl group, a dibenzothiophenyl group, a dibenzosilolyl group, an indeno carbazolyl group, an indolocarbazolyl group, a benzofuracarbazolyl group, a benzothienocarbazolyl group, a benzosilolocarbazolyl group, an imidazolyl group, a pyrazolyl group, a thiazolyl group, an isothiazolyl group, an oxazolyl group, an isoxazolyl group, a pyridinyl group, a pyrazinyl group, a pyridazinyl group, a pyrimidinyl group, an indazolyl group, a purinyl group, a quinolinyl group, an isoquinolinyl group, a benzoquinolinyl group, a benzoisoquinolinyl group, a phthalazinyl group, a naphthyridinyl group, a quinoxalinyl group, a benzoquinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an oxadiazolyl group, a triazinyl group, a thiadiazolyl group, an imidazopyridinyl group, an imidazopyrimidinyl group, an azaindenyl group, an azaindolyl group, an azabenzofuranyl group, an azabenzothiophenyl group, an azabenzosilolyl group, an azafluorenyl group, an azacarbazolyl group, an azadibenzofuranyl group, an azadibenzothiophenyl group, and an azadibenzosilolyl group, each unsubstituted or substituted with at least one selected from deuterium, a $C_1$-$C_{10}$ alkyl group, a $C_1$-$C_{10}$ alkoxy group, a phenyl group, a ($C_1$-$C_{10}$ alkyl)phenyl group, a di($C_1$-$C_{10}$ alkyl)phenyl group, a biphenyl group, a terphenyl group, a di(phenyl)phenyl group, a di(biphenyl)phenyl group, a (pyridinyl)phenyl group, a di(pyridinyl)phenyl group, a (pyrimidinyl)phenyl group, a di(pyridiminyl)phenyl group, a (triazinyl)phenyl group, a di(triazinyl)phenyl group, a pyridinyl group, a ($C_1$-$C_{10}$ alkyl)pyridinyl group, a di($C_1$-$C_{10}$ alkyl)pyridinyl group, a (phenyl)pyridinyl group, a di(phenyl)pyridinyl group, a (biphenyl)pyridinyl group, a di(biphenyl)pyridinyl group, a (terphenyl)pyridinyl group, a bi(terphenyl)pyridinyl group, a (pyridinyl)pyridinyl group, a di(pyridinyl)pyridinyl group, a (pyrimidinyl)pyridinyl group, a di(pyrimidinyl)pyridinyl group, a (triazinyl)pyridinyl group, a di(triazinyl)pyridinyl group, a pyrimidinyl group, a ($C_1$-$C_{10}$ alkyl)pyrimidinyl group, a di($C_1$-$C_{10}$ alkyl)pyrimidinyl group, a (phenyl)pyrimidinyl group, a di(phenyl)pyrimidinyl group, a (biphenyl)pyrimidinyl group, a di(biphenyl)pyrimidinyl group, a (terphenyl)pyrimidinyl group, a bi(terphenyl)pyrimidinyl group, a (pyridinyl)pyrimidinyl group, a di(pyridinyl)pyrimidinyl group, a (pyrimidinyl)pyrimidinyl group, a di(pyrimidinyl)pyrimidinyl group, a (triazinyl)pyrimidinyl group, a di(triazinyl)pyrimidinyl group, a triazinyl group, a ($C_1$-$C_{10}$ alkyl)triazinyl group, a di($C_1$-$C_{10}$ alkyl)triazinyl group, a (phenyl)triazinyl group, a di(phenyl)triazinyl group, a (biphenyl)triazinyl group, a di(biphenyl)triazinyl group, a (terphenyl)triazinyl group, a bi(terphenyl)triazinyl group, a (pyridinyl)triazinyl group, a di(pyridinyl)triazinyl group, a (pyrimidinyl)triazinyl group, a di(pyrimidinyl)triazinyl group, a (triazinyl)triazinyl group, a di(triazinyl)triazinyl group, a fluorenyl group, a di($C_1$-$C_{10}$ alkyl)fluorenyl group, a di(phenyl)fluorenyl group, a di(biphenyl)fluorenyl group, a carbazolyl group, a ($C_1$-$C_{10}$ alkyl) carbazolyl group, a (phenyl)carbazolyl group, a (biphenyl) carbazolyl group, a dibenzofuranyl group, a ($C_1$-$C_{10}$ alkyl) dibenzofuranyl group, a (phenyl)dibenzofuranyl group, a ($C_1$-$C_{10}$ alkyl)dibenzothiophenyl group, a (phenyl)dibenzothiophenyl group, and a (biphenyl)dibenzothiophenyl group, but embodiments of the present disclosure are not limited thereto.

In one or more embodiments, $R_3$ in Formula 11 may be selected from:

a group represented by Formula 13(1) or 13(2);

a phenyl group, a biphenyl group, a terphenyl group, a naphthyl group, a fluorenyl group, a quinolinyl group, an isoquinolinyl group, a carbazolyl group, a dibenzofuranyl group, a dibenzothiophenyl group, and an indolocarbazolyl group; and a phenyl group, a biphenyl group, a terphenyl group, a naphthyl group, a fluorenyl group, a quinolinyl group, an isoquinolinyl group, a carbazolyl group, a dibenzofuranyl group, a dibenzothiophenyl group, and an indolocarbazolyl group, each substituted with at least one selected from deuterium, a $C_1$-$C_{10}$ alkyl group, a $C_1$-$C_{10}$ alkoxy group, a phenyl group, a biphenyl group, a terphenyl group, a naphthyl group, a fluorenyl group, a pyridinyl group, a pyrimidinyl group, a pyrazinyl group, a pyridazinyl group, a triazinyl group, a quinolinyl group, an isoquinolinyl group, a carbazolyl group, a dibenzofuranyl group, a dibenzothiophenyl group, an indolocarbazolyl group, and —Si($Q_{31}$)($Q_{32}$)($Q_{33}$), and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group:

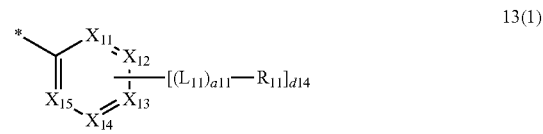

(13)1

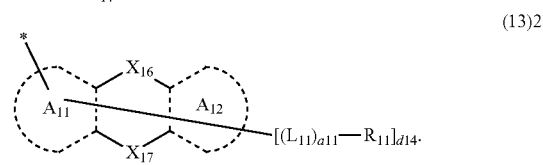

(13)2

$X_{11}$ to $X_{15}$ in Formula 13(1) may each independently be C or N, and at least one of $X_{11}$ to $X_{15}$ may be N.

For example, two or three of $X_{11}$ to $X_{15}$ may each be N.

In Formula 13(2), $A_{11}$ and $A_{12}$ may each independently be a benzene group, a naphthalene group, a pyridine group, a pyrazine group, a pyrimidine group, a pyridazine group, a quinoline group, an isoquinoline group, a quinoxaline group, or a quinazoline group, and at least one of $A_{11}$ and $A_{12}$ may be a pyridine group, a pyrazine group, a pyrimidine group, a pyridazine group, a quinoline group, an isoquinoline group, a quinoxaline group, or a quinazoline group.

For example, $A_{11}$ may be a pyridine group, a pyrimidine group, a quinoline group, an isoquinoline group, a quinoxaline group, or a quinazoline group, and $A_{12}$ may be a benzene group or a naphthalene group, but embodiments of the present disclosure are not limited thereto.

In Formula 13(2), $X_{16}$ may be N-[($L_{12}$)$_{a12}$-$R_{12}$], C($R_{14}$)($R_{15}$), O, or S, and $X_{17}$ may be a single bond, N-[($L_{13}$)$_{a13}$-$R_{13}$], C($R_{16}$)($R_{17}$), O, or S.

For example, $X_{16}$ may be O or S, and $X_{17}$ may be a single bond, but embodiments of the present disclosure are not limited thereto.

In Formulae 13(1) and 13(2), $L_{11}$ to $L_{13}$ are the same as described in connection with $L_3$, a11 to a13 are the same as described in connection with c3, and $R_{11}$ to $R_{17}$ are the same as described in connection with $R_1$.

d16 in Formula 13(2) may be an integer from 0 to 6, and d14 in Formula 13(1) may be an integer from 0 to 4.

* in Formulae 13(1) and 13(2) indicates a binding site to a neighboring atom.

In an embodiment, $R_3$ in Formula 11 may be one of groups represented by Formulae 13-1 to 13-20, but embodiments of the present disclosure are not limited thereto:

13-1 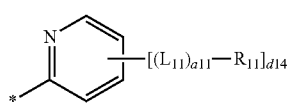
13-2 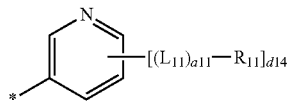
13-3 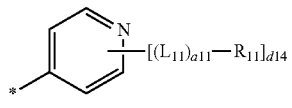
13-4 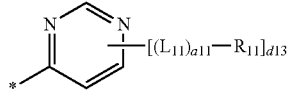
13-5 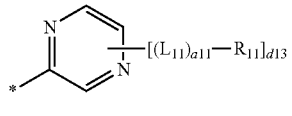
13-6 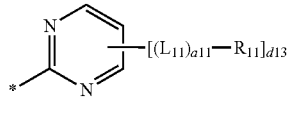
13-7 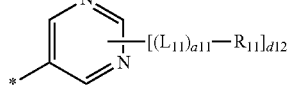
13-8 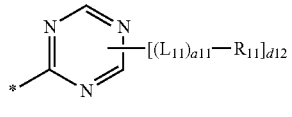
13-9 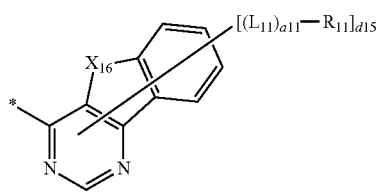
13-10 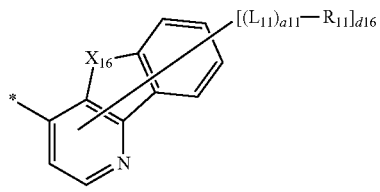
13-11 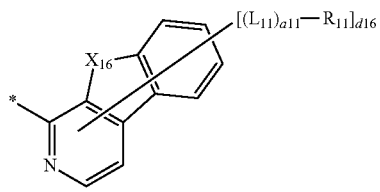
13-12 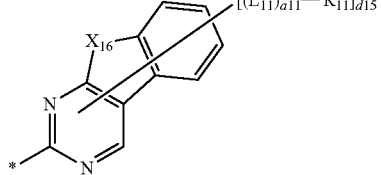
13-13 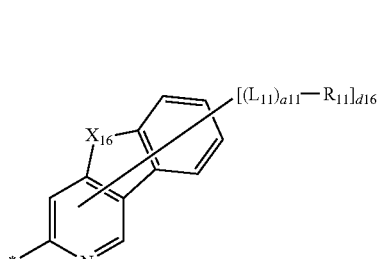
13-14 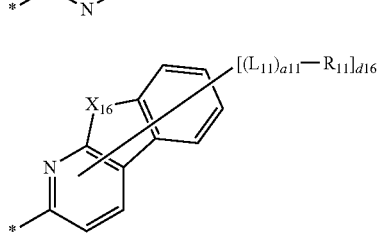
13-15 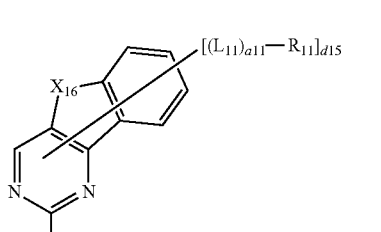
13-16 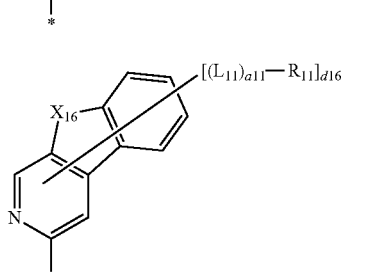
13-17 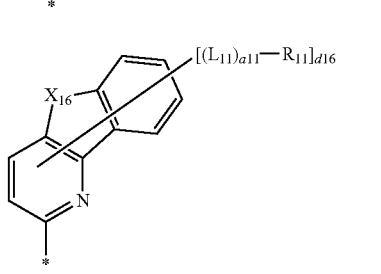
13-18 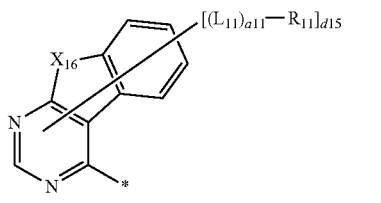

-continued 13-19

13-20
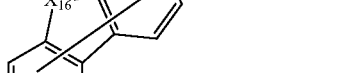

In Formulae 13-1 to 13-20,
$X_{16}$ may be N-[$(L_{12})_{a12}$-$R_{12}$], $C(R_{14})(R_{15})$, O, or S,
$L_{11}$ and $L_{12}$ are the same as described in connection with $L_3$,
a11 and a12 are the same as described in connection with c3,
$R_{11}$, $R_{12}$, $R_{14}$, and $R_{15}$ are the same as described in connection with $R_1$,
d16 may be an integer from 0 to 6,
d15 may be an integer from 0 to 5,
d14 may be an integer from 0 to 4,
d13 may be an integer from 0 to 3,
d12 may be an integer from 0 to 2, and
indicates a binding site to a neighboring atom.

In an embodiment, $R_1$, $R_2$, $R_5$, and $R_6$ in Formula 11 may each independently be selected from hydrogen, deuterium, a $C_1$-$C_{10}$ alkyl group, a $C_1$-$C_{10}$ alkoxy group, a phenyl group, a biphenyl group, a terphenyl group, a naphthyl group, a fluorenyl group, a pyridinyl group, a pyrimidinyl group, a pyrazinyl group, a pyridazinyl group, a triazinyl group, a carbazolyl group, a dibenzofuranyl group, a dibenzothiophenyl group, an indolocarbazolyl group, —Si($Q_1$)($Q_2$)($Q_3$), and —N($Q_4$)($Q_5$), and $Q_1$ to $Q_5$ may each independently be selected from a $C_1$-$C_{10}$ alkyl group, a $C_1$-$C_{10}$ alkoxy group, a phenyl group, a biphenyl group, a terphenyl group, and a naphthyl group.

a1 and a2 in Formula 11 indicate the number of groups $R_1$ and the number of groups $R_2$, respectively, and may each independently be an integer from 0 to 10. When a1 is two or more, two or more groups $R_1$ may be identical to or different from each other, and when a2 is two or more, two or more groups $R_2$ may be identical to or different from each other.

In an embodiment, the third material may include a compound represented by one of Formulae 11-1 to 11-7, but embodiments of the present disclosure are not limited thereto:

11-1
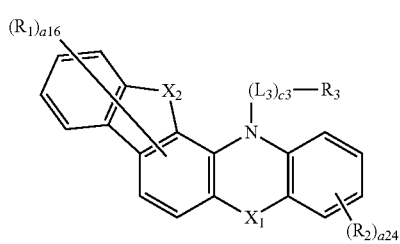

11-2
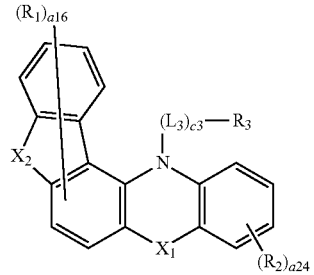

11-3
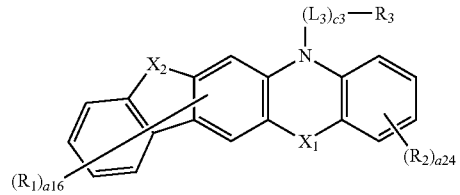

11-4
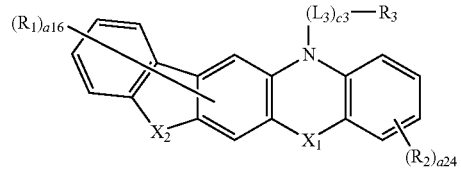

11-5
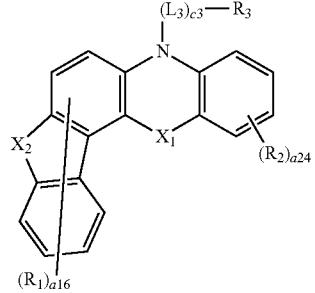

11-6
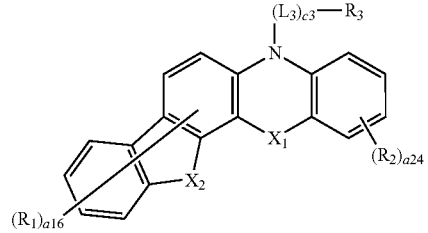

11-7
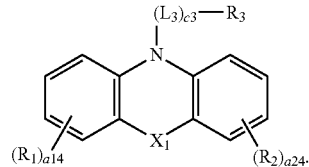

In Formulae 11-1 to 11-7,
$X_1$, $L_3$, c3, and $R_1$ to $R_3$ are the same as described herein,
$X_2$ may be N-[$(L_5)_{c5}$-$R_7$], $C(R_8)(R_9)$, O, or S,
$L_5$ and c5 are the same as described in connection with $L_3$ and c3, R₇ is the same as described in connection with R₃, R₈ and R₉ are the same as described in connection with R₅ and R₆, a16 may be an integer from 0 to 6, and a14 and a24 may each independently be an integer from 0 to 4.

In an embodiment, in Formulae 11-1 to 11-17, 1) $R_3$ when $X_2$ is $C(R_8)(R_9)$, O, or S, and 2) at least one of $R_3$ and $R_7$ when $X_2$ is $N-[(L_5)_{c5}-R_7]$, may each independently include at least one π electron-depleted nitrogen-containing cyclic group as described above.

In one or more embodiments, in Formulae 11-1 to 11-17, 1) $R_3$ when $X_2$ is $C(R_8)(R_9)$, O, or S and 2) $R_3$ and $R_7$ when $X_2$ is $N-[(L_5)_{c5}-R_7]$, may each independently be selected from:

a group represented by Formula 13(1) or 13(2) (for example, one of groups represented by Formulae 13-1 to 13-20);

a phenyl group, a biphenyl group, a terphenyl group, a naphthyl group, a fluorenyl group, a quinolinyl group, an isoquinolinyl group, a carbazolyl group, a dibenzofuranyl group, a dibenzothiophenyl group, and an indolocarbazolyl group; and a phenyl group, a biphenyl group, a terphenyl group, a naphthyl group, a fluorenyl group, a quinolinyl group, an isoquinolinyl group, a carbazolyl group, a dibenzofuranyl group, a dibenzothiophenyl group, and an indolocarbazolyl group, each substituted with at least one selected from deuterium, a $C_1$-$C_{10}$ alkyl group, a $C_1$-$C_{10}$ alkoxy group, a phenyl group, a biphenyl group, a terphenyl group, a naphthyl group, a fluorenyl group, a pyridinyl group, a pyrimidinyl group, a pyrazinyl group, a pyridazinyl group, a triazinyl group, a quinolinyl group, an isoquinolinyl group, a carbazolyl group, a dibenzofuranyl group, a dibenzothiophenyl group, an indolocarbazolyl group, and —Si(Q₃₁)(Q₃₂)(Q₃₃), 1) $R_3$ when $X_2$ is $C(R_8)(R_9)$, O, or S and 2) at least one of $R_3$ and $R_7$ when $X_2$ is $N-[(L_5)_{c5}-R_7]$, may each independently be a group represented by Formula 13(1) or 13(2) (for example, one of groups represented by Formulae 13-1 to 13-20).

a1 and a2 in Formula 11 indicate the number of groups $R_1$ to the number of groups $R_2$, respectively, and may each independently be an integer from 0 to 10. When a1 is two or more, two or more groups $R_1$ may be identical to or different from each other, and when a2 is two or more, two or more groups $R_2$ may be identical to or different from each other. For example, a1 and a2 may each independently be 0, 1, 2, or 3, but they are not limited thereto.

In an embodiment, the third material may include at least one compound selected from Compounds M1-1 to M1-81, M2-1 to M2-81, M3-1 to M3-81, and M201 to M204, but embodiments of the present disclosure are not limited thereto:

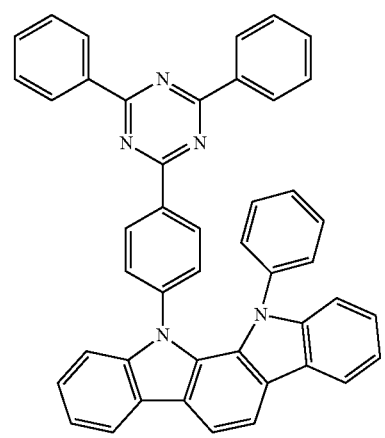

M1-1

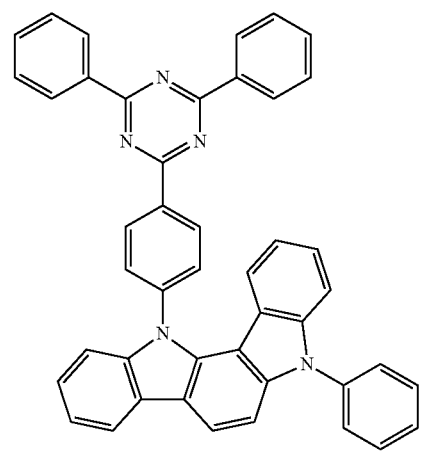

M1-2

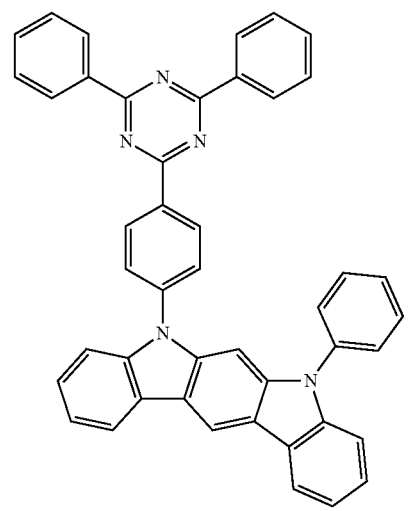

M1-3

M1-4
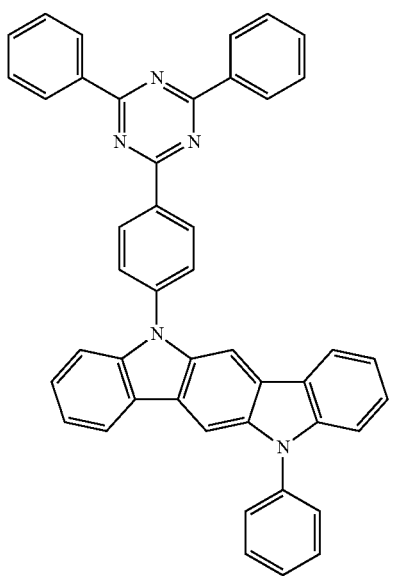
M1-5
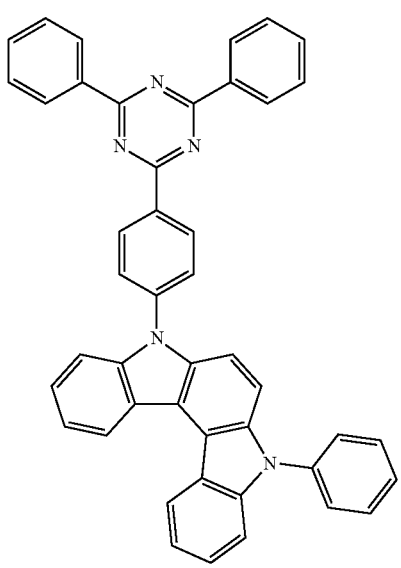
M1-6
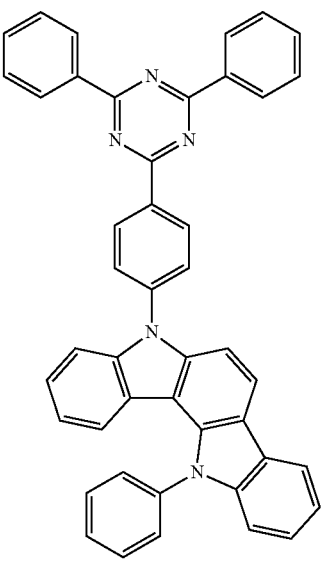
M1-7
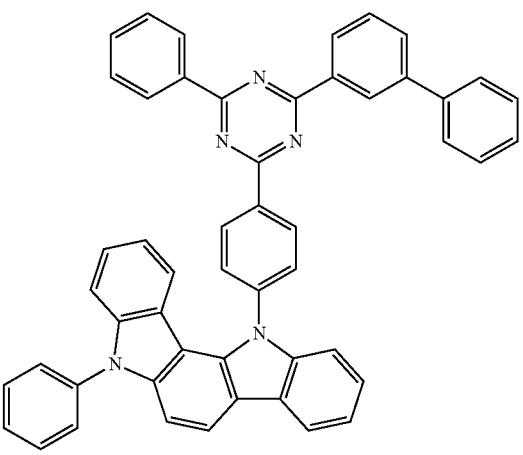
M1-8
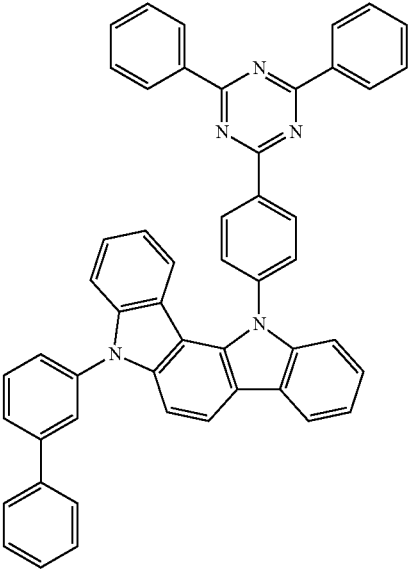

-continued
M1-9
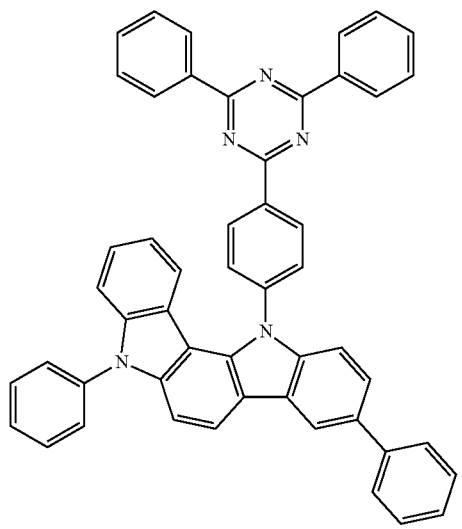
M1-10
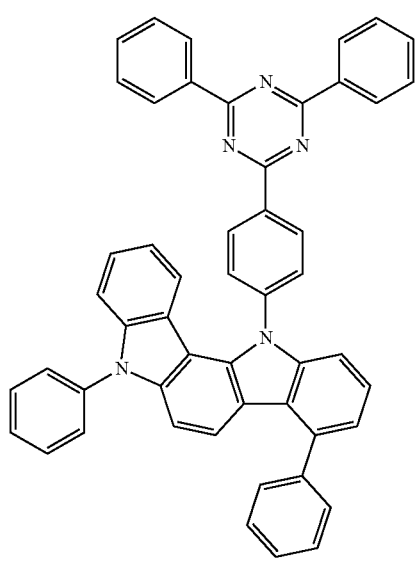
M1-11
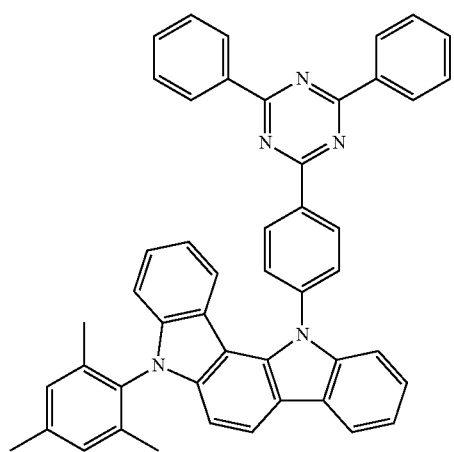
-continued
M1-12
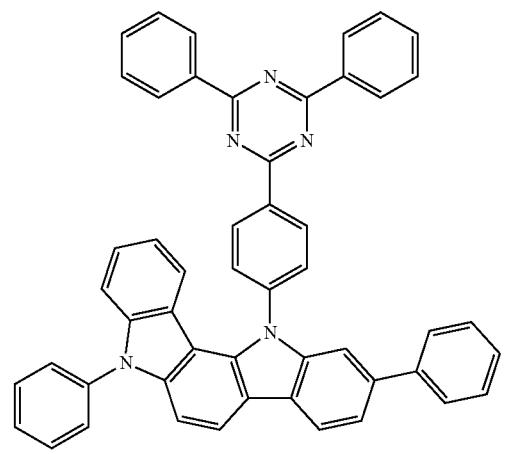
M1-13
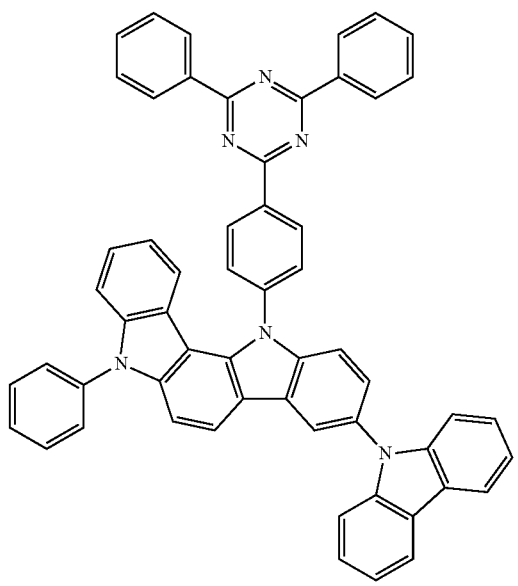
M1-14
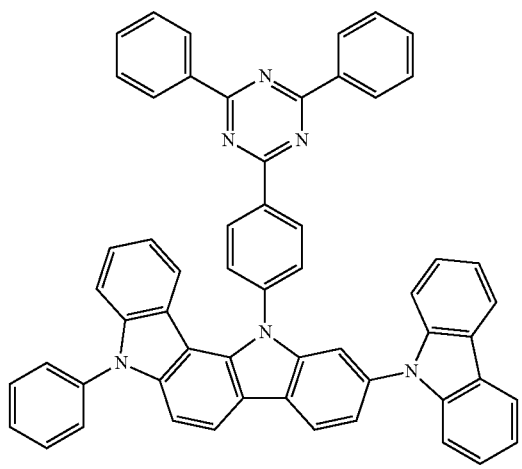

-continued
M1-15
M1-16
M1-17
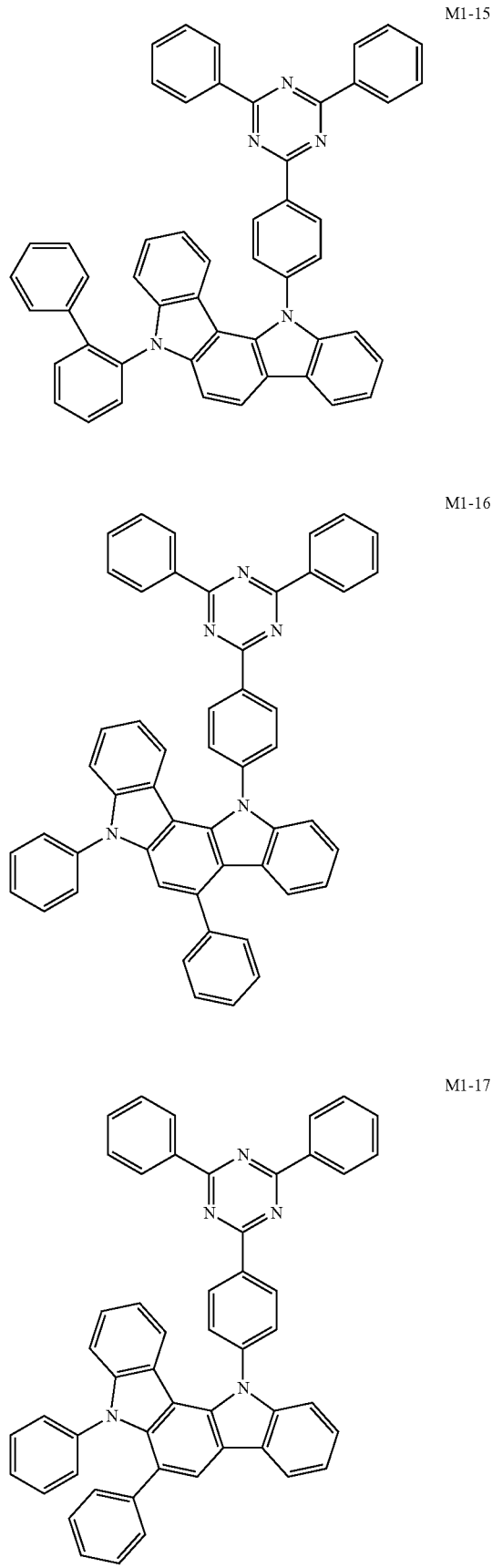
-continued
M1-18
M1-19

M1-20
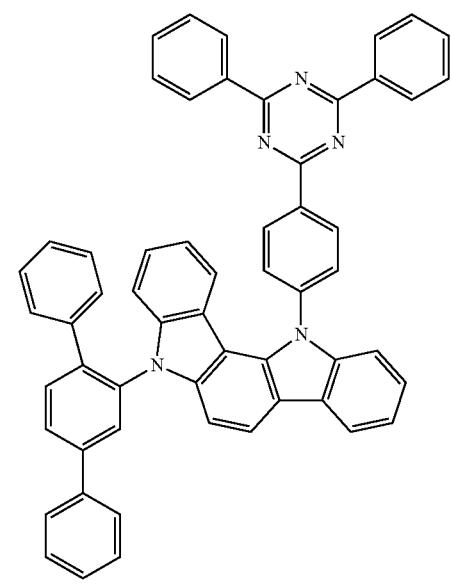
M1-21
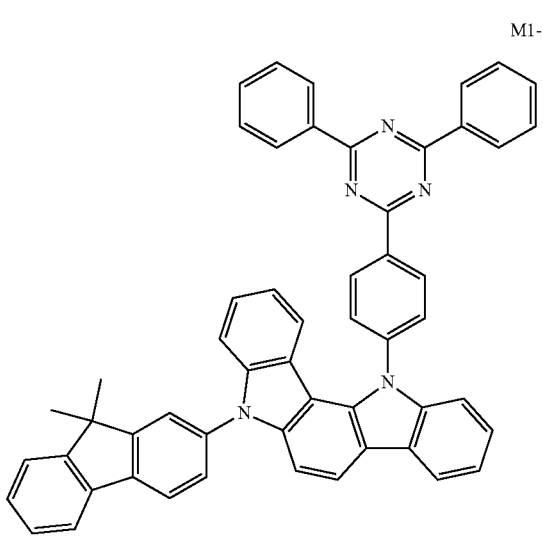
M1-22
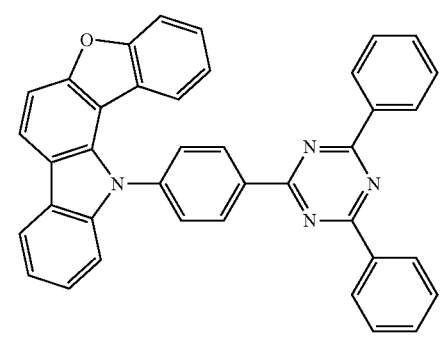
M1-23
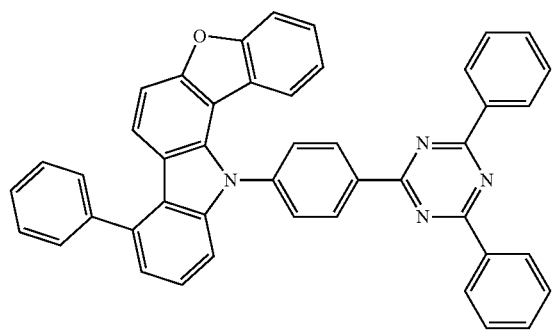
M1-24
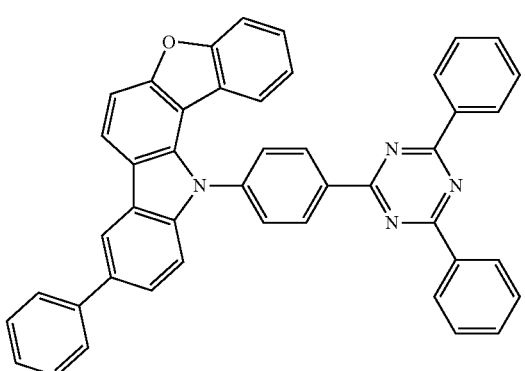
M1-25
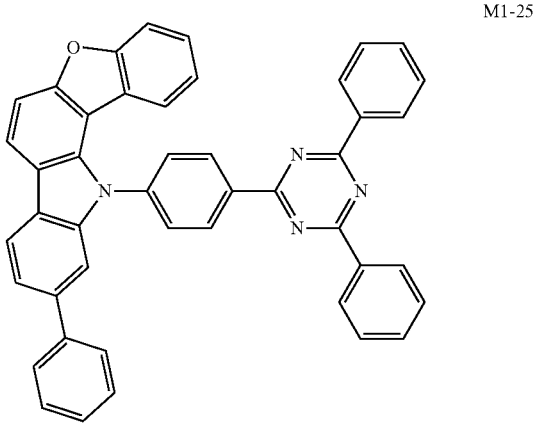
M1-26
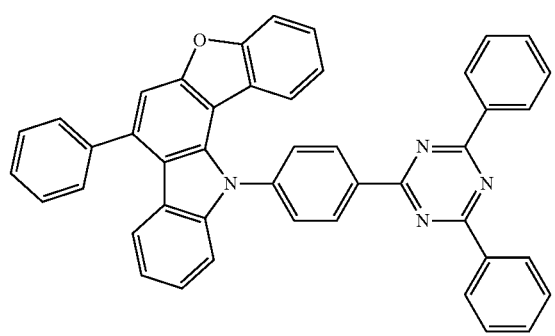

M1-27
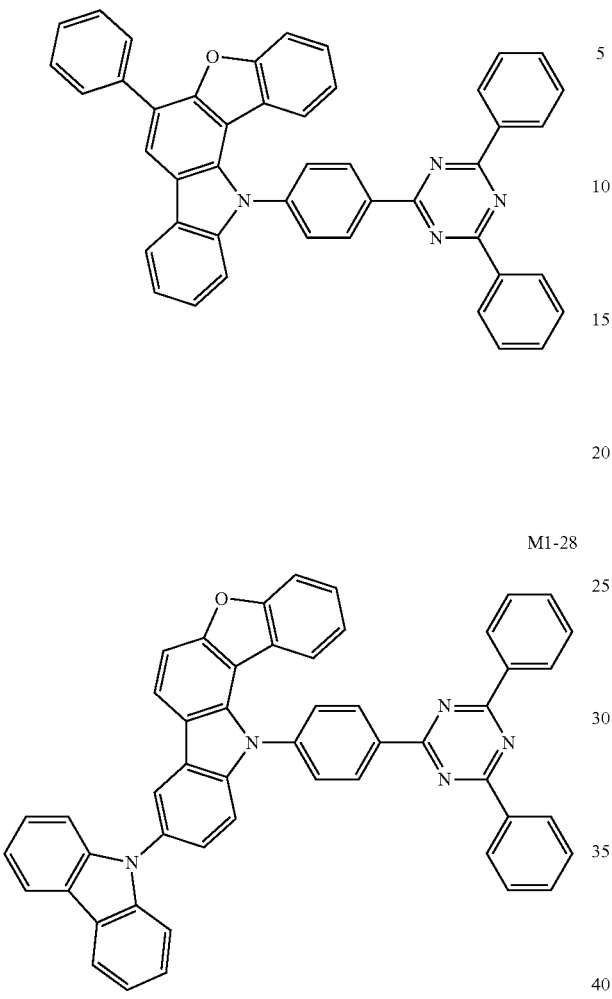
M1-28
M1-29
M1-30
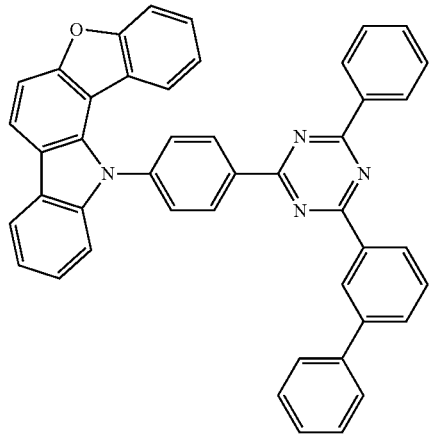
M1-31
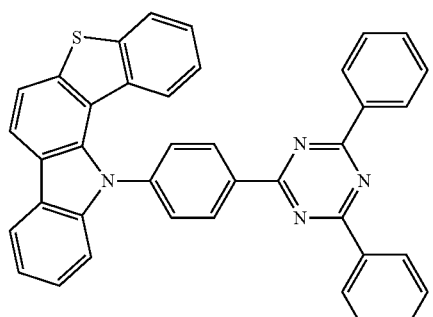
M1-32
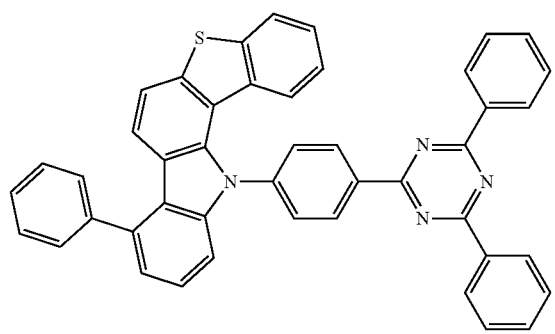
M1-33
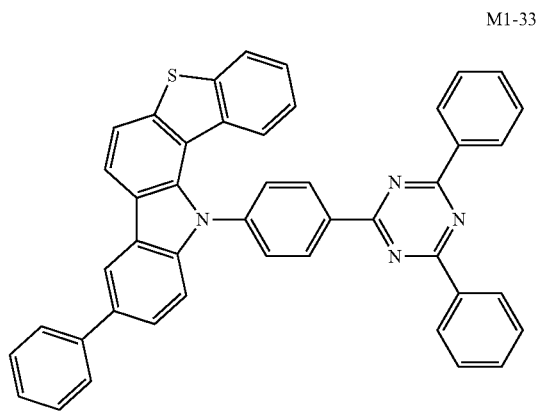
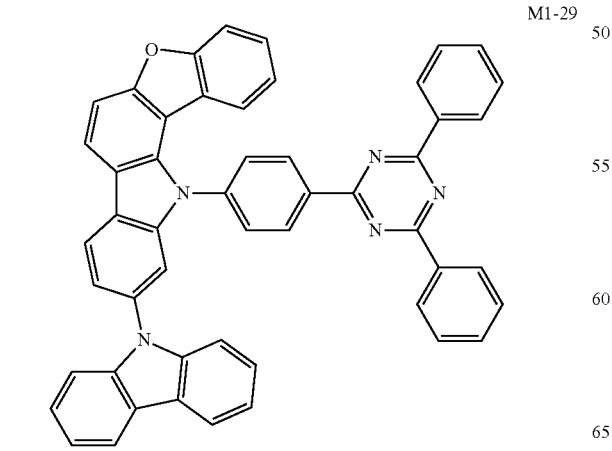

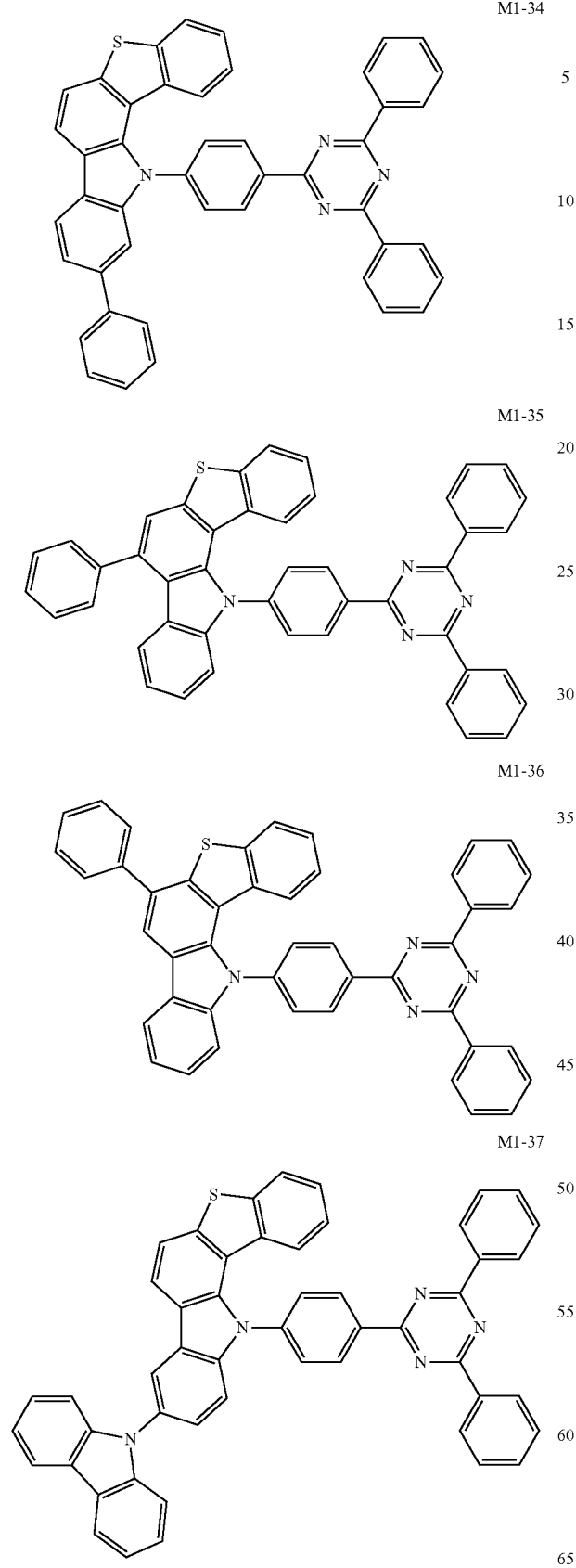
M1-34
M1-35
M1-36
M1-37
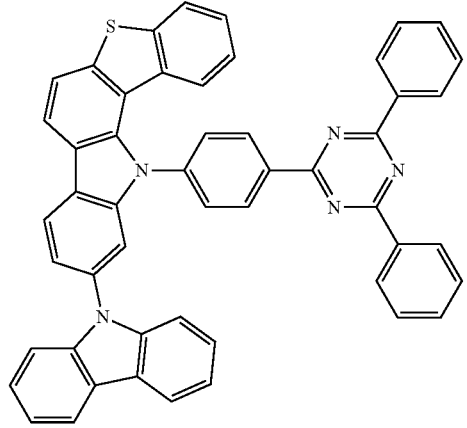
M1-38
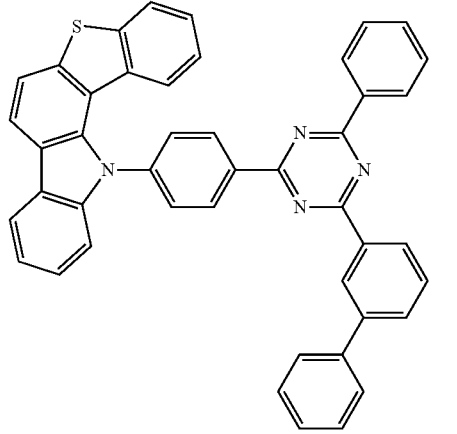
M1-39
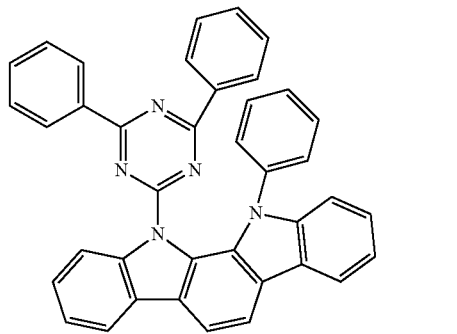
M1-40
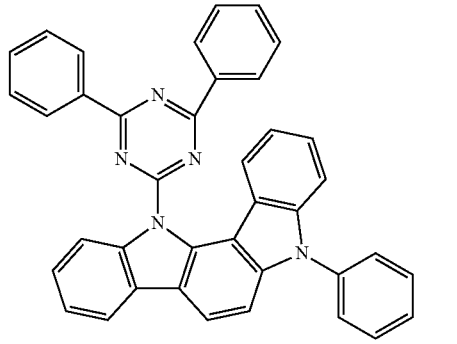
M1-41

M1-42
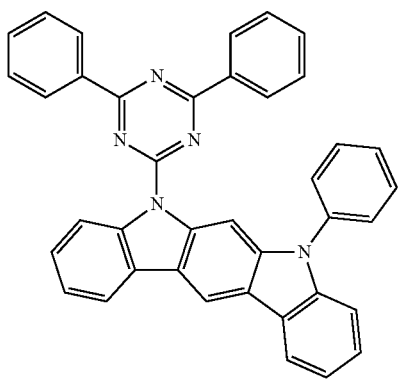
M1-43
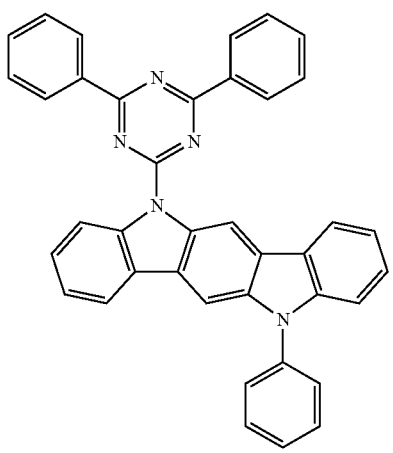
M1-44
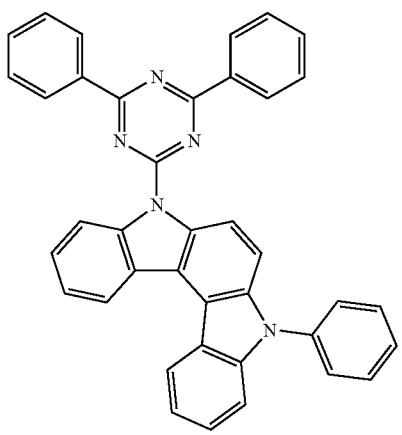
M1-45
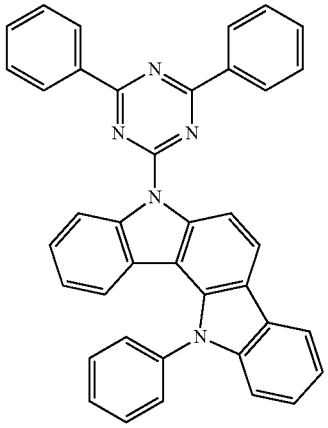
M1-46
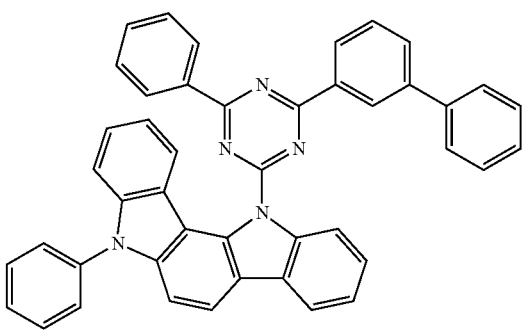
M1-47
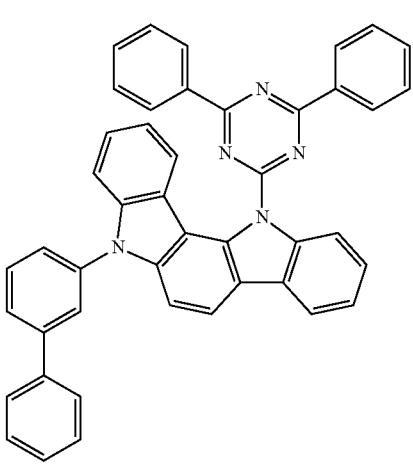
M1-48
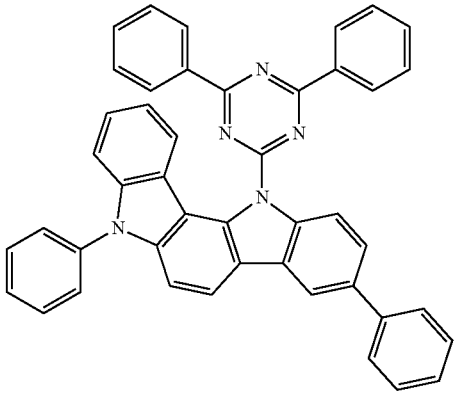

M1-49
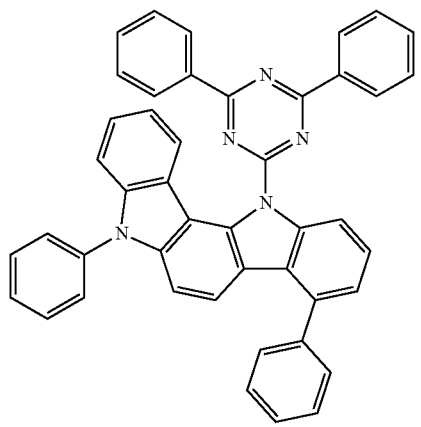
M1-50
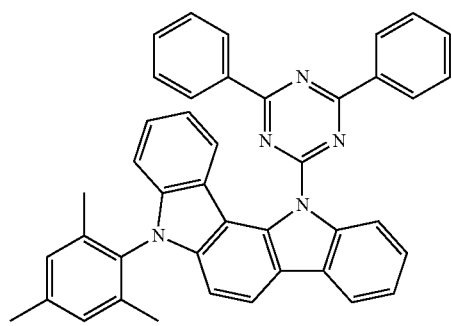
M1-51
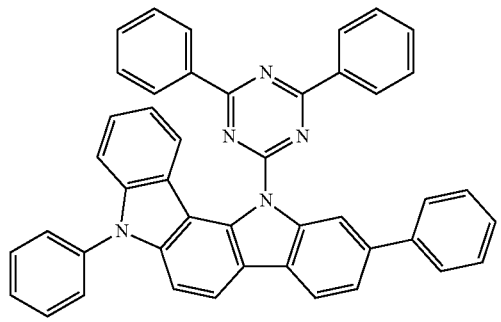
M1-52
M1-53
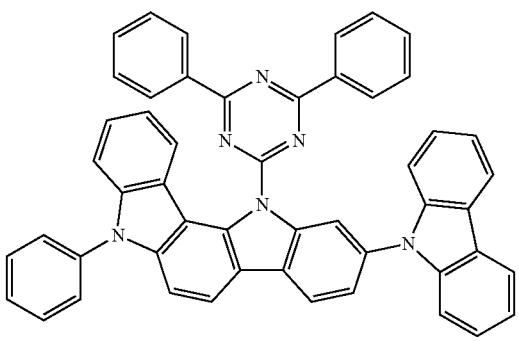
M1-54
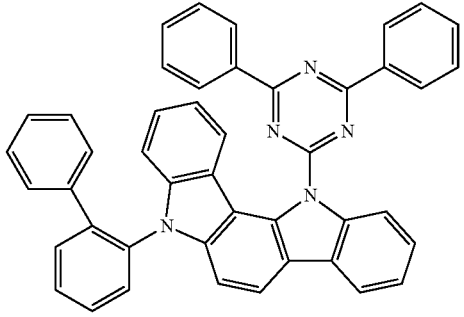
M1-55
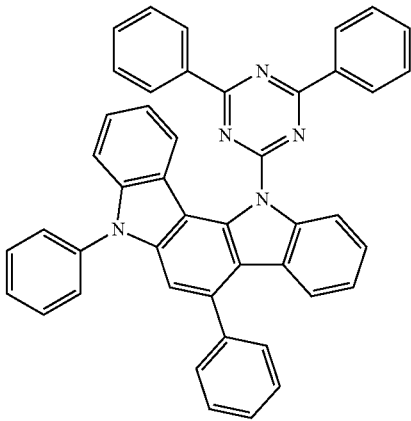
M1-56
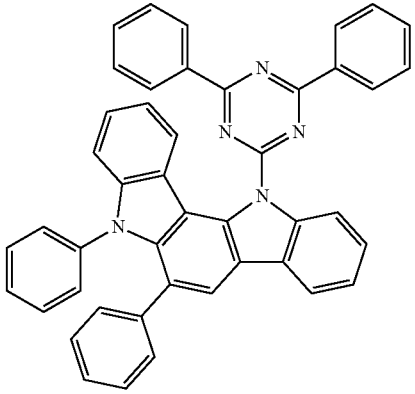

M1-57
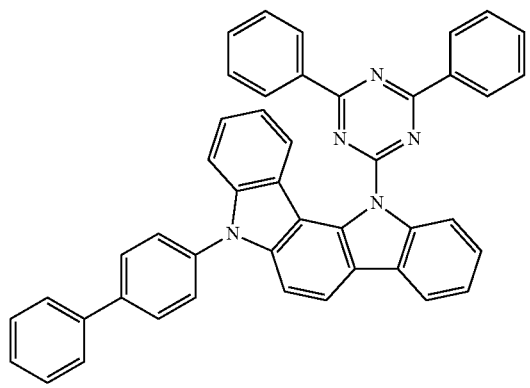
M1-58
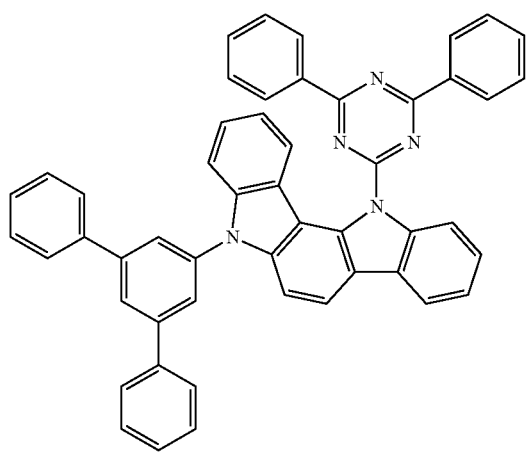
M1-59
M1-60
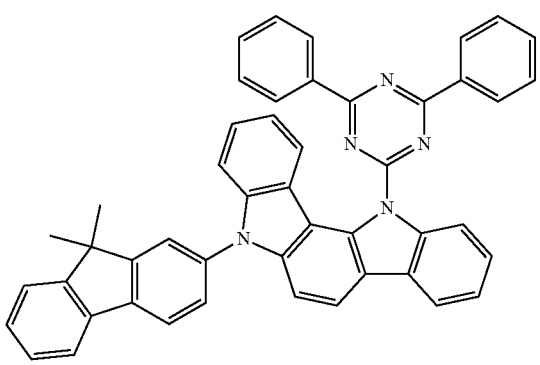
M1-61
M1-62
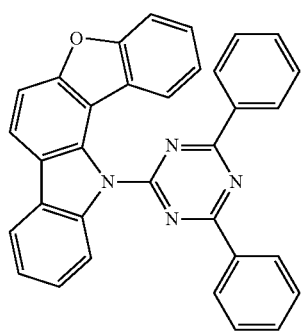
M1-63
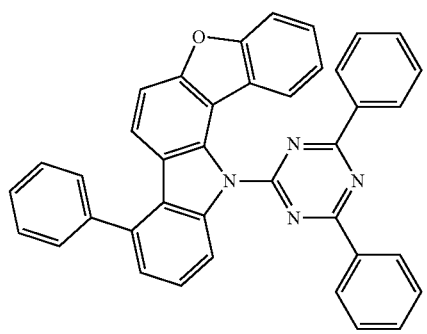
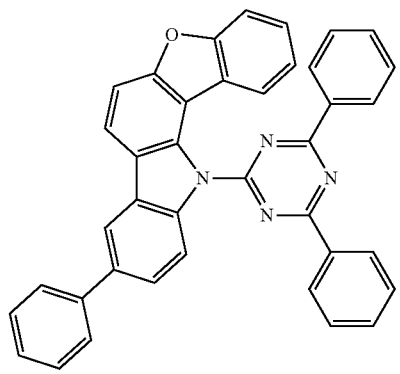

M1-64
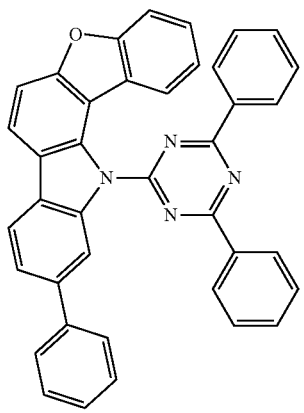
M1-68
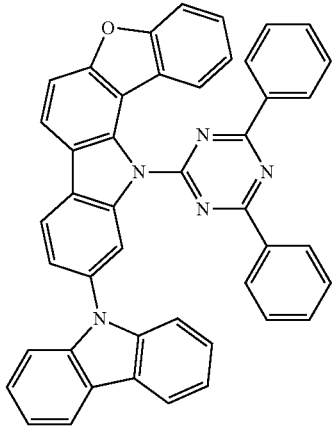
M1-65
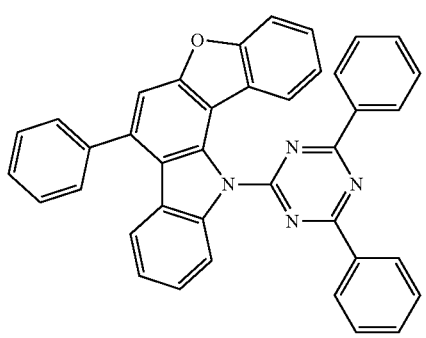
M1-69
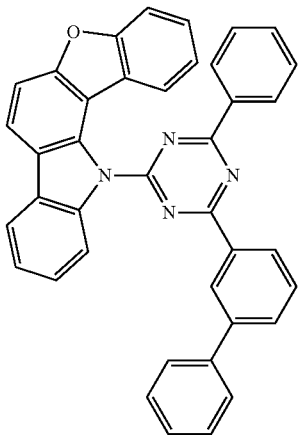
M1-66
M1-70
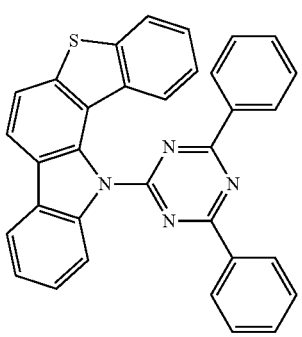
M1-67
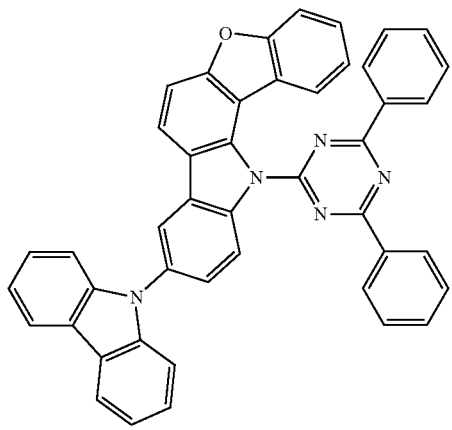
M1-71
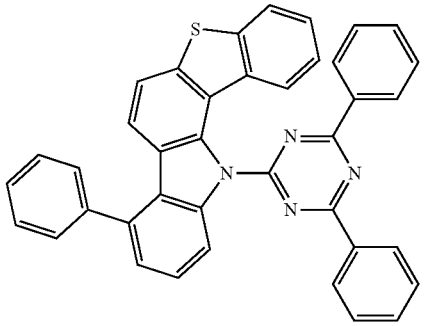

M1-72
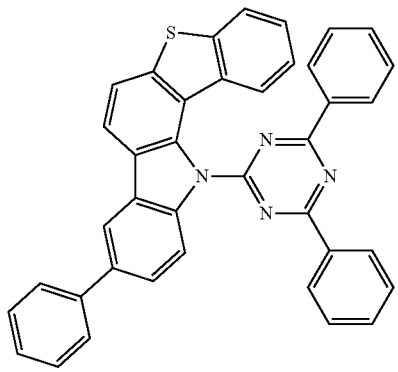
M1-73
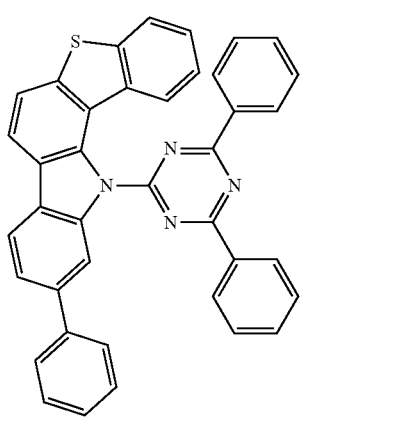
M1-74
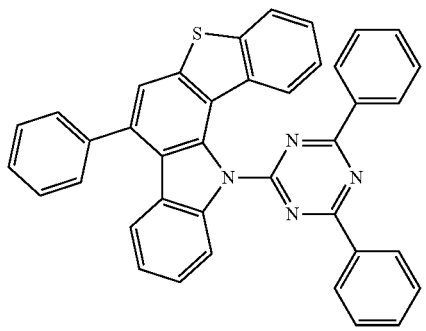
M1-75
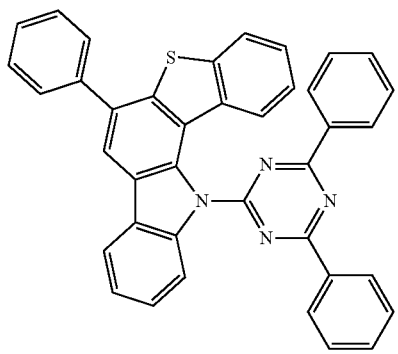
M1-76
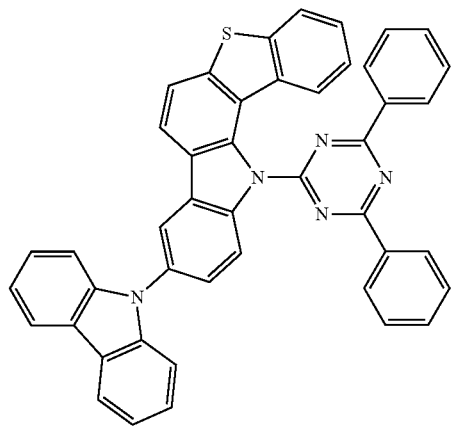
M1-77
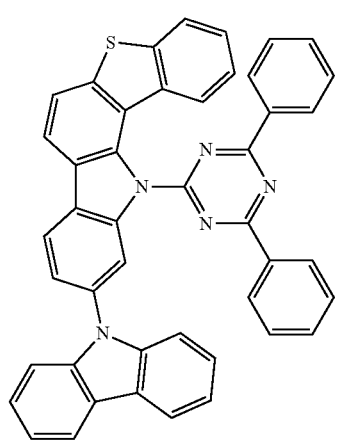
M1-78
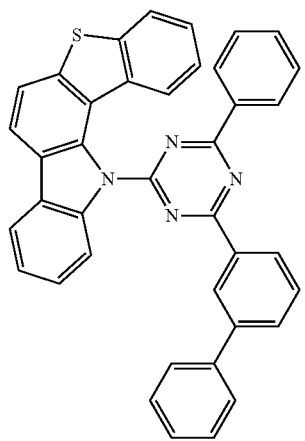

M1-79
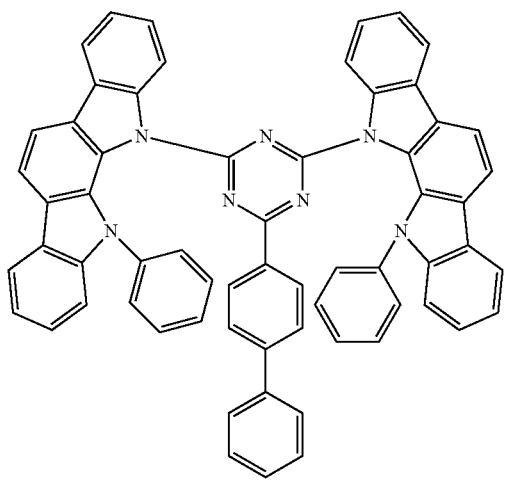
M2-1
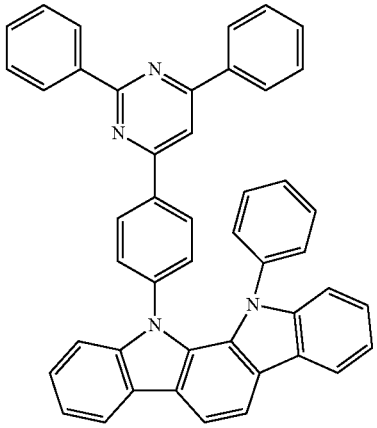
M1-80
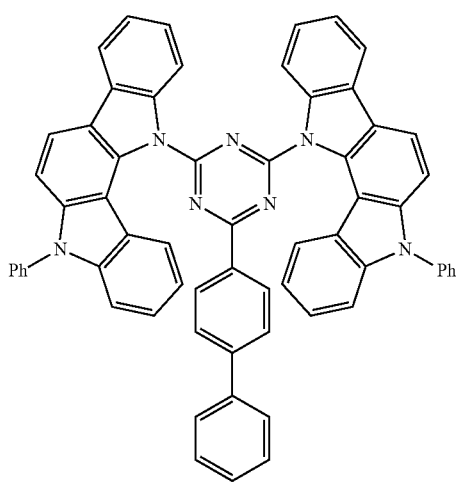
M2-2
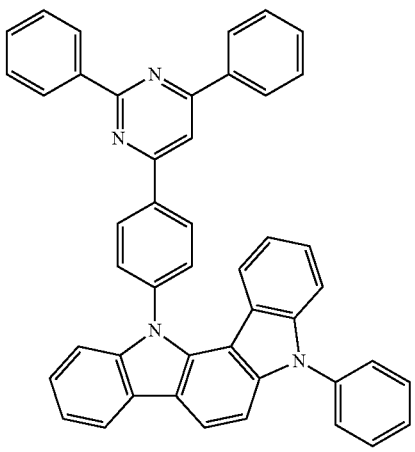
M1-81
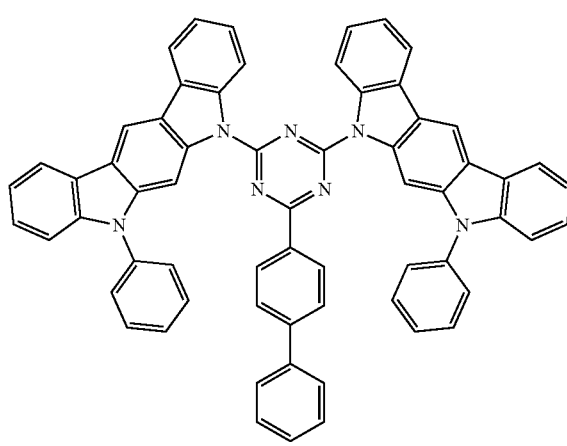
M2-3
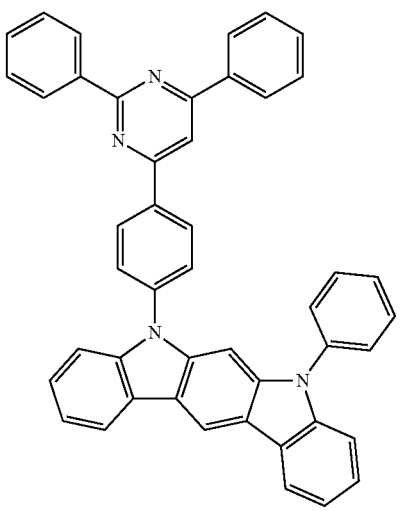

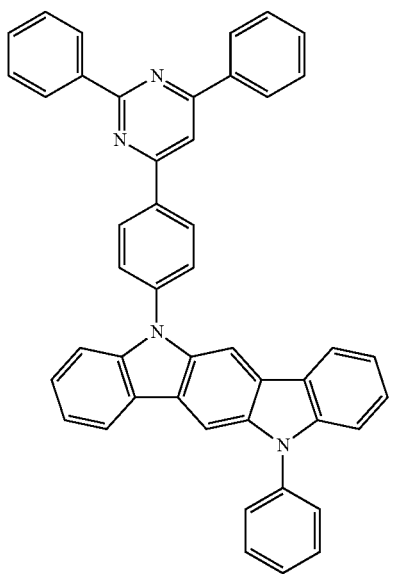
M2-4
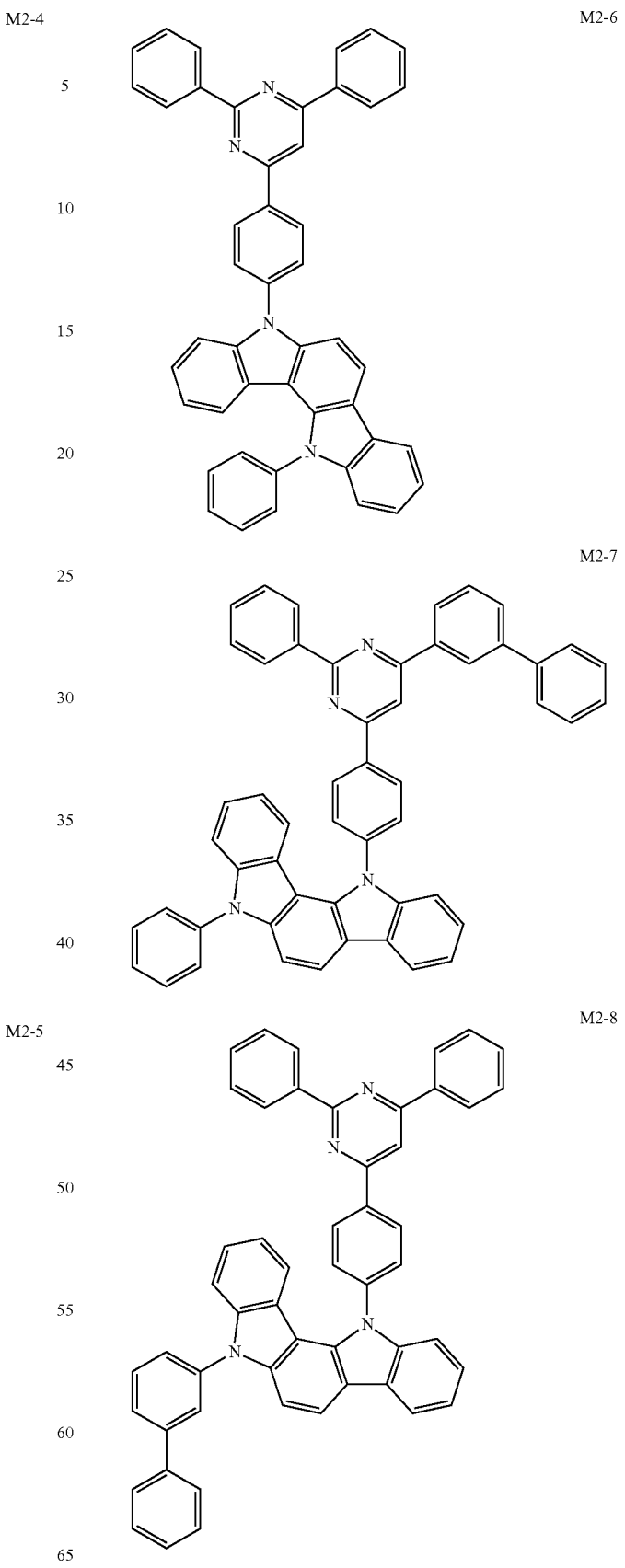

M2-9
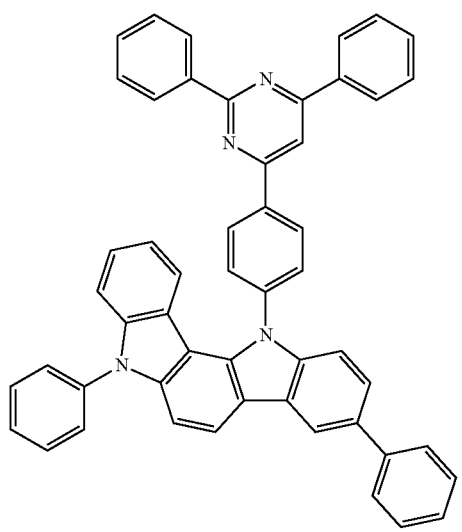
M2-10
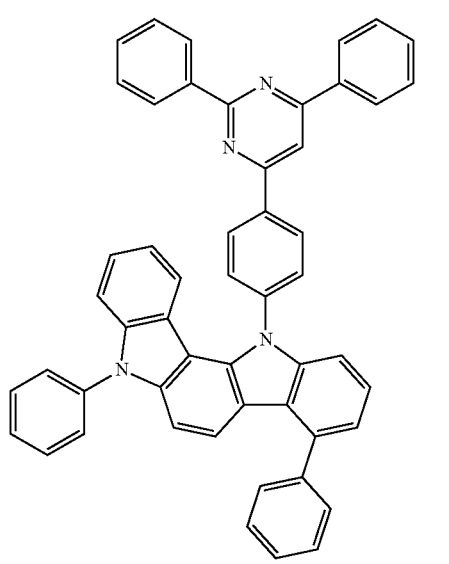
M2-11
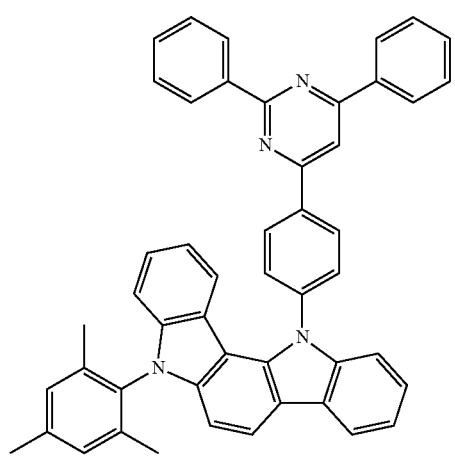
M2-12
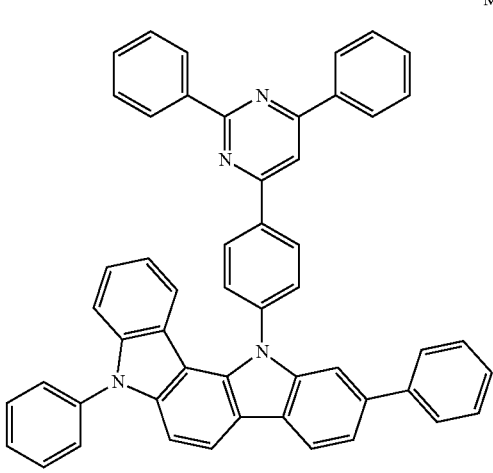
M2-13
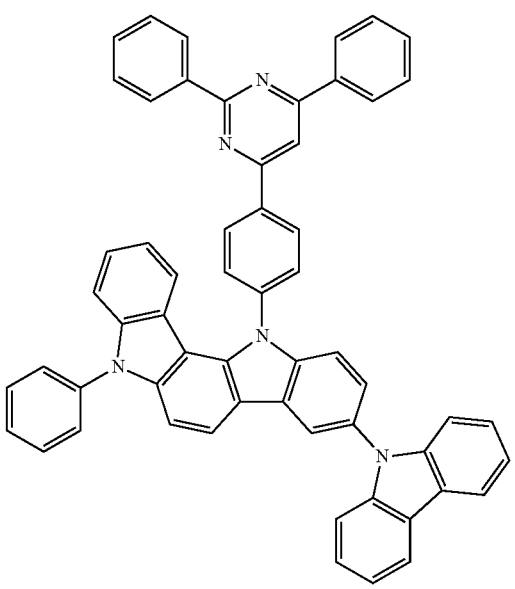
M2-14
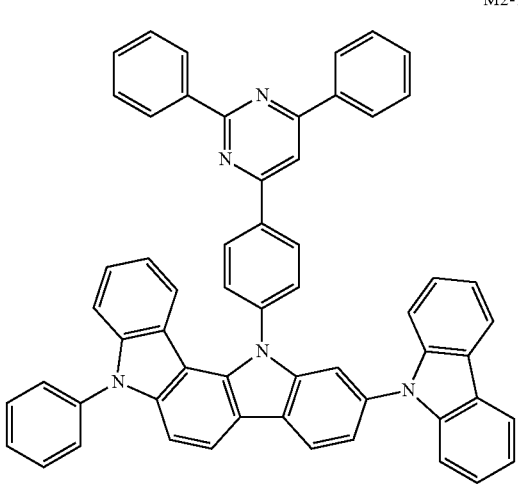

M2-15
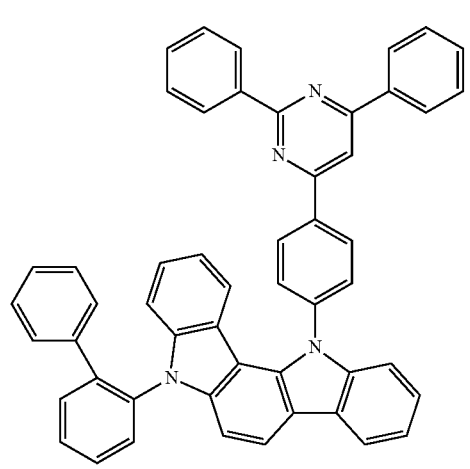
M2-16
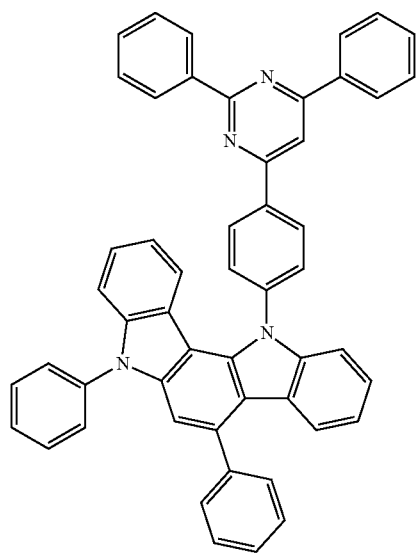
M2-17
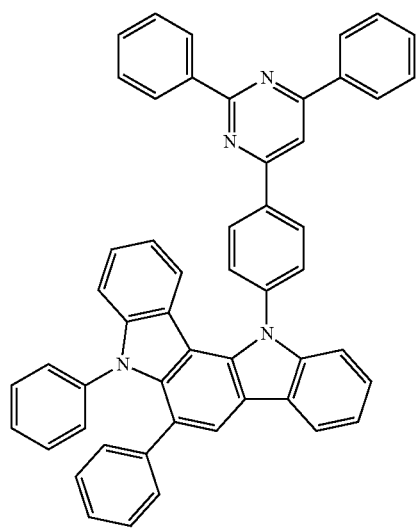
M2-18
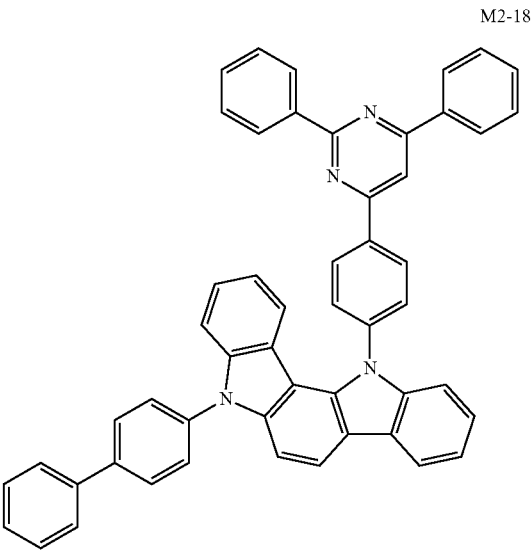
M2-19
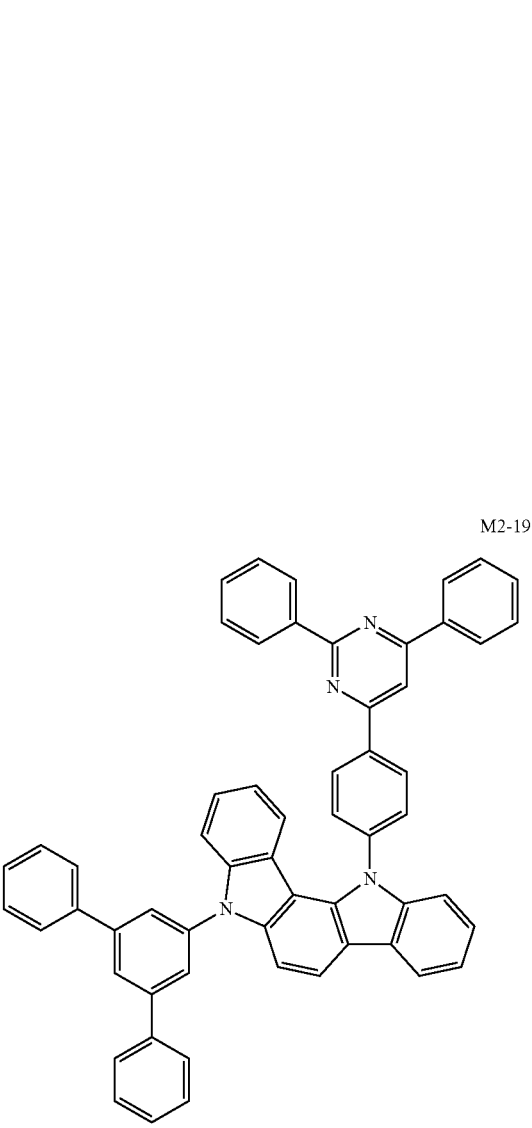

M2-20
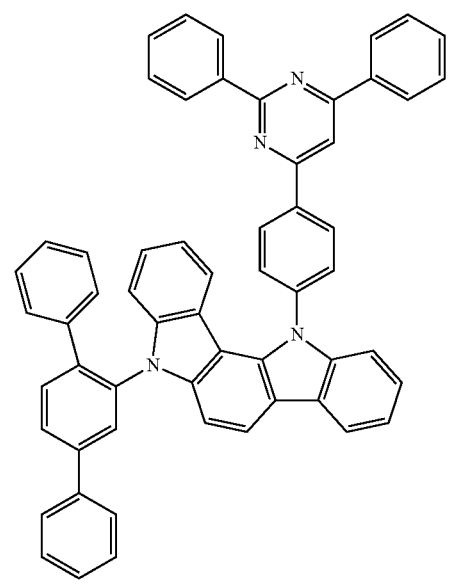
M2-21
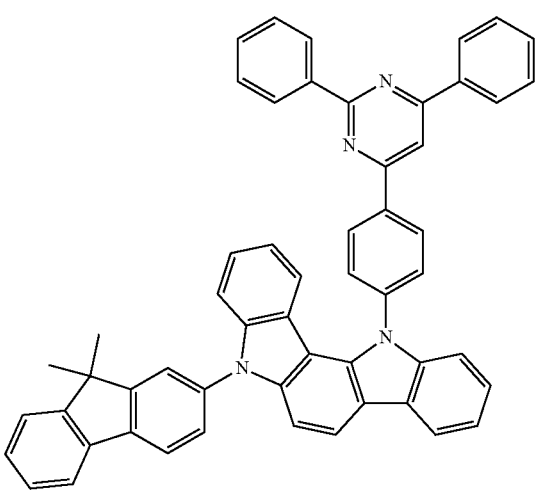
M2-22
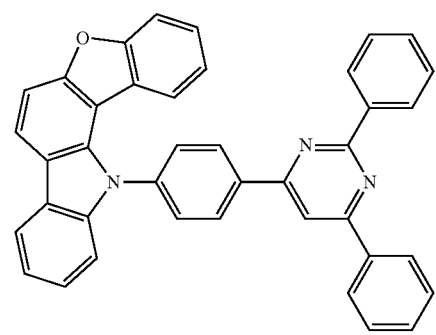
M2-23
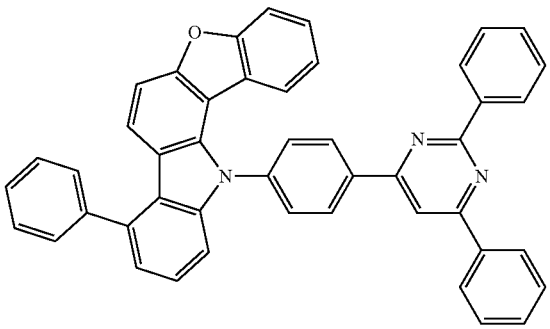
M2-24
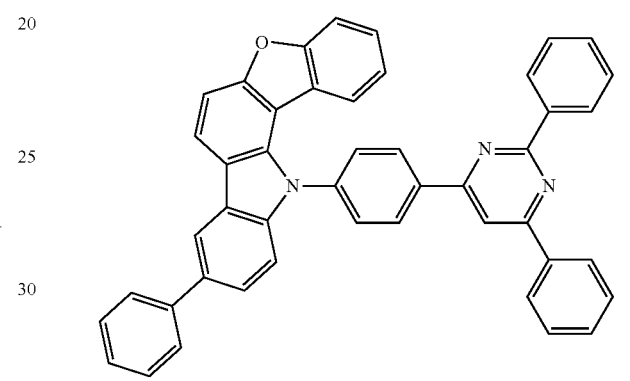
M2-25
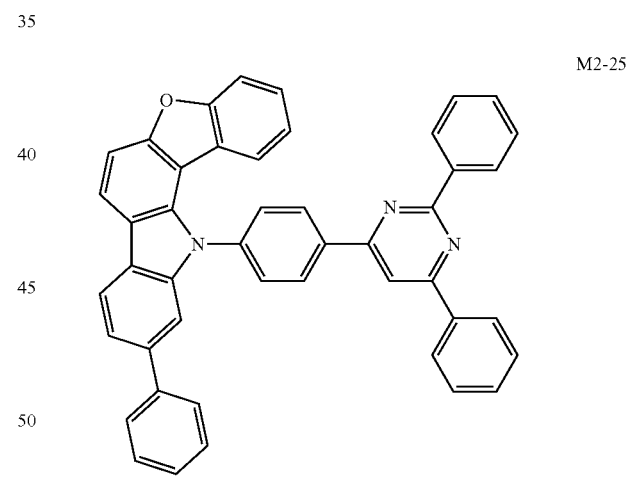
M2-26
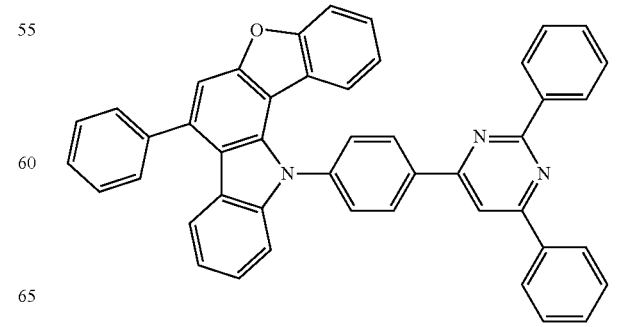

M2-27
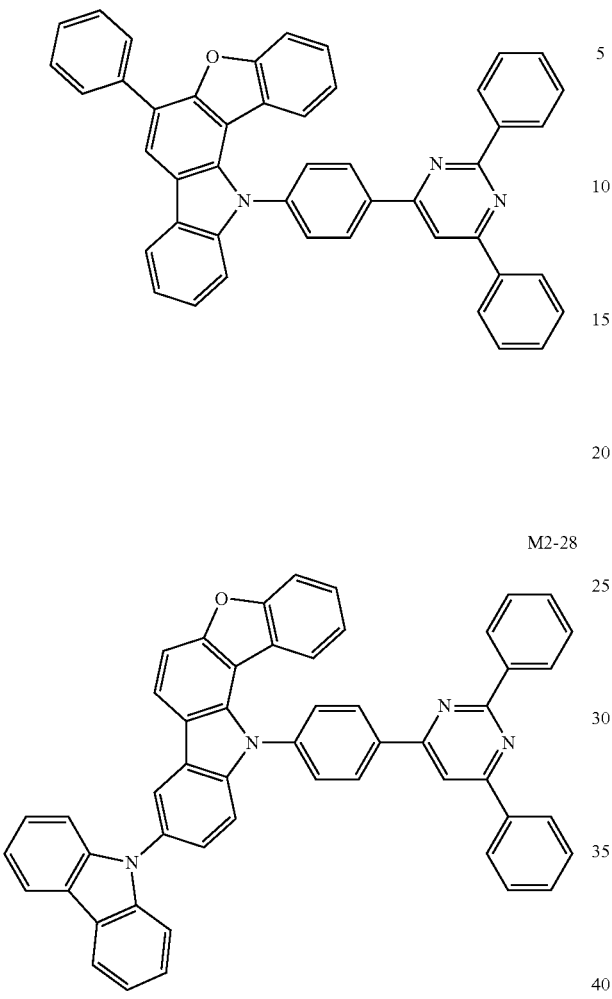
M2-28
M2-29
M2-30
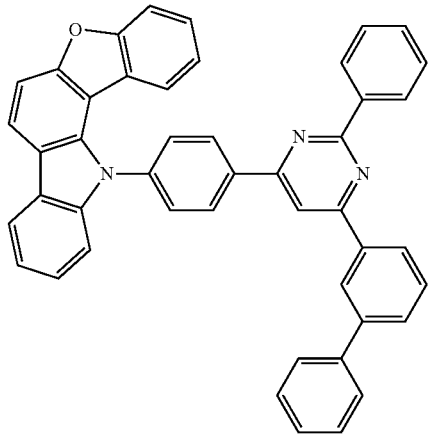
M2-31
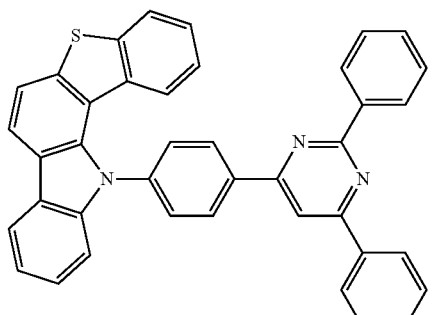
M2-32
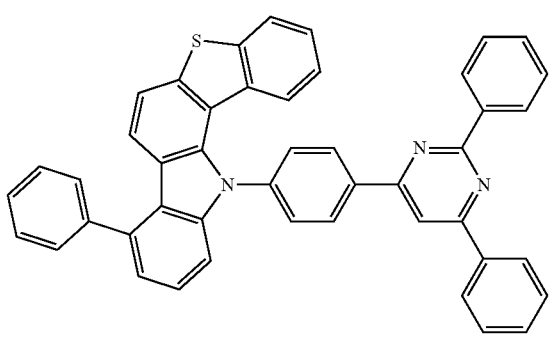
M2-33
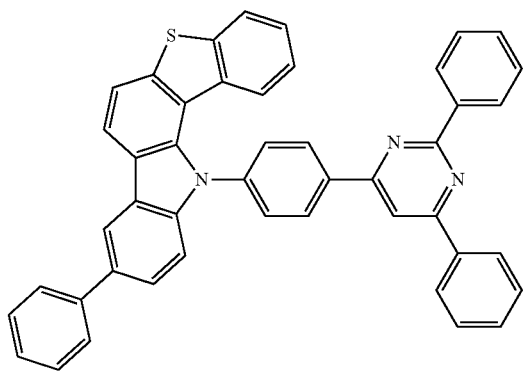

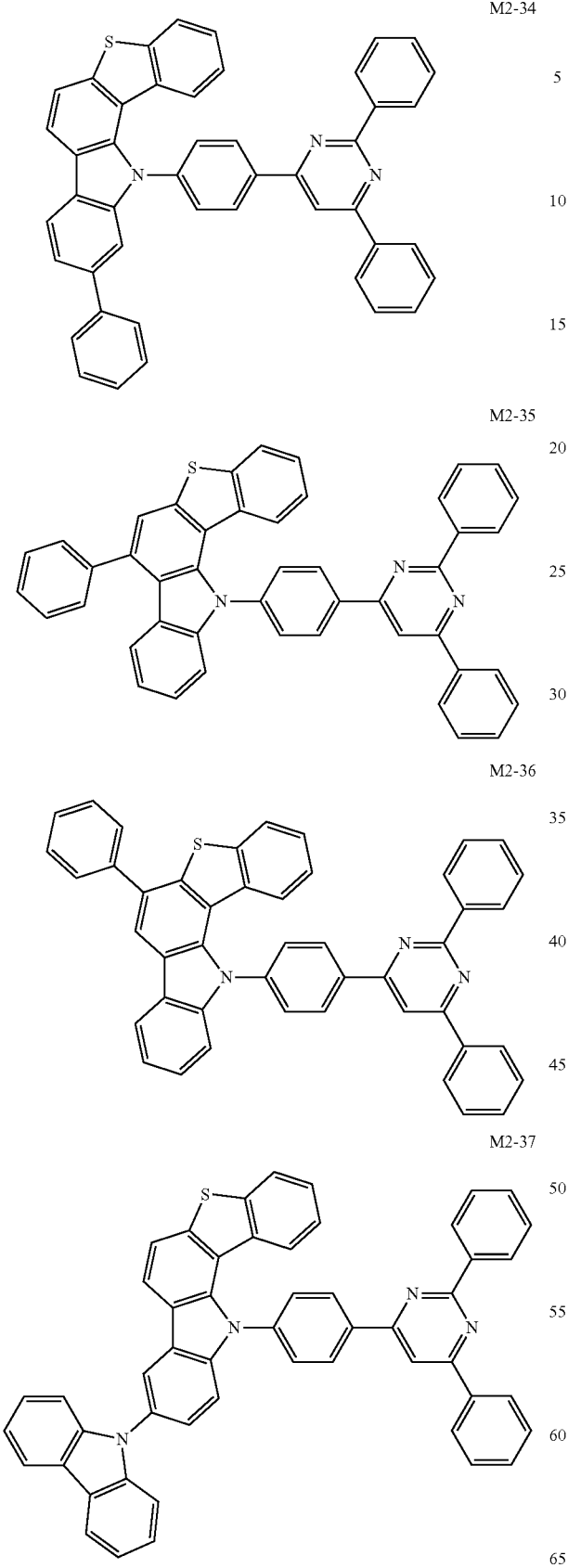
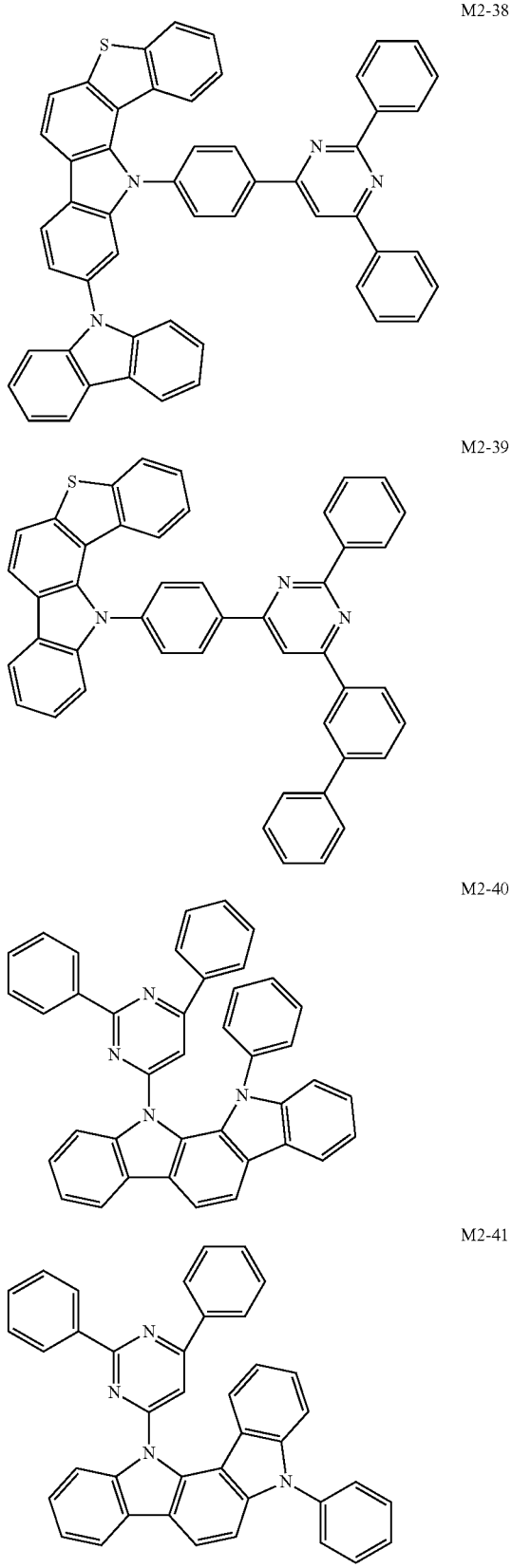

-continued
M2-42
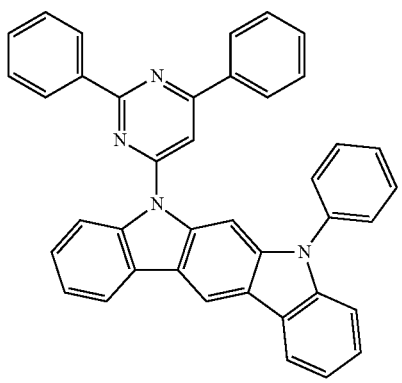
M2-43
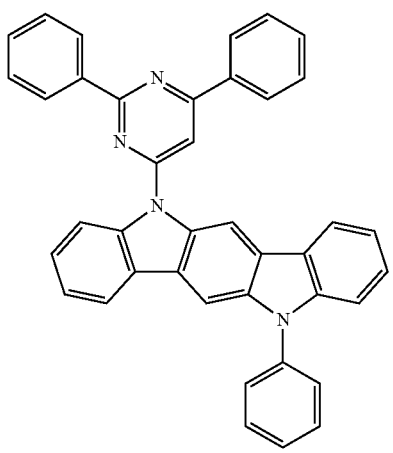
M2-44
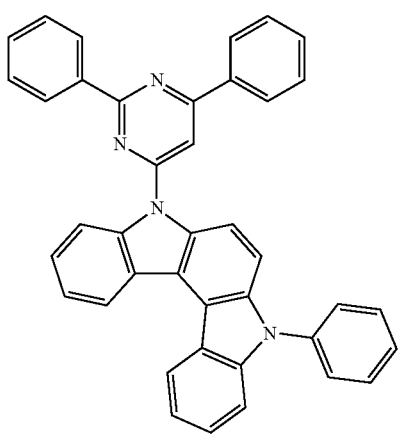
-continued
M2-45
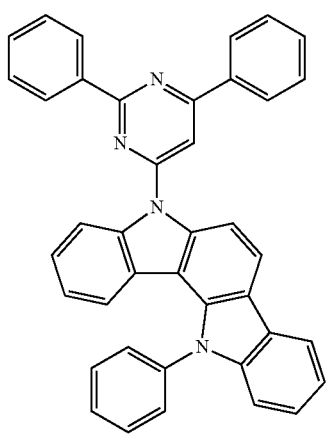
M2-46
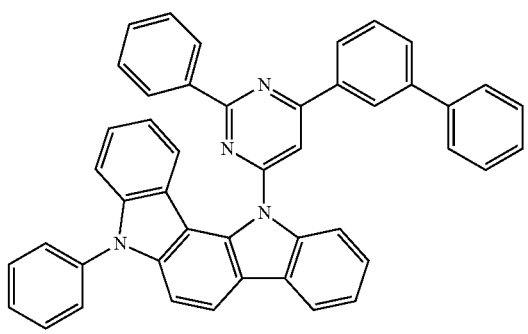
M2-47
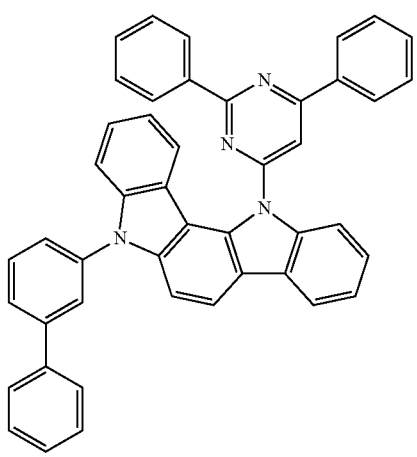
M2-48
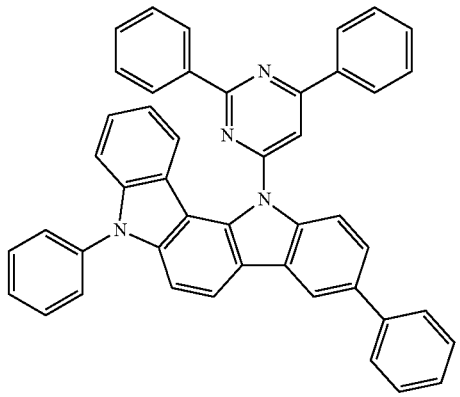

M2-49
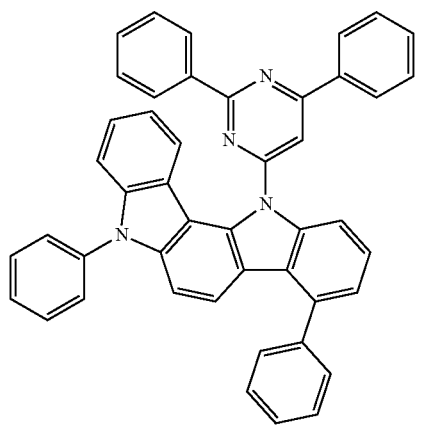
M2-50
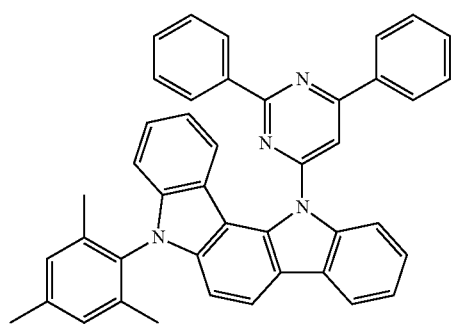
M2-51
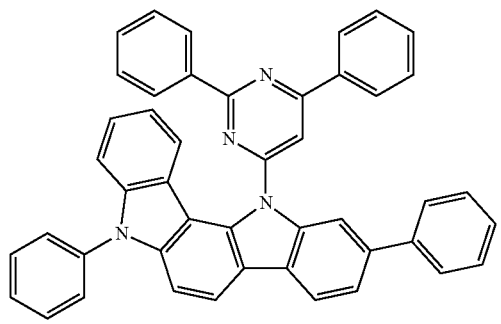
M2-52
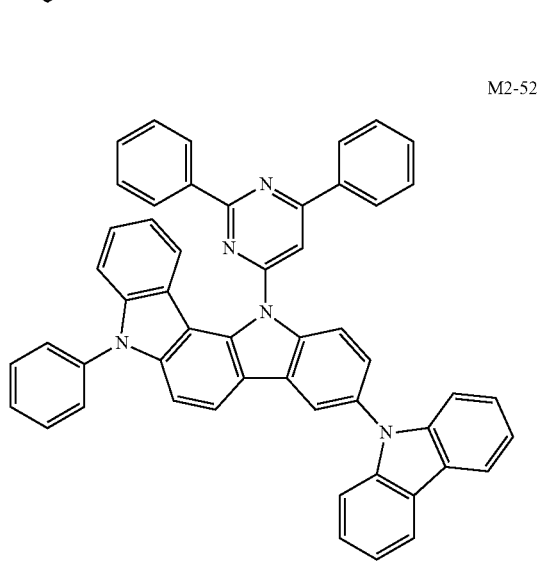
M2-53
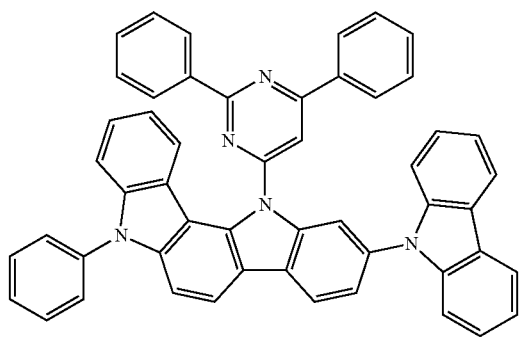
M2-54
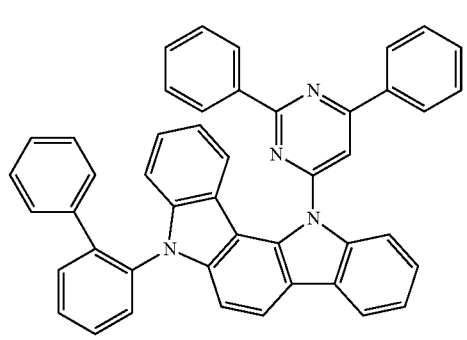
M2-55
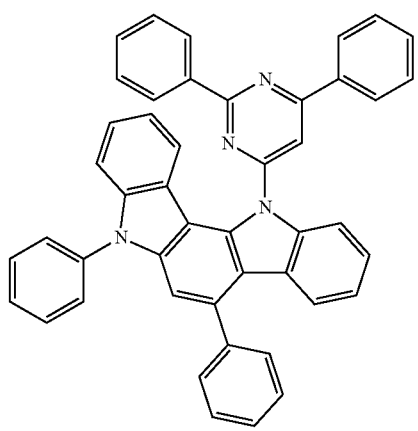
M2-56
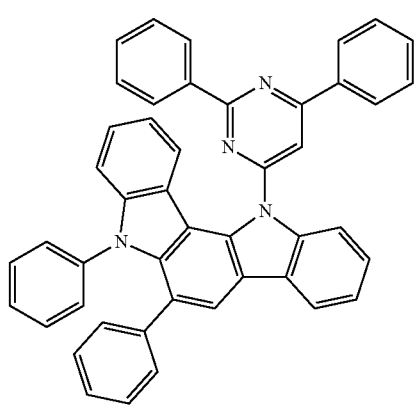

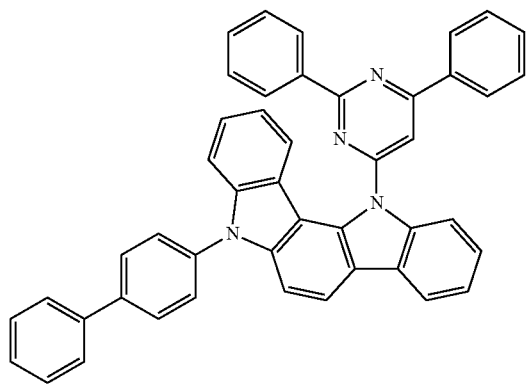
M2-57
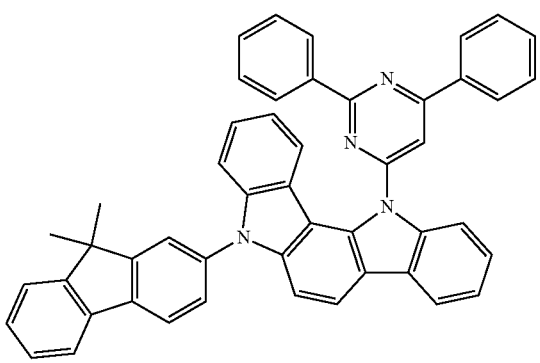
M2-60
M2-58
M2-61
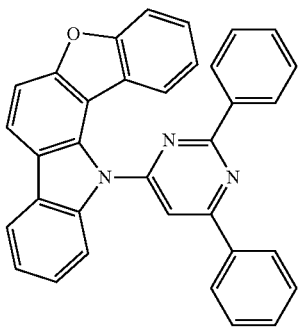
M2-62
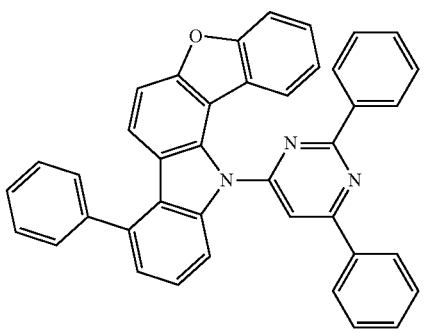
M2-59
M2-63
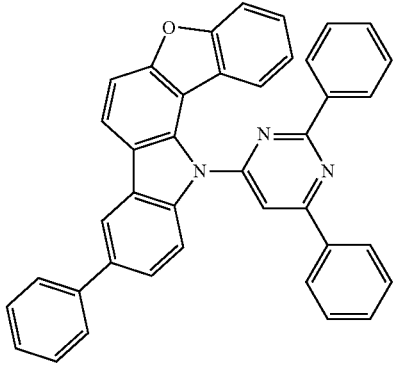

M2-64
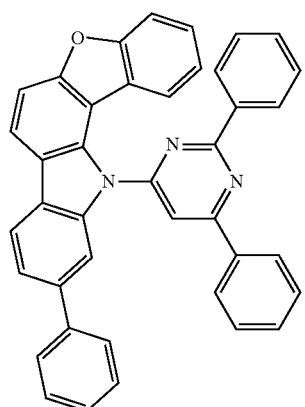
M2-65
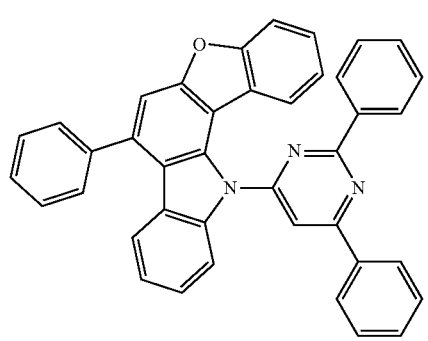
M2-66
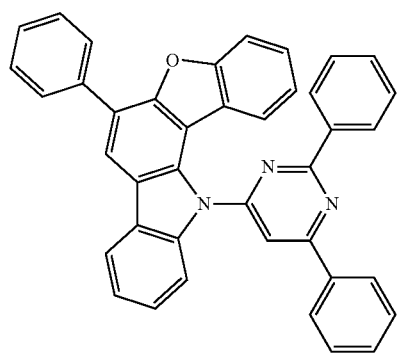
M2-67
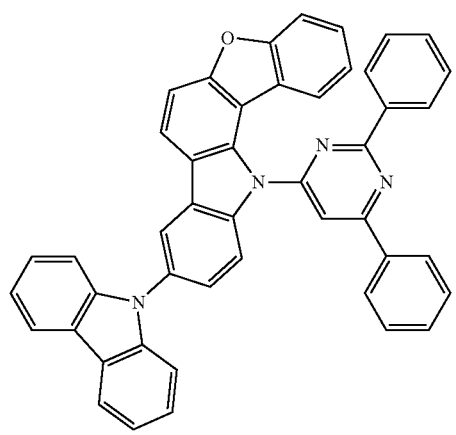
M2-68
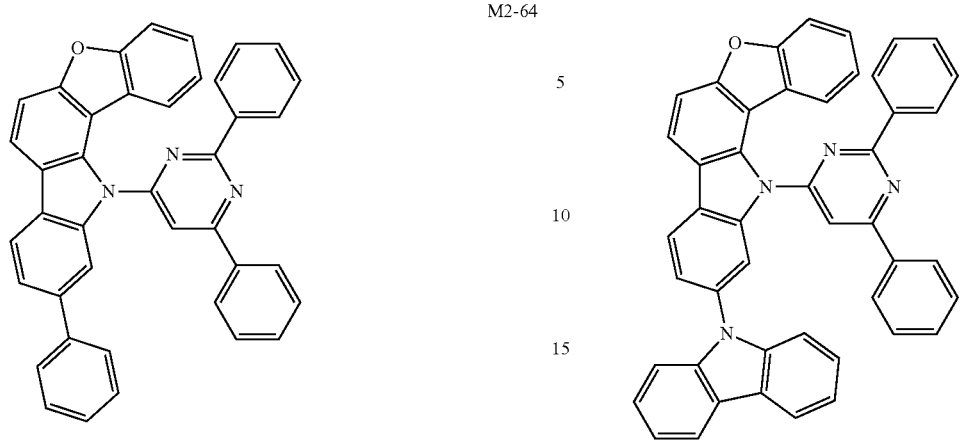
M2-69
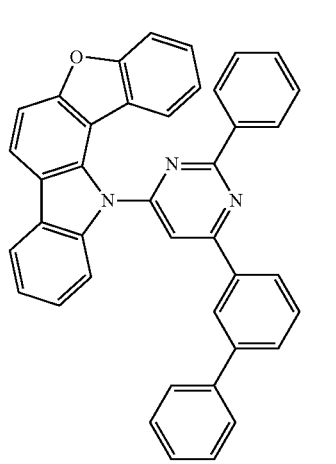
M2-70
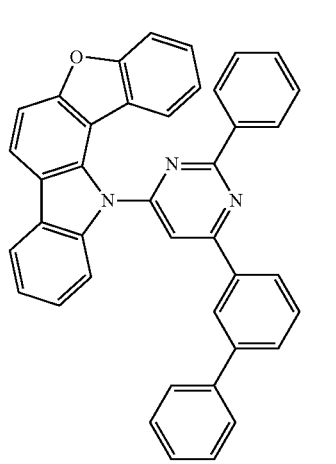
M2-71

-continued
M2-72
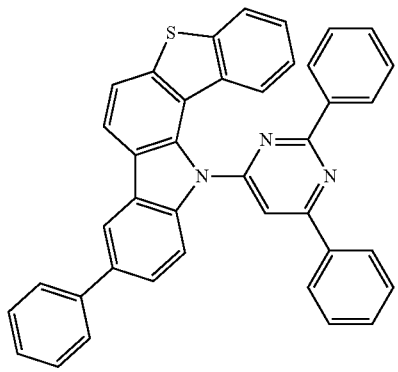
M2-73
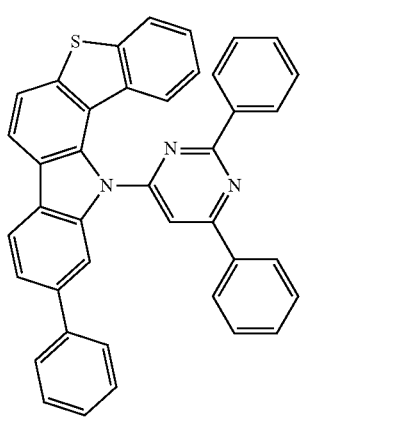
M2-74
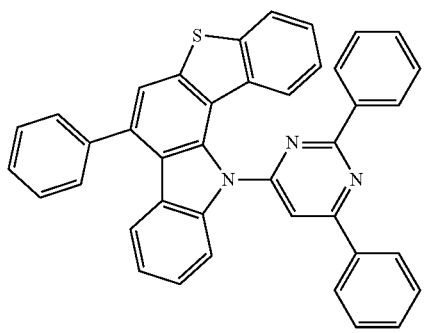
M2-75
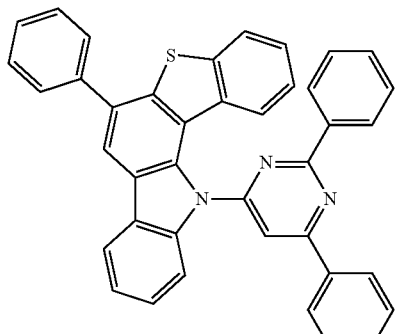
-continued
M2-76
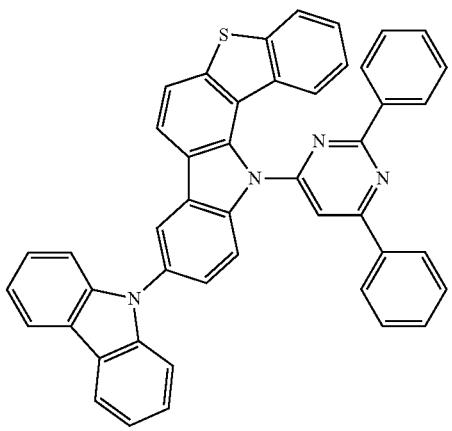
M2-77
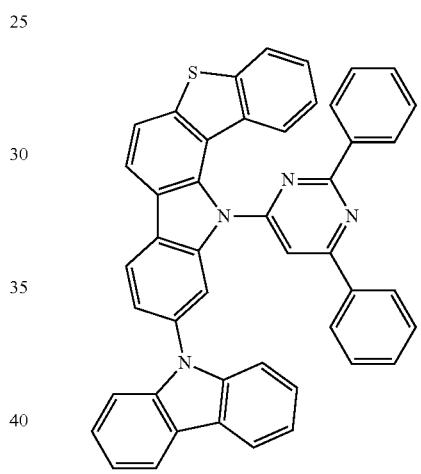
M2-78
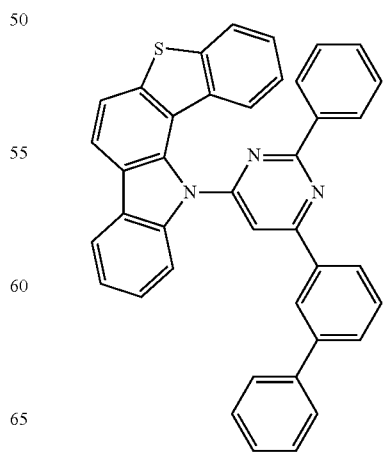

M2-79
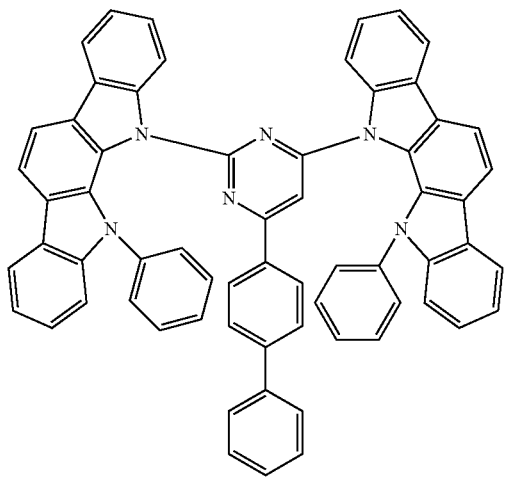
M3-1
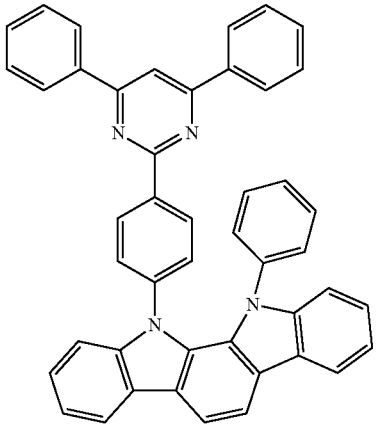
M2-80
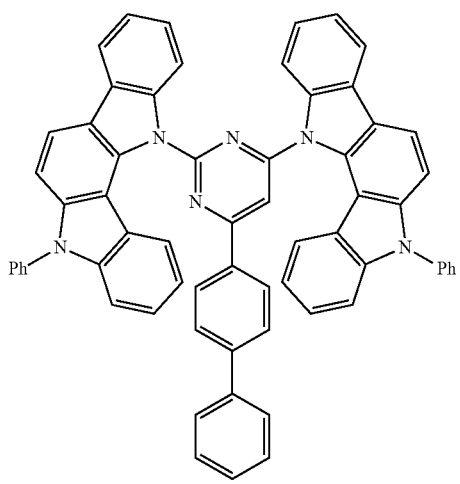
M3-2
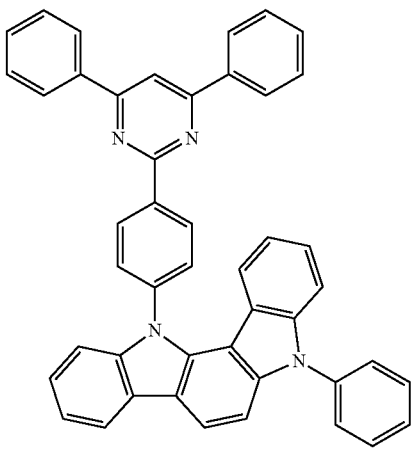
M2-81
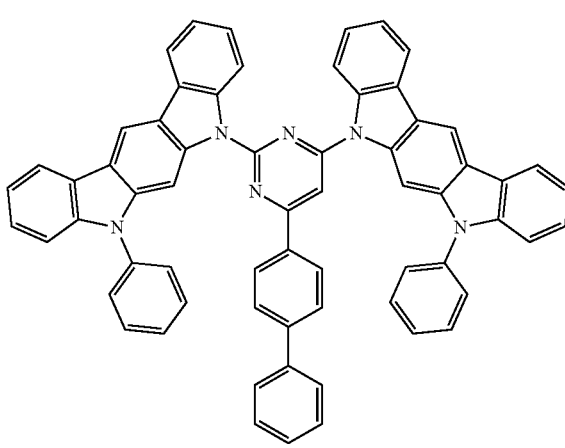
M3-3
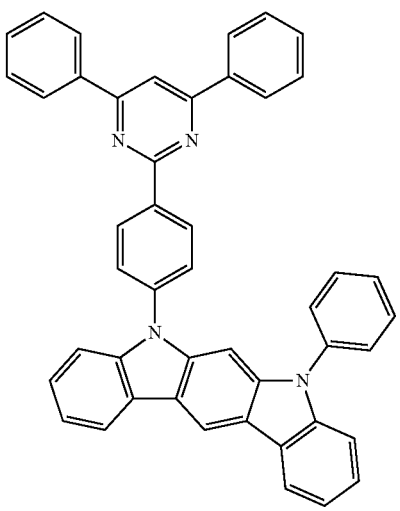

M3-4
M3-5
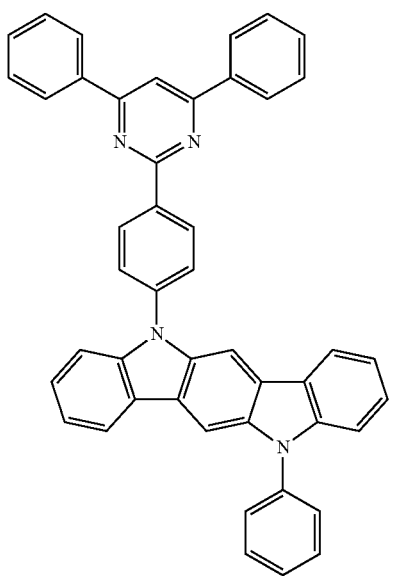
M3-6
M3-7
M3-8
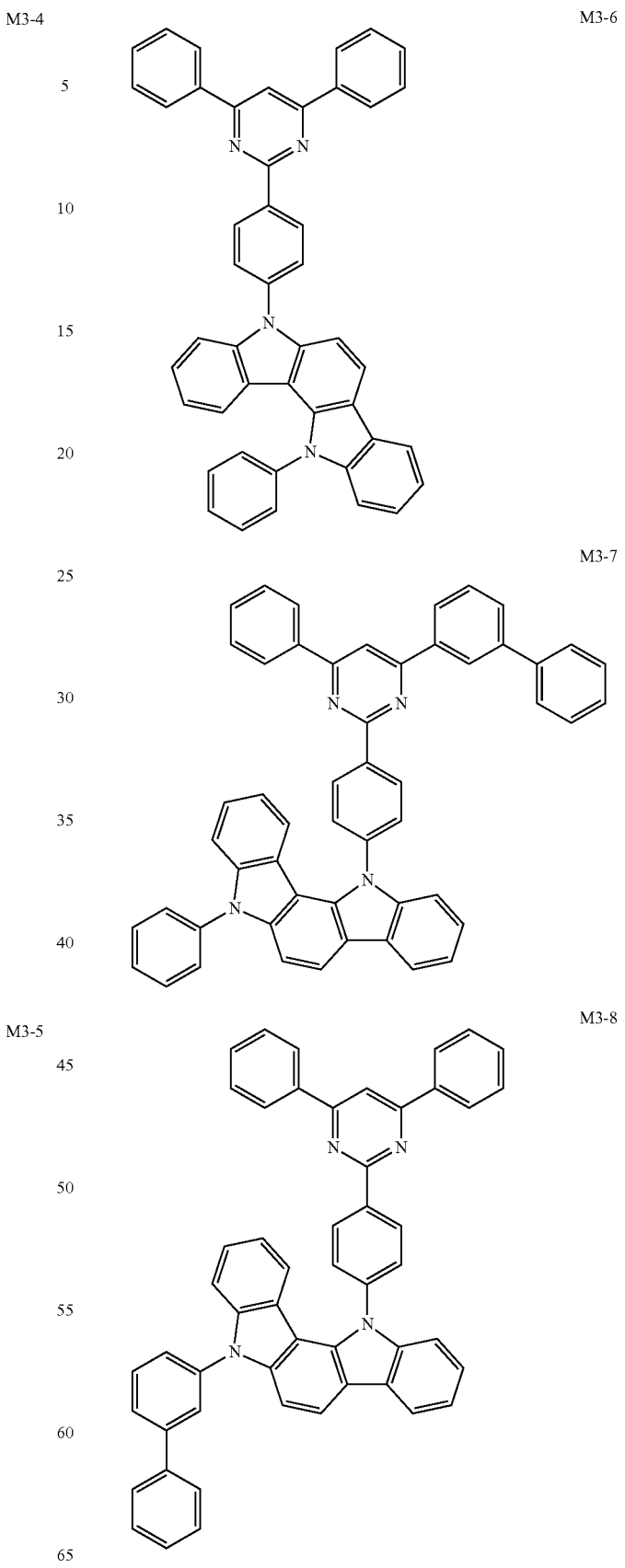

M3-9
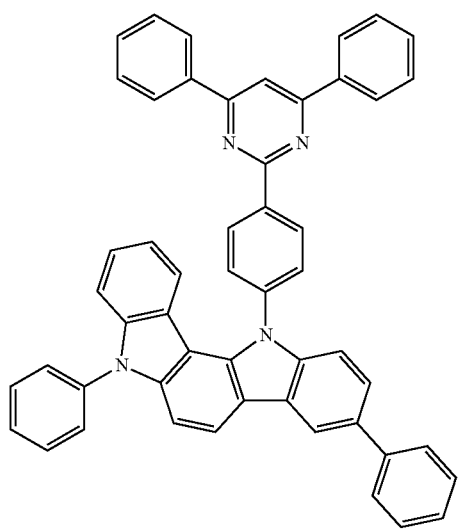
M3-10
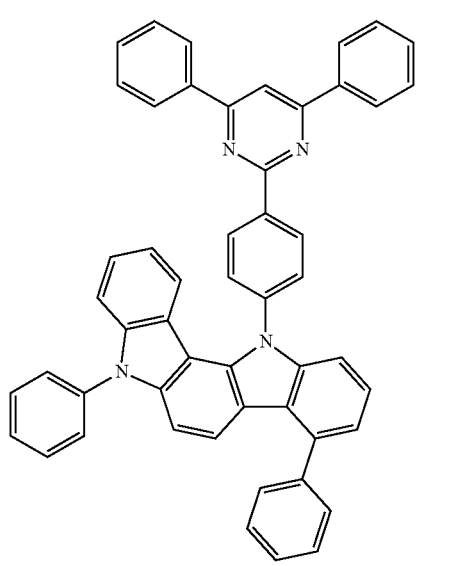
M3-11
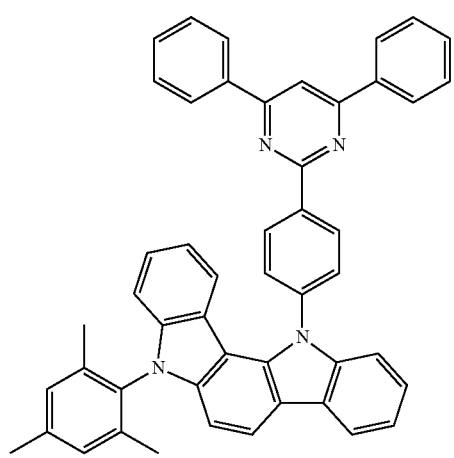
M3-12
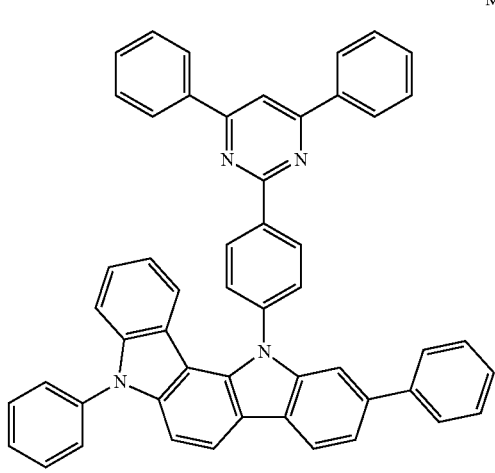
M3-13
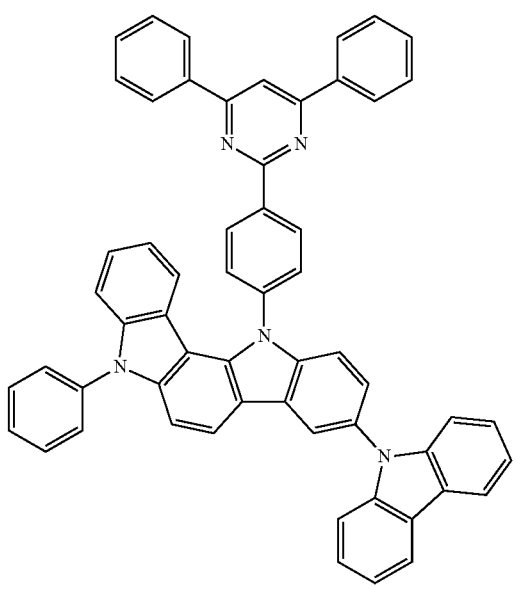
M3-14
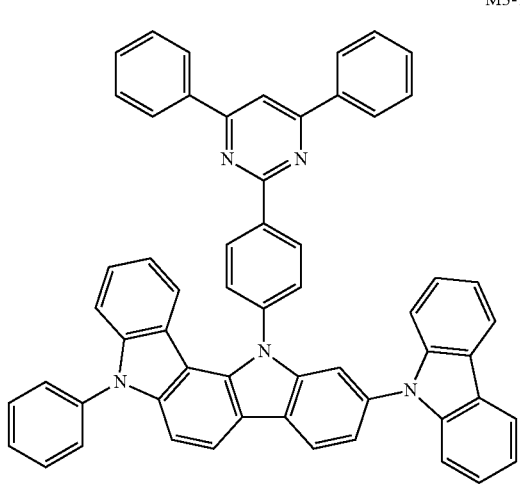

M3-15
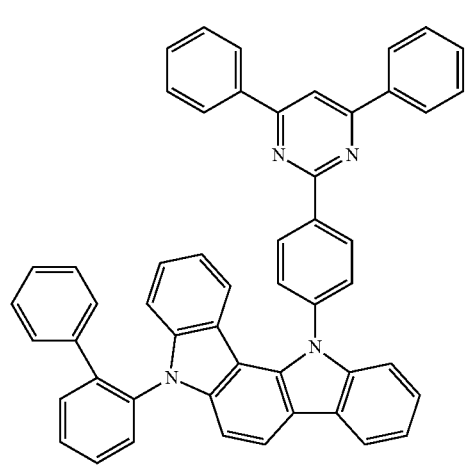
M3-16
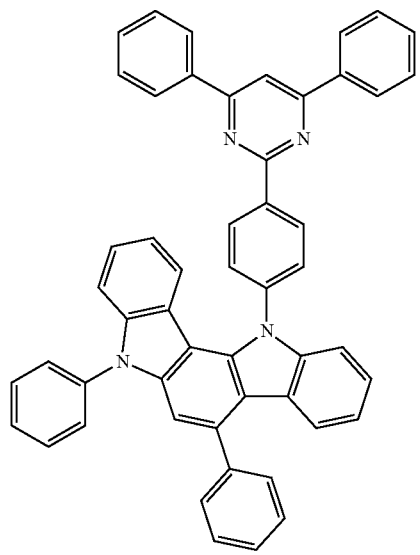
M3-17
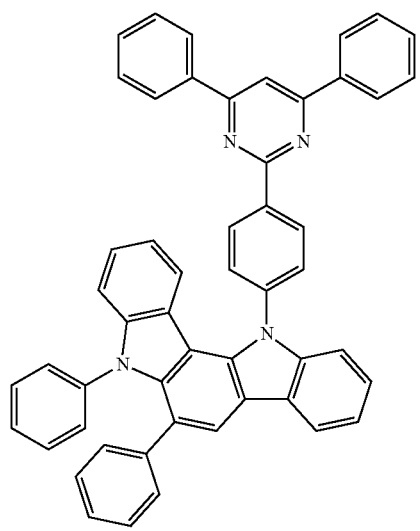
M3-18
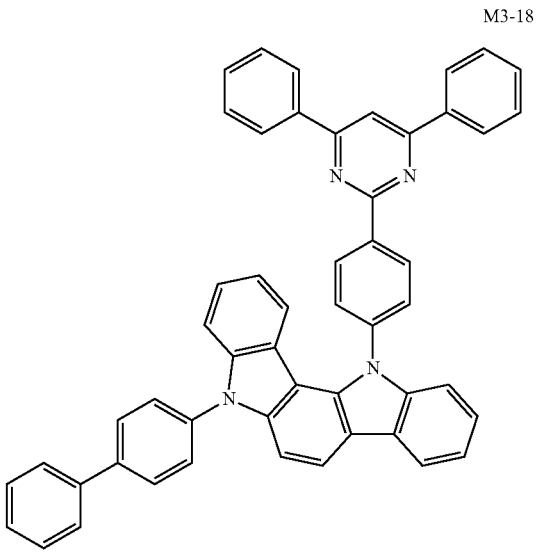
M3-19
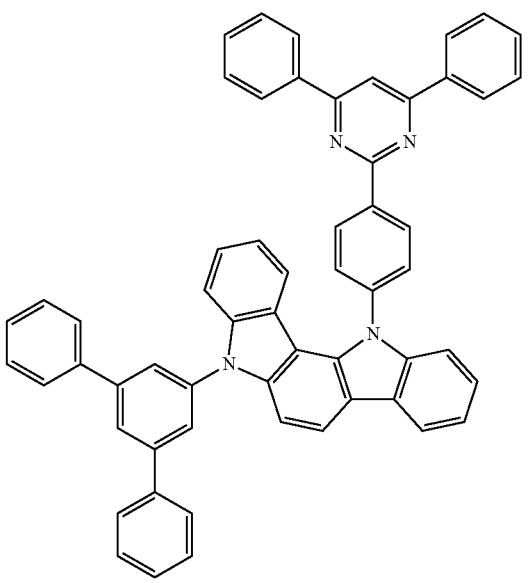

M3-20
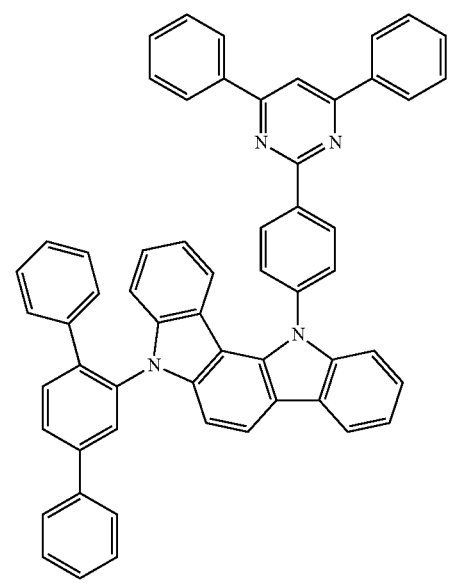
M3-23
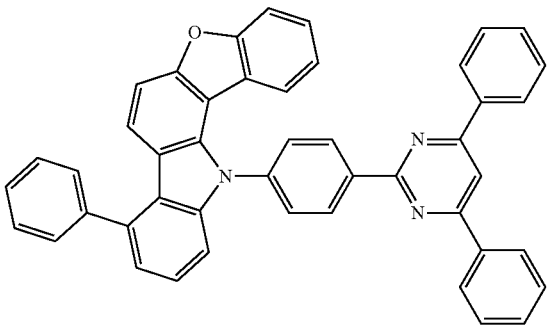
M3-24
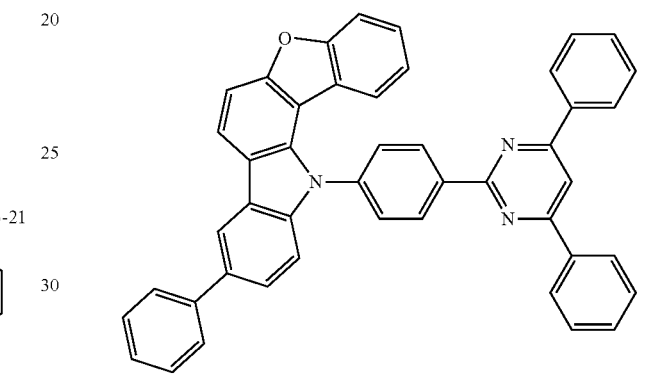
M3-21
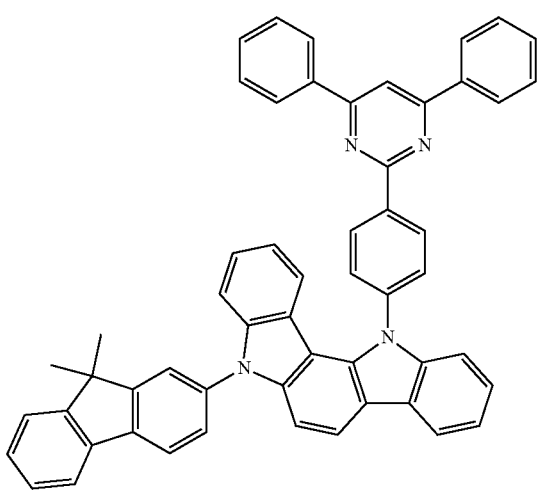
M3-25
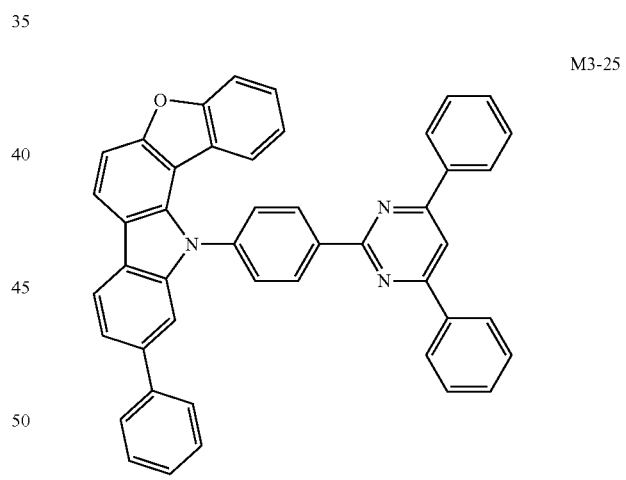
M3-22
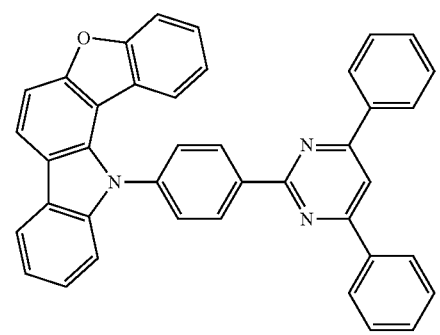
M3-26
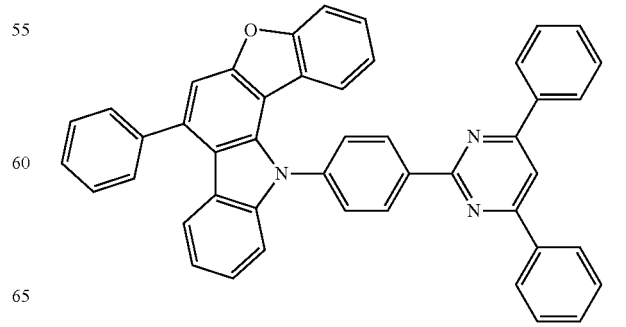

-continued
M3-27
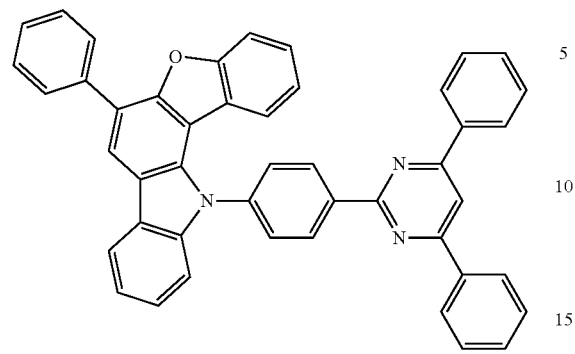
M3-28
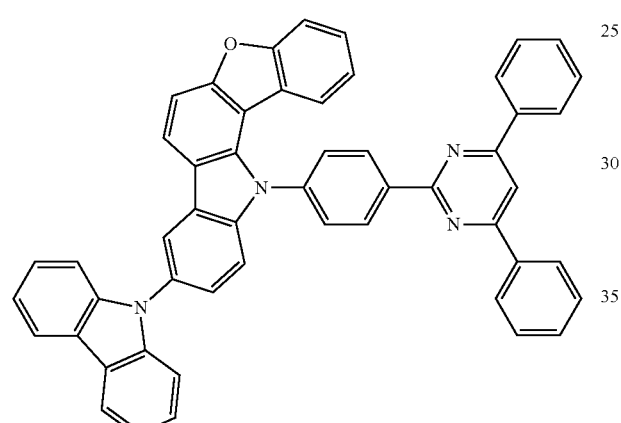
M3-29
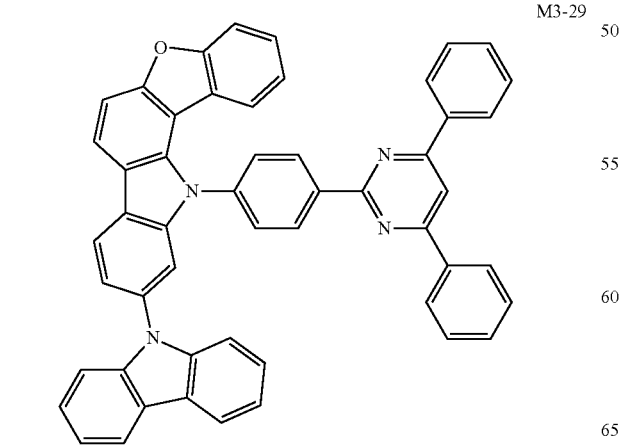
M3-30
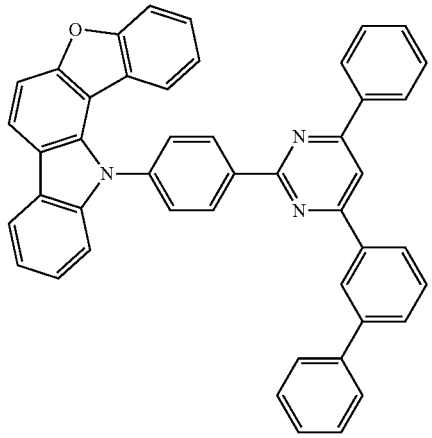
M3-31
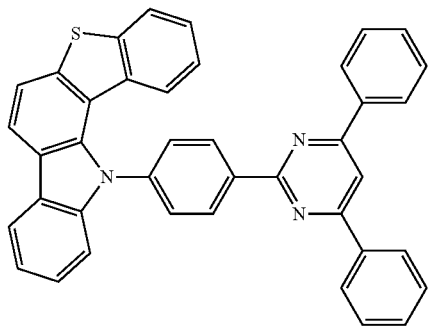
M13-32
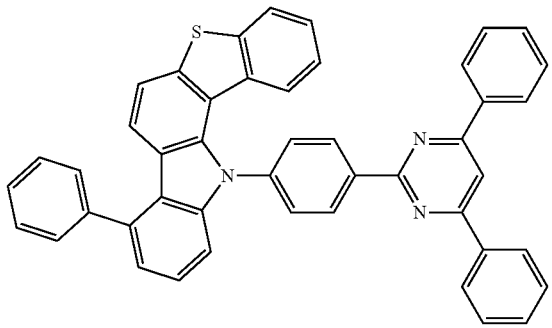
M3-33
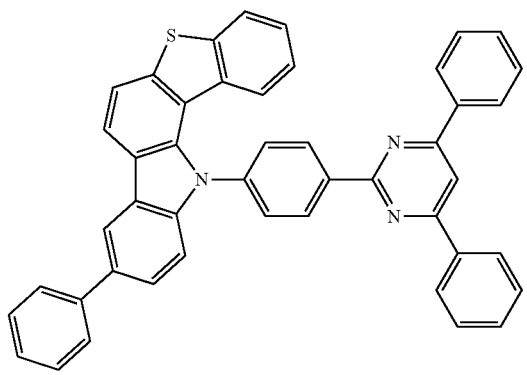

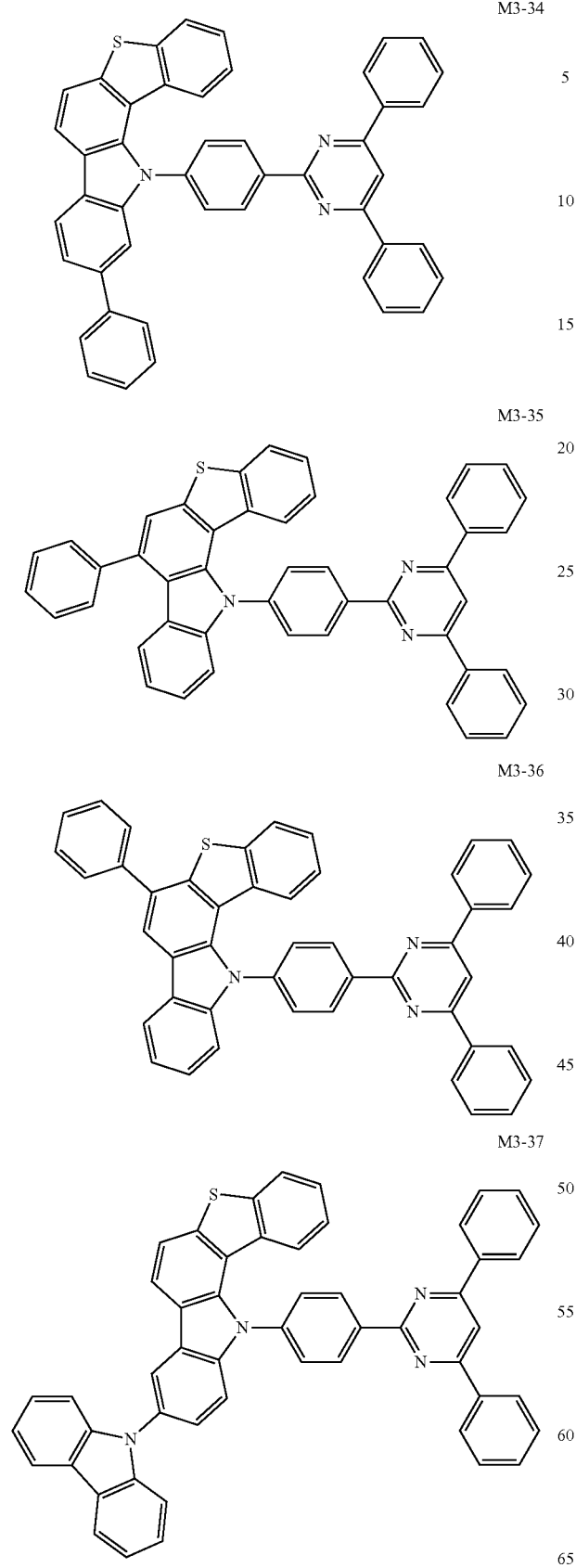
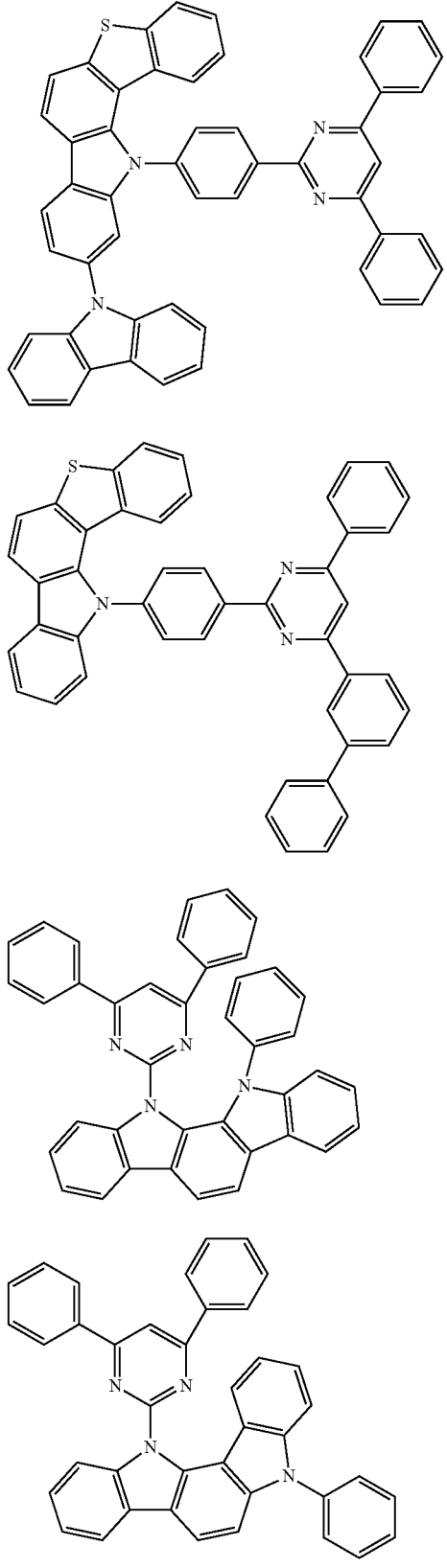

-continued
M3-42
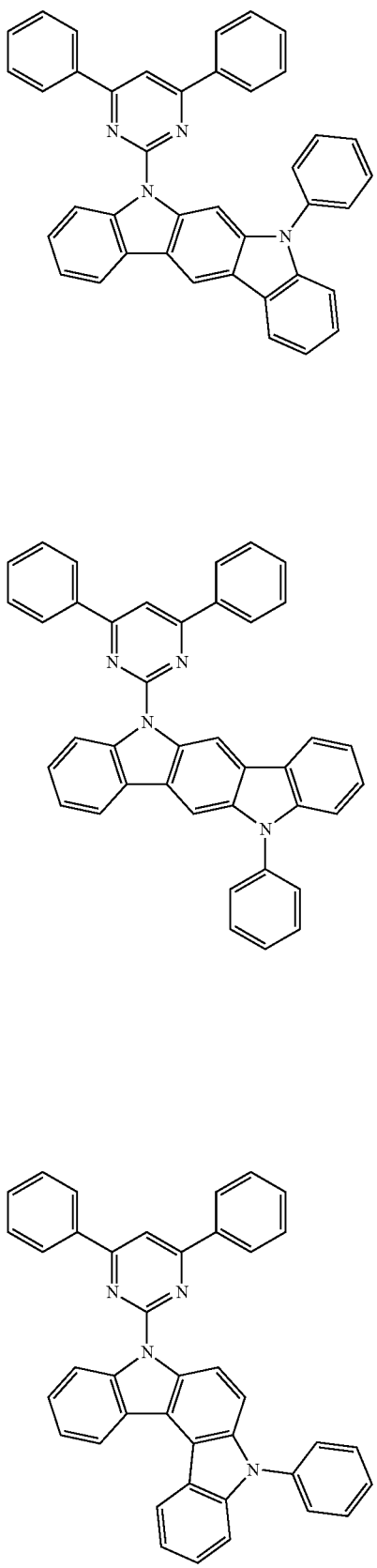
M3-43
M3-44
-continued
M3-45
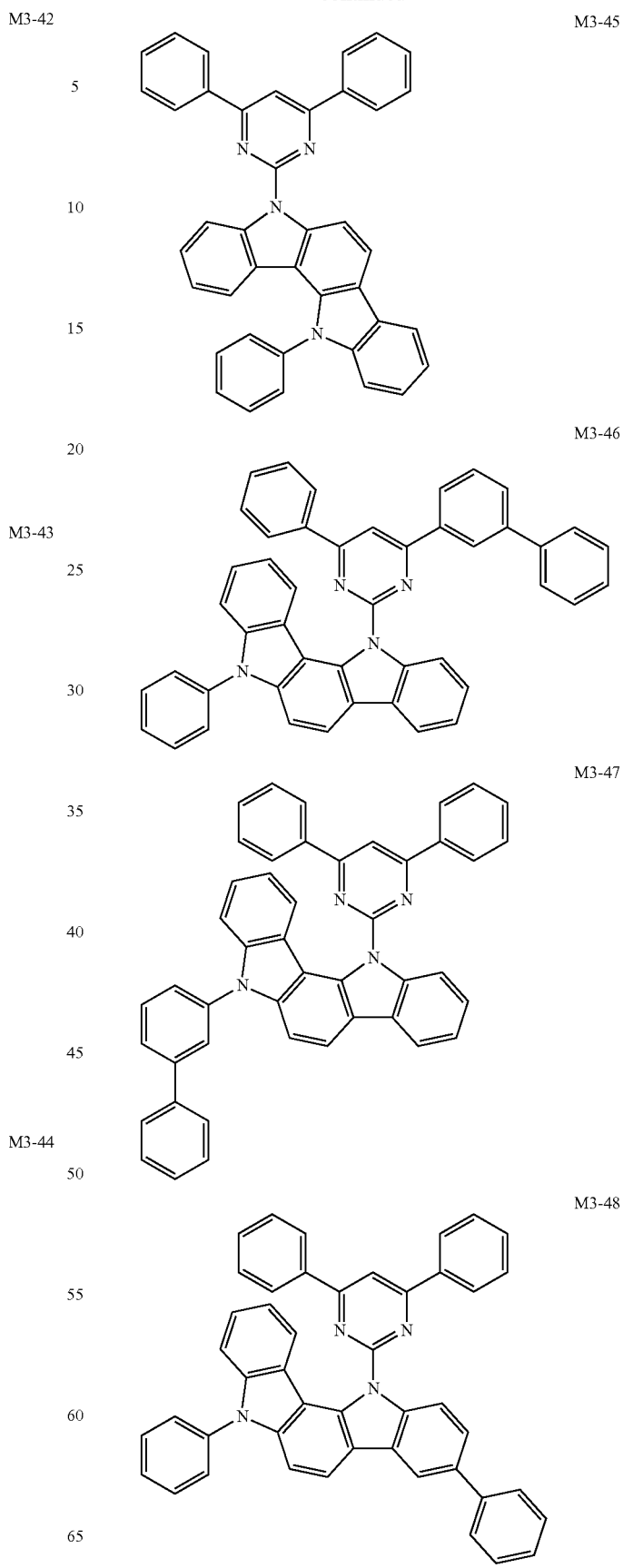
M3-46
M3-47
M3-48

M3-49
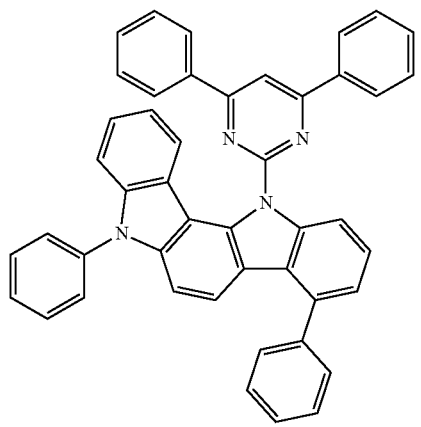
M3-50
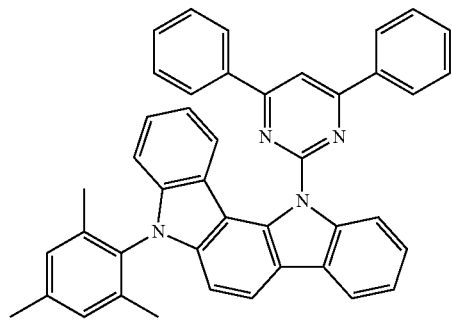
M3-51
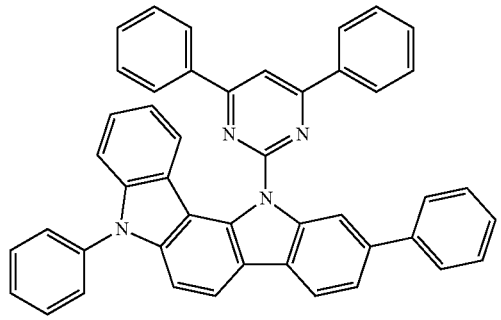
M3-52
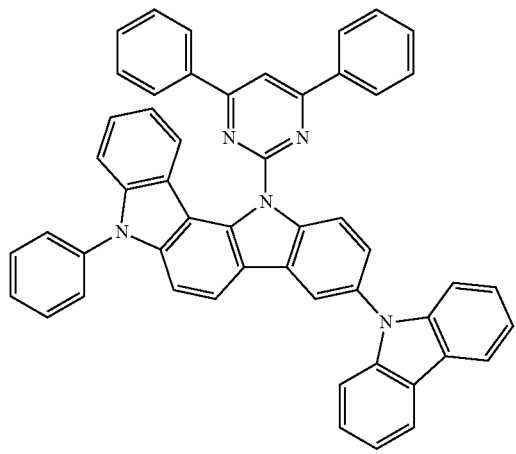
M3-53
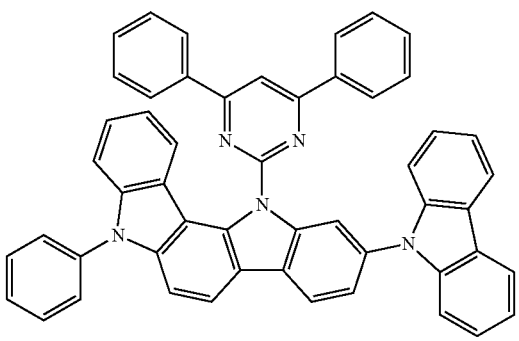
M3-54
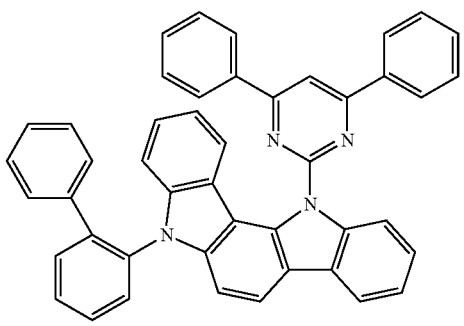
M3-55
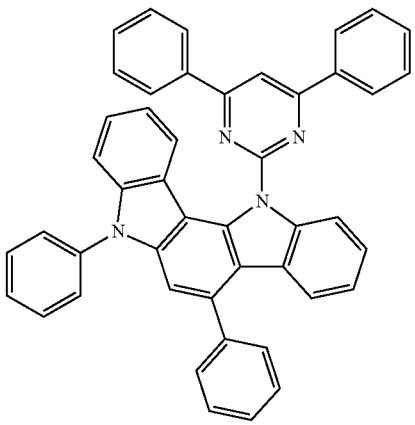
M3-56
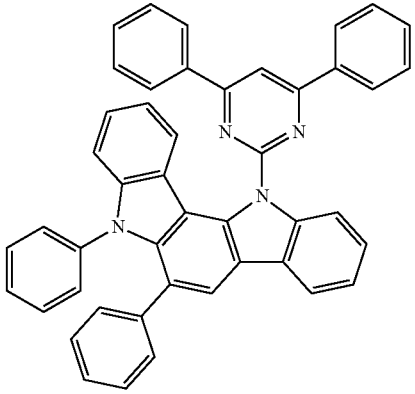

M3-57
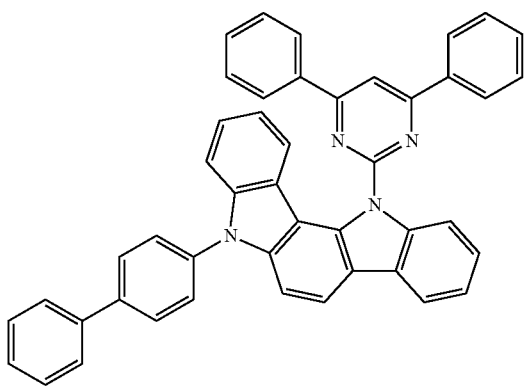
M3-58
M3-59
M3-60
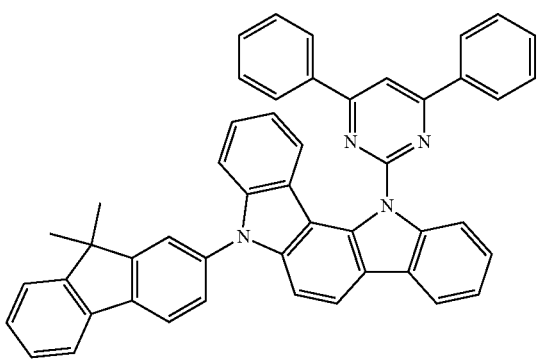
M3-61
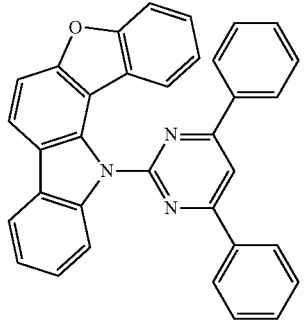
M3-62
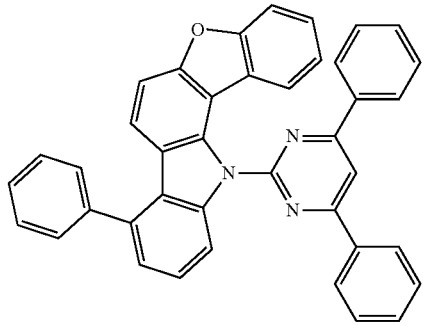
M3-63
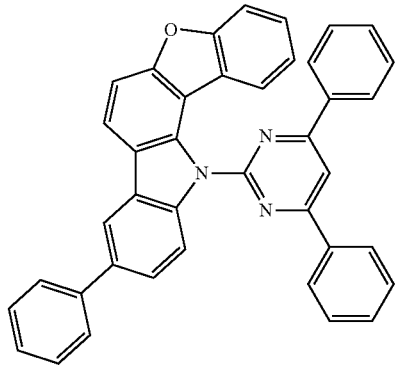

M3-64
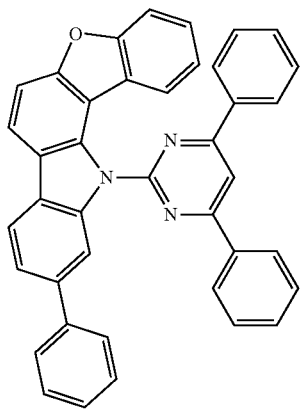
M3-68
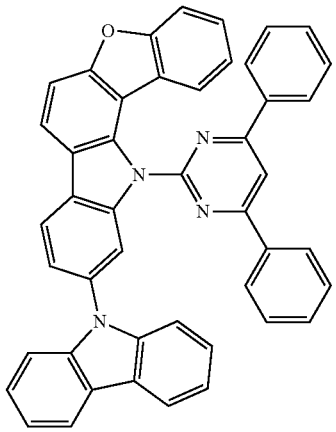
M3-65
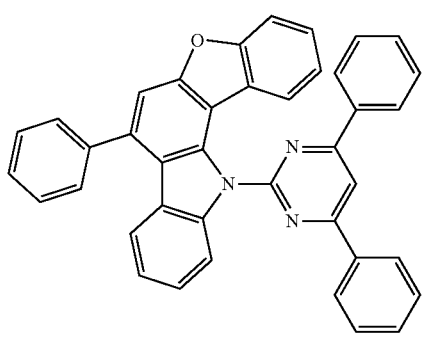
M3-69
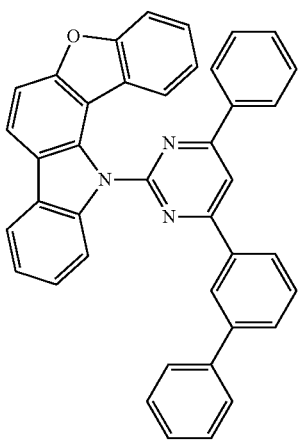
M3-66
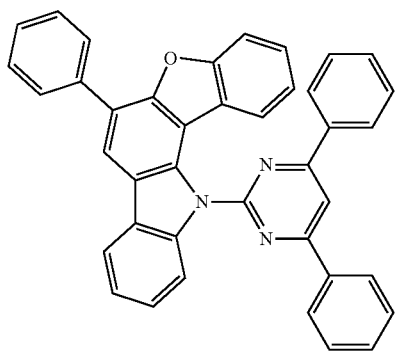
M3-70
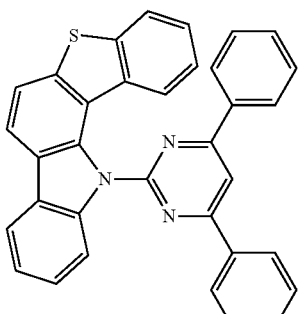
M3-67
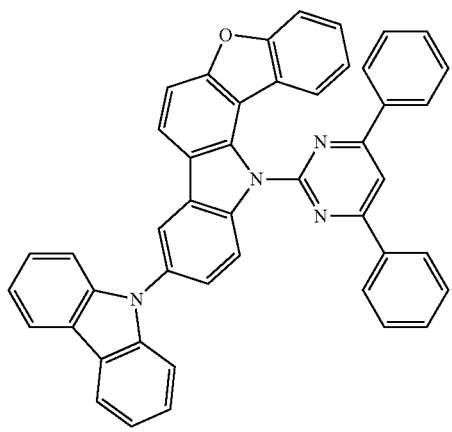
M3-71
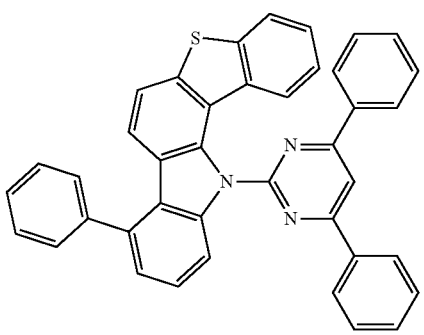

M3-72
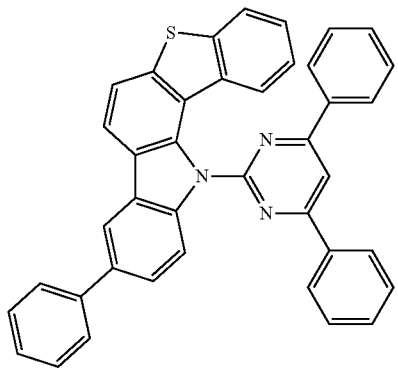
M3-73
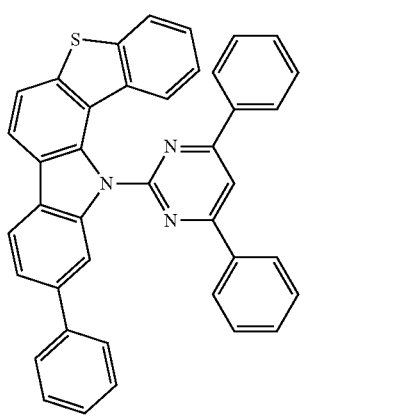
M3-74
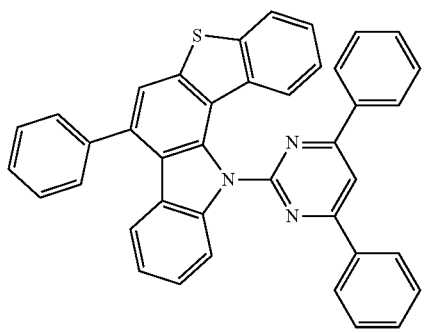
M3-75
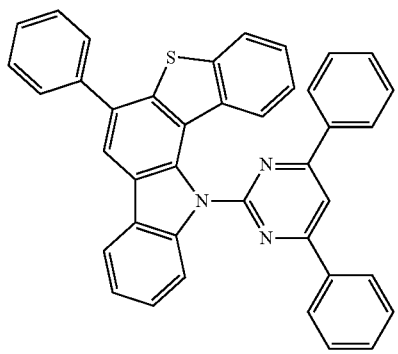
M3-76
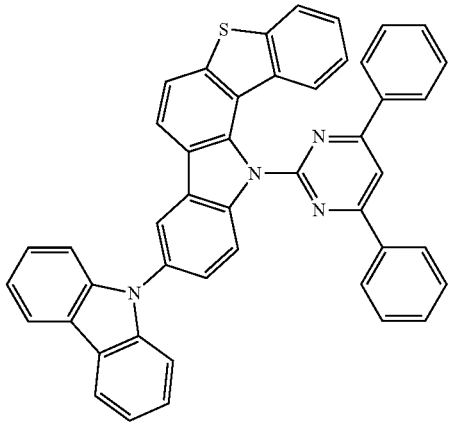
M3-77
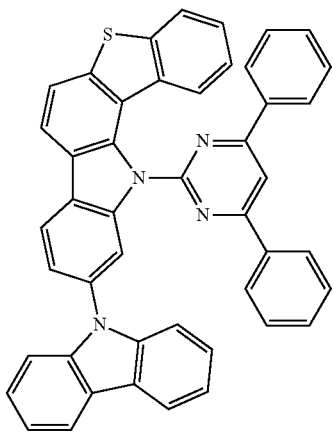
M3-78
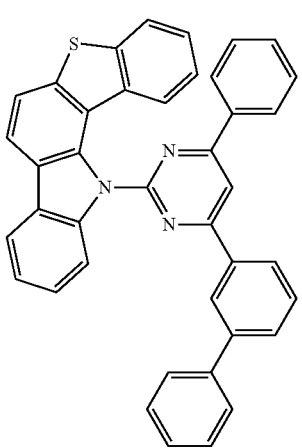

M3-79
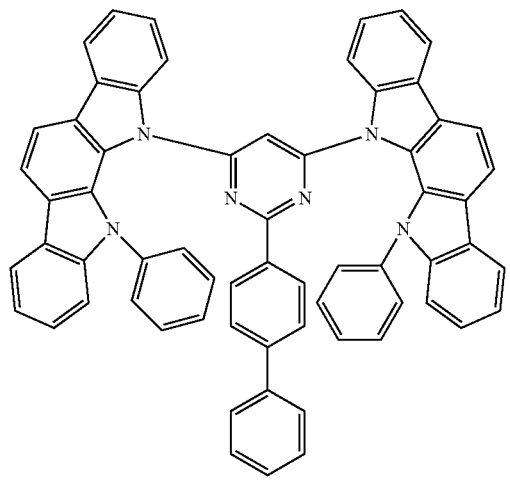
M3-80
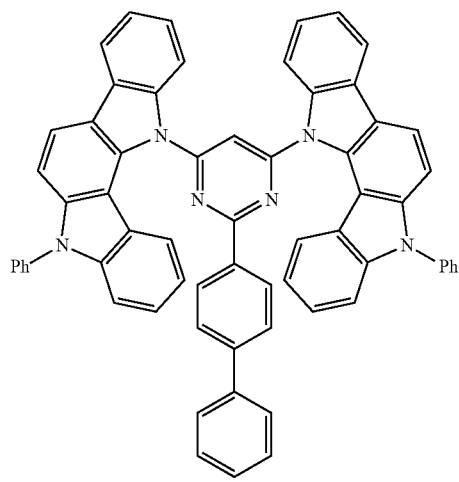
M3-81
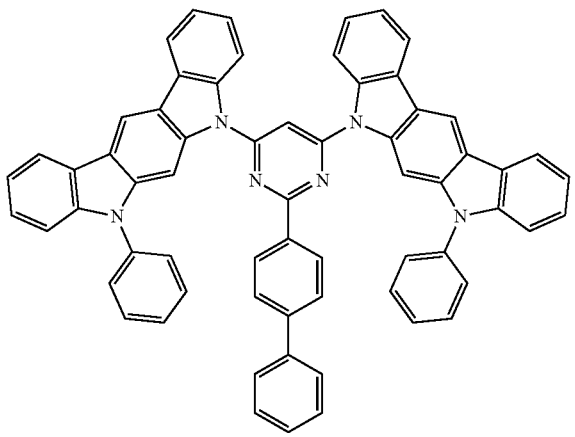
M201
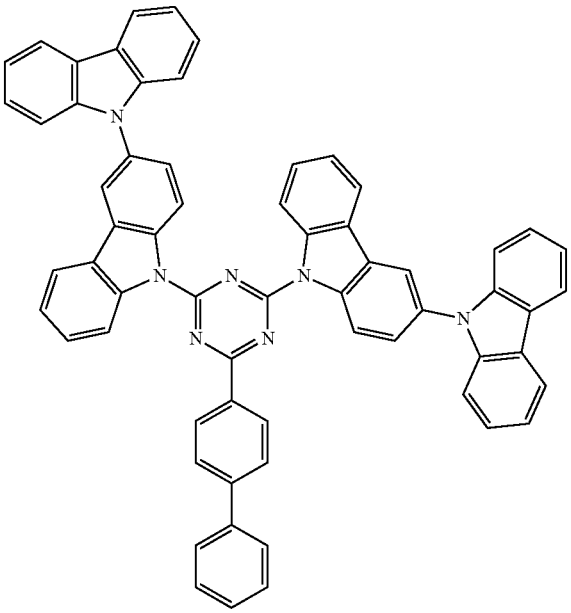
M202
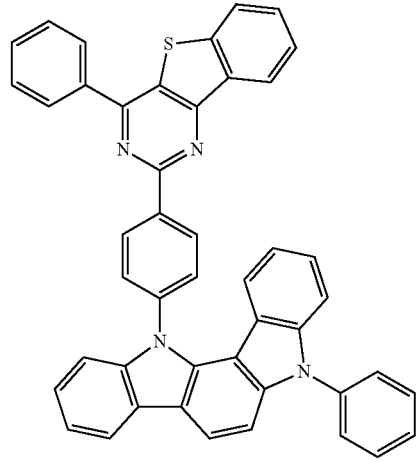
M203
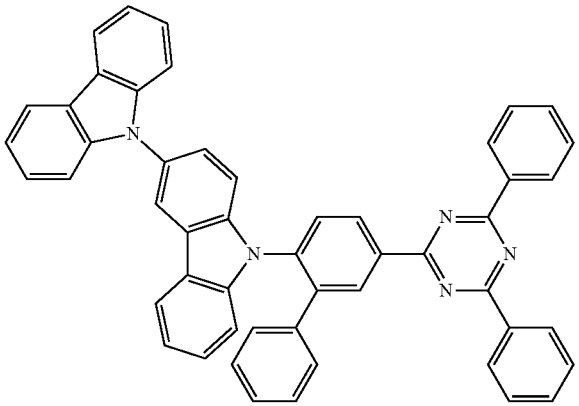

-continued

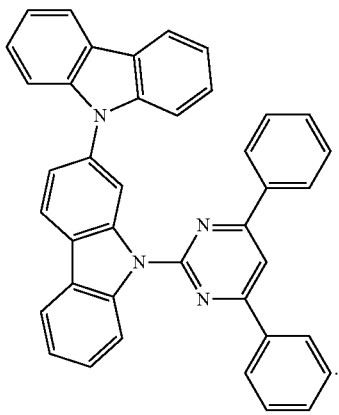

M204

The light-emitting material may include a phosphorescent material. Therefore, the emission layer may emit phosphorescence.

In an embodiment, the light-emitting material may include a transition metal-containing organometallic compound.

The transition metal may be, for example, iridium (Ir), platinum (Pt), osmium (Os), titanium (Ti), zirconium (Zr), hafnium (Hf), europium (Eu), terbium (Tb), thulium (Tm), rhodium (Rh), ruthenium (Ru), rhenium (Re), cobalt (Co), copper (Cu), rhodium (Rh), palladium (Pd), silver (Ag), or gold (Au), but embodiments of the present disclosure are not limited thereto.

In one or more embodiments, the light-emitting material may include a transition metal-containing organometallic compound that emits blue light.

In one or more embodiments, the light-emitting material may include an organometallic compound including a bidentate ligand and a transition metal, the bidentate ligand containing at least one cyano group or at least one fluoro group.

In one or more embodiments, the light-emitting material may include an organometallic compound including a transition metal and a cyano group-containing bidentate ligand.

In one or more embodiments, the light-emitting material may include an organometallic compound including a ligand containing at least one cyano group and at least one deuterium and a transition metal.

In one or more embodiments, the light-emitting material may include a homoleptic organometallic compound including iridium and a cyano group-containing phenylimidazole-based bidentate ligand.

In one or more embodiments, the light-emitting material may include an organometallic compound represented by Formula 1:

Formula 1

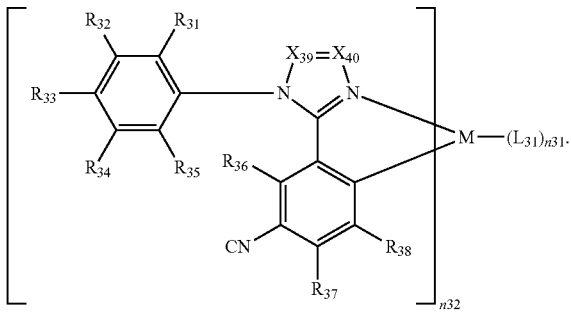

M in Formula 1 may be selected from a first-row transition metal, a second-row transition metal, and a third-row transition metal.

For example, M may be Ir, Os, Re, Pt, Pd, or Au, but embodiments of the present disclosure are not limited thereto.

In Formula 1, $L_{31}$ may be selected from a monodentate ligand and a bidentate ligand, and n31 may be 0, 1, 2, 3, or 4, wherein, when n31 is two or more, two or more groups $L_{31}$ may be identical to or different from each other.

n32 in Formula 1 may be 1, 2, or 3.

For example, when M is Ir or Os, the sum of n31 and n32 may be 3, and when M is Pt, the sum of n31 and n32 may be 2.

In Formula 1, $X_{39}$ may be N or $C(R_{39})$, and $X_{40}$ may be N or $C(R_{40})$.

$R_{31}$ to $R_{40}$ may each independently be selected from hydrogen, deuterium, —F, —Cl, —Br, —I, —SF$_5$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N(Q$_1$)(Q$_2$), —Si(Q$_3$)(Q$_4$)(Q$_5$), —B(Q$_6$)(Q$_7$), and —P(=O)(Q$_8$)(Q$_9$). Q$_1$ to Q$_9$ are the same as described above.

For example, $R_{31}$ to $R_{40}$ may each independently be selected from:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —SF$_5$, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, a naphthyl group, a pyridinyl group, and a pyrimidinyl group;

a cyclopentyl group, a cyclohexyl group, a cycloheptyl group, a cyclooctyl group, an adamantyl group, a norbornanyl group, a norbornenyl group, a cyclopentenyl group, a cyclohexenyl group, a cycloheptenyl group, a phenyl group, a biphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, and isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group;

a cyclopentyl group, a cyclohexyl group, a cycloheptyl group, a cycloctyl group, an adamantanyl group, a norbornanyl group, a norbornenyl group, a cyclopentenyl group, a cyclohexenyl group, a cycloheptenyl group, a phenyl group, a biphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinoinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cycloctyl group, an adamantanyl group, a norbornanyl group, a norbornenyl group, a cyclopentenyl group, a cyclohexenyl group, a cycloheptenyl group, a phenyl group, a biphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; and —N($Q_1$)($Q_2$), —Si($Q_3$)($Q_4$)($Q_5$), —B($Q_6$)($Q_7$), and —P(=O)($Q_8$)($Q_9$), and $Q_1$ to $Q_9$ may each independently be selected from:
—CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, and —CD$_2$CDH$_2$;

an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group; and an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group, each substituted with at least one selected from deuterium, a $C_1$-$C_{10}$ alkyl group, and a phenyl group, but embodiments of the present disclosure are not limited thereto.

Two or more neighboring groups selected from $R_{31}$ to $R_{40}$ may optionally be linked to form a substituted or unsubstituted $C_5$-$C_{30}$ carbocyclic group or a substituted or unsubstituted $C_2$-$C_{30}$ heterocyclic group.

In an embodiment, at least one of $R_{31}$, $R_{33}$, and $R_{35}$ in Formula 1 (for example, $R_{31}$ and $R_{35}$) may each independently be:

deuterium, a cyano group, a $C_1$-$C_{20}$ alkyl group, a phenyl group, a biphenyl group, or a terphenyl group; or a $C_1$-$C_{20}$ alkyl group, a phenyl group, a biphenyl group, or a terphenyl group, each unsubstituted or substituted with at least one selected from deuterium, a cyano group, and a $C_1$-$C_{20}$ alkyl group.

In an embodiment, a maximum emission wavelength of the organometallic compound represented by Formula 1 may be in a range of about 440 nanometers (nm) to about 470 nm (for example, about 440 nm to about 467 nm). When the maximum emission wavelength is in a range of about 440 nm to about 470 nm, an organic light-emitting device emitting a deep blue color may be provided.

In an embodiment, the light-emitting material may include at least one compound selected from Compounds 1 to 24, D1 to D11, and F$_2$IrPic, but embodiments of the present disclosure are not limited thereto:

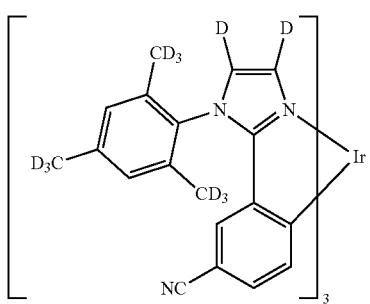
1
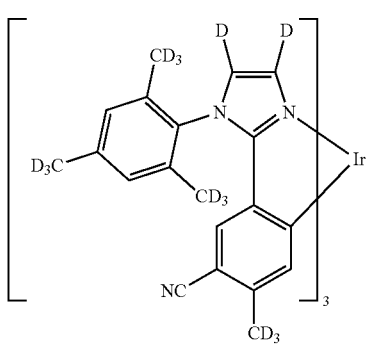
2
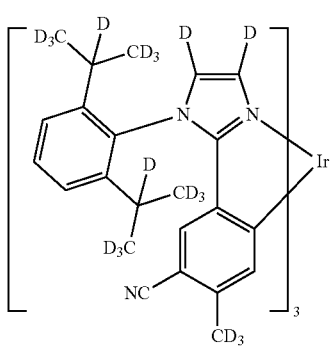
3
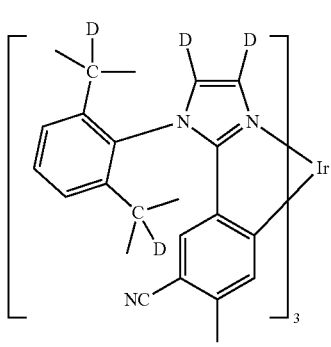
4
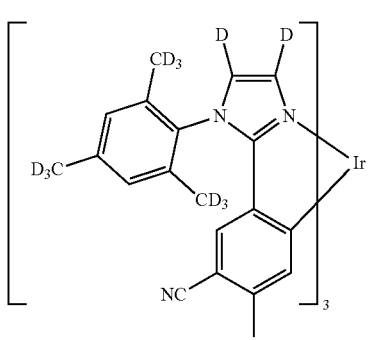
5
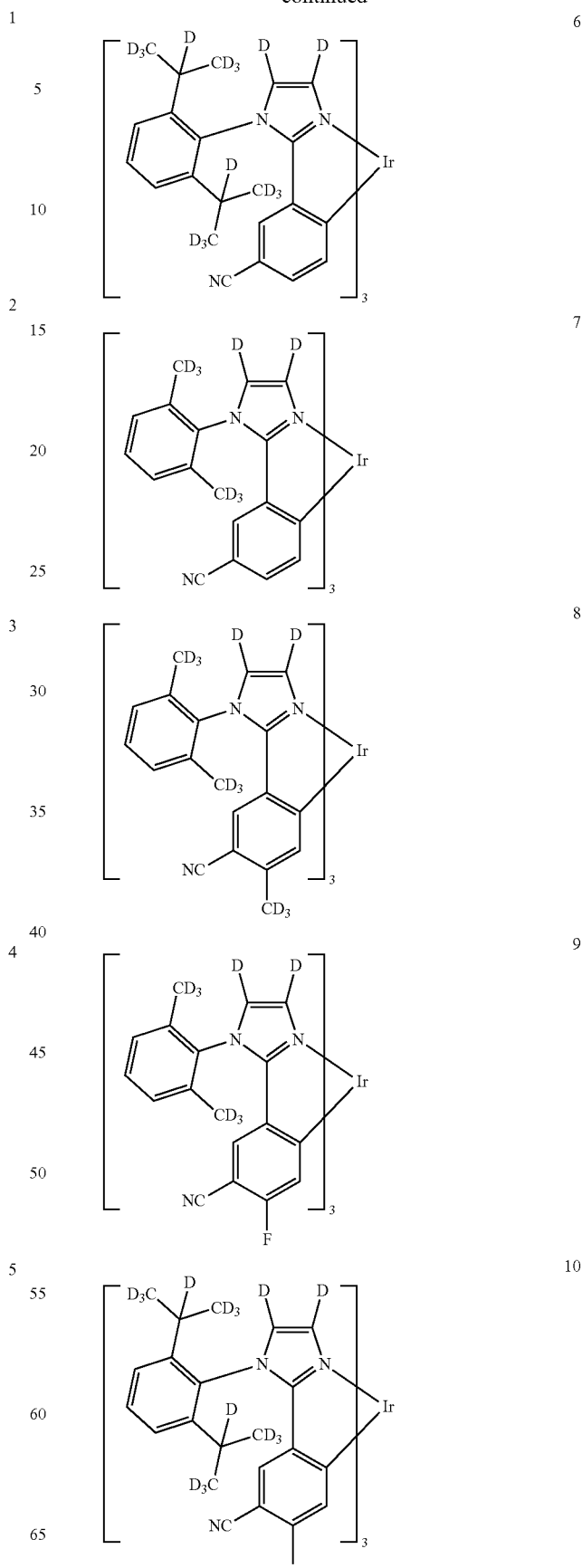

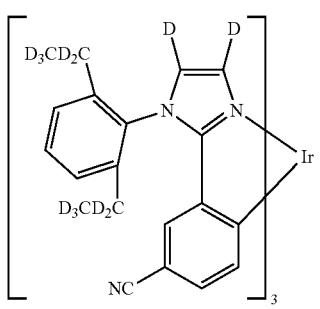
11
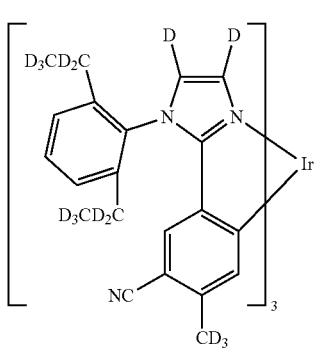
12
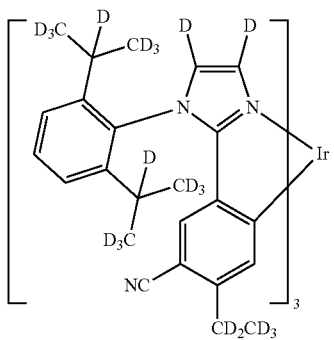
13
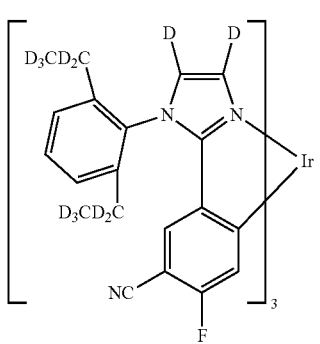
14
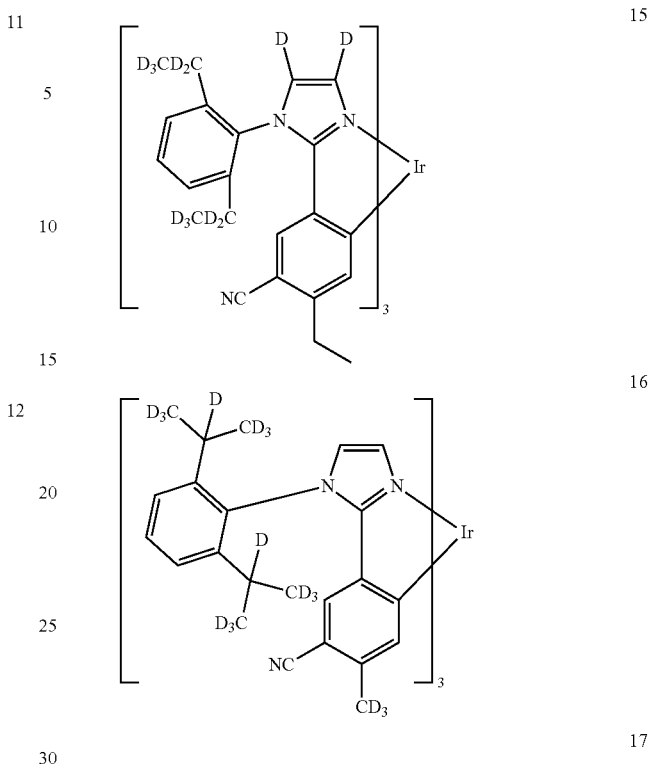
15
16
17
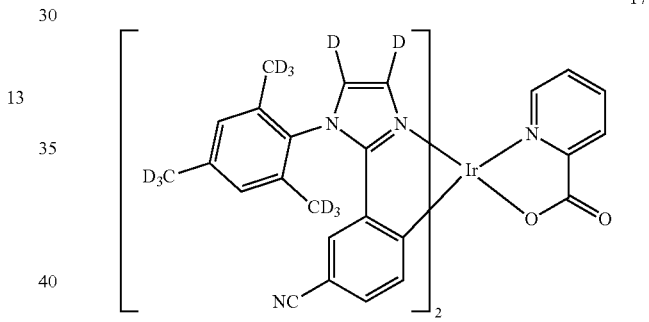
18
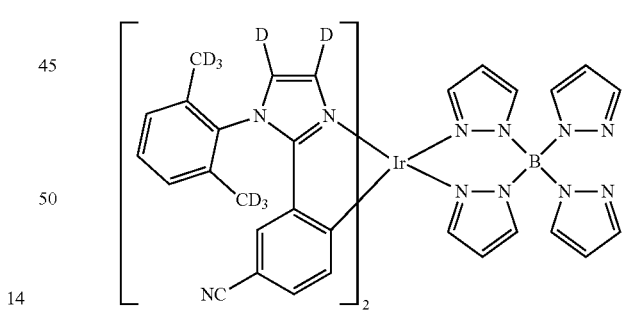
19
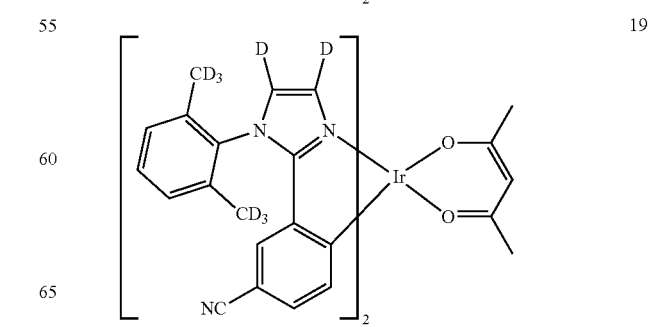

20
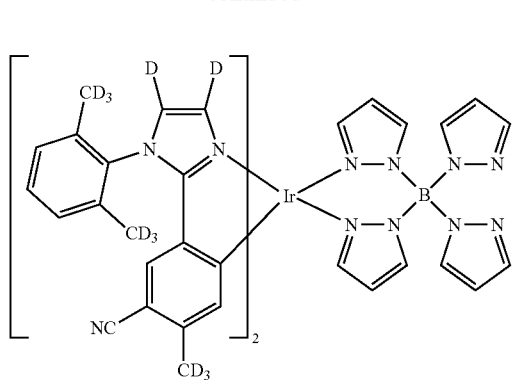
21
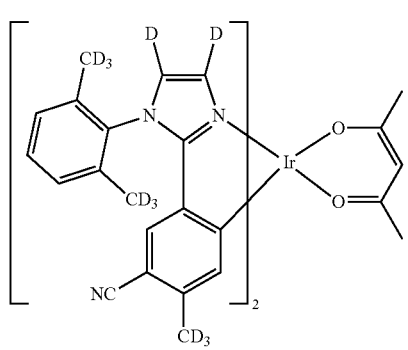
22
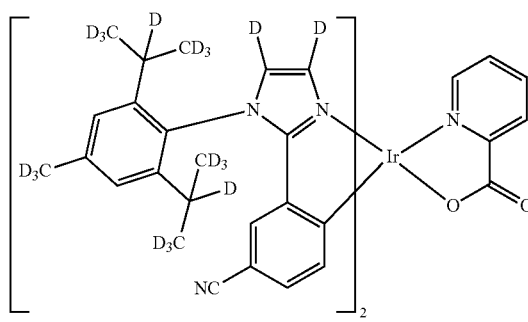
23
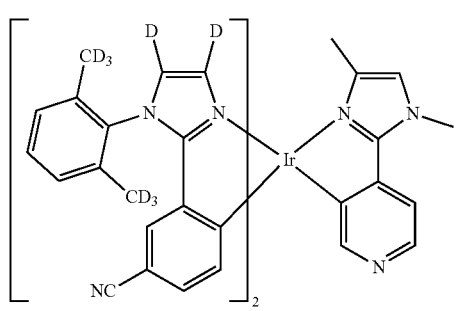
24
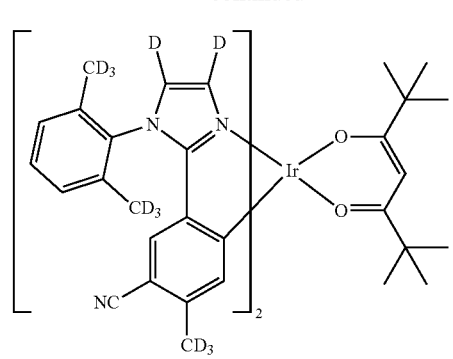
D1
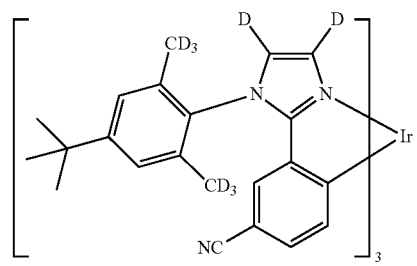
D2
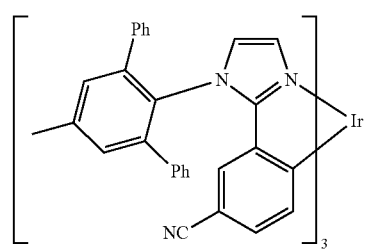
D3
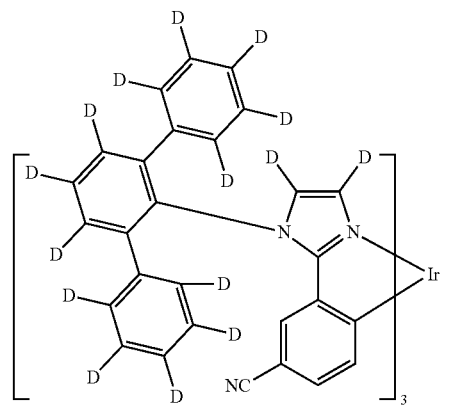
D4
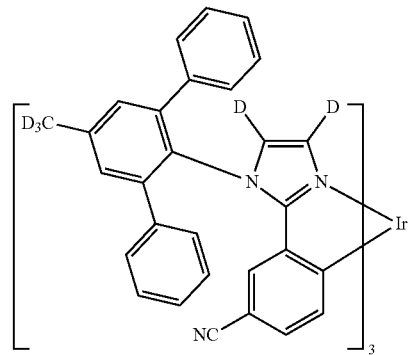

-continued

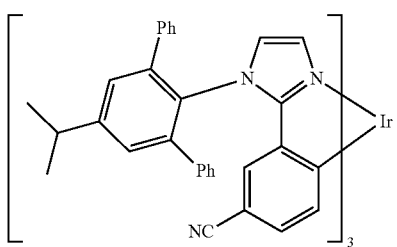
D5

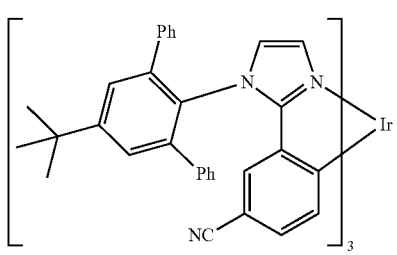
D6

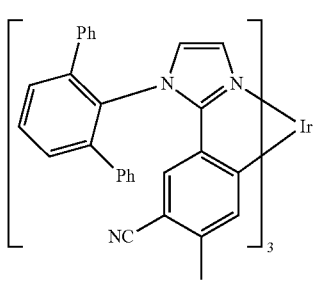
D7

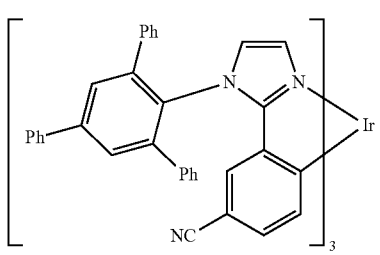
D8

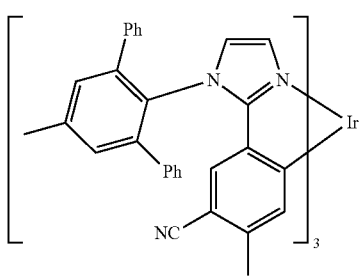
D9

-continued

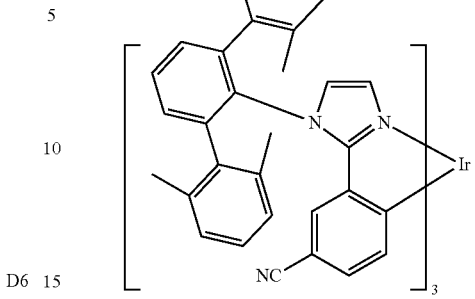
D10

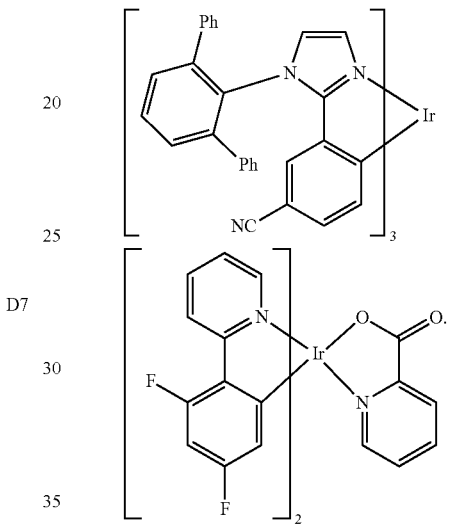
D11

F$_2$Irpic

The first material, the second material, the third material, and the light-emitting material in the emission layer may be different from one another. That is, the emission layer may essentially include four types of different compounds.

A ratio of a light-emitting compound emitted from the light-emitting material to a total light-emitting component emitted from the emission layer may be 90% or more, for example, 92% or more, 94% or more, 96% or more, or 98% or more.

An amount of the third material may be greater than about 0 parts by weight and equal to and less than about 10 parts by weight, for example, about 1 part by weight to about 7 parts by weight, based on 100 parts by weight of the first material, the second material, the third material, and the light-emitting material. While not wishing to be bound by theory, it is understood that when the amount of the third material is within this range, it is possible to achieve an increase in luminescent efficiency from the light-emitting material in the emission layer and achieve an effect of reducing polaron-triplet quenching in the emission layer.

An amount of the light-emitting material may be greater than about 0 parts by weight and equal to and less than about 10 parts by weight, for example, about 0.1 parts by weight to about 5 parts by weight, based on 100 parts by weight of the first material, the second material, the third material, and the light-emitting material. While not wishing to be bound by theory, it is understood that when the amount of the light-emitting material is within this range, it is possible to achieve high luminescent efficiency without concentration quenching.

The total amount of the first material and the second material may be in a range of about 50 parts by weight to about 95 parts by weight, for example, about 60 parts by weight to about 90 parts by weight, based on 100 parts by weight of the first material, the second material, the third material, and the light-emitting material. While not wishing to be bound by theory, it is understood that when the total amount of the first material and the second material is within this range, it is possible to achieve high luminescent efficiency without concentration quenching.

A weight ratio of the first material to the second material may be selected from about 1:9 to about 9:1, about 2:8 to about 8:2, about 3:7 to about 7:3, and about 4:6 to about 6:4.

The first material and the second material may act as a host in the emission layer, the light-emitting material may act as a dopant in the emission layer, and the third material may act as an additive for improvement in lifespan in the emission layer.

Since the emission layer includes the first material, the second material, the third material, and the light-emitting material at the same time as described above, an organic light-emitting device including the emission layer may have both high luminescent efficiency and long lifespan characteristics due to minimization in polaron-triplet quenching.

The FIGURE is a schematic view of an organic light-emitting device 10 according to an embodiment. Hereinafter, the structure of an organic light-emitting device according to an embodiment and a method of manufacturing an organic light-emitting device according to an embodiment will be described in connection with the FIGURE. The organic light-emitting device 10 includes a first electrode 11, an organic layer 15, and a second electrode 19, which are sequentially stacked.

A substrate may be additionally disposed under the first electrode 11 or above the second electrode 19. For use as the substrate, any substrate that is used in general organic light-emitting devices may be used, and the substrate may be a glass substrate or a transparent plastic substrate, each having excellent mechanical strength, thermal stability, transparency, surface smoothness, ease of handling, and water resistance.

The first electrode 11 may be formed by depositing or sputtering a material for forming the first electrode 11 on the substrate. The first electrode 11 may be an anode. The material for forming the first electrode 11 may be selected from materials with a high work function to facilitate hole injection. The first electrode 11 may be a reflective electrode, a semi-transmissive electrode, or a transmissive electrode. The material for forming the first electrode may be, for example, indium tin oxide (ITO), indium zinc oxide (IZO), tin oxide ($SnO_2$), and zinc oxide (ZnO). In one or more embodiments, magnesium (Mg), aluminum (Al), aluminum-lithium (Al—Li), calcium (Ca), magnesium-indium (Mg—In), or magnesium-silver (Mg—Ag) may be used as the material for forming the first electrode.

The first electrode 11 may have a single-layered structure or a multi-layered structure including two or more layers. For example, the first electrode 11 may have a three-layered structure of ITO/Ag/ITO, but the structure of the first electrode 110 is not limited thereto.

The organic layer 15 is disposed on the first electrode 11.

The organic layer 15 may include a hole transport region, an emission layer, and an electron transport region.

The hole transport region may be disposed between the first electrode 11 and the emission layer.

The hole transport region may include at least one selected from a hole injection layer, a hole transport layer, an electron blocking layer, and a buffer layer. The hole transport layer may be a single layer or may include two or more layers.

The hole transport region may include only either a hole injection layer or a hole transport layer. In an embodiment, the hole transport region may include, a hole injection layer/hole transport layer structure, a hole injection layer/hole transport layer/electron blocking layer structure, a hole transport layer/electron blocking layer structure, a hole injection layer/first hole transport layer/second hole transport layer structure, a hole injection layer/first hole transport layer/second hole transport layer/electron blocking layer structure, or a first hole transport layer/second hole transport layer/electron blocking layer structure, which are sequentially stacked in this stated order from the first electrode 11.

A hole injection layer may be formed on the first electrode 11 by using one or more suitable methods selected from vacuum deposition, spin coating, casting, or Langmuir-Blodgett (LB) deposition.

When a hole injection layer is formed by vacuum deposition, the deposition conditions may vary according to a compound that is used to form the hole injection layer, and the structure and thermal characteristics of the hole injection layer. For example, the deposition conditions may include a deposition temperature of about 100° C. to about 500° C., a vacuum pressure of about $10^{-8}$ torr to about $10^{-3}$ torr, and a deposition rate of about 0.01 Angstroms per second (Å/sec) to about 100 Å/sec. However, the deposition conditions are not limited thereto.

When the hole injection layer is formed using spin coating, coating conditions may vary according to the material used to form the hole injection layer, and the structure and thermal properties of the hole injection layer. For example, a coating speed may be from about 2,000 revolutions per minute (rpm) to about 5,000 rpm, and a temperature at which a heat treatment is performed to remove a solvent after coating may be from about 80° C. to about 200° C. However, the coating conditions are not limited thereto.

Conditions for forming a hole transport layer and an electron blocking layer may be understood by referring to conditions for forming the hole injection layer.

The hole transport region may include at least one selected from m-MTDATA, TDATA, 2-TNATA, NPB, β-NPB, TPD, Spiro-TPD, Spiro-NPB, methylated-NPB, TAPC, HMTPD, 4,4',4"-tris(N-carbazolyl)triphenylamine (TCTA), polyaniline/dodecylbenzene sulfonic acid (PANI/DBSA), poly(3,4-ethylenedioxythiophene)/poly(4-styrene sulfonate) (PEDOT/PSS), polyaniline/camphor sulfonic acid (PANI/CSA), polyaniline/poly(4-styrene sulfonate) (PANI/PSS), a compound represented by Formula 201 below, and a compound represented by Formula 202 below:

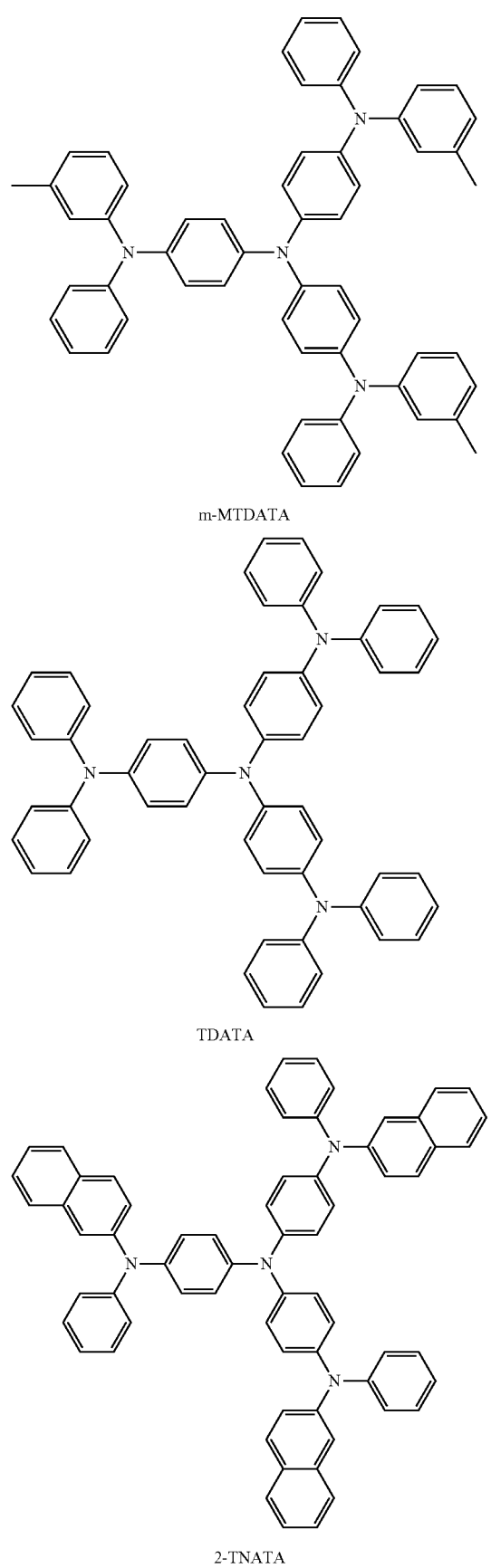
m-MTDATA
TDATA
2-TNATA
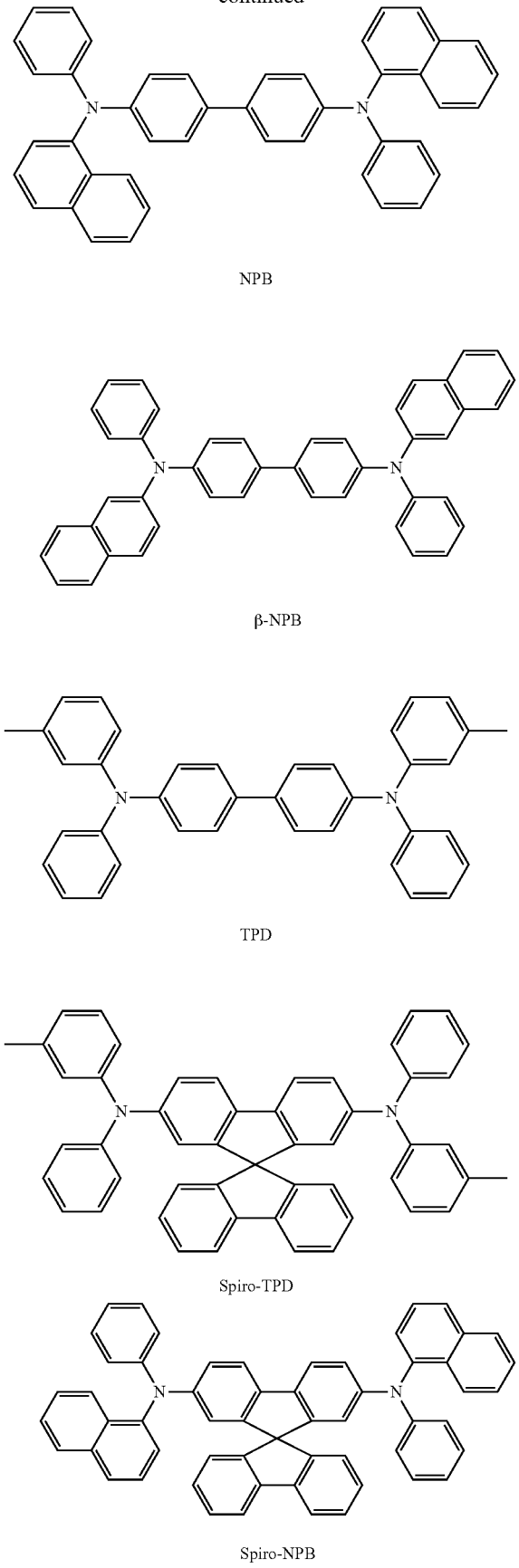
NPB
β-NPB
TPD
Spiro-TPD
Spiro-NPB

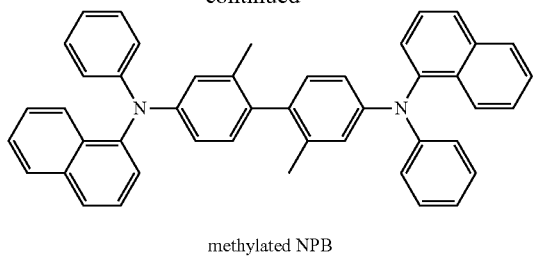

methylated NPB

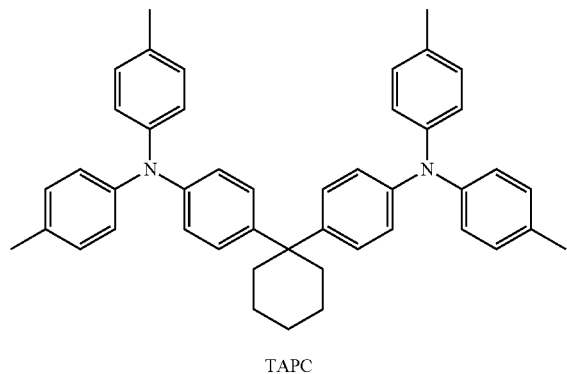

TAPC

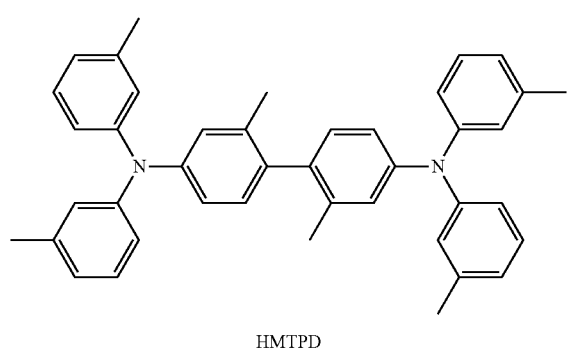

HMTPD

Formula 201

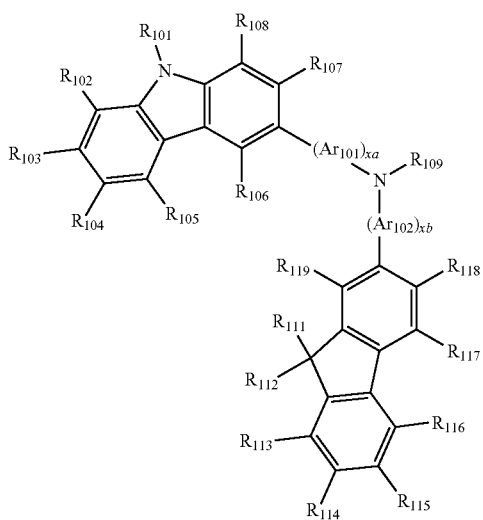

Formula 202

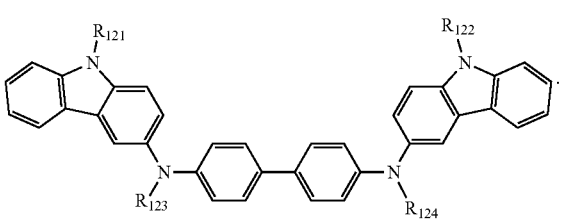

In Formula 201, $Ar_{101}$ and $Ar_{102}$ may each independently be selected from:

a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group; and a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_1$-$C_{10}$ heterocycloalkyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

In Formula 201, xa and xb may each independently be an integer of 0 to 5, or may be 0, 1, or 2. For example, xa is 1 and xb is 0, but xa and xb are not limited thereto.

In Formulae 201 and 202, $R_{101}$ to $R_{108}$, $R_{111}$ to $R_{119}$, and $R_{121}$ to $R_{124}$ may each independently be selected from:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group (for example, a methyl group, an ethyl group, a propyl group, a butyl group, pentyl group, a hexyl group, and the like), and a $C_1$-$C_{10}$ alkoxy group (for example, a methoxy group, an ethoxy group, a propoxy group, a butoxy group, a pentoxy group, and the like);

a $C_1$-$C_{10}$ alkyl group and a $C_1$-$C_{10}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a naphthyl group, an anthracenyl group, a fluorenyl group, and a pyrenyl group; and a phenyl group, a naphthyl group, an anthracenyl group, a fluorenyl group, and a pyrenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group, but embodiments of the present disclosure are not limited thereto.

In Formula 201, $R_{109}$ may be selected from:

a phenyl group, a naphthyl group, an anthracenyl group, and a pyridinyl group; and a phenyl group, a naphthyl group, an anthracenyl group, and a pyridinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a alkoxy group, a phenyl group, a naphthyl group, an anthracenyl group, and a pyridinyl group.

In an embodiment, the compound represented by Formula 201 may be represented by Formula 201A, but embodiments of the present disclosure are not limited thereto:

Formula 201A

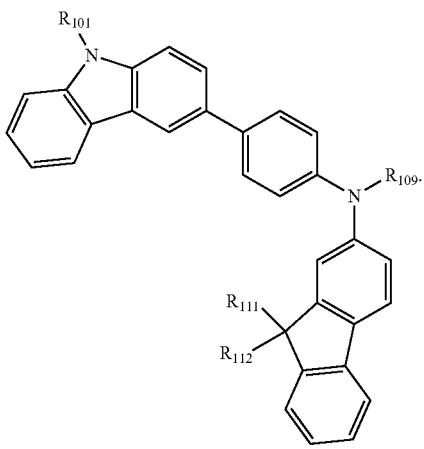

$R_{101}$, $R_{111}$, $R_{112}$, and $R_{109}$ in Formula 201A may be understood by referring to the description provided herein.

For example, the compound represented by Formula 201, and the compound represented by Formula 202 may include compounds HT1 to HT20 illustrated below, but are not limited thereto:

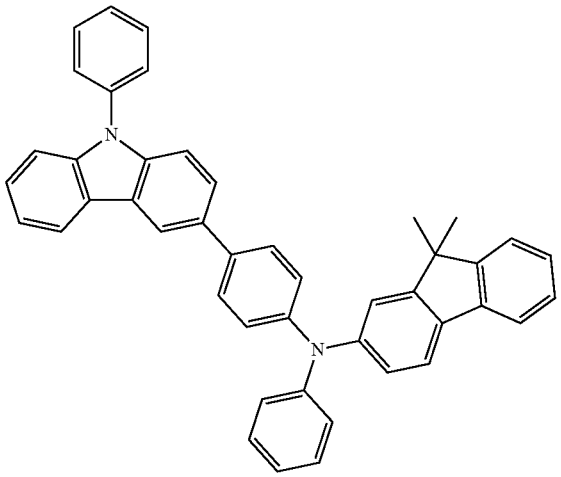

HT1

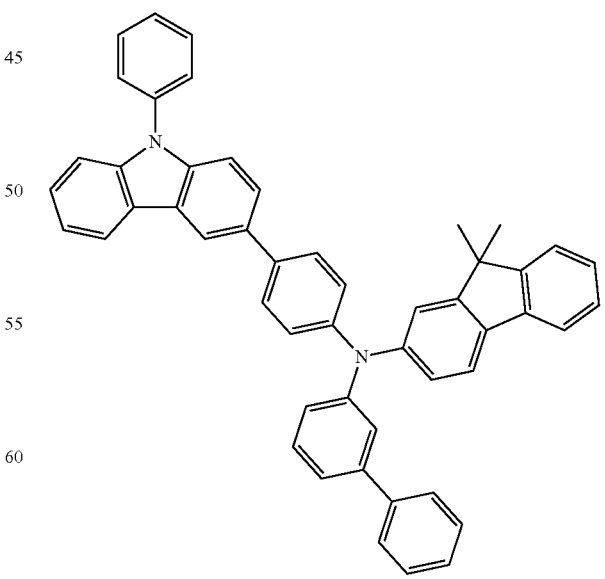

HT2

HT3
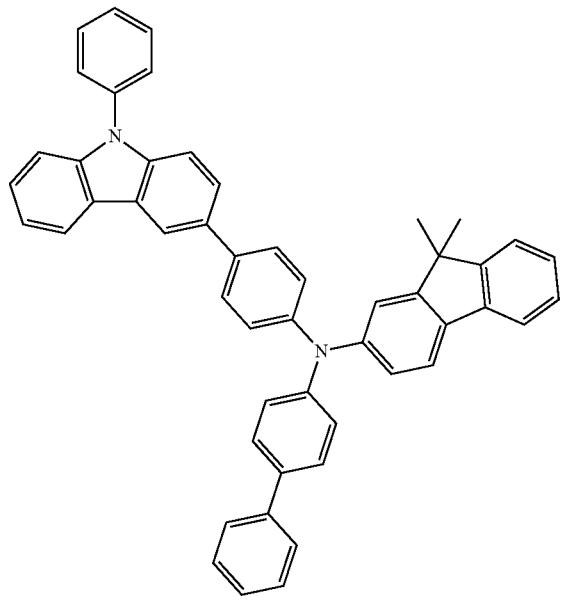
HT5
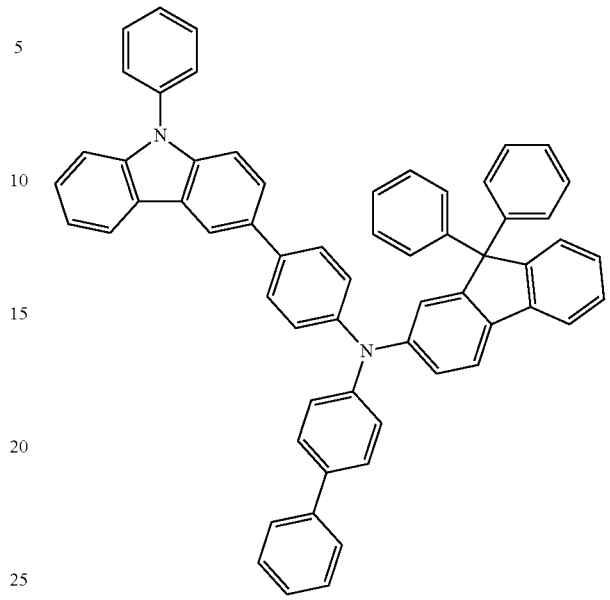
HT4
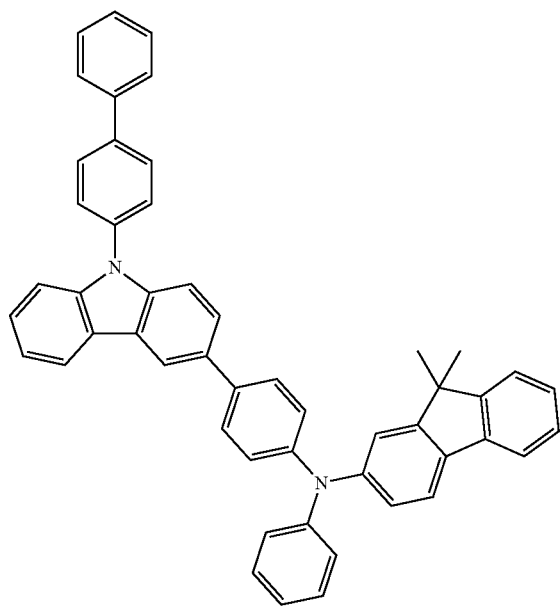
HT6
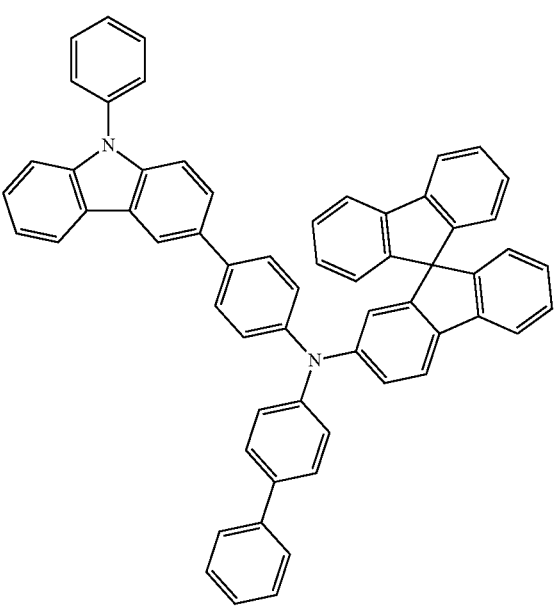

-continued
HT7
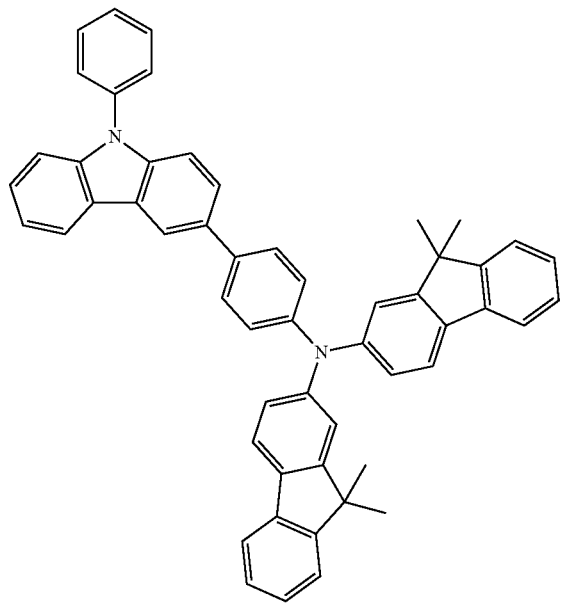
HT8
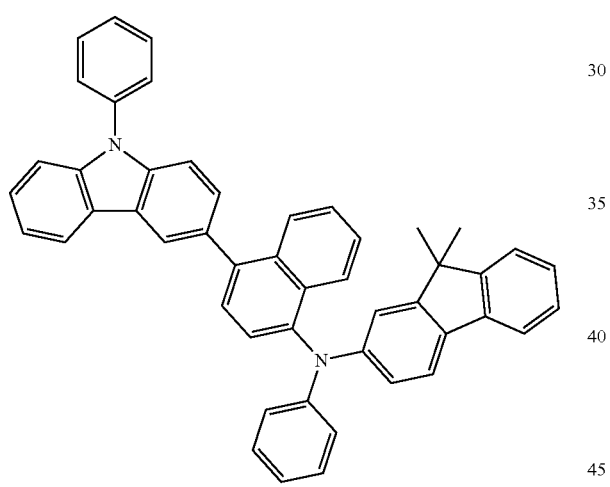
HT9
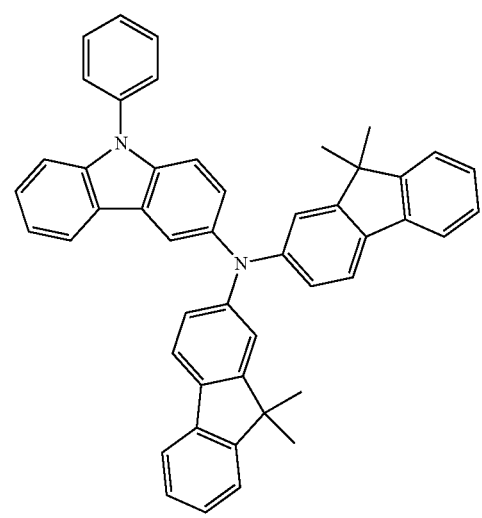
-continued
HT10
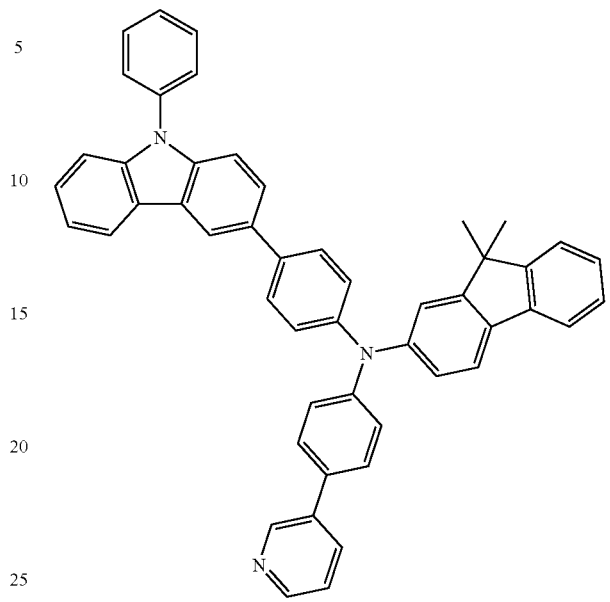
HT11
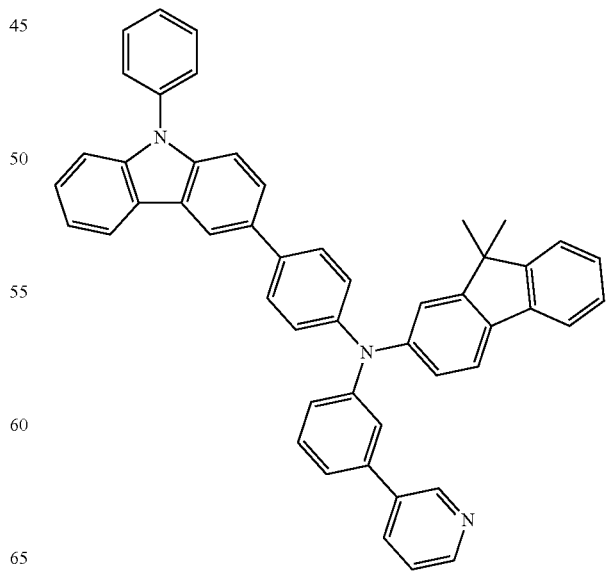

-continued
HT12
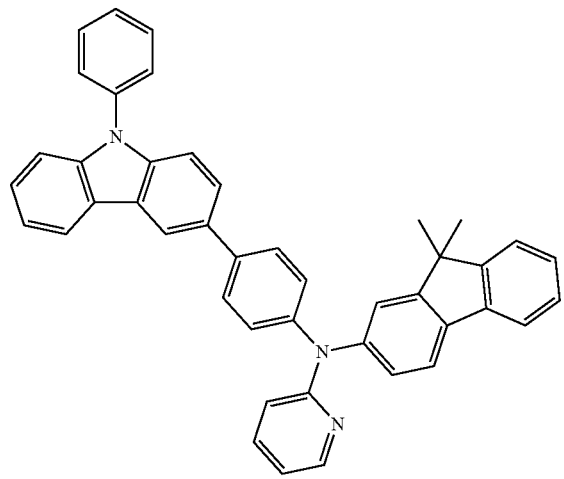
HT13
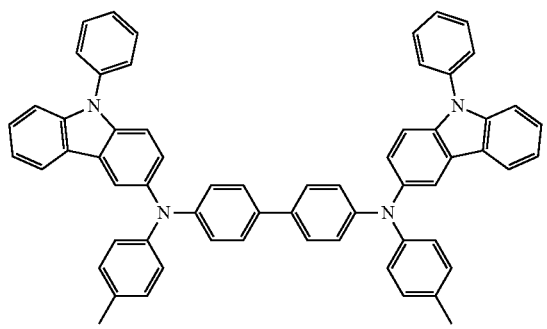
HT14
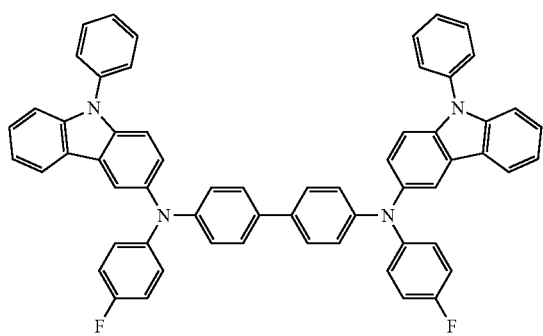
HT15
HT16
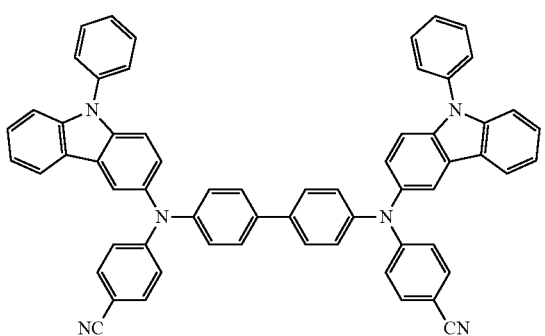
HT17
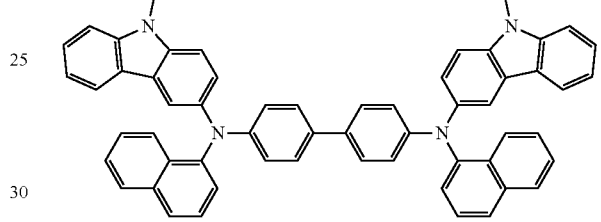
HT18
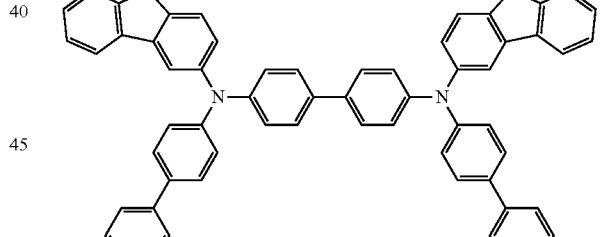
HT19
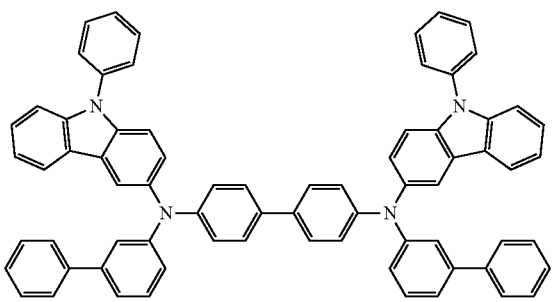

HT20

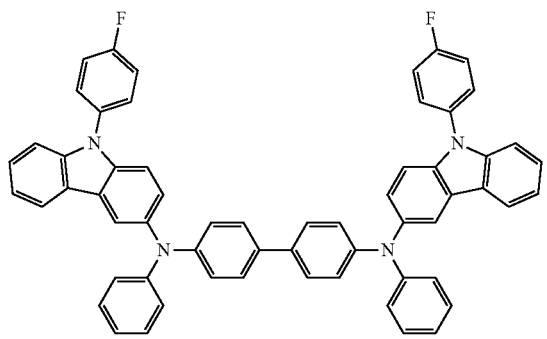

A thickness of the hole transport region may be in a range of about 100 Angstroms (Å) to about 10,000 Å, for example, about 100 Å to about 1,000 Å. When the hole transport region includes a hole injection layer and a hole transport layer, the thickness of the hole injection layer may be in a range of about 100 Å to about 10,000 Å, and for example, about 100 Å to about 1,000 Å, and the thickness of the hole transport layer may be in a range of about 50 Å to about 2,000 Å, and for example, about 100 Å to about 1,500 Å. While not wishing to be bound by theory, it is understood that when the thicknesses of the hole transport region, the hole injection layer, and the hole transport layer are within these ranges, satisfactory hole transporting characteristics may be obtained without a substantial increase in driving voltage.

The hole transport region may further include, in addition to these materials, a charge-generation material for the improvement of conductive properties. The charge-generation material may be homogeneously or non-homogeneously dispersed in the hole transport region.

The charge-generation material may be, for example, a p-dopant. The p-dopant may be one selected from a quinone derivative, a metal oxide, and a cyano group-containing compound, but embodiments of the present disclosure are not limited thereto. Non-limiting examples of the p-dopant are a quinone derivative, such as tetracyanoquinonedimethane (TCNQ) or 2,3,5,6-tetrafluoro-tetracyano-1,4-benzoquinonedimethane (F4-TCNQ); a metal oxide, such as a tungsten oxide or a molybdenium oxide; and a cyano group-containing compound, such as Compound HT-D1 or Compound HT-D2 below, but are not limited thereto.

HT-D1

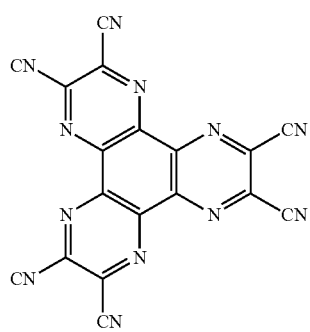

F4-TCNQ

HT-D2

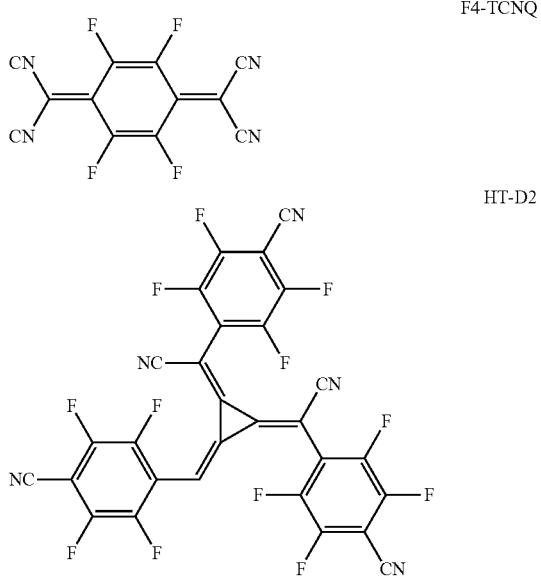

The hole transport region may include a buffer layer.

Also, the buffer layer may compensate for an optical resonance distance according to a wavelength of light emitted from the emission layer, and thus, efficiency of a formed organic light-emitting device may be improved.

Then, an emission layer may be formed on the hole transport region by vacuum deposition, spin coating, casting, LB deposition, or the like. When the emission layer is formed by vacuum deposition or spin coating, the deposition or coating conditions may be similar to those applied in forming the hole injection layer although the deposition or coating conditions may vary according to a compound that is used to form the emission layer.

Meanwhile, when the hole transport region includes an electron blocking layer, a material for the electron blocking layer may be selected from materials for the hole transport region described above and materials for a host to be explained later. However, the material for the electron blocking layer is not limited thereto. For example, when the hole transport region includes an electron blocking layer, a material for the electron blocking layer may be mCP.

mCP

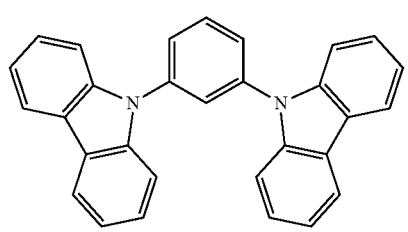

The emission layer may include the first material, the second material, the third material, and the light-emitting material as described above.

When the organic light-emitting device is a full-color organic light-emitting device, the emission layer may be patterned into a red emission layer, a green emission layer, and a blue emission layer. In one or more embodiments, due to a stacked structure including a red emission layer, a green emission layer, and/or a blue emission layer, the emission layer may emit white light.

A thickness of the emission layer may be in a range of about 100 Å to about 1,000 Å, for example, about 200 Å to about 600 Å. While not wishing to be bound by theory, it is understood that when the thickness of the emission layer is within this range, excellent light-emission characteristics may be obtained without a substantial increase in driving voltage.

Then, an electron transport region may be disposed on the emission layer.

The electron transport region may include at least one selected from a hole blocking layer, an electron transport layer, and an electron injection layer.

For example, the electron transport region may have a hole blocking layer/electron transport layer/electron injection layer structure or an electron transport layer/electron injection layer structure, but the structure of the electron transport region is not limited thereto. The electron transport layer may have a single-layered structure or a multi-layered structure including two or more different materials.

Conditions for forming the hole blocking layer, the electron transport layer, and the electron injection layer which constitute the electron transport region may be understood by referring to the conditions for forming the hole injection layer.

When the electron transport region includes a hole blocking layer, the hole blocking layer may include, for example, at least one of BCP, Bphen, and BAlq but embodiments of the present disclosure are not limited thereto:

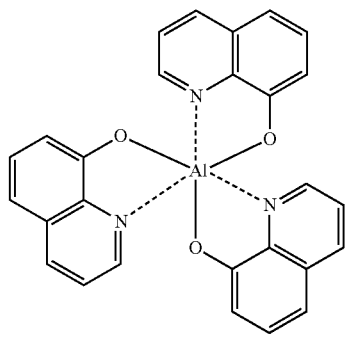

Alq₃

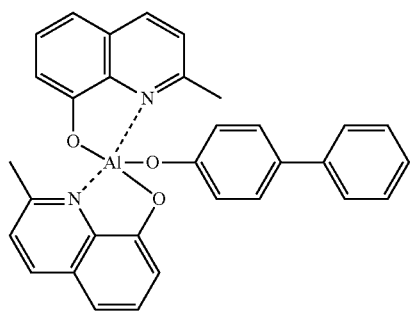

BAlq

BCP

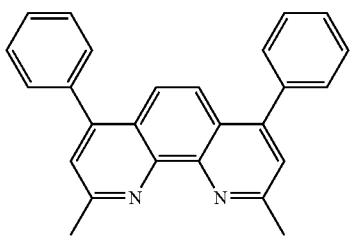

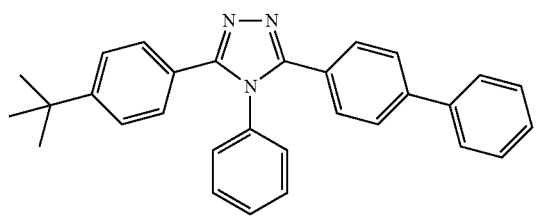

TAZ

Bphen

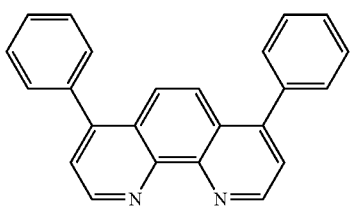

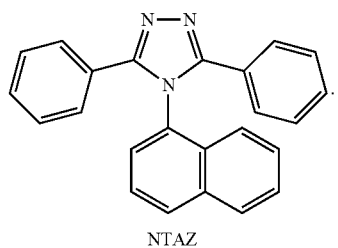

NTAZ

A thickness of the hole blocking layer may be in a range of about 20 Å to about 1,000 Å, for example, about 30 Å to about 300 Å. While not wishing to be bound by theory, it is understood that when the thickness of the hole blocking layer is within these ranges, the hole blocking layer may have improved hole blocking ability without a substantial increase in driving voltage.

The electron transport layer may further include at least one selected from BCP, Bphen, Alq₃, BAlq, TAZ, and NTAZ:

In one or more embodiments, the electron transport layer may include at least one of ET1 and ET25, but are not limited thereto:

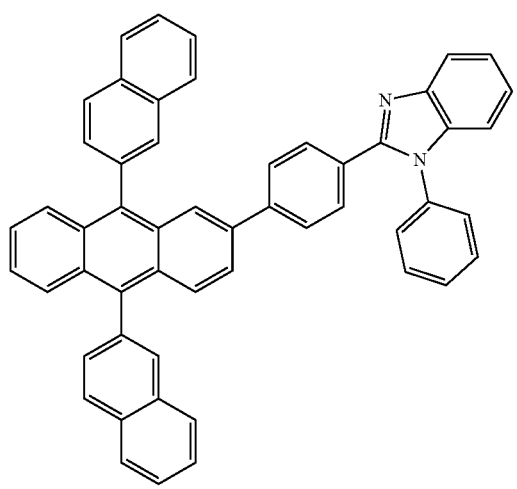
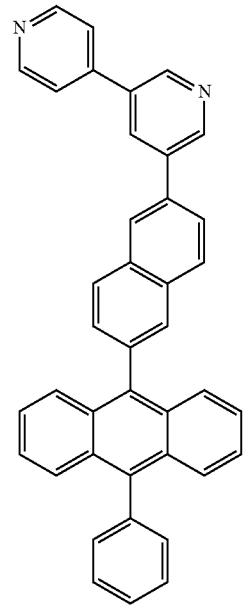
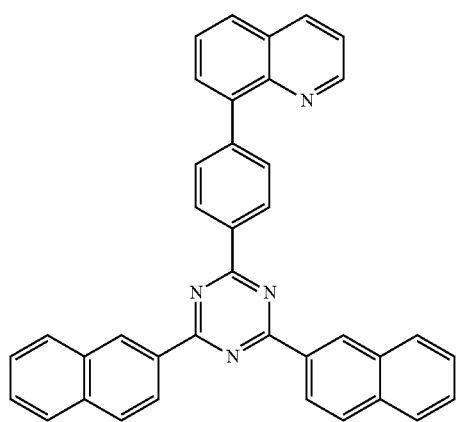

ET7
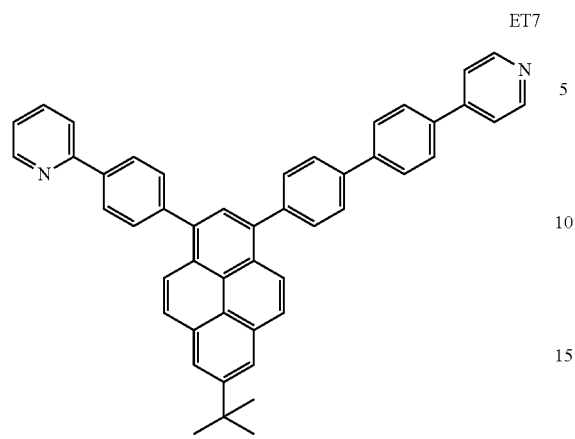
ET10
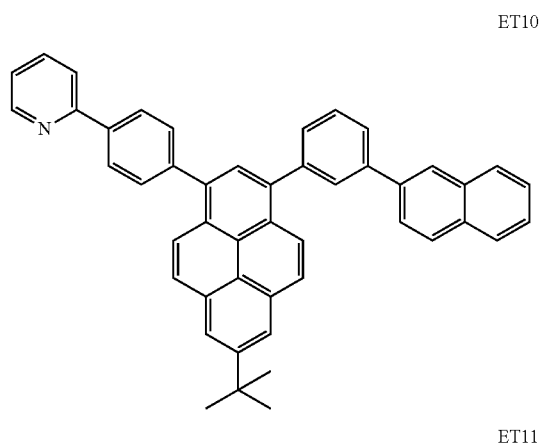
ET8
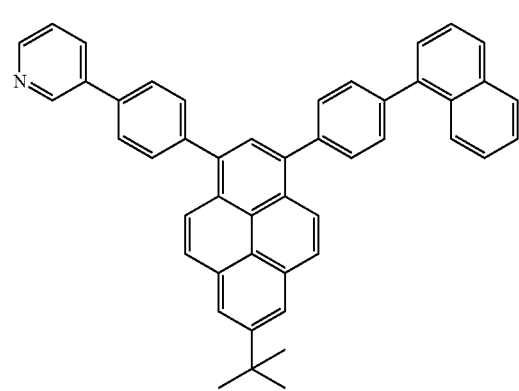
ET11
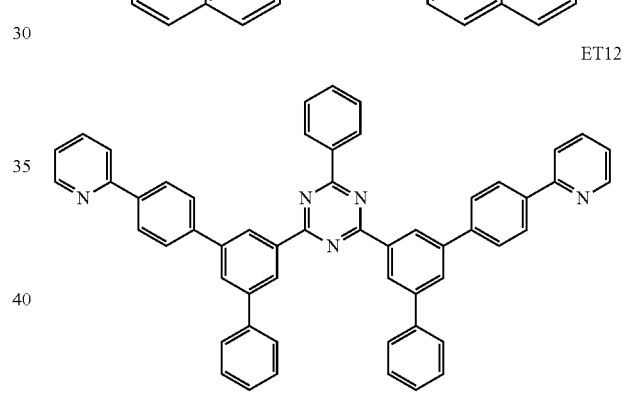
ET12
ET9
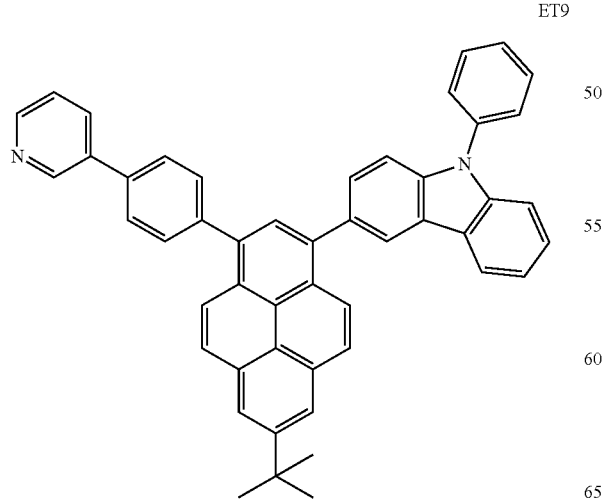
ET13
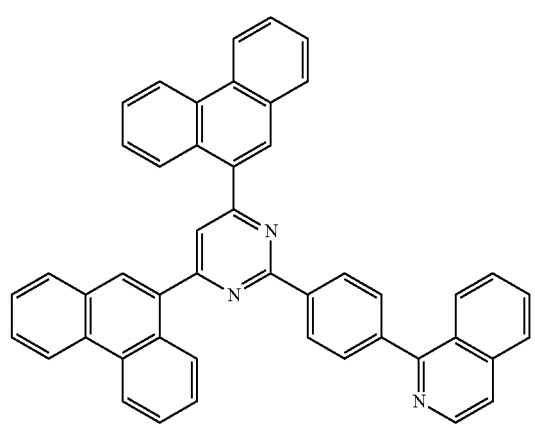

ET14
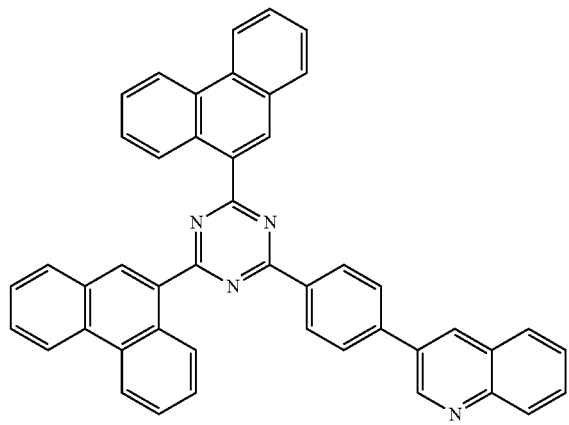
ET15
ET16
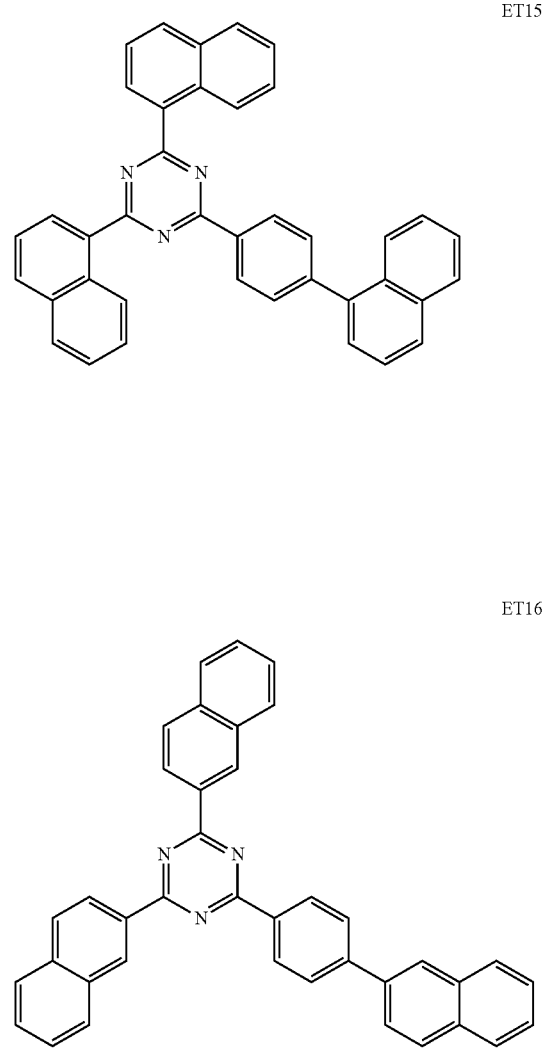
ET17
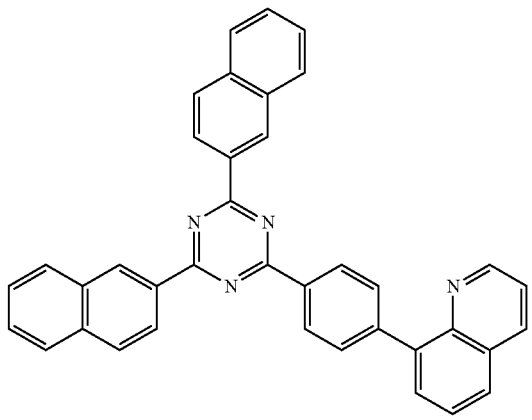
ET18
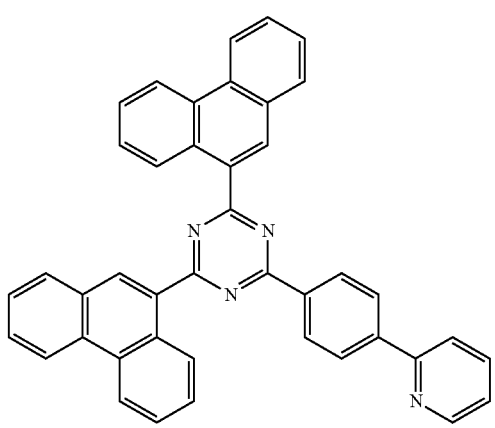
ET19
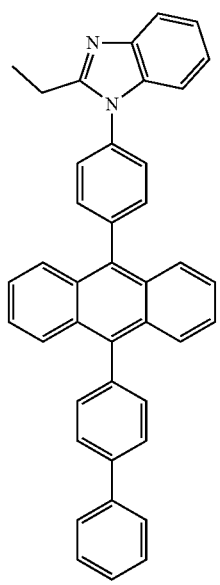

ET20
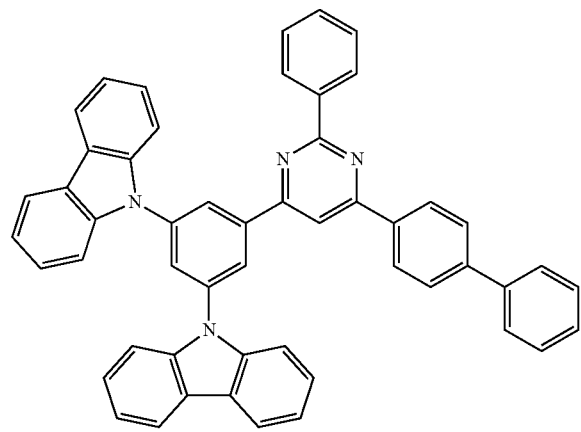
ET23
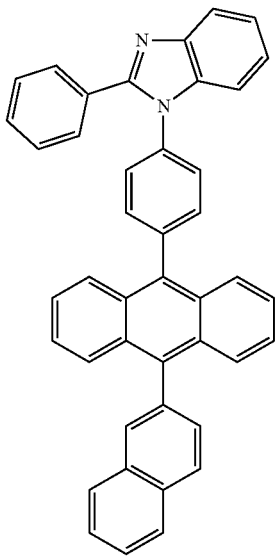
ET21
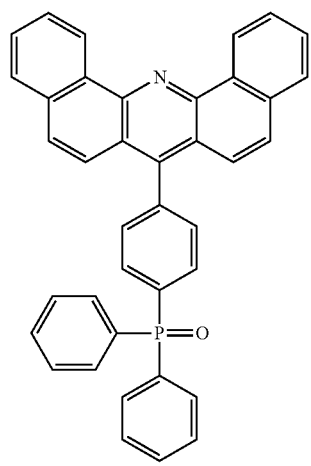
ET24
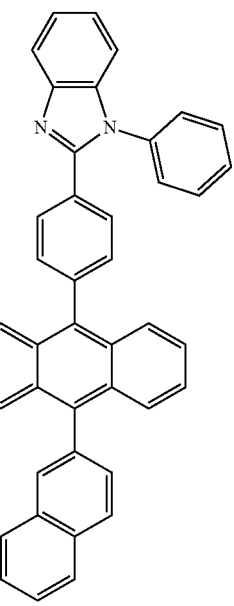
ET22
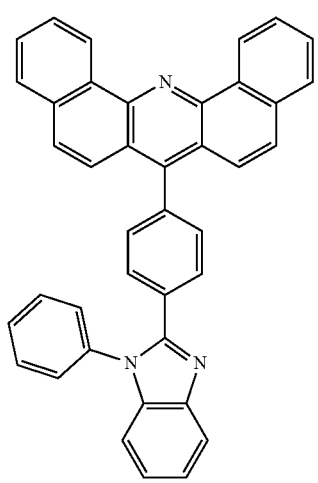
ET25
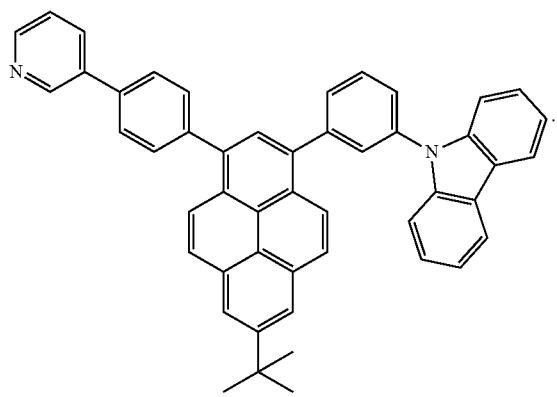
A thickness of the electron transport layer may be in a range of about 100 Å to about 1,000 Å, for example, about 150 Å to about 500 Å. While not wishing to be bound by theory, it is understood that when the thickness of the electron transport layer is within the range described above, the electron transport layer may have satisfactory electron transport characteristics without a substantial increase in driving voltage.

Also, the electron transport layer may further include, in addition to the materials described above, a metal-containing material.

The metal-containing material may include a Li complex. The Li complex may include, for example, Compound ET-D1 (lithium quinolate, LiQ) or ET-D2:

ET-D1

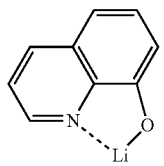

ET-D2

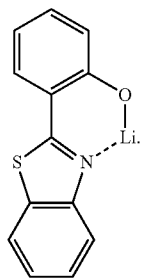

The electron transport region may include an electron injection layer that promotes flow of electrons from the second electrode 19 thereinto.

The electron injection layer may include at least one selected from LiF, NaCl, CsF, Li$_2$O, and BaO.

A thickness of the electron injection layer may be in a range of about 1 Å to about 100 Å, for example, about 3 Å to about 90 Å. While not wishing to be bound by theory, it is understood that when the thickness of the electron injection layer is within the range described above, the electron injection layer may have satisfactory electron injection characteristics without a substantial increase in driving voltage.

The second electrode 19 is disposed on the organic layer 15. The second electrode 19 may be a cathode. A material for forming the second electrode 19 may be selected from metal, an alloy, an electrically conductive compound, and a combination thereof, which have a relatively low work function. For example, lithium (Li), magnesium (Mg), aluminum (Al), aluminum-lithium (Al—Li), calcium (Ca), magnesium-indium (Mg—In), or magnesium-silver (Mg—Ag) may be used as a material for forming the second electrode 19. In one or more embodiments, to manufacture a top-emission type light-emitting device, a transmissive electrode formed using ITO or IZO may be used as the second electrode 19.

Hereinbefore, the organic light-emitting device has been described with reference to the FIGURE, but embodiments of the present disclosure are not limited thereto.

The term "$C_1$-$C_{60}$ alkyl group" as used herein refers to a linear or branched saturated aliphatic hydrocarbon monovalent group having 1 to 60 carbon atoms, and non-limiting examples thereof include a methyl group, an ethyl group, a propyl group, an iso-butyl group, a sec-butyl group, a tert-butyl group, a pentyl group, an iso-amyl group, and a hexyl group. The term "$C_1$-$C_{60}$ alkylene group" as used herein refers to a divalent group having the same structure as the $C_1$-$C_{60}$ alkyl group.

The term "$C_1$-$C_{60}$ alkoxy group" as used herein refers to a monovalent group represented by —OA$_{101}$ (wherein A$_{101}$ is the $C_1$-$C_{60}$ alkyl group), and non-limiting examples thereof include a methoxy group, an ethoxy group, and an iso-propyloxy group.

The term "$C_2$-$C_{60}$ alkenyl group" as used herein refers to a hydrocarbon group formed by including at least one carbon-carbon double bond in the middle or at the terminus of the $C_2$-$C_{60}$ alkyl group, and examples thereof include an ethenyl group, a propenyl group, and a butenyl group. The term "$C_2$-$C_{60}$ alkenylene group" as used herein refers to a divalent group having the same structure as the $C_2$-$C_{60}$ alkenyl group.

The term "$C_2$-$C_{60}$ alkynyl group" as used herein refers to a hydrocarbon group formed by including at least one carbon-carbon triple bond in the middle or at the terminus of the $C_2$-$C_{60}$ alkyl group, and examples thereof include an ethynyl group, and a propynyl group. The term "$C_2$-$C_{60}$ alkynylene group" as used herein refers to a divalent group having the same structure as the $C_2$-$C_{60}$ alkynyl group.

The term "$C_3$-$C_{10}$ cycloalkyl group" as used herein refers to a monovalent saturated hydrocarbon monocyclic group having 3 to 10 carbon atoms, and non-limiting examples thereof include a cyclopropyl group, a cyclobutyl group, a cyclopentyl group, a cyclohexyl group, and a cycloheptyl group. The term "$C_3$-$C_{10}$ cycloalkylene group" as used herein refers to a divalent group having the same structure as the $C_3$-$C_{10}$ cycloalkyl group.

The term "$C_1$-$C_{10}$ heterocycloalkyl group" as used herein refers to a monovalent saturated monocyclic group having at least one heteroatom selected from N, O, P, Si and S as a ring-forming atom and 1 to 10 carbon atoms, and non-limiting examples thereof include a tetrahydrofuranyl group, and a tetrahydrothiophenyl group. The term "$C_1$-$C_{10}$ heterocycloalkylene group" as used herein refers to a divalent group having the same structure as the $C_1$-$C_{10}$ heterocycloalkyl group.

The term "$C_3$-$C_{10}$ cycloalkenyl group" as used herein refers to a monovalent monocyclic group that has 3 to 10 carbon atoms and at least one carbon-carbon double bond in the ring thereof and no aromaticity, and non-limiting examples thereof include a cyclopentenyl group, a cyclohexenyl group, and a cycloheptenyl group. The term "$C_3$-$C_{10}$ cycloalkenylene group" as used herein refers to a divalent group having the same structure as the $C_3$-$C_{10}$ cycloalkenyl group.

The term "$C_1$-$C_{10}$ heterocycloalkenyl group" as used herein refers to a monovalent monocyclic group that has at least one heteroatom selected from N, O, P, Si, and S as a ring-forming atom, 1 to 10 carbon atoms, and at least one carbon-carbon double bond in its ring. Examples of the $C_1$-$C_{10}$ heterocycloalkenyl group are a 2,3-dihydrofuranyl group, and a 2,3-dihydrothiophenyl group. The term "$C_1$-$C_{10}$ heterocycloalkenylene group" as used herein refers to a divalent group having the same structure as the $C_1$-$C_{10}$ heterocycloalkenyl group.

The term "$C_6$-$C_{60}$ aryl group" used herein refers to a monovalent group having a carbocyclic aromatic system having 6 to 60 carbon atoms, and a $C_6$-$C_{60}$ arylene group used herein refers to a divalent group having a carbocyclic aromatic system having 6 to 60 carbon atoms. Non-limiting examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

The term "$C_1$-$C_{60}$ heteroaryl group" as used herein refers to a monovalent group having a heterocyclic aromatic system that has at least one heteroatom selected from N, O, P, Si, and S as a ring-forming atom, and 1 to 60 carbon atoms. The term "$C_1$-$C_{60}$ heteroarylene group," as used herein refers to a divalent group having a heterocyclic aromatic system that has at least one heteroatom selected from N, O, P, Si, and S as a ring-forming atom, and 1 to 60 carbon atoms. Non-limiting examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include two or more rings, the rings may be fused to each other.

The term "$C_6$-$C_{60}$ aryloxy group" used herein indicates —$OA_{102}$ (wherein $A_{102}$ is the $C_6$-$C_{60}$ aryl group), and a $C_6$-$C_{60}$ arylthio group used herein indicates —$SA_{103}$ (wherein $A_{103}$ is the $C_6$-$C_{60}$ aryl group).

The term "monovalent non-aromatic condensed polycyclic group" as used herein refers to a monovalent group (for example, having 8 to 60 carbon atoms) having two or more rings condensed to each other, only carbon atoms as ring-forming atoms, and no aromaticity in its entire molecular structure. Examples of the monovalent non-aromatic condensed polycyclic group include a fluorenyl group. The term "divalent non-aromatic condensed polycyclic group" as used herein refers to a divalent group having the same structure as the monovalent non-aromatic condensed polycyclic group.

The term "monovalent non-aromatic condensed heteropolycyclic group" as used herein refers to a monovalent group (for example, having 2 to 60 carbon atoms) having two or more rings condensed to each other, a heteroatom selected from N, O, P, Si, and S, other than carbon atoms, as a ring-forming atom, and no aromaticity in its entire molecular structure. Non-limiting examples of the monovalent non-aromatic condensed heteropolycyclic group include a carbazolyl group. The term "divalent non-aromatic condensed heteropolycyclic group" as used herein refers to a divalent group having the same structure as the monovalent non-aromatic condensed heteropolycyclic group.

The term "$C_5$-$C_{30}$ carbocyclic group" as used herein refers to a saturated or unsaturated cyclic group having, as a ring-forming atom, 5 to 30 carbon atoms only. The term "$C_5$-$C_{30}$ carbocyclic group" as used herein refers to a monocyclic group or a polycyclic group, and, according to its chemical structure, a monovalent, divalent, trivalent, tetravalent, pentavalent, or hexavalent group.

The term "$C_2$-$C_{30}$ heterocyclic group" as used herein refers to a saturated or unsaturated cyclic group having, as a ring-forming atom, at least one heteroatom selected from N, O, Si, P, and S other than 2 to 30 carbon atoms. The term "$C_2$-$C_{30}$ heterocyclic group" as used herein refers to a monocyclic group or a polycyclic group, and, according to its chemical structure, a monovalent, divalent, trivalent, tetravalent, pentavalent, or hexavalent group.

At least one substituent of the substituted $C_5$-$C_{30}$ carbocyclic group, the substituted $C_2$-$C_{30}$ heterocyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{11})(Q_{12})$, —$Si(Q_{13})(Q_{14})(Q_{15})$, —$B(Q_{16})(Q_{17})$, and —$P(=O)(Q_{18})(Q_{19})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{21})(Q_{22})$, —$Si(Q_{23})(Q_{24})(Q_{25})$, —$B(Q_{26})(Q_{27})$ and —$P(=O)(Q_{28})(Q_{29})$; and —$N(Q_{31})(Q_{32})$, —$Si(Q_{33})(Q_{34})(Q_{35})$, —$B(Q_{36})(Q_{37})$, and —$P(=O)(Q_{38})(Q_{39})$, and $Q_1$ to $Q_9$, $Q_{11}$ to $Q_{19}$, $Q_{21}$ to $Q_{29}$, and $Q_{31}$ to $Q_{39}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with at least one selected from a $C_1$-$C_{60}$ alkyl group and a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

Hereinafter, a compound and an organic light-emitting device according to embodiments are described in detail with reference to Synthesis Example and Examples. However, the organic light-emitting device is not limited thereto. The wording "B was used instead of A" used in describing Synthesis Examples means that an amount of A used was identical to an amount of B used, in terms of a molar equivalent.

EXAMPLES

Synthesis Example 1

Synthesis of Compound D1

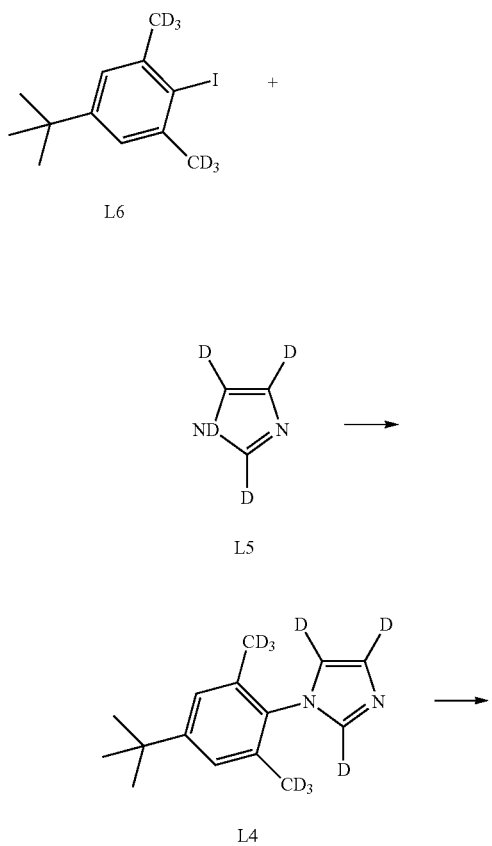

L6

L5

L4

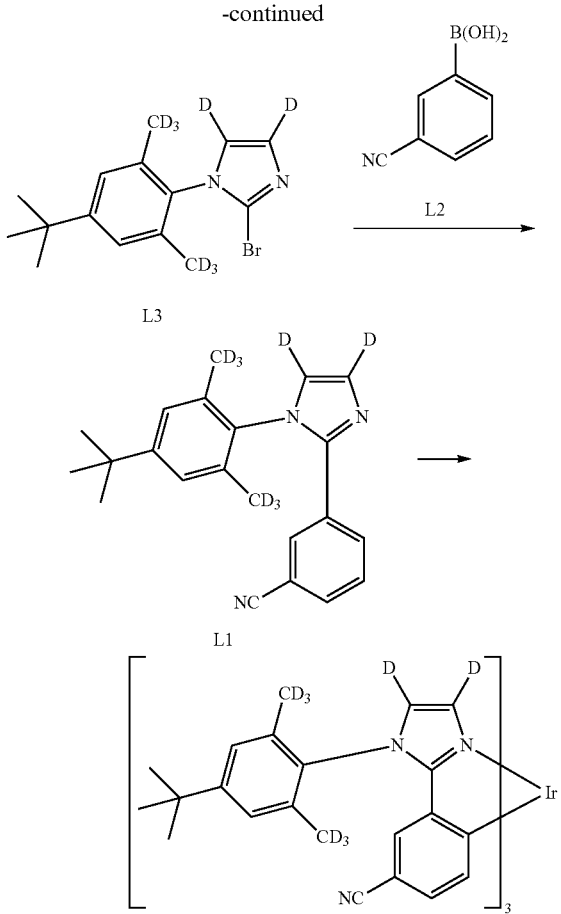

L3

L1

D1

(1) Synthesis of Compound L4

Compound L6 (34.70 millimoles, mmol), Compound L5 (41.64 mmol), $K_2CO_3$ (173.51 mmol), CuI (1.74 mmol), 1,10-phenanthroline (3.47 mmol), and 500 milliliters (mL) of DMF were added to a 1-L reaction container and refluxed for 12 hours in a nitrogen atmosphere. After the reaction was completed, the reaction mixture was cooled to room temperature. Then, the organic layer was separated therefrom by adding dichloromethane and distilled water thereto. The separated organic layer was washed twice by using distilled water and dried by using $MgSO_4$, and the solvent was removed therefrom. The crude product was purified by silica gel column chromatography (eluent: ethyl acetate and n-hexane) to obtain 26.37 mmol of Compound L4. The obtained Compound L4 was identified by LC-MS.

LC-MS (m/z): 237.22 [M+1].

(2) Synthesis of Compound L3

Compound L4 (26.37 mmol) and tetrahydrofuran were added to a reaction container and cooled to a temperature of −78° C. in a nitrogen atmosphere. n-BuLi (2.5 M in n-hexane, 27.69 mmol) was slowly added thereto at a temperature of −78° C. and then stirred. After stirring for 1 hour, $Br_2$ (52.74 mmol) was slowly added thereto at a temperature of −78° C. After 30 minutes, the reaction mixture was heated by removing a cooler and stirred at room temperature for 6 hours. After the reaction was completed, the organic layer was separated therefrom by adding dichloromethane and pure water thereto. The separated organic layer was washed twice by using distilled water and dried by using MgSO$_4$, and the solvent was removed therefrom. The crude product was purified by silica gel column chromatography (eluent: ethyl acetate and n-hexane) to obtain Compound L3 (18.72 mmol). The obtained Compound L3 was identified by LC-MS.

LC-MS (m/z): 314.12 [M+1].

(3) Synthesis of Compound L1

Compound L3 (18.72 mmol), Compound L2 (28.08 mmol), Pd(PPh$_3$)$_4$ (1.87 mmol), K$_2$CO$_3$ (210.63 mmol), and THF:distilled water (=2:1) were added to a reaction container and refluxed for 12 hours in a nitrogen atmosphere. After the reaction was completed, the reaction mixture was cooled to room temperature. Then, the organic layer was separated therefrom by adding dichloromethane and distilled water thereto. The separated organic layer was washed twice by using distilled water and dried by using MgSO$_4$, and the solvent was removed therefrom. The crude product was purified by silica gel column chromatography (eluent: ethyl acetate and n-hexane) to obtain Compound L1 (16.47 mmol). The obtained Compound L1 was identified by LC-MS.

LC-MS (m/z): 337.24 [M+1].

(4) Synthesis of Compound D1

Ir(acac)$_3$ (3.29 mmol), Compound L1 (16.47 mmol), and glycerol were added to a reaction container and refluxed for 12 hours in a nitrogen atmosphere. After the reaction was completed, the reaction mixture was cooled to room temperature. Then, the organic layer was separated therefrom by adding dichloromethane and distilled water thereto. The separated organic layer was washed twice by using distilled water and dried by using MgSO$_4$, and the solvent was removed therefrom. The crude product was purified by silica gel column chromatography (eluent: dichloromethane and n-hexane) to obtain Compound D1 (0.49 mmol). The obtained Compound D1 was identified by MALDI-TOF.

MALDI-TOF (m/z): 529.19 [M]$^+$.

Evaluation Example 1

Evaluation of Reorganization Energy

Reorganization energy was evaluated by applying a density function theory (PBE0/def2-SVP) using quantum chemical software (TURBOMOLE). Specifically, after optimizing a lowest singlet ground state of a neutral molecule (S$_0$) and a lowest doublet ground state of an ionic state (D$_0$), hole reorganization energy ($\lambda_h$) and electron reorganization energy ($\lambda_e$) were calculated by using the following equations:

$$\lambda_h = IP(v) - HEP$$

$$\lambda_e = EEP - EA(v).$$

In the equations, IP(v) (electron volts, eV) represents vertical ionization potential, EA(v) (eV) represents electron affinity, HEP (eV) represents hole extraction potential, and EEP (eV) represents electron extraction potential.

Reorganization energies of Compounds M1-41, M204, A, B, and C were evaluated by the above-described method, and results thereof are shown in Table 1.

TABLE 1

| Compound No. | Reorganization energy (eV) |
|---|---|
| M1-41 | 0.43 |
| M204 | 0.43 |
| A | 0.32 |
| B | 0.29 |
| C | 0.25 |

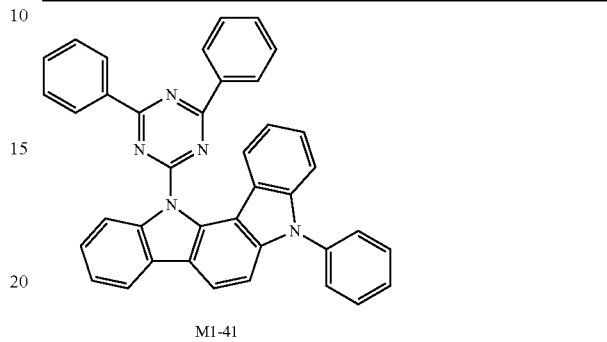

M1-41

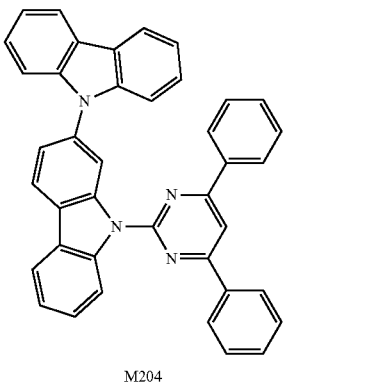 [SMILES: c1ccc(-c2cc(-c3ccccc3)nc(-n3c4ccccc4c4ccc(-n5c6ccccc6c6ccccc65)cc43)n2)cc1 ; "M204"]

M204

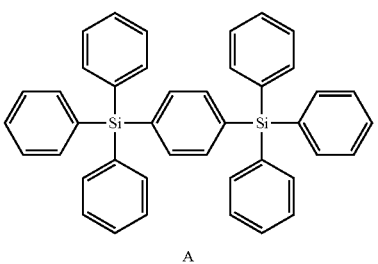

A

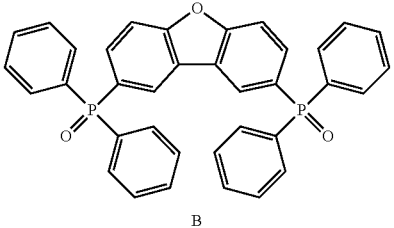

B

TABLE 1-continued

| Compound No. | Reorganization energy (eV) |
|---|---|

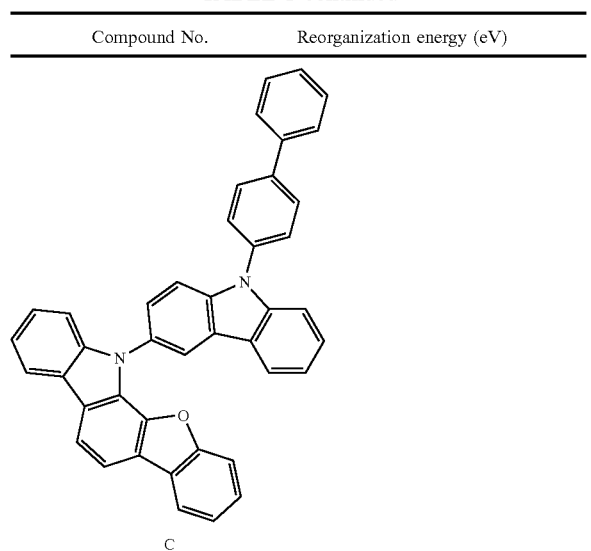

C

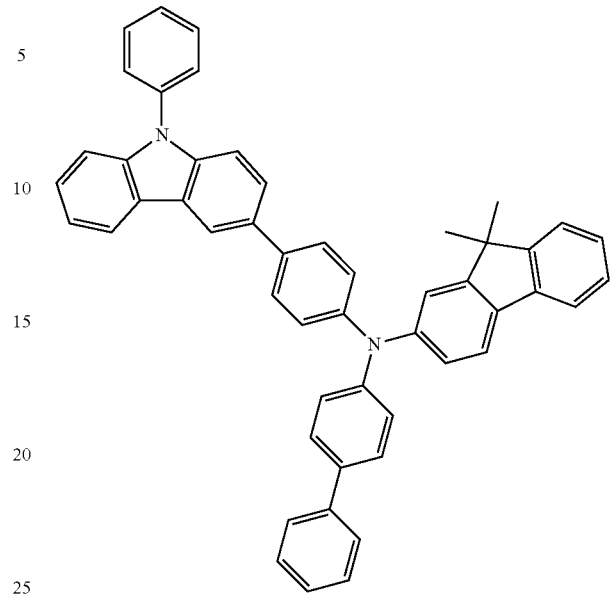

HT3

Referring to Table 1, it is confirmed that Compounds M1-41 and M204 have high reorganization energy, as compared with Compounds A, B, and C.

Example 1

A glass substrate, on which an ITO electrode (first electrode, anode) having a thickness of 1,500 Angstroms (Å) was formed, was cleaned by distilled water ultrasound. After the distilled water cleaning was completed, the glass substrate was ultrasonically cleaned by using iso-propyl alcohol, acetone, and methanol in sequence and then dried. The glass substrate was provided to a plasma cleanser so that the glass substrate was cleaned for 5 minutes by using oxygen plasma. Then, the glass substrate was provided to a vacuum deposition apparatus.

Compound HT3 was vacuum-deposited on the ITO electrode of the glass substrate to form a first hole injection layer having a thickness of 3,500 Å, Compound HT-D1 was vacuum-deposited on the first hole injection layer to form a second hole injection layer having a thickness of 300 Å, TAPC was vacuum-deposited on the second hole injection layer to form an electron blocking layer having a thickness of 100 Å, thereby forming a hole transport region.

Compound H19 (first material), Compound E4 (second material), Compound M1-41 (third material), and $F_2$Irpic (light-emitting material) were co-deposited on the hole transport region, such that i) an amount of the third material was 10 percent by weight (wt %) based on 100 wt % of the emission layer, ii) an amount of the light-emitting material was 1 wt % based on 100% of the emission layer, iii) a total amount of the first material, the second material, and the third material was 99 wt % based on 100 wt % of the emission layer, and iv) a weight ratio of the first material to the second material was 5:5, thereby forming an emission layer having a thickness of 300 Å.

Compound ET3 was vacuum-deposited on the emission layer to form an electron transport layer having a thickness of 250 Å, ET-D1 (LiQ) was deposited on the electron transport layer to form an electron injection layer having a thickness of 5 Å, Al was deposited on the electron injection layer to form a second electrode (cathode) having a thickness of 1,000 Å, thereby completing the manufacture of an organic light-emitting device.

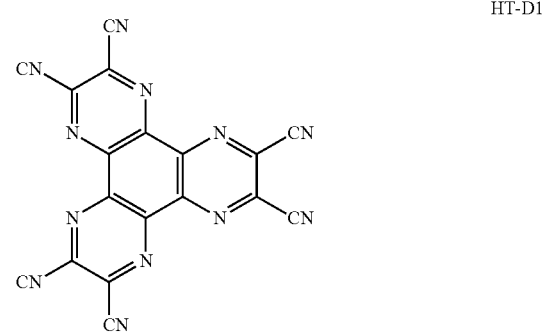

HT-D1

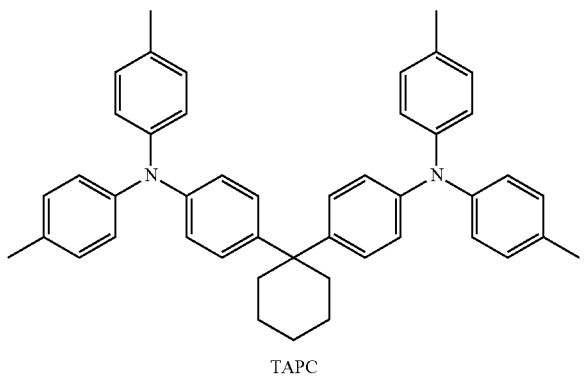

TAPC

ET3

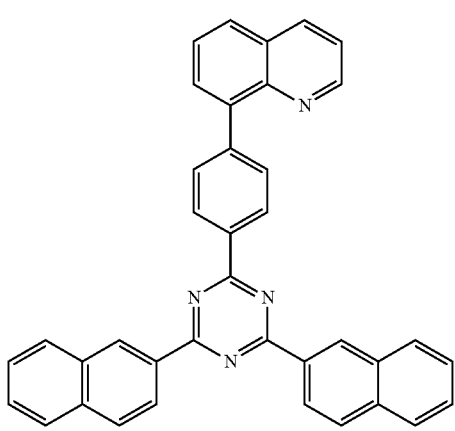

H19

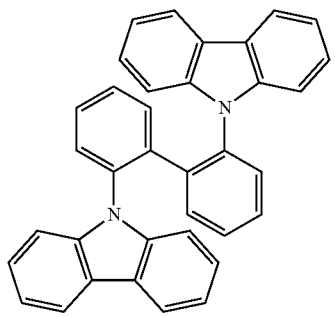

E4

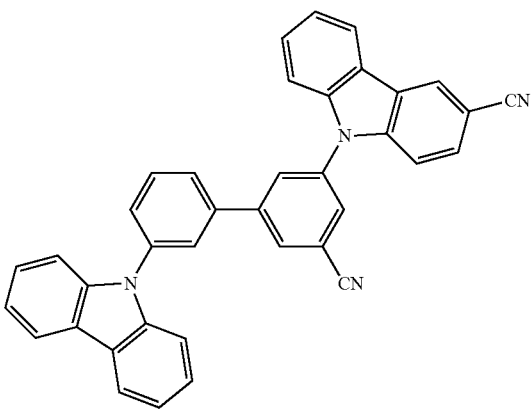

M1-41

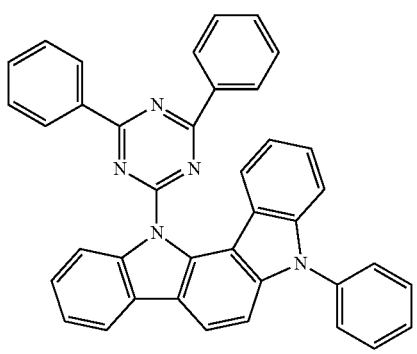

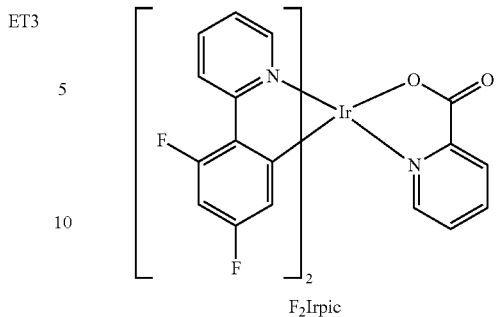

F$_2$Irpic

Example 2 and Comparative Examples A to F

Organic light-emitting devices were manufactured in the same manner as in Example 1, except that Compounds shown in Table 2 were each used as a first material, a second material, a third material, and a light-emitting material in forming an emission layer. In Comparative Examples E and F, a weight ratio of the first material (or, the second material) and the third material was 5:5.

Evaluation Example 2

Evaluation of Characteristics of Organic Light-Emitting Device

Lifespans ($T_{95}$) of the organic light-emitting devices manufactured according to Examples 1 and 2 and Comparative Examples A to F were evaluated, and results thereof are shown in Table 2. The lifespan ($T_{95}$) indicates an amount of time that lapsed when luminance was 95% of initial luminance (100%) (the measurement of the luminance was performed by using a luminance meter (Minolta Cs-1000A)). The lifespan ($T_{95}$) was indicated by a relative value of data of Comparative Example D.

TABLE 2

| | Emission layer | | | | Lifespan ($T_{95}$) |
|---|---|---|---|---|---|
| | First material | Second material | Third material | Light-emitting material | (at 1000 cd/m$^2$) (%) |
| Example 1 | H19 | E4 | M1-41 | F$_2$Irpic | 120 |
| Example 2 | H19 | E4 | M204 | F$_2$Irpic | 110 |
| Comparative Example A | H19 | E4 | A | F$_2$Irpic | 70 |
| Comparative Example B | H19 | E4 | B | F$_2$Irpic | 64 |
| Comparative Example C | H19 | E4 | C | F$_2$Irpic | 62 |
| Comparative Example D | H19 | E4 | — | F$_2$Irpic | 100 |
| Comparative Example E | H19 | — | M1-41 | F$_2$Irpic | 60 |
| Comparative Example F | — | E4 | M1-41 | F$_2$Irpic | 40 |

TABLE 2-continued

| | Emission layer | | | Lifespan (T₉₅) |
|---|---|---|---|---|
| First material | Second material | Third material | Light-emitting material | (at 1000 cd/m²) (%) |

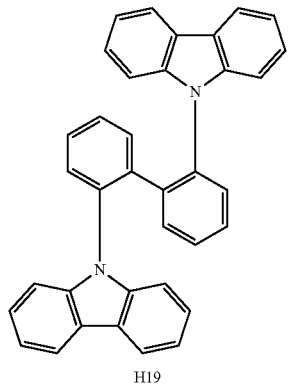

H19

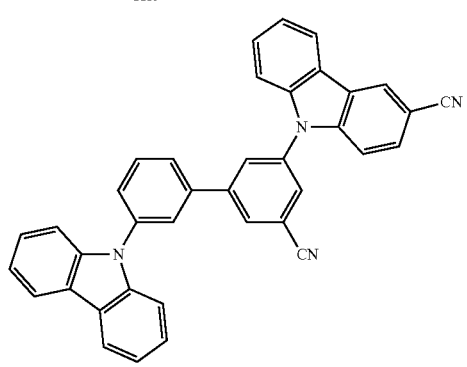

E4

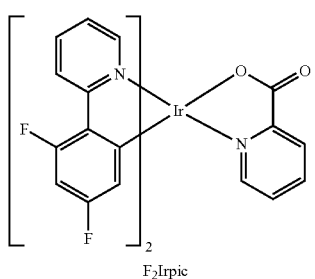

F₂Irpic

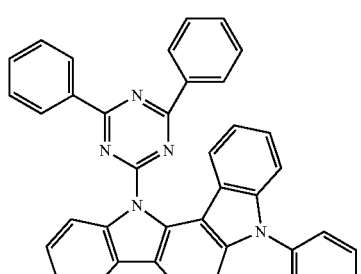

M1-41

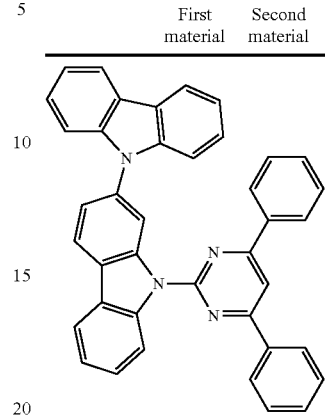

M204

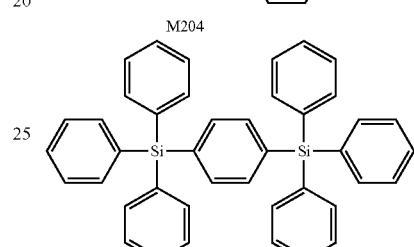

A

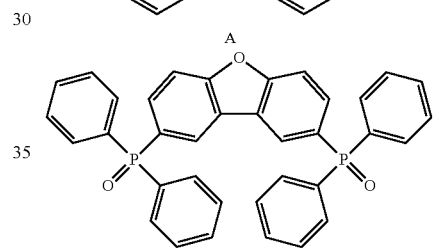

B

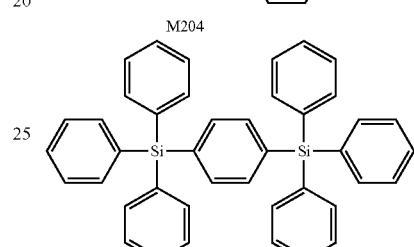

C

Referring to Table 2, it is confirmed that Examples 1 and 2 have an excellent lifespan, as compared with Comparative Examples A to F.

Examples 3 and 4

Organic light-emitting devices were manufactured in the same manner as in Example 1, except that Compounds shown in Table 3 were each used as a light-emitting material in forming an emission layer.

Evaluation Example 3

Evaluation of Characteristics of Organic Light-Emitting Device

Lifespans ($T_{95}$) of the organic light-emitting devices manufactured according to Examples 3 and 4 were evaluated in the same manner as in Evaluation Example 2, and results thereof are shown in Table 3. The lifespan ($T_{95}$) was indicated by a relative value of data of Comparative Example D.

TABLE 3

| | Emission layer | | | |
|---|---|---|---|---|
| | First material | Second material | Third material | Light-emitting material | Lifespan ($T_{95}$) (at 1000 cd/m$^2$) (%) |
| Example 3 | H19 | E4 | M1-41 | D1 | 143 |
| Example 4 | H19 | E4 | M204 | D1 | 122 |

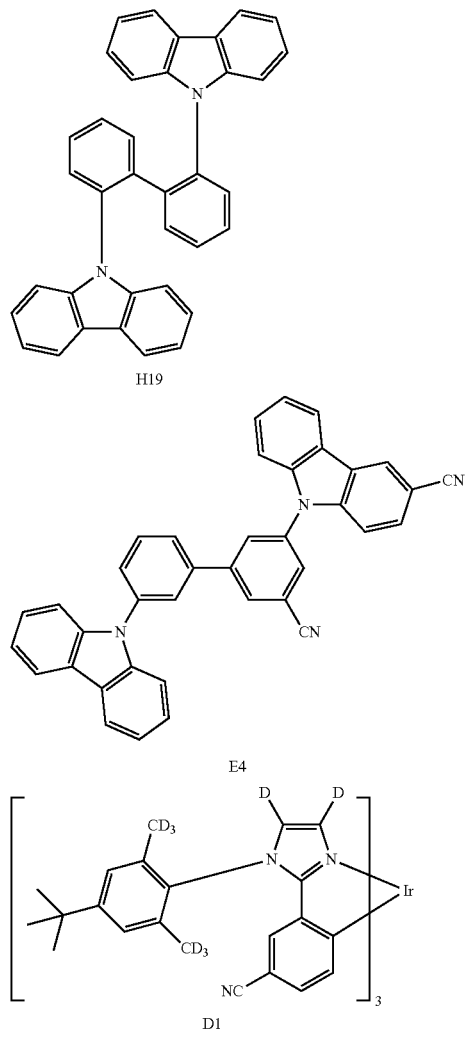

Referring to Table 3, it is confirmed that Examples 3 and 4 have an excellent lifespan, as compared with Comparative Examples A to F.

Since the organic light-emitting device includes the first material, the second material, the third material, and the light-emitting material in a predetermined condition, the organic light-emitting device may have a long lifespan.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the FIGURES, it will be understood by those of ordinary skill in the art that various changes in form and details may be made therein without departing from the spirit and scope of the present description as defined by the following claims.

What is claimed is:

1. An organic light-emitting device comprising:
a first electrode;
a second electrode facing the first electrode; and
an emission layer disposed between the first electrode and the second electrode,
wherein the emission layer comprises a first material, a second material, a third material, and a light-emitting material,
the first material does not comprise an electron transport moiety,
the second material comprises at least one electron transport moiety, the third material has reorganization energy of about 0.4 electron volts or more,
the first material, the second material, the third material, and the light-emitting material are different from one another, and
a ratio of a light-emitting component emitted from the light-emitting material to a total of light-emitting components emitted from the emission layer is about 90% or more,
wherein the second material comprises at least one of a compound represented by Formula E-1(1), a compound represented by Formula E-1(2), and a compound represented by Formula E-1(3):

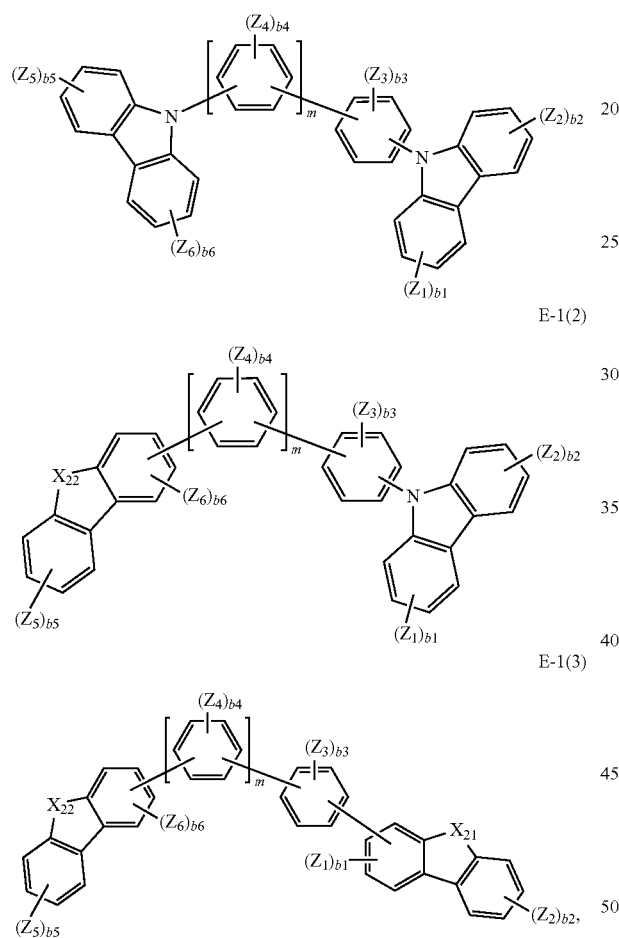

wherein, in Formulae E-1(1) to E-1(3),
$Z_1$ to $Z_6$ are each independently:
hydrogen, deuterium, or a cyano group (CN);
a $C_1$-$C_{20}$ alkyl group, a phenyl group, a biphenyl group, a terphenyl group, a dibenzofuranyl group, or a dibenzothiophenyl group, each unsubstituted or substituted with at least one selected from deuterium, a cyano group, an unsubstituted phenyl group, and an unsubstituted biphenyl group,
b1 to b6 are each independently 1, 2, or 3,
at least one of groups $Z_1$ in the number of b1, groups $Z_2$ in the number of b2, groups $Z_3$ in the number of b3, groups $Z_4$ in the number of b4, groups $Z_5$ in the number of b5, and groups $R_6$ in the number of b6 is a cyano group, $X_{21}$ and $X_{22}$ are each independently O or S, and
m is 0 or 1,
provided that when the second material comprises a compound represented by Formula E-1(1), then m is 1,
wherein the third material comprises a compound represented by Formula 11:

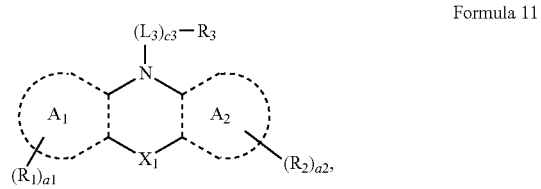

Formula 11 wherein, in Formula 11,
$X_1$ is a single bond, $N$-$[(L_4)_{c4}$-$R_4]$, $C(R_5)(R_6)$, O, or S,
$A_1$ and $A_2$ are each independently a benzene group, a naphthalene group, an indene group, an indole group, a benzofuran group, a benzothiophene group, a benzosilole group, a fluorene group, a carbazole group, a dibenzofuran group, a dibenzothiophene group, or a dibenzosilole group,
$L_3$ and $L_4$ are each independently selected from a single bond, a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group,
c3 and c4 are each independently an integer from 1 to 4,
$R_1$ to $R_6$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —$Si(Q_1)(Q_2)(Q_3)$, —$N(Q_4)(Q_5)$, and —$B(Q_6)(Q_7)$,
a1 and a2 are each independently an integer from 0 to 10,
provided that $L_3$ is not a dibenzofuranylene group and $R_3$ is not a substituted triazine group,
at least one substituent of the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group is selected from:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{14}$)($Q_{15}$), and —B($Q_{16}$)($Q_{17}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{24}$)($Q_{25}$), and —B($Q_{26}$)($Q_{27}$); and —Si($Q_{31}$)($Q_{32}$)($Q_{33}$), —N($Q_{34}$)($Q_{35}$), and —B($Q_{36}$)($Q_{37}$), at least one substituent of the substituted $C_1$-$C_{60}$ alkyl group, the substituted $C_2$-$C_{60}$ alkenyl group, the substituted $C_2$-$C_{60}$ alkynyl group is selected from:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, and a $C_1$-$C_{60}$ alkoxy group;

a $C_1$-$C_{60}$ alkoxy group substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{14}$)($Q_{15}$), and —B($Q_{16}$)($Q_{17}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{24}$)($Q_{25}$), and —B($Q_{26}$)($Q_{27}$); —Si($Q_{31}$)($Q_{32}$)($Q_{33}$), —N($Q_{34}$)($Q_{35}$), and —B($Q_{36}$)($Q_{37}$), and $Q_1$ to $Q_7$, $Q_{11}$ to $Q_{17}$, $Q_{21}$ to $Q_{27}$, and $Q_{31}$ to $Q_{37}$ are each independently selected from hydrogen, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group wherein the light-emitting material comprises F2Irpic, an organometallic compound represented by Formula 1, or a combination thereof:

Formula 1

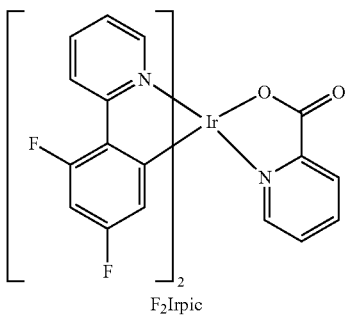

F2Irpic

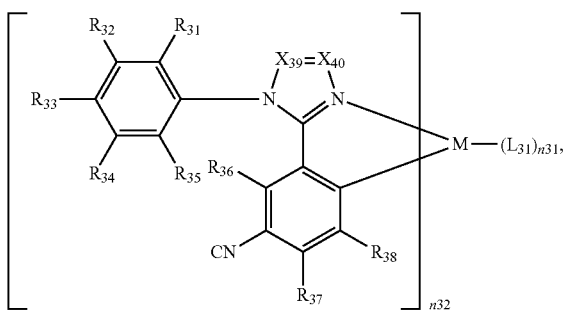

wherein, in Formula 1,

M is selected from a first-row transition metal, a second-row transition metal, and a third-row transition metal, $L_{31}$ is selected from a monodentate ligand and a bidentate ligand, n31 is 0, 1, 2, 3, or 4, wherein, when n31 is two or more, two or more groups $L_{31}$ are identical to or different from each other, n32 is 1, 2, or 3, $X_{39}$ is N or $C(R_{39})$, and $X_{40}$ is N or $C(R_{40})$, $R_{31}$ to $R_{35}$ are each independently selected from hydrogen, deuterium, a hydroxyl group, an amino group, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —$CD_3$, —$CD_2H$, —$CDH_2$, a hydroxyl group, an amino group, an amidino group, a $C_1$-$C_{10}$ alkyl group, a cyclopentyl group, a cyclohexyl group, a cycloheptyl group, a 8yclooctyl group, an adamantanyl group, a norbornanyl group, a norbornenyl group, a cyclopentenyl group, a cyclohexenyl group, a cycloheptenyl group, a phenyl group, a biphenyl group, a naphthyl group, a pyridinyl group, and a pyrimidinyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, 9yclooctyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each unsubstituted;

a cyclopentyl group, a cyclohexyl group, a cycloheptyl group, a 9yclooctyl group, an adamantanyl group, a norbornanyl group, a norbornenyl group, a cyclopentenyl group, a cyclohexenyl group, a cycloheptenyl group, a phenyl group, a biphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, 9yclooctyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from deuterium, —$CD_3$, —$CD_2H$, —$CDH_2$, a hydroxyl group, an amino group, a $C_1$-$C_{20}$ alkyl group, a $C_1$-$C_{20}$ alkoxy group, a cyclopentyl group, a cyclohexyl group, a cycloheptyl group, a 9yclooctyl group, an adamantanyl group, a norbornanyl group, a norbornenyl group, a cyclopentenyl group, a cyclohexenyl group, a cycloheptenyl group, a phenyl group, a biphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; and
—$N(Q_1)(Q_2)$, —$Si(Q_3)(Q_4)(Q_5)$, —$B(Q_6)(Q_7)$, and —$P(=O)(Q_8)(Q_9)$, and $Q_1$ to $Q_9$ may each independently be selected from:
—$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$, —$CHDCD_2H$, —$CHDCDH_2$, —$CHDCD_3$, —$CD_2CD_3$, —$CD_2CD_2H$, and —$CD_2CDH_2$;

an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group; and an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group, each substituted with at least one selected from deuterium, a $C_1$-$C_{10}$ alkyl group, and a phenyl group, $R_{36}$ to $R_{40}$ are each independently selected from hydrogen, deuterium, —F, —Cl, —Br, —I, —$SF_5$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —$N(Q_1)(Q_2)$, —$Si(Q_3)(Q_4)(Q_5)$, —$B(Q_6)(Q_7)$, and —$P(=O)(Q_8)(Q_9)$, at least one of $R_{31}$, $R_{33}$, and $R_{35}$ in Formula 1 is independently:

deuterium; or a $C_1$-$C_{20}$ alkyl group, a phenyl group, a biphenyl group, or a terphenyl group, each substituted with deuterium, two or more neighboring groups selected from $R_{31}$ to $R_{40}$ are optionally linked to form a substituted or unsubstituted $C_5$-$C_{30}$ carbocyclic group or a substituted or unsubstituted $C_2$-$C_{30}$ heterocyclic group, at least one substituent of the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group is selected from:

deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{11})(Q_{12})$, —$Si(Q_{13})(Q_{14})(Q_{15})$, —$B(Q_{16})(Q_{17})$, and —$P(=O)(Q_{18})(Q_{19})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{21})(Q_{22})$, —$Si(Q_{23})(Q_{24})(Q_{25})$, —$B(Q_{26})(Q_{27})$, and —$P(=O)(Q_{28})(Q_{29})$; and —$N(Q_{31})(Q_{32})$, —$Si(Q_{33})(Q_{34})(Q_{35})$, —$B(Q_{36})(Q_{37})$, and —$P(=O)(Q_{38})(Q_{39})$, at least one substituent of the substituted $C_1$-$C_{60}$ alkyl group, the substituted $C_2$-$C_{60}$ alkenyl group, the substituted $C_2$-$C_{60}$ alkynyl group is selected from:

deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, and a $C_1$-$C_{60}$ alkoxy group;

a $C_1$-$C_{60}$ alkoxy group substituted with at least one selected from deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N(Q$_{11}$)(Q$_{12}$), —Si(Q$_{13}$)(Q$_{14}$)(Q$_{15}$), —B(Q$_{16}$)(Q$_{17}$), and —P(=O)(Q$_{18}$)(Q$_{19}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N(Q$_{21}$)(Q$_{22}$), —Si(Q$_{23}$)(Q$_{24}$)(Q$_{25}$), —B(Q$_{26}$)(Q$_{27}$), and —P(=O)(Q$_{28}$)(Q$_{29}$); and —N(Q$_{31}$)(Q$_{32}$), —Si(Q$_{33}$)(Q$_{34}$)(Q$_{35}$), —B(Q$_{36}$)(Q$_{37}$), and —P(=O)(Q$_{38}$)(Q$_{39}$) and Q$_1$ to Q$_9$, Q$_{11}$ to Q$_{19}$, Q$_{21}$ to Q$_{29}$, and Q$_{31}$ to Q$_{39}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with at least one selected from a $C_1$-$C_{60}$ alkyl group and a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

2. The organic light-emitting device of claim 1, wherein the first material comprises at least one π electron-depleted nitrogen-free cyclic group and does not comprise an electron transport moiety, the second material comprises at least one π electron-depleted nitrogen-free cyclic group and at least one electron transport moiety, and the electron transport moiety is selected from a cyano group, a π electron-depleted nitrogen-containing cyclic group, and a group represented by one of the following Formulae:

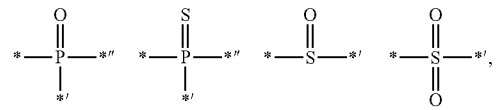

wherein *, *', and *" in the Formulae each indicate a binding site to a neighboring atom.

3. The organic light-emitting device of claim 1, wherein the first material comprises at least one of a compound represented by Formula H-1(1), a compound represented by Formula H-1(2), and a compound represented by Formula H-1(3):

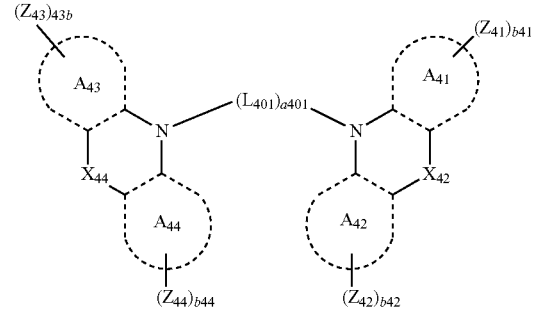

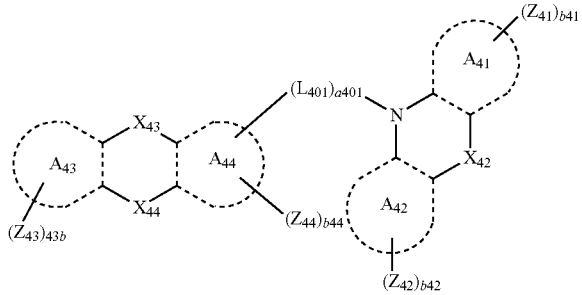

-continued

H-1(3)

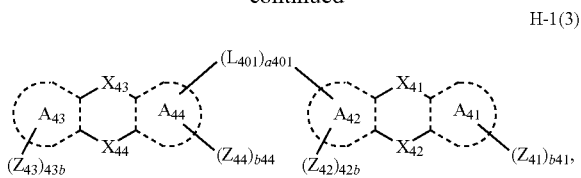

wherein, in Formulae H-1(1) to H-1(3), $A_{41}$ to $A_{44}$ are each independently a benzene group, a naphthalene group, an indene group, an indole group, a benzofuran group, a benzothiophene group, a benzosilole group, a fluorene group, a carbazole group, a dibenzofuran group, a dibenzothiophene group, or a dibenzosilole group, $X_{41}$ is $N-[(L_{411})_{c411}-Z_{411}]$, $C(Z_{415})(Z_{416})$, O, or S, $X_{42}$ is a single bond, $N-[(L_{412})_{c412}-Z_{412}]$, $C(Z_{417})(Z_{418})$, O, or S, $X_{43}$ is $N-[(L_{413})_{c413}-Z_{413}]$, $C(Z_{419})(Z_{420})$, O, or S, $X_{44}$ is a single bond, $N-[(L_{414})_{c414}-Z_{414}]$, $C(Z_{421})(Z_{422})$, O, or S, $L_{401}$ and $L_{411}$ to $L_{414}$ are each independently selected from:

a single bond; and a π electron-depleted nitrogen-free cyclic group, unsubstituted or substituted with at least one selected from deuterium, a $C_1$-$C_{10}$ alkyl group, a $C_1$-$C_{10}$ alkoxy group, a phenyl group, a naphthyl group, a fluorenyl group, a carbazolyl group, a dibenzofuranyl group, a dibenzothiophenyl group, a triphenylenyl group, a biphenyl group, a terphenyl group, a tetraphenyl group, and $-Si(Q_{401})(Q_{402})(Q_{403})$, a401 and c411 to c414 are each independently an integer from 1 to 10, wherein, when a401 is two or more, two or more groups L401 are identical to or different from each other, when c411 is two or more, two or more groups L411 are identical to or different from each other, when c412 is two or more, two or more groups $L_{412}$ are identical to or different from each other, when c413 is two or more, two or more groups $L_{413}$ are identical to or different from each other, and when c414 is two or more, two or more groups $L_{414}$ are identical to or different from each other, $Z_{41}$ to $Z_{44}$ and $Z_{411}$ to $Z_{422}$ are each independently selected from:

hydrogen, deuterium, a $C_1$-$C_{10}$ alkyl group, and a $C_1$-$C_{10}$ alkoxy group; and a π electron-depleted nitrogen-free cyclic group, unsubstituted or substituted with at least one selected from deuterium, a $C_1$-$C_{10}$ alkyl group, a $C_1$-$C_{10}$ alkoxy group, a phenyl group, a naphthyl group, a fluorenyl group, a carbazolyl group, a dibenzofuranyl group, a dibenzothiophenyl group, a triphenylenyl group, a biphenyl group, a terphenyl group, a tetraphenyl group, and $-Si(Q_{401})(Q_{402})(Q_{403})$, b41 to b44 are each independently 1, 2, 3, or 4, and $Q_{401}$ to $Q_{403}$ are each independently hydrogen, deuterium, a $C_1$-$C_{10}$ alkyl group, a $C_1$-$C_{10}$ alkoxy group, a phenyl group, a naphthyl group, a fluorenyl group, a carbazolyl group, a dibenzofuranyl group, a dibenzothiophenyl group, a triphenylenyl group, a biphenyl group, a terphenyl group, or a tetraphenyl group.

4. The organic light-emitting device of claim 3, wherein $L_{401}$ and $L_{411}$ to $L_{414}$ are each independently selected from:

a single bond; and a benzene group, a fluorene group, a dibenzofuran group, a dibenzothiophene group, a carbazole group, a dibenzosilole group, an indenocarbazole group, an indolocarbazole group, a benzofurocarbazole group, a benzothienocarbazole group, a benzosilolocarbazole group, an acridine group, or a dihydroacridine group, each unsubstituted or substituted with at least one selected from deuterium, a $C_1$-$C_{10}$ alkyl group, a $C_1$-$C_{10}$ alkoxy group, a phenyl group, a naphthyl group, a fluorenyl group, a carbazolyl group, a dibenzofuranyl group, a dibenzothiophenyl group, a triphenylenyl group, a biphenyl group, a terphenyl group, and a tetraphenyl group, $Z_{41}$ to $Z_{44}$ and $Z_{411}$ to $Z_{422}$ are each independently selected from:

hydrogen, deuterium, a $C_1$-$C_{10}$ alkyl group, and a $C_1$-$C_{10}$ alkoxy group; and a phenyl group, a biphenyl group, a terphenyl group, a tetraphenyl group, a fluorenyl group, a dibenzocarbazolyl group, a dibenzofuranyl group, a dibenzothiophenyl group, a carbazolyl group, a dibenzosilolyl group, an indenocarbazolyl group, an indolocarbazolyl group, a benzofurocarbazolyl group, a benzothienocarbazolyl group, a benzosilolocarbazolyl group, an acridinyl group, or a dihydroacridinyl group, each unsubstituted or substituted with at least one selected from deuterium, a $C_1$-$C_{10}$ alkyl group, a $C_1$-$C_{10}$ alkoxy group, a phenyl group, a naphthyl group, a fluorenyl group, a carbazolyl group, a dibenzofuranyl group, a dibenzothiophenyl group, a triphenylenyl group, a biphenyl group, a terphenyl group, and a tetraphenyl group.

5. The organic light-emitting device of claim 1, wherein the second material comprises at least one cyano group.

6. The organic light-emitting device of claim 1, wherein, in Formulae E-1(1) to E-1(3), at least one of groups $Z_1$ in the number of b1 and groups $Z_2$ in the number of b2 is a cyano group, at least one of groups $Z_3$ in the number of b3 and groups $Z_4$ in the number of b4 is a cyano group, at least one of groups $Z_5$ in the number of b5 and groups $Z_6$ in the number of b6 is a cyano group, at least one of groups $Z_1$ in the number of b1 and groups $Z_2$ in the number of b2 is a cyano group, and at least one of groups $Z_3$ in the number of b3 and groups $Z_4$ in the number of b4 is a cyano group, at least one of groups $Z_1$ in the number of b1 and groups $Z_2$ in the number of b2 is a cyano group, and at least one of groups $Z_5$ in the number of b5 and groups $Z_6$ in the number of b6 is a cyano group, at least one of groups $Z_3$ in the number of b3 and groups $Z_4$ in the number of b4 is a cyano group, and at least one of groups $Z_5$ in the number of b5 and groups $Z_6$ in the number of b6 is a cyano group, or at least one of groups $Z_1$ in the number of b1 and groups $Z_2$ in the number of b2 is a cyano group, at least one of groups $Z_3$ in the number of b3 and groups $Z_4$ in the number of b4 is a cyano group, and at least one of groups $Z_5$ in the number of b5 and groups $Z_6$ in the number of b6 is a cyano group.

7. The organic light-emitting device of claim 1, wherein a group represented by

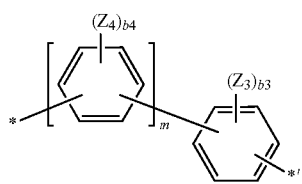
in Formulae E-1(1) to E-1(3) is one of groups represented by Formulae PO1 to PO25, PM1 to PM25, PP1 to PP18, MO1 to MO37, MM1 to MM37, MP1 to MP25, OO1 to OO37, OM1 to OM37, OP1 to OP25, O1 to O16, M1 to M16, and P1 to P9:
PO1
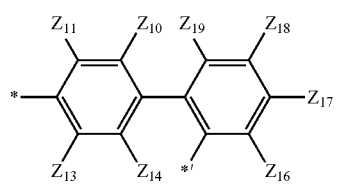
PO2
PO3
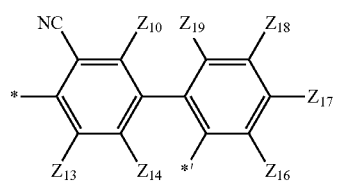
PO4
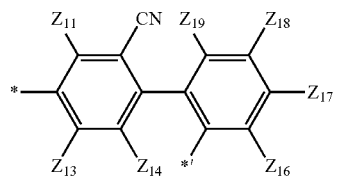
PO5
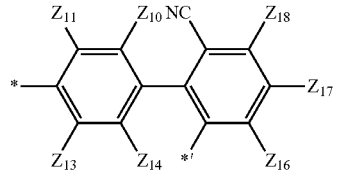
PO6
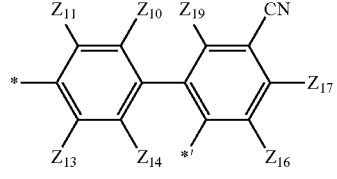
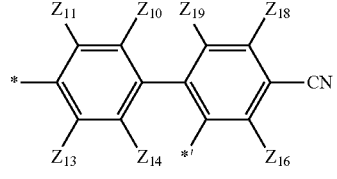
PO7
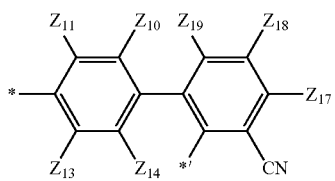
PO8
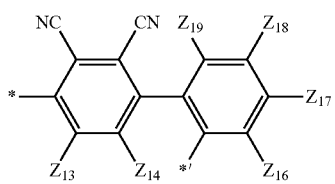
PO9
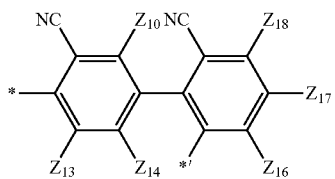
PO10
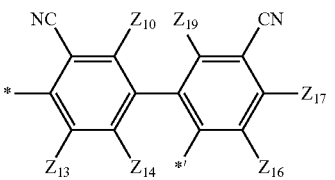
PO11
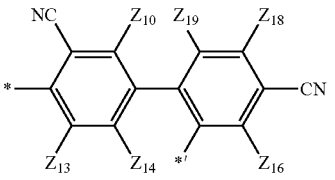
PO12
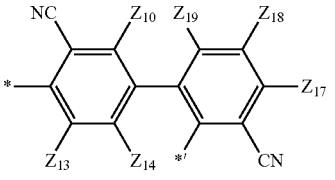
PO13
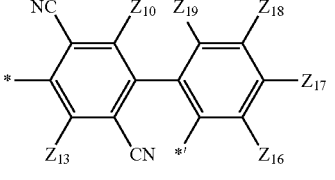
PO14
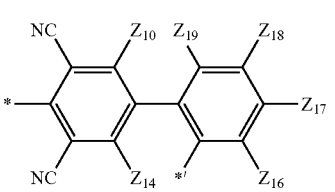

215
-continued
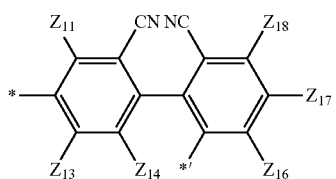
PO15
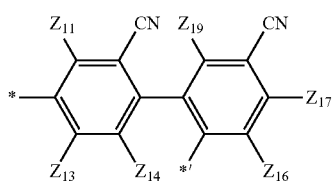
PO16
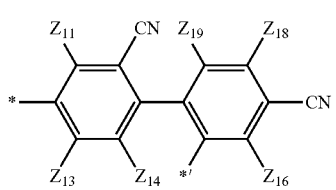
PO17
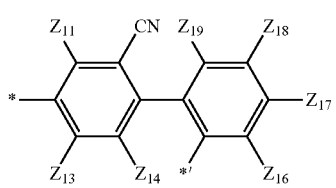
PO18
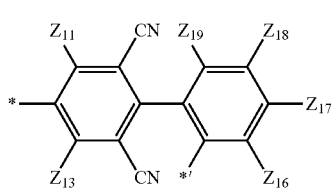
PO19
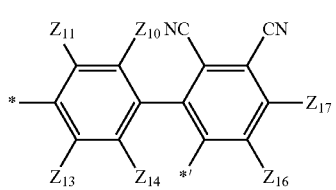
PO20
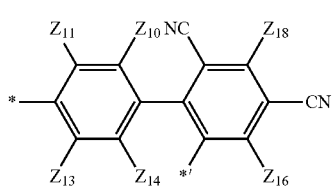
PO21
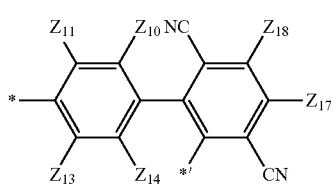
PO22
216
-continued
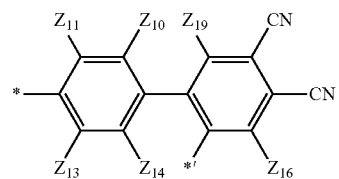
PO23
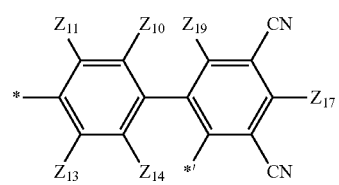
PO24
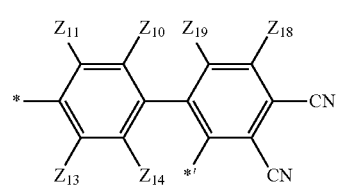
PO25
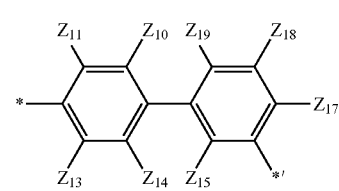
PM1
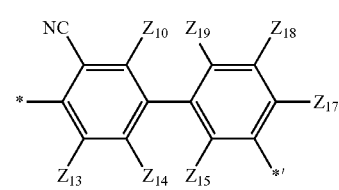
PM2
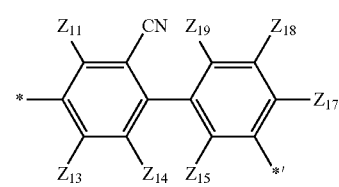
PM3
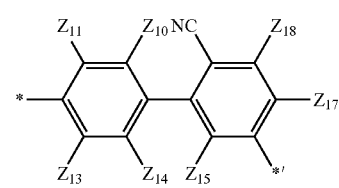
PM4
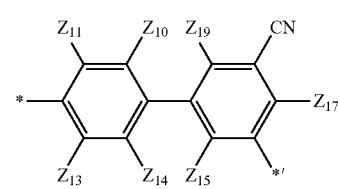
PM5

-continued
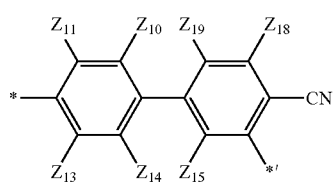
PM6
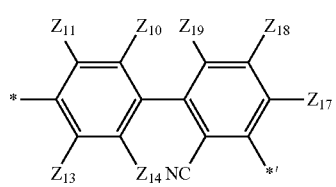
PM7
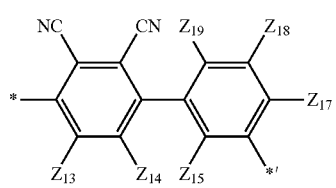
PM8
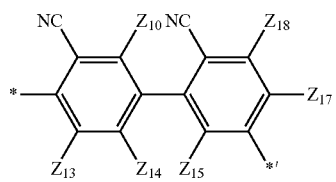
PM9
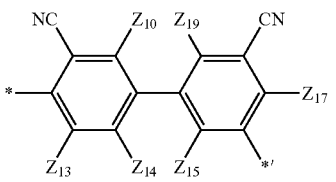
PM10
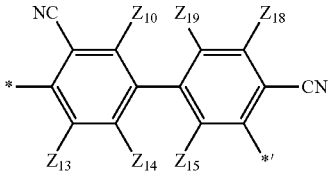
PM11
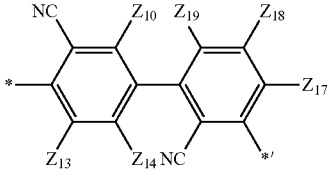
PM12
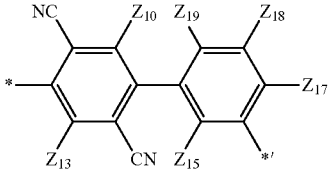
PM13
-continued
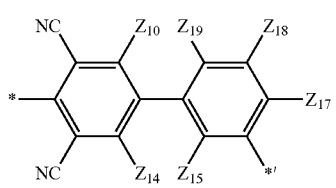
PM14
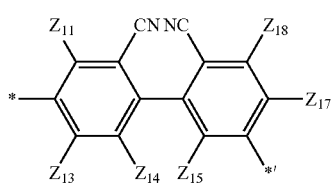
PM15
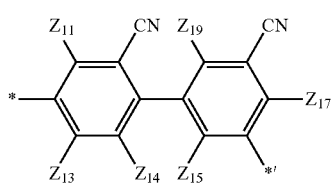
PM16
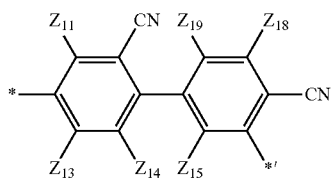
PM17
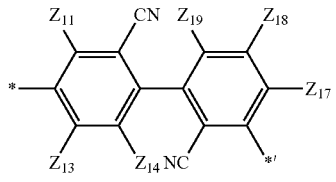
PM18
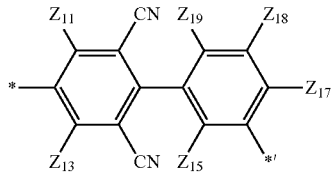
PM19
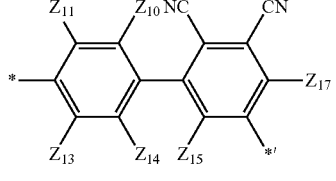
PM20
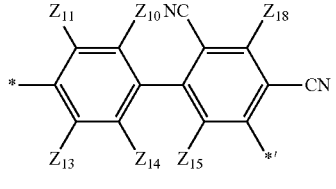
PM21

PM22 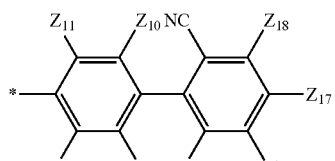
PM23 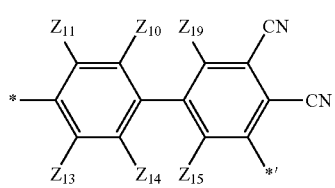
PM24 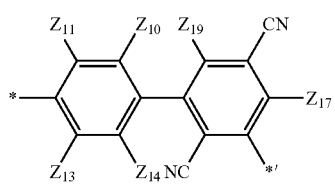
PM25 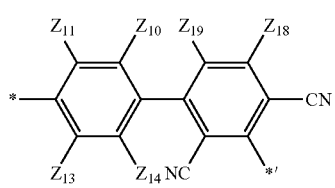
PP1 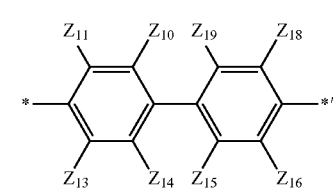
PP2 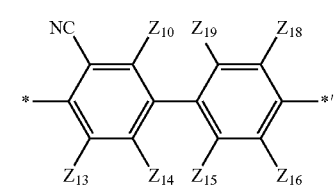
PP3 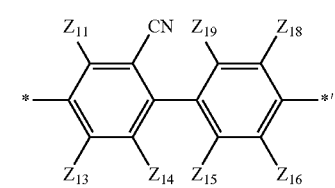
PP4 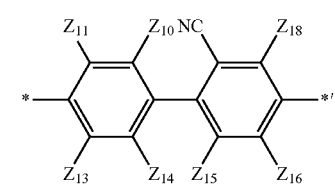
PP5 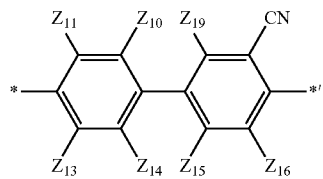
PP6 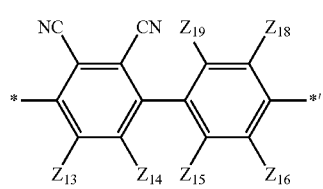
PP7 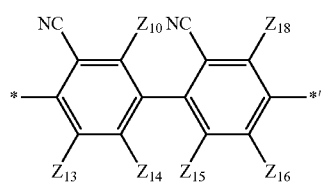
PP8 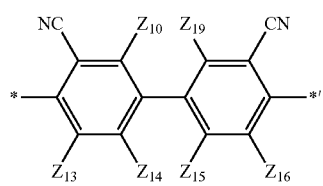
PP9 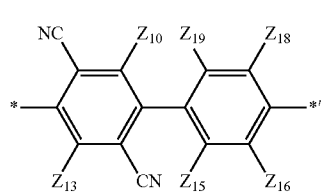
PP10 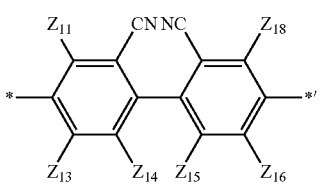
PP11 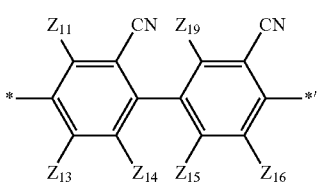
PP12 

US 12,069,879 B2
221
-continued
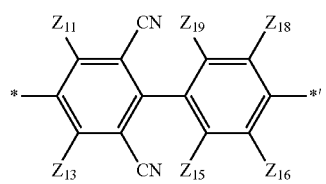
PP13
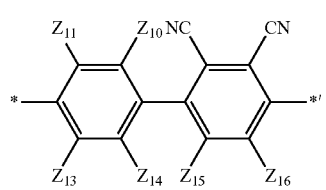
PP14
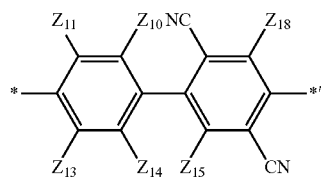
PP15
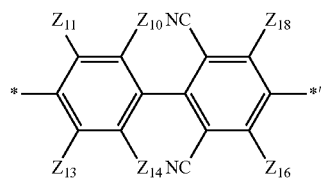
PP16
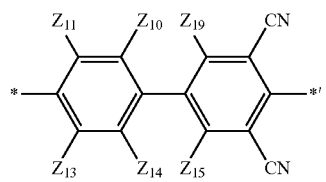
PP17
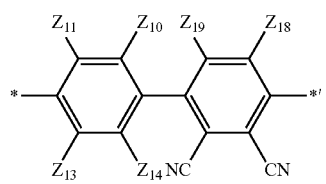
PP18
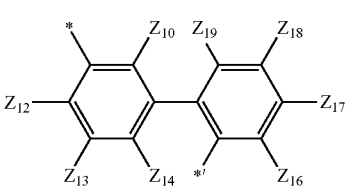
MO1
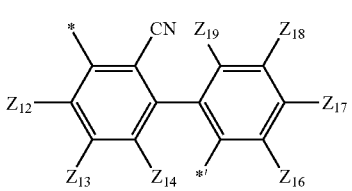
MO2
222
-continued
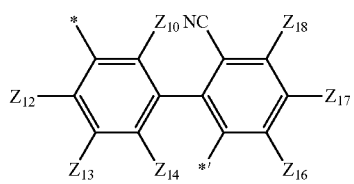
MO3
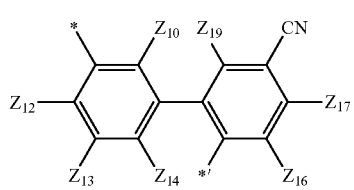
MO4
MO5
MO6
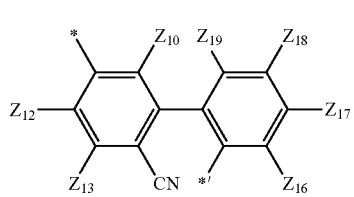
MO7
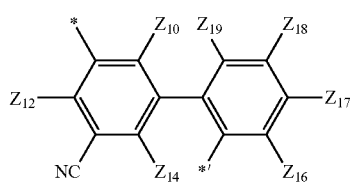
MO8
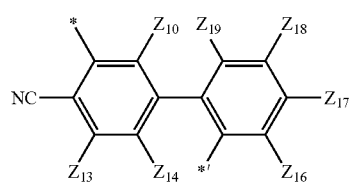
MO9
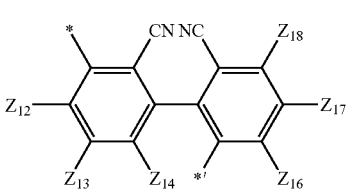
MO10

-continued
MO11 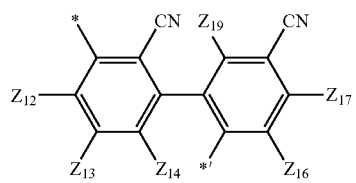
MO12 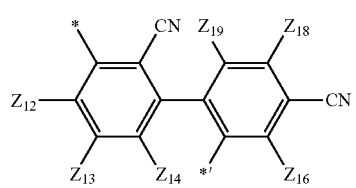
MO13 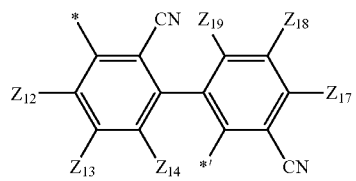
MO14 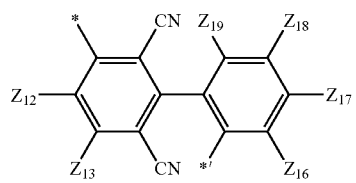
MO15 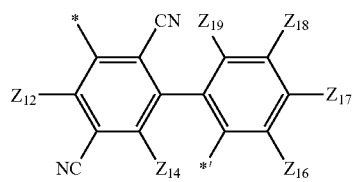
MO16 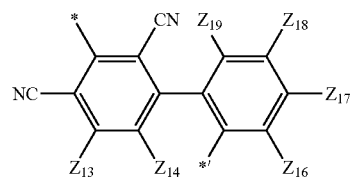
MO17 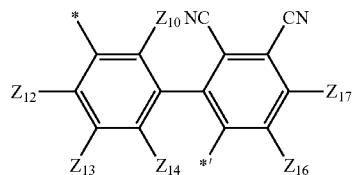
MO18 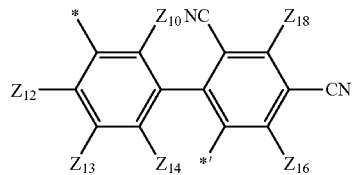
-continued
MO19 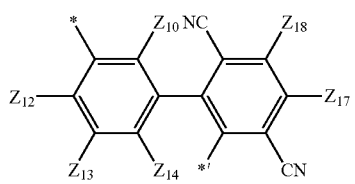
MO20 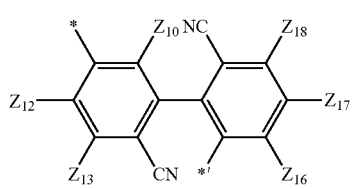
MO21 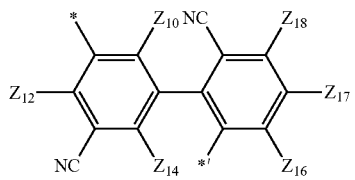
MO22 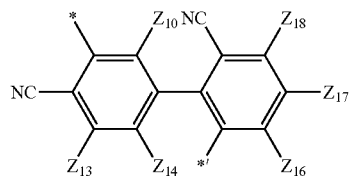
MO23 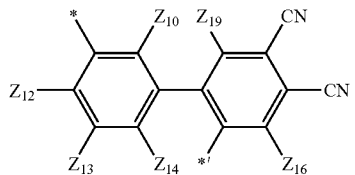
MO24 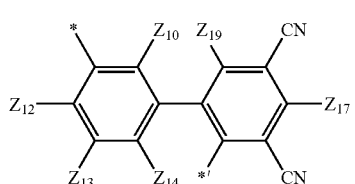
MO25 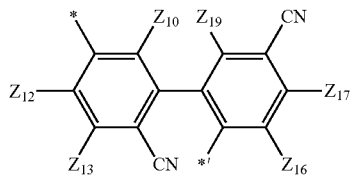
MO26 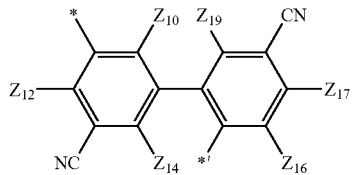

-continued
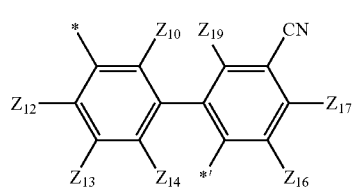
MO27
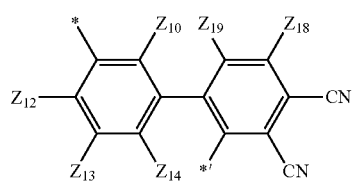
MO28
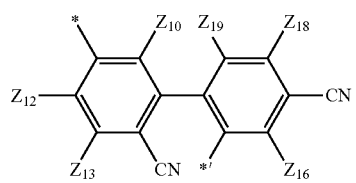
MO29
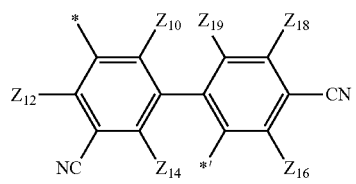
MO30
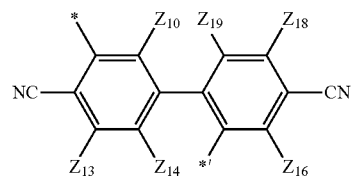
MO31
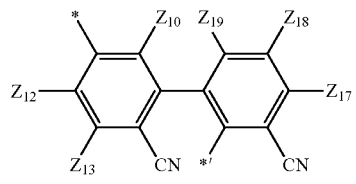
MO32
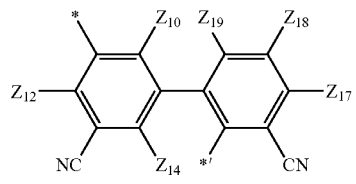
MO33
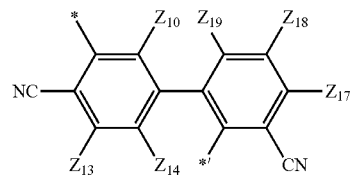
MO34
-continued
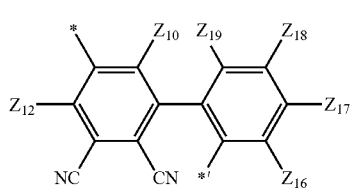
MO35
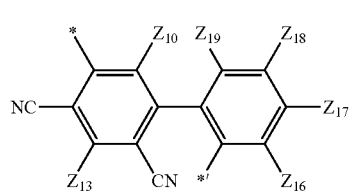
MO36
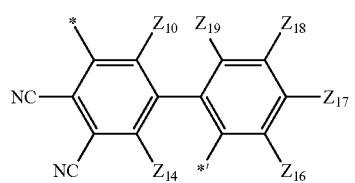
MO37
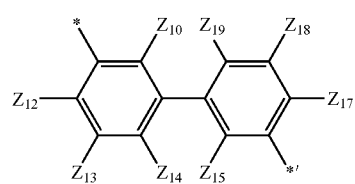
MM1
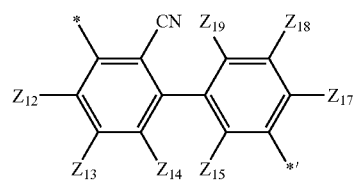
MM2
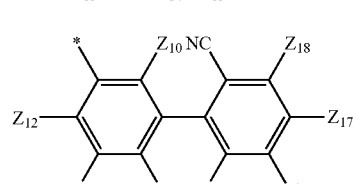
MM3
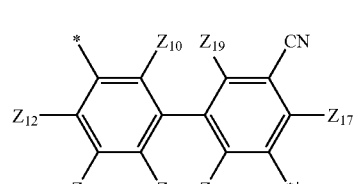
MM4
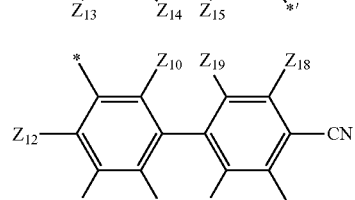
MM5

227
-continued

MM6, MM7, MM8, MM9, MM10, MM11, MM12, MM13

228
-continued

MM14, MM15, MM16, MM17, MM18, MM19, MM20, MM21

| | |
|---|---|
| 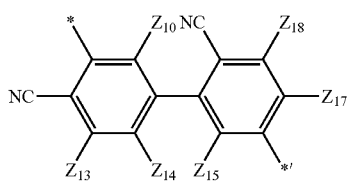 MM22 | 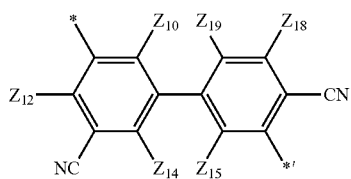 MM30 |
| 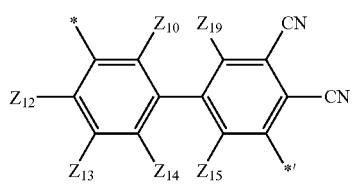 MM23 | 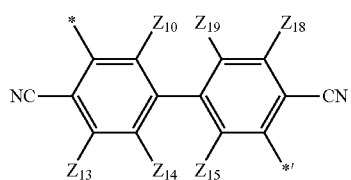 MM31 |
| 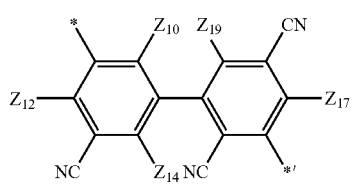 MM24 | 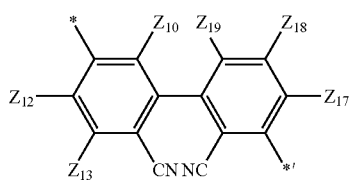 MM32 |
| 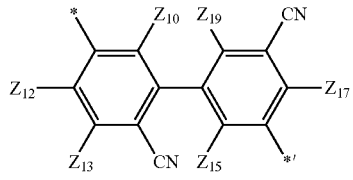 MM25 | 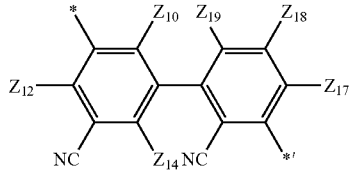 MM33 |
| 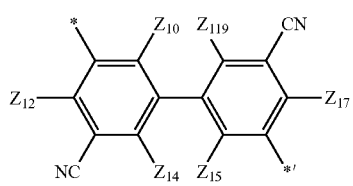 MM26 | 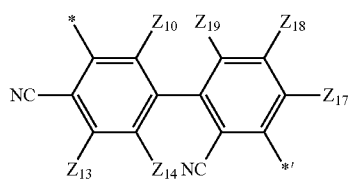 MM34 |
| 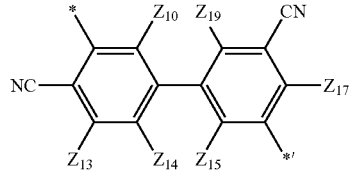 MM27 | 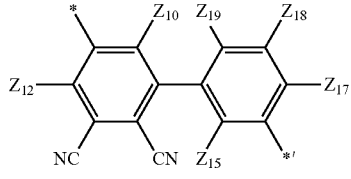 MM35 |
| 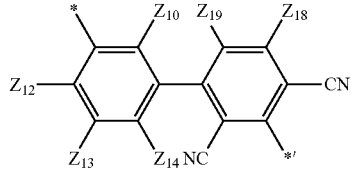 MM28 | 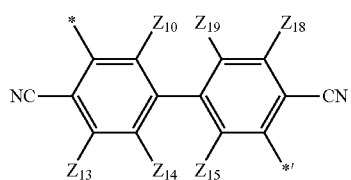 MM36 |
| 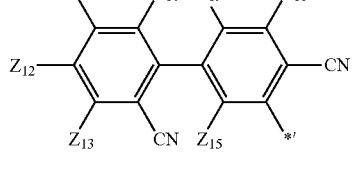 MM29 | 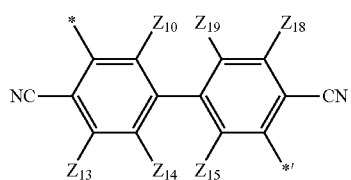 MM37 |

MP1 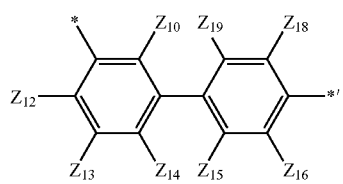
MP2 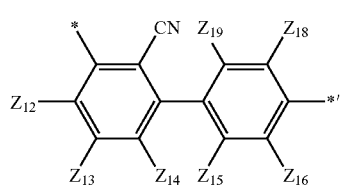
MP3 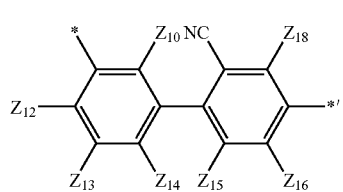
MP4 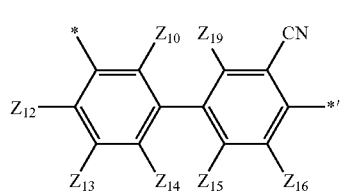
MP5 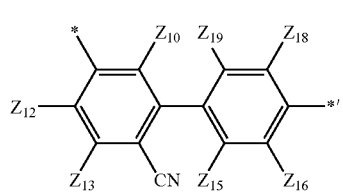
MP6 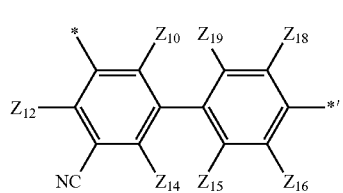
MP7 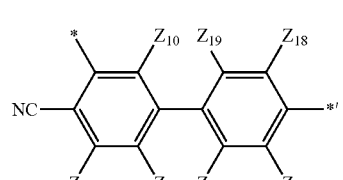
MP8 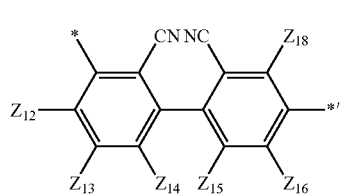
MP9 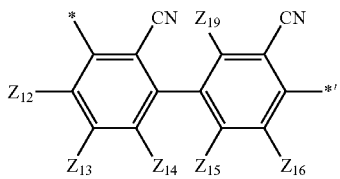
MP10 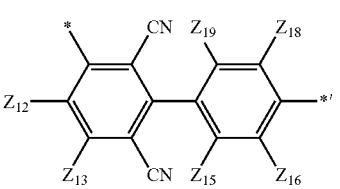
MP11 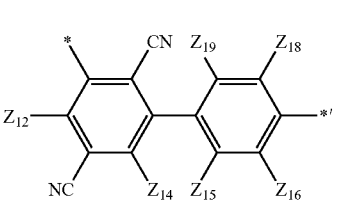
MP12 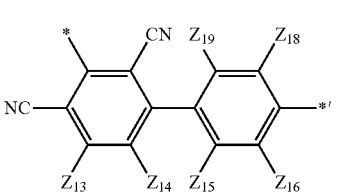
MP13 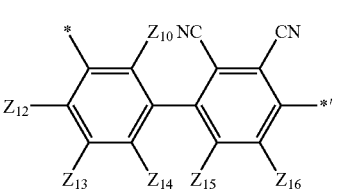
MP14 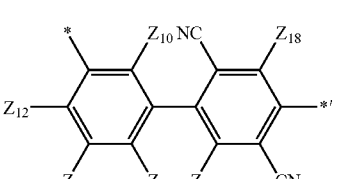
MP15 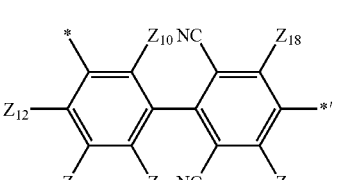
MP16 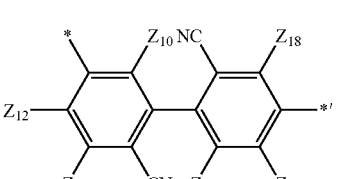

MP17 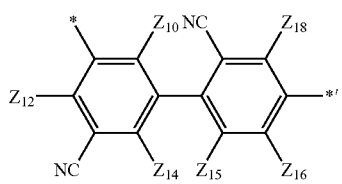
MP18 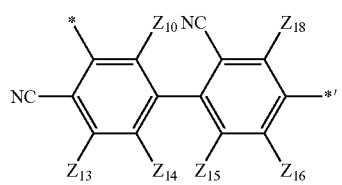
MP19 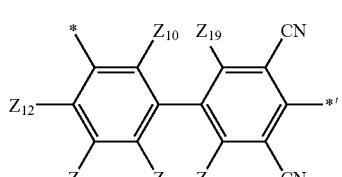
MP20 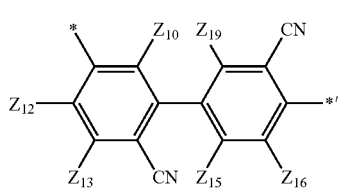
MP21 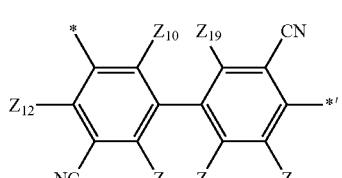
MP22 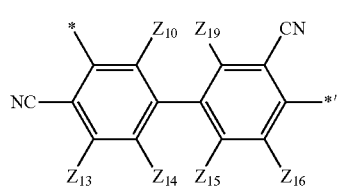
MP23 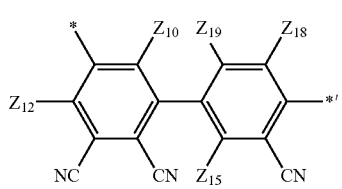
MP24 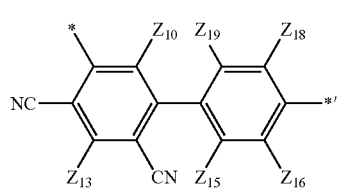
MP25 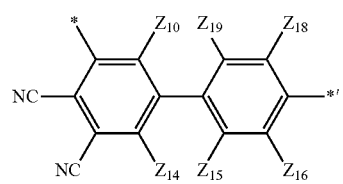
OO1 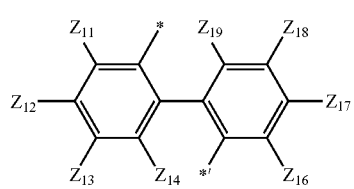
OO2 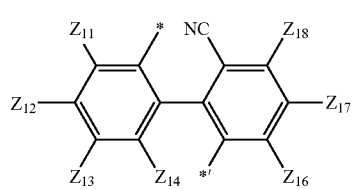
OO3 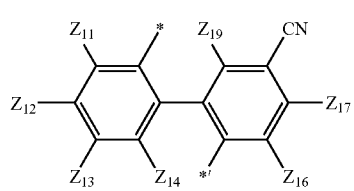
OO4 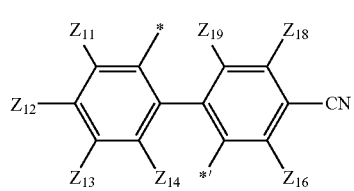
OO5 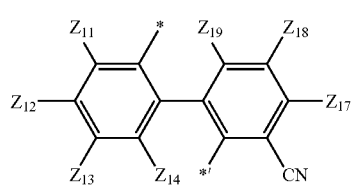
OO6 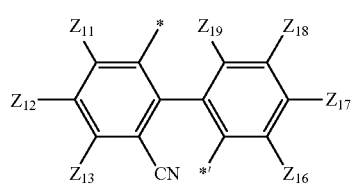
OO7 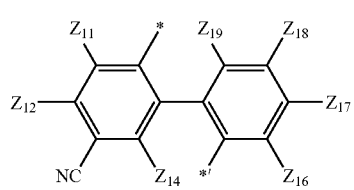

OO8
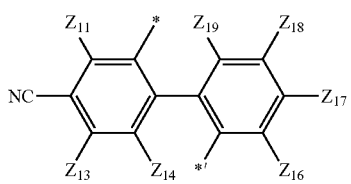
OO9
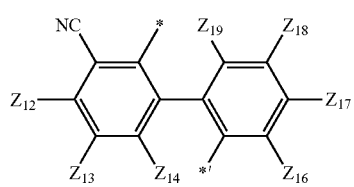
OO10
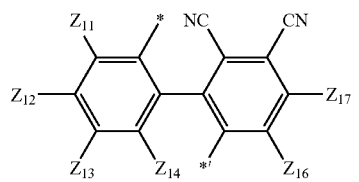
OO11
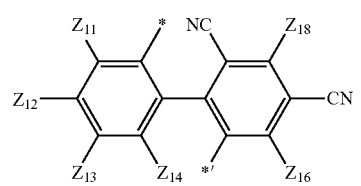
OO12
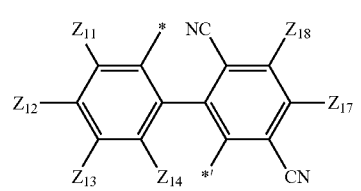
OO13
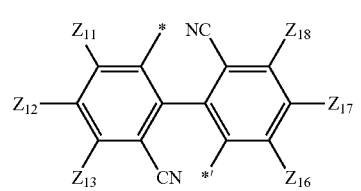
OO14
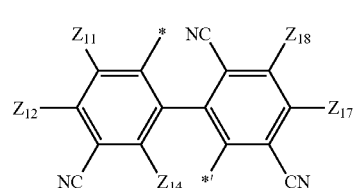
OO15
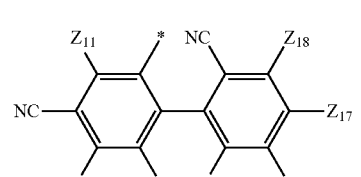
OO16
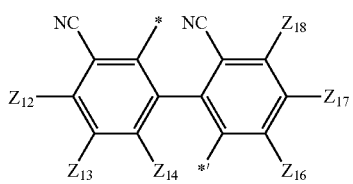
OO17
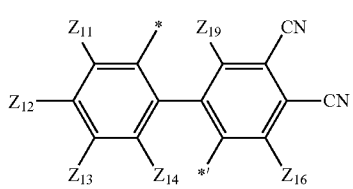
OO18
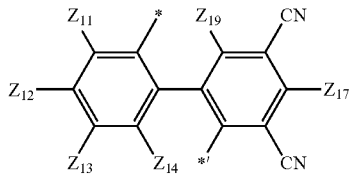
OO19
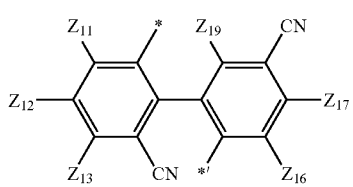
OO20
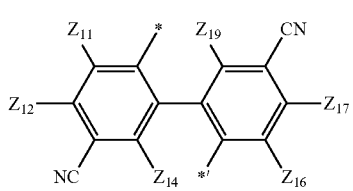
OO21
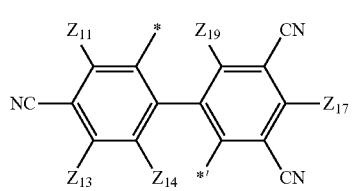
OO22
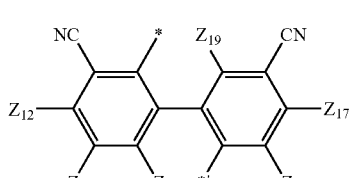
OO23
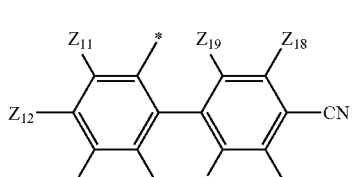

OO24 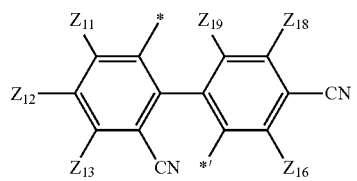
OO25 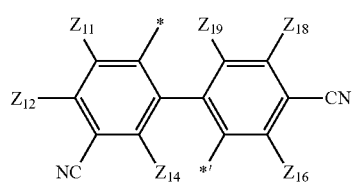
OO26 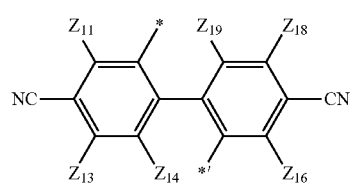
OO27 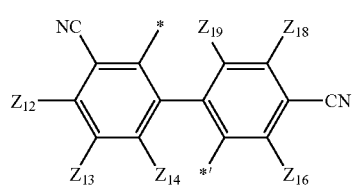
OO28 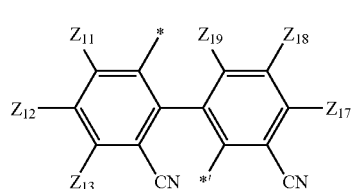
OO29 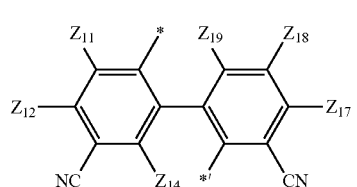
OO30 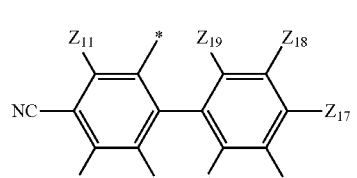
OO31 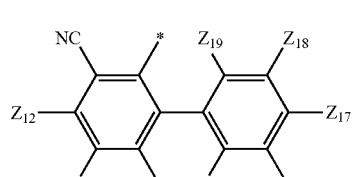
OO32 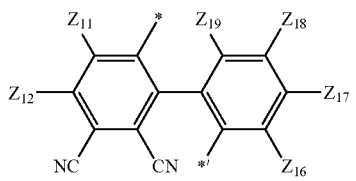
OO33 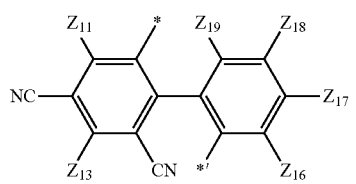
OO34 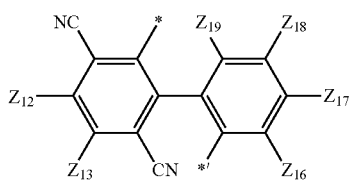
OO35 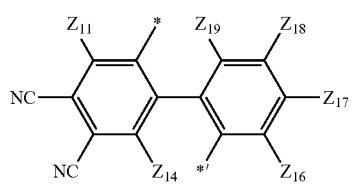
OO36 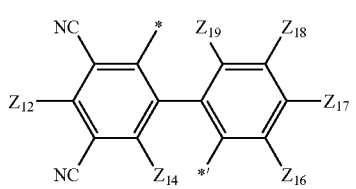
OO37 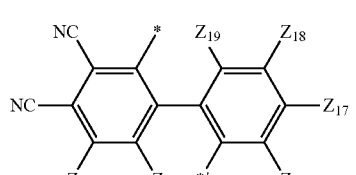
OM1 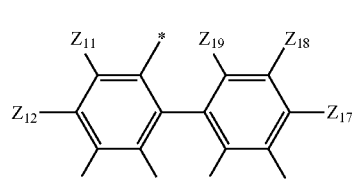
OM2 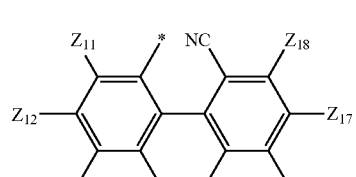

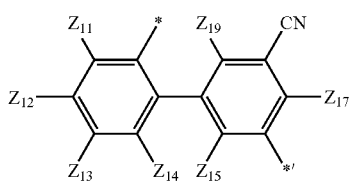 OM3
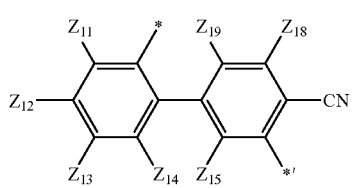 OM4
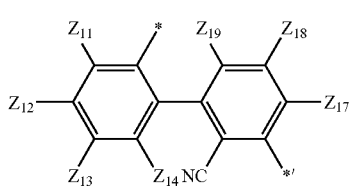 OM5
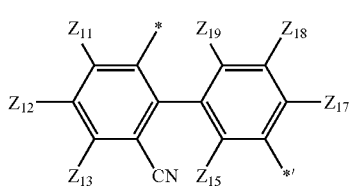 OM6
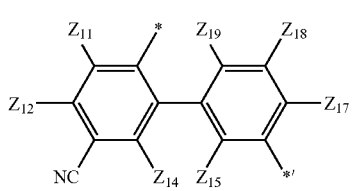 OM7
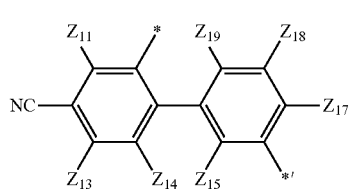 OM8
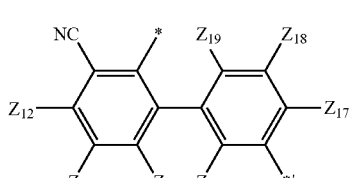 OM9
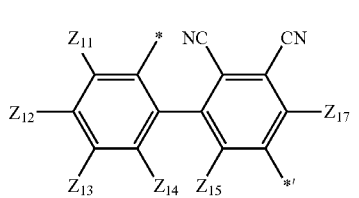 OM10
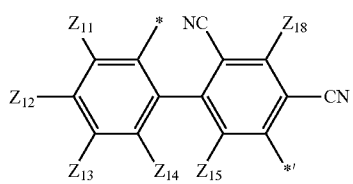 OM11
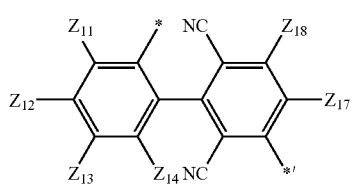 OM12
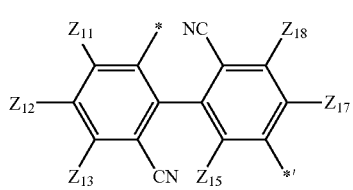 OM13
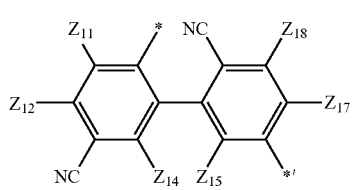 OM14
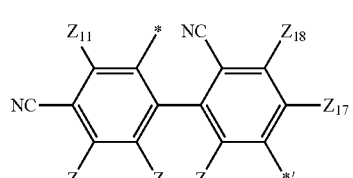 OM15
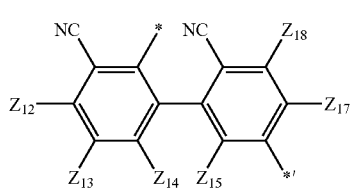 OM16
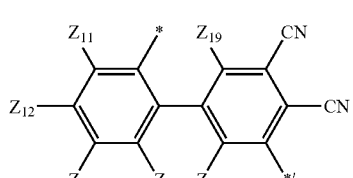 OM17
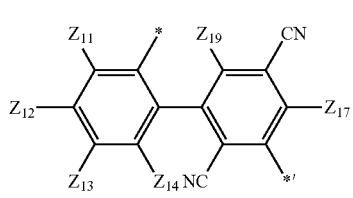 OM18

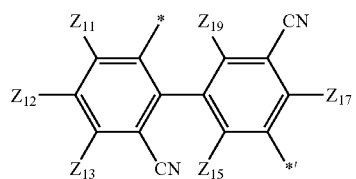 OM19
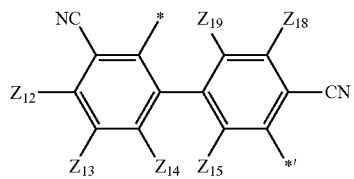 OM27
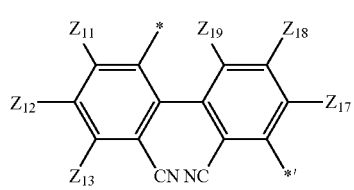 OM28
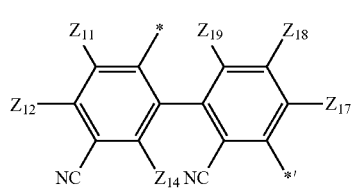 OM29
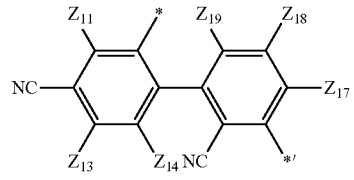 OM30
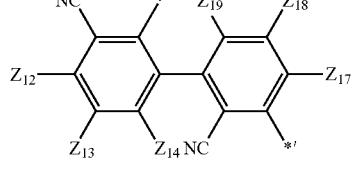 OM31
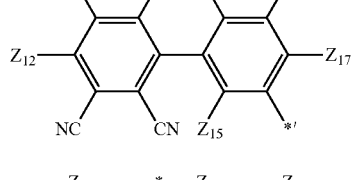 OM32
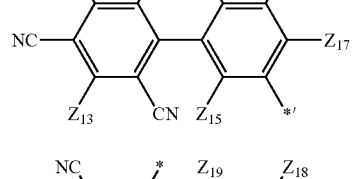 OM33
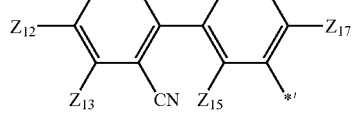 OM34

OM35 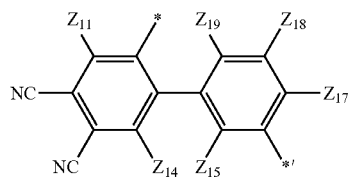
OM36 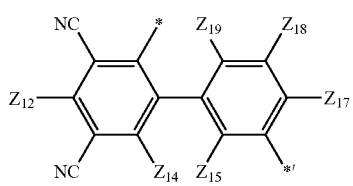
OM37 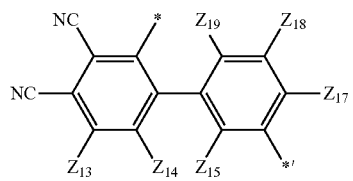
OP1 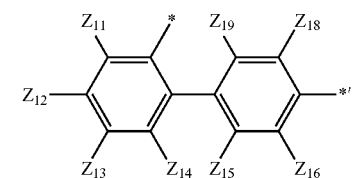
OP2 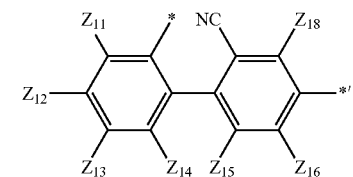
OP3 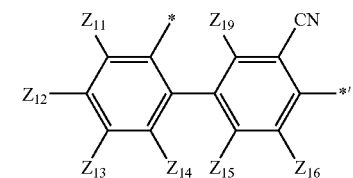
OP4 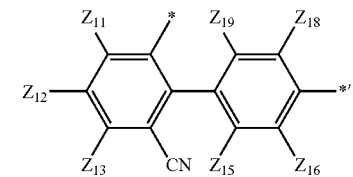
OP5 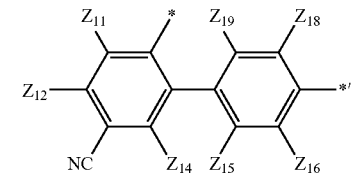
OP6 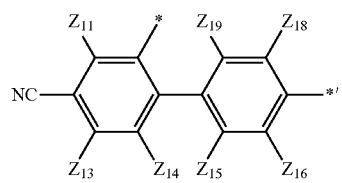
OP7 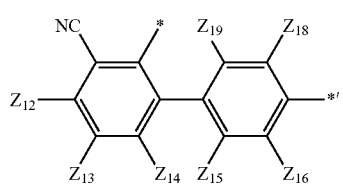
OP8 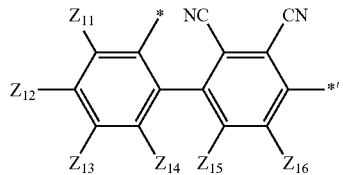
OP9 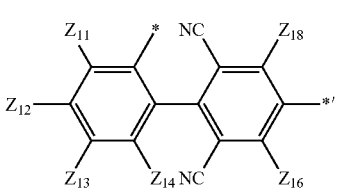
OP10 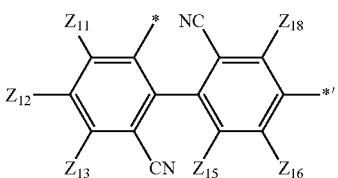
OP11 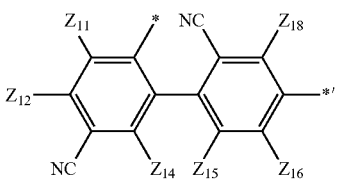
OP12 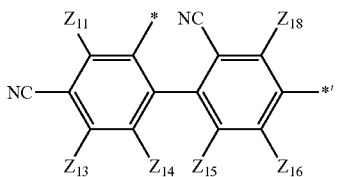
OP13

245
-continued
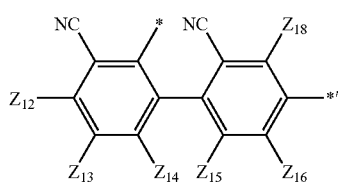
OP14
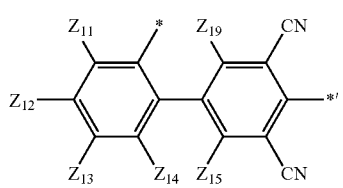
OP15
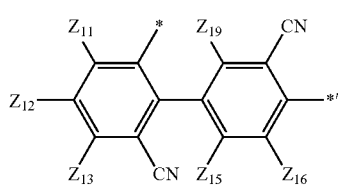
OP16
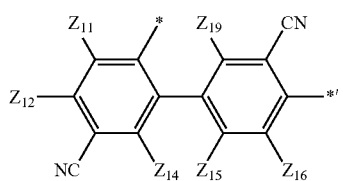
OP17
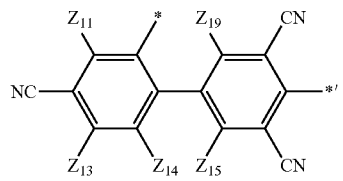
OP18
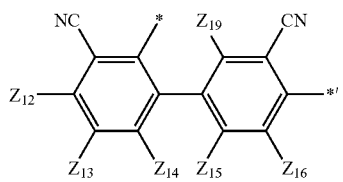
OP19
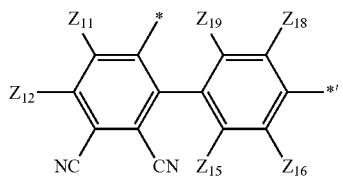
OP20
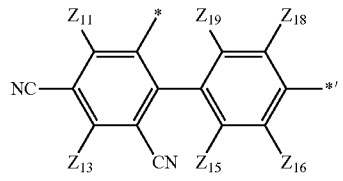
OP21
246
-continued
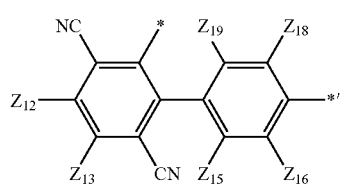
OP22
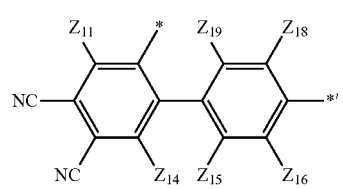
OP23
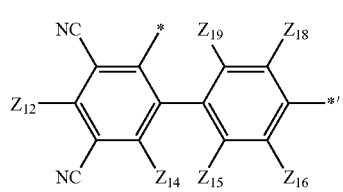
OP24
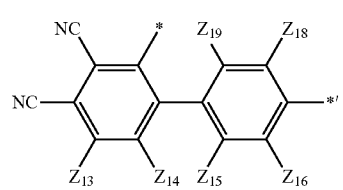
OP25
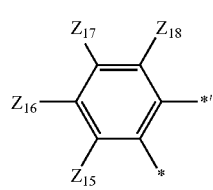
O1
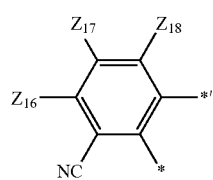
O2
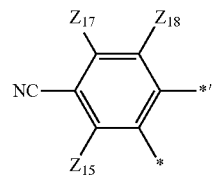
O3
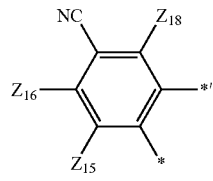
O4

-continued
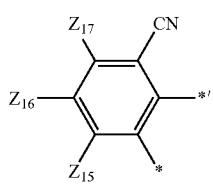 O5
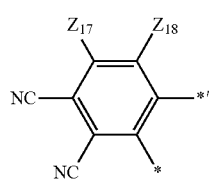 O6
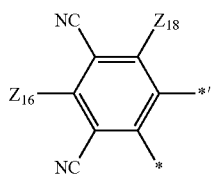 O7
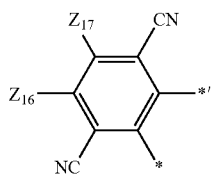 O8
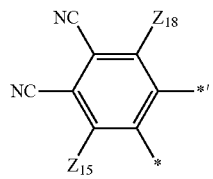 O9
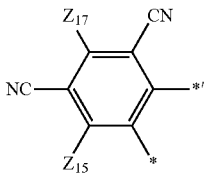 O10
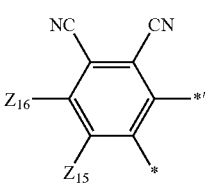 O11
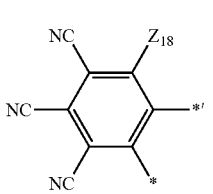 O12
-continued
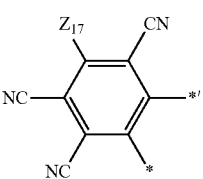 O13
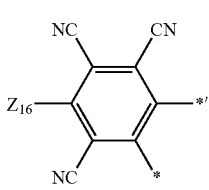 O14
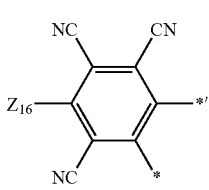 O15
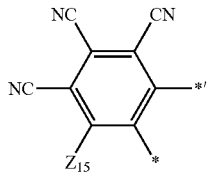 O16
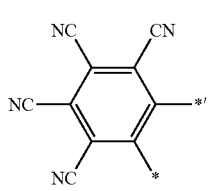 M1
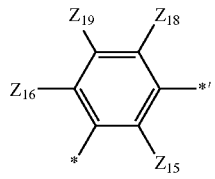 M2
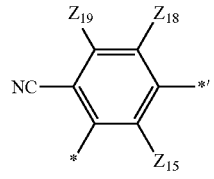 M3
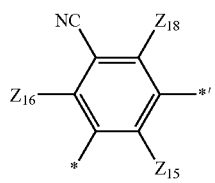 M4
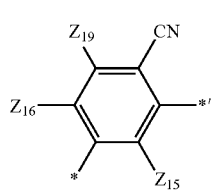

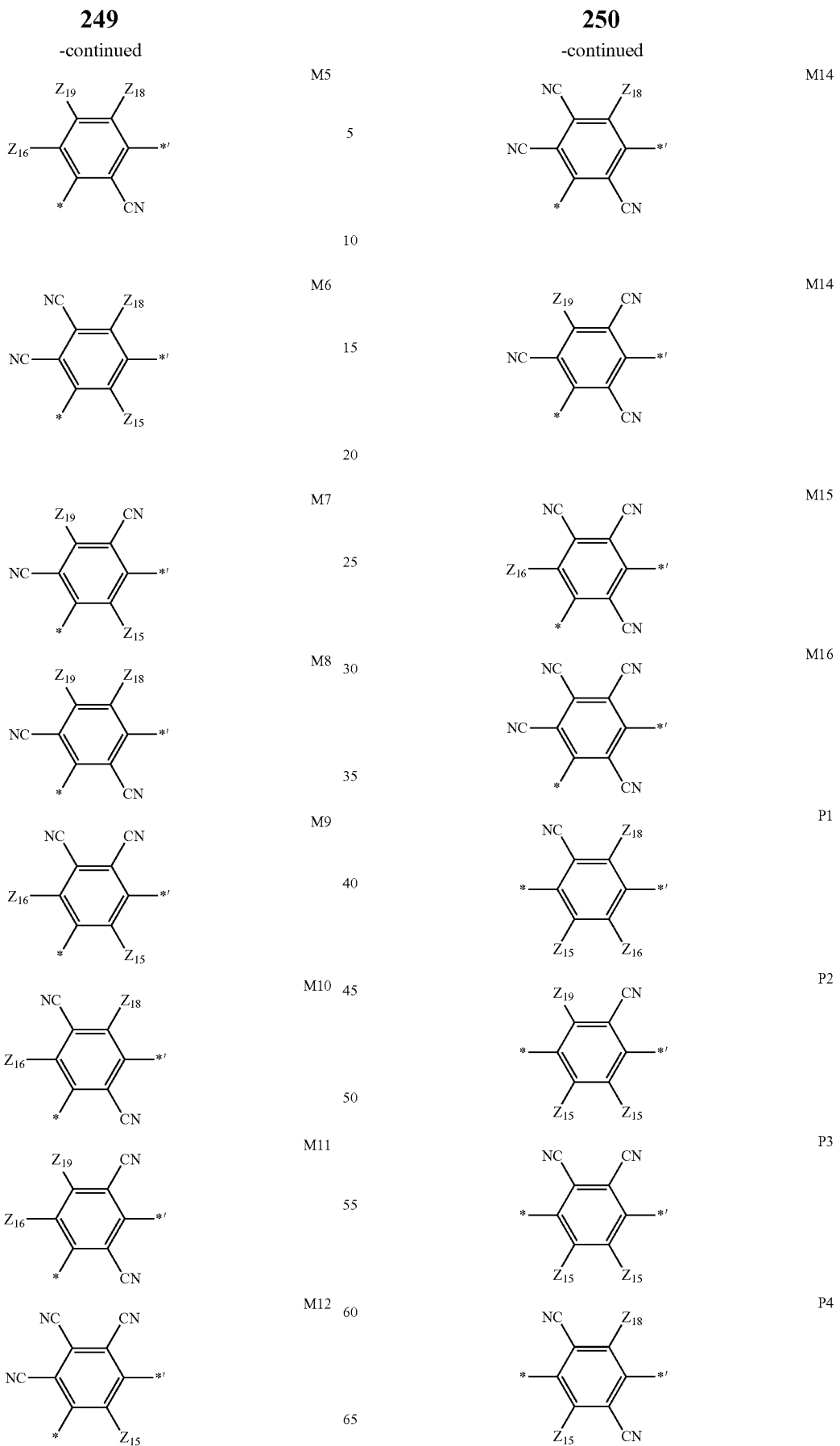

-continued

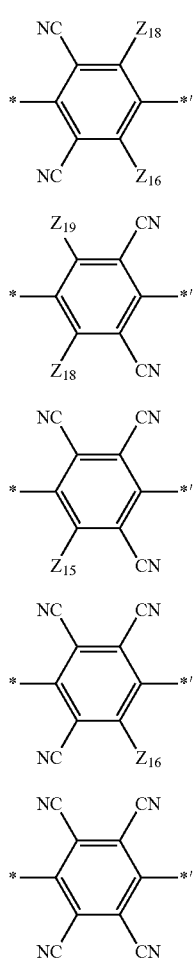

wherein, in Formulae PO1 to PO25, PM1 to PM25, PP1 to PP18, MO1 to MO37, MM1 to MM37, MP1 to MP25, OO1 to OO37, OM1 to OM37, OP1 to OP25, O1 to O16, M1 to M16, and P1 to P9, $Z_{10}$ to $Z_{19}$ are each independently:

hydrogen, deuterium, or a cyano group; or a $C_1$-$C_{20}$ alkyl group, a phenyl group, a biphenyl group, a terphenyl group, a dibenzofuranyl group, or a dibenzothiophenyl group, each unsubstituted or substituted with at least one selected from deuterium, a cyano group, a phenyl group, and a biphenyl group, and and *' each indicate a binding site to a neighboring atom.

8. The organic light-emitting device of claim 1, wherein a group represented by

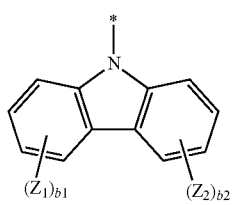

in Formulae E-1(1) and E-1(2) is one of groups represented by Formulae A1-1 to A1-3, a group represented by

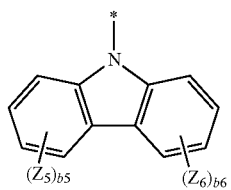

in Formula E-1(1) is one of groups represented by Formulae A2-1 to A2-3, a group represented by

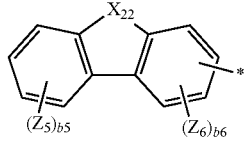

in Formulae E-1(2) and E-1(3) is one of groups represented by Formulae A2-4 to A2-17, and a group represented by

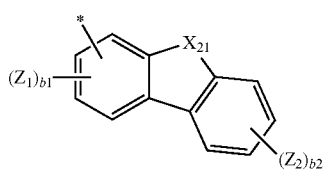

in Formula E-1(3) is one of groups represented by Formulae A1-4 to A1-17:

A1-1

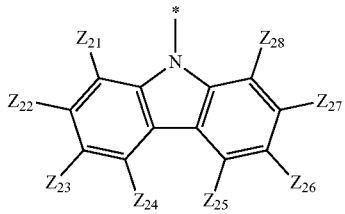

A1-2

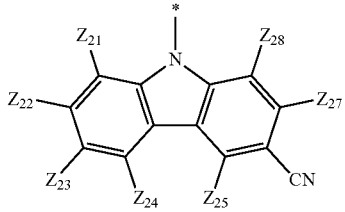

A1-3

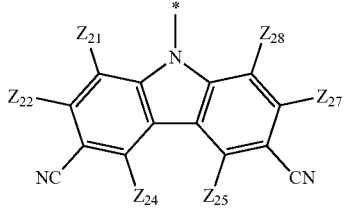

-continued
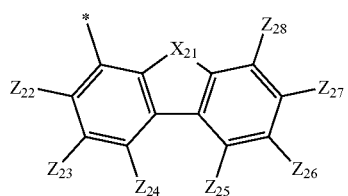
A1-4
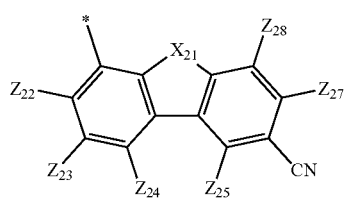
A1-5
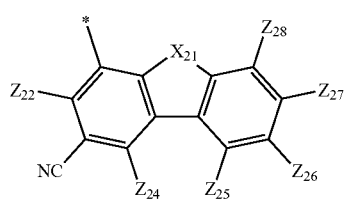
A1-6
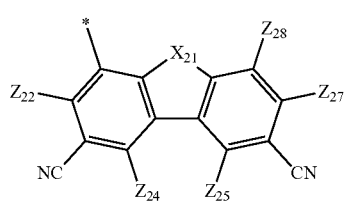
A1-7
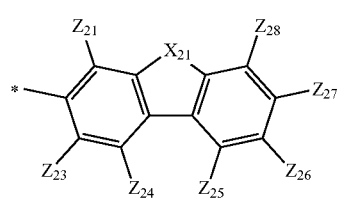
A1-8
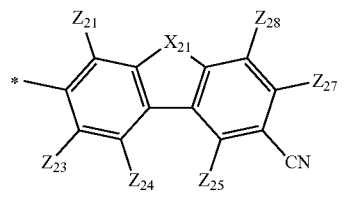
A1-9
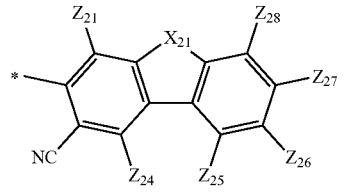
A1-10
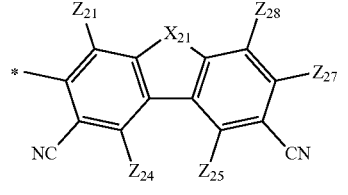
A1-11
-continued
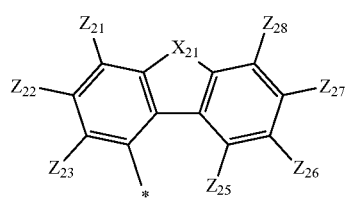
A1-12
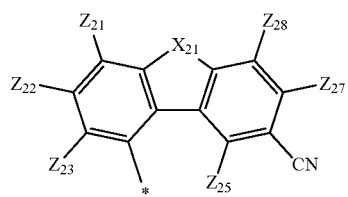
A1-13
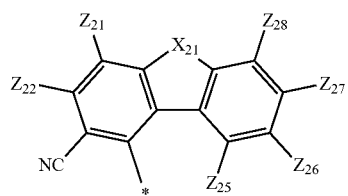
A1-14
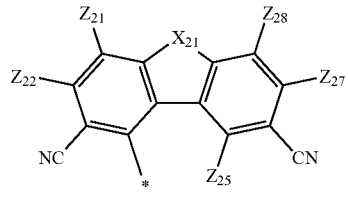
A1-15
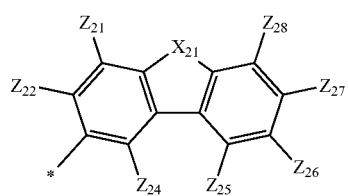
A1-16
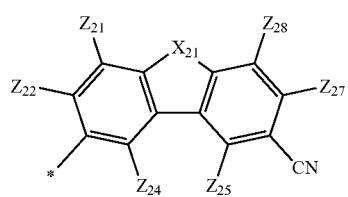
A1-17
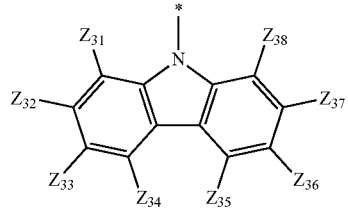
A2-1

-continued
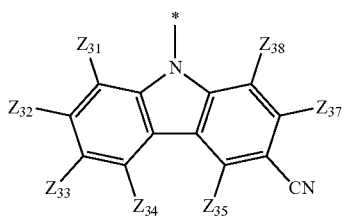
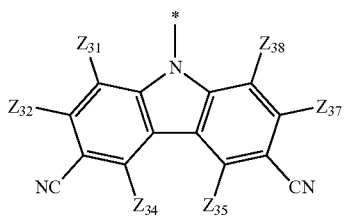
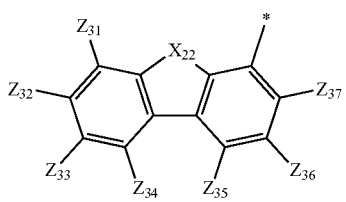
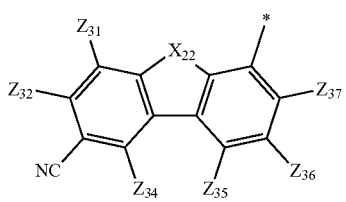
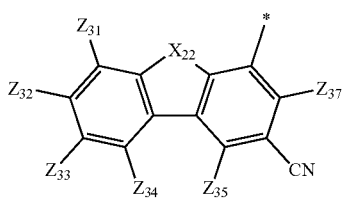
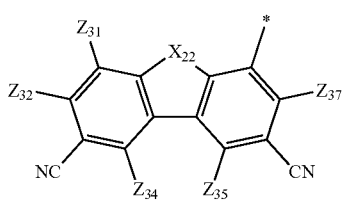
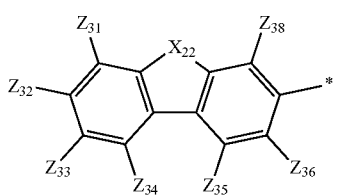
-continued
A2-2
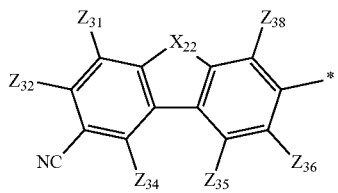
A2-3
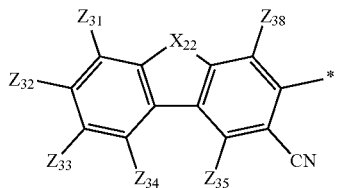
A2-4
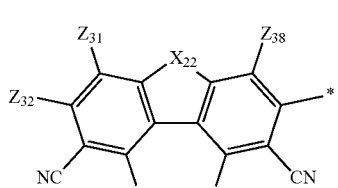
A2-5
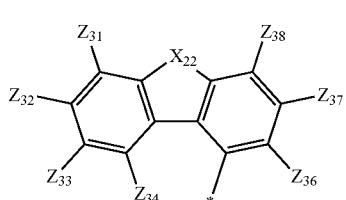
A2-6
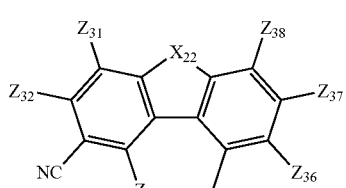
A2-7
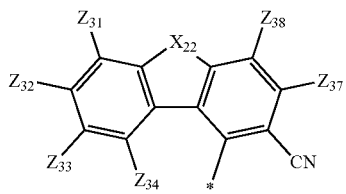
A2-8
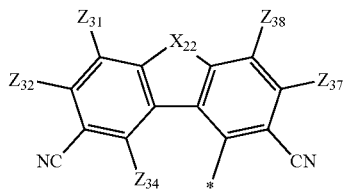
A2-9
A2-10
A2-11
A2-12
A2-13
A2-14
A2-15
A2-16
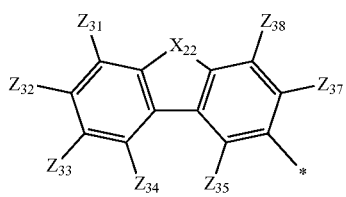

-continued

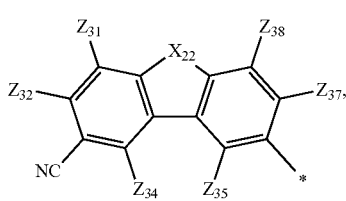

A2-17 wherein, in Formulae A1-1 to A1-17 and A2-1 to A2-17,
$Z_{21}$ to $Z_{28}$ and $Z_{31}$ to $Z_{38}$ are each independently:
hydrogen, deuterium, or a cyano group;
or
a $C_1$-$C_{20}$ alkyl group, a phenyl group, a biphenyl group, a terphenyl group, a dibenzofuranyl group, or a dibenzothiophenyl group, each unsubstituted or substituted with at least one selected from deuterium, a cyano group, a phenyl group, and a biphenyl group, and
and *' each indicate a binding site to a neighboring atom.

9. The organic light-emitting device of claim 1, wherein the third material has reorganization energy of about 0.4 electron volts to about 1 electron volt.

10. The organic light-emitting device of claim 1, wherein $R_3$ comprises at least one π electron-depleted nitrogen-containing cyclic group.

11. The organic light-emitting device of claim 1, wherein $R_3$ is selected from:
a group represented by Formula 13(1) or 13(2);
a phenyl group, a biphenyl group, a terphenyl group, a naphthyl group, a fluorenyl group, a quinolinyl group, an isoquinolinyl group, a carbazolyl group, a dibenzofuranyl group, a dibenzothiophenyl group, and an indolocarbazolyl group; and
a phenyl group, a biphenyl group, a terphenyl group, a naphthyl group, a fluorenyl group, a quinolinyl group, an isoquinolinyl group, a carbazolyl group, a dibenzofuranyl group, a dibenzothiophenyl group, and an indolocarbazolyl group, each substituted with at least one selected from deuterium, a $C_1$-$C_{10}$ alkyl group, a $C_1$-$C_{10}$ alkoxy group, a phenyl group, a biphenyl group, a terphenyl group, a naphthyl group, a fluorenyl group, a pyridinyl group, a pyrimidinyl group, a pyrazinyl group, a pyridazinyl group, a triazinyl group, a quinolinyl group, an isoquinolinyl group, a carbazolyl group, a dibenzofuranyl group, a dibenzothiophenyl group, an indolocarbazolyl group, and —Si($Q_{31}$)($Q_{32}$)($Q_{33}$), and $Q_{31}$ to $Q_{33}$ are each independently selected from a $C_1$-$C_{10}$ alkyl group, a $C_1$-$C_{10}$ alkoxy group, a phenyl group, a biphenyl group, a terphenyl group, and a naphthyl group:

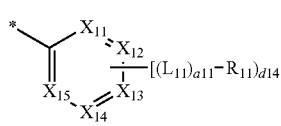

13(1)

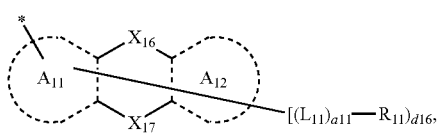

13(2)

wherein, in Formulae 13(1) and 13(2),
$X_{11}$ to $X_{15}$ are each independently C or N, and at least one of $X_{11}$ to $X_{15}$ is N,
$A_{11}$ and $A_{12}$ are each independently a benzene group, a naphthalene group, a pyridine group, a pyrazine group, a pyrimidine group, a pyridazine group, a quinoline group, an isoquinoline group, a quinoxaline group, or a quinazoline group, wherein at least one of $A_{11}$ and $A_{12}$ is a pyridine group, a pyrazine group, a pyrimidine group, a pyridazine group, a quinoline group, an isoquinoline group, a quinoxaline group, or a quinazoline group,
$X_{16}$ is N-[($L_{12}$)$_{a12}$-$R_{12}$], C($R_{14}$)($R_{15}$), O, or S,
$X_{17}$ is a single bond, N-[($L_{13}$)$_{a13}$-$R_{13}$], C($R_{16}$)($R_{17}$), O, or S,
$L_{11}$ to $L_{13}$ are the same as described in connection with $L_3$ in claim 1,
a11 to a13 are the same as described in connection with c3 in claim 1,
$R_{11}$ to $R_{17}$ are the same as described in connection with $R_1$ in claim 1,
d16 is an integer from 0 to 6,
d14 is an integer from 0 to 4, and
indicates a binding site to a neighboring atom.

12. The organic light-emitting device of claim 1, wherein the third material comprises a compound represented by one of Formulae 11-1 to 11-7:

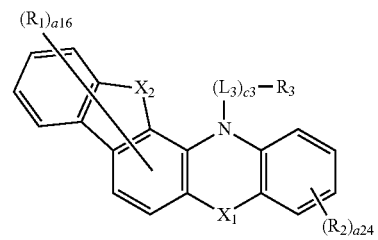

11-1

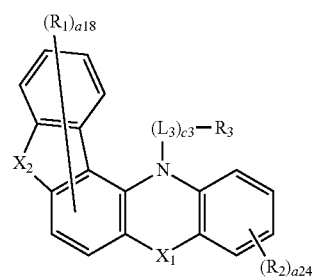

11-2

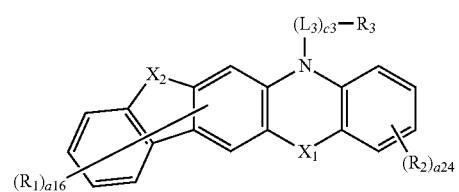

11-3

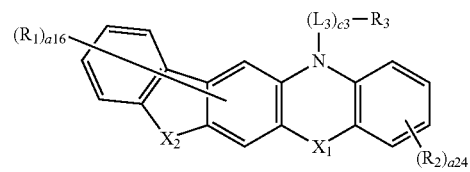

11-4

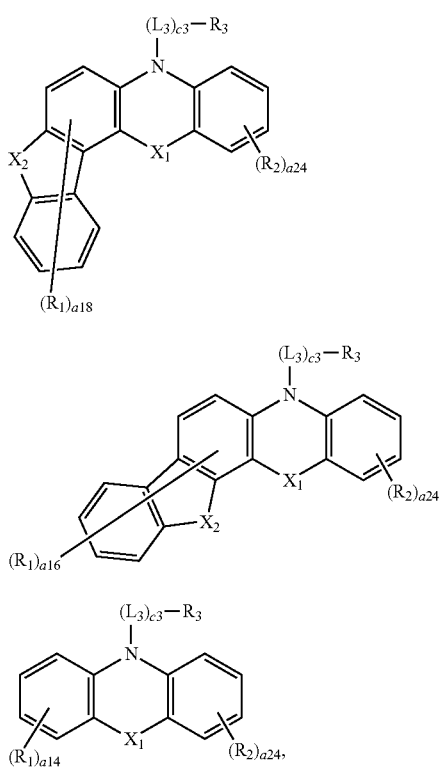

wherein, in Formulae 11-1 to 11-7,
$X_1$, $L_3$, c3, and $R_1$ to $R_3$ are the same as described in claim 1,
$X_2$ is N-$[(L_5)_{c5}$-$R_7]$, C$(R_8)(R_9)$, O, or S,
$L_5$ and c5 are the same as described in connection with $L_3$ and c3 in claim 1,
$R_7$ is the same as described in connection with $R_3$ in claim 1,
$R_8$ and $R_9$ are the same as described in connection with $R_5$ and $R_6$ in claim 1,
a16 is an integer from 0 to 6, and
a14 and a24 are each independently an integer from 0 to 4.

13. The organic light-emitting device of claim 1, wherein the light-emitting material comprises a transition metal-containing organometallic compound that emits blue light.

14. The organic light-emitting device of claim 1, wherein the light-emitting material comprises an organometallic compound comprising a bidentate ligand and a transition metal, the bidentate ligand containing at least one cyano group or at least one fluoro group.

15. The organic light-emitting device of claim 1, wherein an amount of the third material is greater than about 0 parts by weight and equal to or less than about 10 parts by weight based on 100 parts by weight of the first material, the second material, the third material, and the light-emitting material.

16. The organic light-emitting device of claim 1, wherein an amount of the light-emitting material is greater than about 0 parts by weight and equal to or less than about 5 parts by weight based on 100 parts by weight of the first material, the second material, the third material, and the light-emitting material.

\* \* \* \* \*